United States Patent
Bhuniya et al.

(10) Patent No.: US 9,340,506 B2
(45) Date of Patent: *May 17, 2016

(54) ACETAMIDE DERIVATIVES AS GLUCOKINASE ACTIVATORS, THEIR PROCESS AND MEDICINAL APPLICATIONS

(75) Inventors: Debnath Bhuniya, Maharashtra (IN); Anil Deshpande, Maharashtra (IN); Sachin Kandalkar, Maharashtra (IN); Balasaheb Kobal, Maharashtra (IN); Santosh Kurhade, Maharashtra (IN); Vinod Vyavahare, Maharashtra (IN); Rahul Kaduskar, Maharashtra (IN)

(73) Assignee: ADVINUS THERAPEUTICS LIMITED, Bangalore (IN)

(*) Notice: Subject to any disclaimer, the term of this patent is extended or adjusted under 35 U.S.C. 154(b) by 1047 days.

This patent is subject to a terminal disclaimer.

(21) Appl. No.: 13/399,721

(22) Filed: Feb. 17, 2012

(65) Prior Publication Data
US 2012/0214735 A1 Aug. 23, 2012

Related U.S. Application Data

(63) Continuation-in-part of application No. 12/681,845, filed as application No. PCT/IN2008/000650 on Oct. 7, 2008, now Pat. No. 8,501,955.

(30) Foreign Application Priority Data
Oct. 8, 2007 (IN) ............................ 2266/CHE/2007

(51) Int. Cl.
| C07D 277/34 | (2006.01) |
|---|---|
| C07D 277/38 | (2006.01) |
| C07D 513/04 | (2006.01) |
| A61K 31/397 | (2006.01) |
| A61K 31/44 | (2006.01) |
| A61K 31/437 | (2006.01) |
| A61K 31/427 | (2006.01) |
| C07D 213/80 | (2006.01) |
| C07D 241/26 | (2006.01) |
| C07D 277/46 | (2006.01) |
| C07D 277/54 | (2006.01) |
| C07D 401/04 | (2006.01) |
| C07D 405/12 | (2006.01) |
| C07D 405/14 | (2006.01) |
| C07D 413/12 | (2006.01) |
| C07D 417/04 | (2006.01) |
| C07D 417/12 | (2006.01) |
| C07D 417/14 | (2006.01) |
| A61K 38/26 | (2006.01) |

(52) U.S. Cl.
CPC ............ *C07D 213/80* (2013.01); *C07D 241/26* (2013.01); *C07D 277/46* (2013.01); *C07D 277/54* (2013.01); *C07D 401/04* (2013.01); *C07D 405/12* (2013.01); *C07D 405/14* (2013.01); *C07D 413/12* (2013.01); *C07D 417/04* (2013.01); *C07D 417/12* (2013.01); *C07D 417/14* (2013.01); *C07D 513/04* (2013.01); *A61K 38/26* (2013.01)

(58) Field of Classification Search
CPC combination set(s) only.
See application file for complete search history.

(56) References Cited

U.S. PATENT DOCUMENTS

2010/0144772 A1  6/2010  Mookhtiar et al.

FOREIGN PATENT DOCUMENTS

| WO | 02/08209 | 1/2002 |
|---|---|---|
| WO | 03/015774 | 2/2003 |
| WO | 03/055482 | 7/2003 |
| WO | 2008/104994 | 9/2008 |

OTHER PUBLICATIONS

Office action for corresponding Application No. EP 08 838 336 dated Jan. 23, 2012.
Written Opinion for International Application No. PCT/IN2008/000650 dated Apr. 13, 2010.
International Search Report for Application No. PCT/IN2008/000650 dated Apr. 15, 2009.

*Primary Examiner* — Nyeemah A Grazier
(74) *Attorney, Agent, or Firm* — Perkins Coie LLP

(57) ABSTRACT

Acetamide derivatives, their stereoisomers, tautomers, prodrugs, pharmaceutically acceptable salts, polymorphs, solvates and formulations thereof for the prophylaxis, management, treatment, control of progression, or adjunct treatment of diseases and/or medical conditions where the activation of glucokinase would be beneficial, are disclosed.

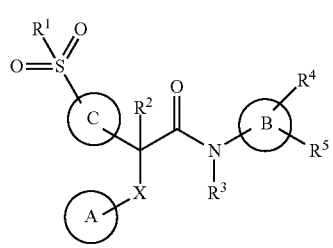

The disclosure also provides process of preparation of these acetamide derivatives.

18 Claims, No Drawings

ACETAMIDE DERIVATIVES AS GLUCOKINASE ACTIVATORS, THEIR PROCESS AND MEDICINAL APPLICATIONS

CROSS-REFERENCE TO RELATED APPLICATIONS

The present application is a continuation in part of U.S. patent application Ser. No. 12/681,845, filed on Aug. 23, 2010, which is a 371 of International Patent Application No. PCT/IN2008/000650, filed Oct. 7, 2008, which claims priority to and the benefit of India Patent Application No. 22661CHE/2007, filed Oct. 8, 2007, the disclosures of each of which are incorporated by reference herein in their entirety.

TECHNICAL FIELD

This disclosure relates to a series of acetamide derivatives, their stereoisomers, tautomers, prodrugs, pharmaceutically acceptable salts, polymorphs, solvates and formulations thereof. The disclosure also relates to the process of preparation of acetamide derivatives along with their glucokinase activating effects, which are beneficial for the prophylaxis, management, treatment, control of progression, or adjunct treatment of diseases and/or medical conditions where the activation of glucokinase would be beneficial, such as diabetes, metabolic syndrome, and/or diabetes-related complications including retinopathy, nephropathy, neuropathy, ischemic heart disease, arteriosclerosis, β-cell dysfunction, and as therapeutic and/or prophylactic agents for obesity.

It also relates to compounds with liver selective Glucokinase activation, useful for the treatment of hyperglycemia, diabetes, obesity, dyslipidemia, metabolic syndrome and like, in mammals and have minimum hypoglycemic potential.

BACKGROUND

Diabetes mellitus is a metabolic disorder characterized by recurrent or persistent hyperglycemia (high blood glucose) and other signs, as distinct from a single disease or condition. Glucose level abnormalities can result in serious long-term complications, which include cardiovascular disease, chronic renal failure, retinal damage, nerve damage (of several kinds), microvascular damage and obesity.

Type 1 diabetes, also known as Insulin Dependent Diabetes Mellitus (IDDM), is characterized by loss of the insulin-producing β-cells of the islets of Langerhans of the pancreas leading to a deficiency of insulin. Type-2 diabetes previously known as adult-onset diabetes, maturity-onset diabetes, or Non-Insulin Dependent Diabetes Mellitus (NIDDM)—is due to a combination of increased hepatic glucose output, defective insulin secretion, and insulin resistance or reduced insulin sensitivity (defective responsiveness of tissues to insulin).

Chronic elevation of blood glucose level leads to damage of blood vessels. In diabetes, the resultant problems are grouped under "microvascular disease" (due to damage of small blood vessels) and "macrovascular disease" (due to damage of the arteries). Examples of microvascular disease include diabetic retinopathy, neuropathy and nephropathy, while examples of macrovascular disease include coronary artery disease, stroke, peripheral vascular disease, and diabetic myonecrosis.

Diabetic retinopathy, characterized by the growth of weakened blood vessels in the retina as well as macular edema (swelling of the macula), can lead to severe vision loss or blindness. Retinal damage (from microangiopathy) makes it the most common cause of blindness among non-elderly adults in the US. Diabetic neuropathy is characterized by compromised nerve function in the lower extremities. When combined with damaged blood vessels, diabetic neuropathy can lead to diabetic foot. Other forms of diabetic neuropathy may present as mononeuritis or autonomic neuropathy. Diabetic nephropathy is characterized by damage to the kidney, which can lead to chronic renal failure, eventually requiring dialysis. Diabetes mellitus is the most common cause of adult kidney failure worldwide. A high glycemic diet (i.e., a diet that consists of meals that give high postprandial blood sugar) is known to be one of the causative factors contributing to the development of obesity.

Glucokinase (GK), also known as hexokinase IV or D, is one of four glucose-phosphorylating enzymes called hexokinases that catalyze the first step of glycolysis, the conversion of glucose to glucose 6-phosphate (G6P), in vertebrate tissues. GK functions in a dual role, with distinct functions in the pancreas and liver; (a) as a molecular glucose sensor in the insulin-producing pancreatic β-cells, and (b) as the high-capacity enzymatic step initiating the storage of glucose in the form of glycogen in the liver and uptake of glucose during hyperglycemia. Therefore, GK plays a central role in glucose homeostasis, through the phosphorylation of glucose in the liver, and the modulation of insulin secretion in the pancreas (Postic, C. et al (1999) *J. Biol. Chem.* 274: 305-315). GK also functions as a sensor in other neuroendocrine cells of the gastrointestinal tract and in various brain cells including specific cells in the hypothalamus (Jetton, T. A. et al (1994) *J. Biol. Chem.* 269: 3641-3654).

The physiological concentration of glucose in human plasma is approximately 5.5 mM under fasting conditions, and increases to about 12 mM in the fed state. This concentration is dependent on and maintained by the activity of GK, which senses glucose and controls metabolic flux in key cell types. The glucose concentration, at which GK activity is at half of its maximal velocity or $V_{max}$, is defined as its $S_{0.5}$. The $S_{0.5}$ of GK for glucose lies in the middle of the physiological glucose concentration range at approximately 8 mM, allowing this enzyme to act as a molecular glucose sensor crucial for glucose homeostasis. The limited tissue distribution and unique kinetic properties of GK allow it to play a critical role in pancreatic β-cell insulin secretion and hepatic glucose utilization. GK differs from the other members of the mammalian hexokinase family in its unique sigmoidal kinetics with respect to glucose, a high $S_{0.5}$ that lies in the physiological glucose concentration range (the other three mammalian hexokinases have $S_{0.5}$ values less than 0.5 mM), the lack of product inhibition by G6P, and its tissue distribution in cell types that are thought to be responsive to changing plasma glucose levels.

Tissue-specific differences have been observed between the regulation of GK in the liver and the pancreas. In the liver, GK is allosterically inhibited by the glucokinase regulatory protein (GKRP), which results in its sequestration in the nucleus and subsequent protection from proteolytic degradation. This inhibition is reversed by high concentrations of glucose and by fructose 1-phosphate, and is potentiated by fructose 6-phosphate. In the pancreatic β-cells, GK expression is believed to be constitutive. GK is also known to be expressed in the hypothalamus, where it may exert effects on feeding behavior, and in the intestine K and L cells, where it may contribute to the secretion of enteroincretins such as glucagon-like peptide-1 (GLP-1), glucose dependent insulinotropic peptide (GIP) (Matschinsky F. M. et al (2006) *Diabetes* 55: 1-12; Theodorakis M. J. et al (2006) *Am. J. Physiol. Endocrinol. Metab.* 290: E550-E559). Given the role of GK as a molecular glucose sensor, it is not surprising that GK mutations have a profound influence on glucose homeostasis. About 2000 GK mutations that have been identified in humans result in impaired glucose-mediated insulin secretion and maturity-onset diabetes of the young type 2 (MODY-2). Some of these mutations result in decreased accumulation of hepatic glycogen, while others decrease GK activity by reducing the stability of the enzyme or by decreasing its $V_{max}$. Mutations that result in activation of GK are implicated in the onset of persistent hyperinsulinemic hypoglycemia of infancy (PHHI). Single point mutations (e.g. V62M, D158A, Y214A, V455M, and F456V) in regions distinct from the substrate binding site of the enzyme lead to modulation of GK activity (Glaser, B. et al (1998) *N. Engl. J. Med.* 338: 226-230; Gloyn, A. L. (2003) *Hum. Mutat.* 22: 353-362; Gloyn, A. L. et al (2003) *Diabetes* 52: 2433-2440). These observations highlight that GK activity can be regulated through allosteric modulation.

Homozygous knock out of GK in mice results in severe diabetes and death, while heterozygous disruption results in a milder diabetic phenotype, decreased hepatic glucose uptake and impaired insulin secretion in response to glucose. Conversely, over-expression of GK in fat-induced diabetic as well as non-diabetic mice results in improved glucose tolerance. Transgenic mice over-expressing GK in the liver show a modest (20%) increase in fasting GK activity, which correlates with lower fasting plasma glucose and insulin, and improved glucose tolerance (Hariharan, N. et al (1997) *Diabetes* 46: 11-16).

The enzymatic properties of GK can be described in terms of its velocity (i.e. its rate of converting glucose to G6P) and its $S_{0.5}$ for glucose (i.e. the apparent glucose concentration at which GK converts glucose to G6P at half of its maximal velocity). The $S_{0.5}$ of human GK for glucose is approximately 8 mM in enzyme based assay. GKAs induce increased conversion by GK of glucose to G6P by either decreasing the $S_{0.5}$ of GK for glucose, increasing its $V_{max}$, or by a combination of both, and can potentially lower blood glucose concentrations to hypoglycemic levels.

Several patent applications and publications describe the discovery of small-molecule glucokinase activators (GKAs) that allosterically modulate or activate the activity of GK (Kamata, K. et al (2004) *Structure* 12: 429-438; WO 2003/055482 A1; WO 2005/123132 A2; WO 2004/002481 A2; U.S. Pat. No. 6,486,184 B2; WO 2006/040528 A1; Fyfe, M. C. T. (2007) *Diabetologia*, 50: 1277-1287; McKerrecher, D. et al *Bioorg. Med. Chem. Lett.* 15 (2005) 2103-2106; Efanov, A. M. et al (2005) *Endocrinology* 146: 3696-3701; Printz, R. L. and Granner, D. K. (2005) *Endocrinology* 146: 3693-3695; Brocklehurst, K. J. et al (2004) *Diabetes*, 53: 535-541; Grimsby, J. et al (2003) *Science* 301: 370-373). These GKAs increase GK activity by decreasing its $S_{0.5}$ for glucose, and, in some cases, also increasing its $V_{max}$. However, for many of these compounds, hypoglycemia has been reported in animal studies which may be a consequence of excessive GK activation. For example, GK activators like Ro-28-1675 cause hypoglycemia in animal efficacy models (Kamata, K. et al (2004) *Structure* 12: 429-438). Similar hypoglycemic potential is seen in another GK activator, PSN-GK1, at higher dose (Fyfe, M. C. T. (2007) *Diabetologia*, 50: 1277-1287).

Rat liver glucokinase is inhibited by long chain acyl-CoA. Deinhibition of such inhibition may also result into glucokinase activation (Tippett P. S. et. al (1982) *J. Biol. Chem.* 25712839-12845, Tippett P. S. et. al (1982) *J. Biol. Chem.* 257, 12846-12852.

A concept of minimizing hypoglycemic potential by liver selective glucokinase activation has been mentioned in patent application no. WO 2005/123123 wherein, compounds described in WO 2004/002481 are identified as liver selective glucokinase activators which increase glucose utilization in the liver without inducing an increase in insulin secretion in response to glucose.

The present disclosure provides a novel class of compounds characterized as glucokinase activators or modulators, and their potential use as medicament for the prophylactic or therapeutic treatment of hyperglycemia, diabetes, obesity, dyslipidemia, metabolic syndrome and like.

SUMMARY OF THE INVENTION

The present disclosure relates to a series of acetamide derivatives described by formula (I), their stereoisomers, tautomers, prodrugs, pharmaceutically acceptable salts, polymorphs, solvates and formulations thereof as glucokinase activators (GKAs);

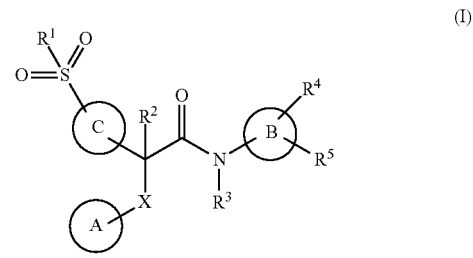

wherein
ring A and ring C are monocyclic ring independently selected from aryl, heteroaryl or heterocyclyl;
wherein rings A and C are optionally substituted with 1 to 4 substituents independently selected from halogen, monohaloalkyl, dihaloalkyl or perhaloalkyl, monohaloalkoxy, dihaloalkoxy or perhaloalkoxy, cyano, nitro, alkyl, alkenyl, alkynyl, methylenedioxy, amidino —NR$^6$R$^7$, —OR$^6$, —NR$^6$C(O)R$^7$, —(CR$^8$R$^9$)$_n$—C(O)OR$^6$, —(CR$^8$R$^9$)$_n$C(O)NR$^6$R$^7$, —(CR$^8$R$^9$)$_n$C(O)R$^6$, cycloalkyl, heterocyclyl, aryl or heteroaryl groups;
n=0-4;
R$^6$ and R$^7$ are independently selected from the group consisting of hydrogen, alkyl, alkenyl, alkynyl, aryl, arylalkyl, heteroaryl, heteroarylalkyl, cycloalkyl, cycloalkylalkyl, heterocyclyl and heterocyclylalkyl; wherein R$^6$ and R$^7$ is each optionally substituted with one or more substituents selected from halo, straight chain or branched chain alkyl, cycloalkyl, aryl, heteroaryl, heterocycle, alkylsulfonyl, oxo, nitro, cyano, —(CR$^8$R$^9$)$_n$COOR$^6$, —(CR$^8$R$^9$)$_n$C(O)NR$^6$R$^7$, —OR$^6$, —SR$^6$ or —NR$^6$R$^7$; or
R$^6$ and R$^7$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, nitro, cyano, —OR$^6$, —SR$^6$, —NR$^6$R$^7$, oxo, alkylsulfonyl, —COOR$^6$, —C(O)NR$^6$R$^7$, cycloalkyl, aryl, heterocyclyl or heteroaryl;
wherein R$^6$ and R$^7$ are as described above;
R$^8$ and R$^9$ are independently selected from the group consisting of hydrogen, fluorine, OR$^6$, alkyl and perfluoroalkyl; or
R$^8$ and R$^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, nito, cyano, oxo, —OR$^6$, —SR$^6$, —NR$^6$R$^7$, alkylsulfonyl, —COOR$^6$, —C(O)NR$^6$R$^7$, cycloalkyl, aryl, heterocyclyl or heteroaryl; wherein R$^6$ and R$^7$ are as described above;

Ring-B is an optionally substituted 4-12 membered mono or bicyclic ring containing 1-4 hetero atoms selected from N, O, S with at least one nitrogen in the ring;

X represents 0 or NR$^6$; wherein R$^6$ is as described above;

R$^1$ is selected from cycloalkyl or heterocyclyl;

R$^2$ is hydrogen;

R$^3$ is selected from the group consisting of hydrogen, alkyl and perfluoroalkyl;

R$^4$ and R$^5$ are independently selected from the group consisting of hydrogen, halogen, alkyl, alkenyl, alkynyl, cycloalkyl, cycloalkylalkyl, heterocyclyl, heterocycloalkyl, aryl, arylalkyl, heteroaryl, heteroarylalkyl, mono, di or tri substituted haloalkyl, nitrile, nitro, oxo, —NR$^6$R$^7$, —OR$^6$, —S(O)$_p$R$^6$, —S(O)$_p$NR$^6$R$^7$, —NR$^6$S(O)$_p$R$^7$, —NR$^6$C(O)R$^7$, —OS(O)$_p$R$^7$, —NR$^6$C(O)OR$^7$, —(CR$^8$R$^9$)$_n$C(O)OR$^6$, —(CR$^8$R$^9$)$_n$(CO)NR$^6$R$^7$, —(CR$^8$R$^9$)$_n$S(O)$_p$NR$^6$R$^7$, —(CR$^8$R$^9$)$_n$N(R$^6$)C(O)R$^6$, —(CR$^8$R$^9$)$_n$OR$^6$, —C(CR$^8$R$^9$)$_n$NR$^6$R$^7$, —C(R$^8$R$^9$)$_n$CO(R$^6$) and —S(O)$_p$C(R$^8$R$^9$)$_n$C(O)OR$^6$, wherein R$^4$ and R$^5$ is each optionally substituted with one or more substituents selected from halo, straight chain or branched chain alkyl, alkenyl, alkynyl, cycloalkyl, aryl, heteroaryl, heterocycle, alkylsulfonyl, oxo, nitro, cyano, —(CR$^8$R$^9$)$_n$COOR$^6$, —(CR$^8$R$^9$)$_n$C(O)NR$^6$R$^7$, —OR$^6$, —SR$^6$ or —NR$^6$R$^7$;

wherein n=0-4;

R$^6$, R$^7$, R$^8$ and R$^9$ are as described in the text;

in addition to R$^4$ and R$^5$, ring-B is further optionally substituted with one or more substituents selected from halo, straight chain or branched chain alkyl, alkenyl, alkynyl, cycloalkyl, aryl, heteroaryl, heterocyclyl, alkylsulfonyl, oxo, nitro, cyano, —COOR$^6$, —C(O)NR$^6$R$^7$, —OR$^6$, —SR$^6$ or —NR$^6$R$^7$.

The disclosure also relates to the process of preparation of acetamide derivatives of formula-I.

These GKAs are beneficial for the prophylaxis, management, treatment, control of progression, or adjunct treatment of diseases and/or medical conditions such as Type-I and Type-II diabetes, obesity, dyslipidemia, metabolic syndrome and/or diabetes-related complications including retinopathy, nephropathy, neuropathy, ischemic heart disease, arteriosclerosis, n-cell dysfunction, and as therapeutic and/or prophylactic agents for obesity where the activation of glucokinase would be beneficial.

The present disclosure also relates to the compounds of formula (I) that are liver selective GK activators. Such liver selective GK activators may be useful for the treatment of hyperglycemia, diabetes, obesity, dyslipidemia, metabolic syndrome and the like, in mammals and have minimum hypoglycemic potential.

Surprisingly, compounds of the present invention were found to have superior glucokinase activating properties over the compounds disclosed in co-pending application 409/CHE/2007.

These and other features, aspects, and advantages of the present subject matter will become better understood with reference to the following description and appended claims. This Summary is provided to introduce a selection of concepts in a simplified form. This Summary is not intended to identify key features or essential features of the claimed subject matter, nor is it intended to be used to limit the scope of the claimed subject matter.

DETAILED DESCRIPTION OF THE INVENTION

Definitions

In the structural formulae given herein and throughout the present disclosure, the following terms have the indicated meaning:

The term "optionally substituted" as used herein means that the group in question is either unsubstituted or substituted with one or more of the substituents specified. When the group in question is substituted with more than one substituent, the substituent may be same or different.

The term "mono or bicyclic ring" refers to a carbocycle, an aryl, a heterocycle or a heteroaryl which can be aromatic or non-aromatic, saturated or unsaturated, 3 to 18 ring atoms system including 0 to 5 heteroatoms independently selected from S, N, O; the said rings can be optionally substituted with common substituents.

The term "aryl", alone or in combination with any other term, refers to a monocyclic or a polycyclic aromatic ring system containing carbon-ring atoms, such as phenyl, biphenyl, naphthyl or anthryl which optionally carries one or more substituents, preferably one to three, each independently selected from halogen, trifluoromethyl, trifluoromethoxy, amino, alkyl, alkenyl, alkynyl, alkoxy, alkylcarbonyl, alkoxycarbamoyl, aminocarbonyl, cycloalkyl, cycloalkenyl, acyl, cyano, carbamoyl, methylendioxy, carboxy, alkoxycarbonyl, aryloxy, alkylaminocarbonyl, dialkylaminocarbonyl, hydroxy, heteroaryl, heterocyclyl, nitro, SO$_2$alkyl, SO$_2$cycloalkyl and the like.

"Heteroaryl", alone or in combination with any other term, refers to a monocyclic aromatic ring structure containing 5 or 6 ring atoms, or a bicyclic aromatic group having 8 to 12 atoms, containing one or more heteroatoms independently selected from O, S, and N, and optionally substituted with 1 to 3 groups or substituents such as halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. "Heteroaryl" is also intended to include oxidized S or N, such as sulfinyl, sulfonyl and N-oxide of tertiary ring nitrogen. A carbon or hetero-atom is the point of attachment of the heteroaryl ring structure such that a stable aromatic ring is retained. Examples of heteroaryl groups are azepinyl, benzimidazolyl, benisoxazolyl, benzofurazanyl, benzopyranyl, benzothiazolyl, benzothienyl, benzoxazolyl, cinnolinyl, pyridinyl, pyridazinyl, pyrazinyl, quinazolinyl, purinyl, indolyl, quinolinyl, pyrimidinyl, pyrrolyl, oxazolyl, oxadiazolyl, thiazolyl, thienyl, isooxazolyl, oxathiadiazolyl, isothiazolyl, tetrazolyl, imidazolyl, triazinyl, furanyl, benzofuryl, naphthyridinyl, thiadiazolyl, triazolyl, oxazolopyridinyl, imidazopyridinyl, thiazolopyridinyl, thiazolotraizinyl, thiazolopyrazinyl, quinoxalinyl and the like. A substituted heteroaryl contains a substituent attached to an available carbon or heteroatom to produce a stable compound. "Heteroaryl" is also intended to encompass compounds where a heteroaryl is attached to another non-aromatic cyclyl or heterocyclyl rings. Non-limiting examples include chromanyl, dihydrobenzofuranyl, indalinyl, dihydrobenzothienyl, benzodioxolyl dihydrobenzothienyl, dihydrobenzothiopyranyl, isochromanyl, dihydrobenzothiopyranyl sulfone, 1,3-dioxolanyl, benzofuryl, and the like.

As used herein, "heterocycle" or "heterocyclyl" refers to a stable 4 to 7-membered monocyclic or stable 8 to 12 membered bicyclic heterocyclic non-aromatic ring which is either saturated or unsaturated, and which consists of carbon atoms and from one to five heteroatoms selected from the group consisting of N, O, and S. "Heterocyclyl" is also intended to include oxidized S or N, such as sulfinyl, sulfonyl and N-oxide of tertiary ring nitrogen. The heterocyclic ring may be attached at any heteroatom or carbon atom which results in the creation of a stable structure. Non-limiting examples include imidazolidinyl, imidazolinyl, indolinyl, isoindolinyl, isoquinolinyl, isothiazolidinyl, isothiazolidinyl, morpholinyl, 2-oxopiperazinyl, 2-oxopiperdinyl, 2-oxopyrrolidinyl, piperidyl, piperazinyl, pyrazolidinyl, pyrrolidinyl, quinoxalinyl, dihydroimidazole-one, tetrahydrofuryl, tetrahydroisoquinolinyl, tetrahydroquinolinyl, tetrahydroquinoxalinyl, thiamorpholinyl sulfoxide, thiazolinyl, thiazolidine, benzooxazinone, benzothiazinone, isoxazoline, oxazolidin, dihydropyrazinyl, dihydrobezoxazinyl, dihydrobenzothiazinyl, benzodioxolyl, dihydrobenzodioxolyl, dihydropyridyl and dihydrobenzodiazepinone.

"Alkyl" refers to straight or branched chain having 1 to 10 carbon atoms which is/are further substituted with one or more common substituents. Examples of alkyl groups include, but are not limited to methyl, ethyl, propyl, isopropyl, butyl, t-butyl and the like.

"Cycloalkyl" refers to a cyclic or polycyclic alkyl group containing 3 to 15 carbon atoms which are further substituted with one or more common substituents. Examples of cycloalkyl groups include, but are not limited to cyclopropyl, cyclobutyl, cyclopentyl, bicyclo[4.4.0]decane, adamantanyl, and the like. "Cycloalkyl" is also intended to encompass cyclic alkyl group attached to an aryl group such as 1,2,3,4-tetrahydronaphthalenyl, indanyl and the like.

"Alkenyl", alone or in combination refers to a straight, branched, mono cyclic or polycyclic unsaturated hydrocarbon preferably containing 2 to 10 carbon atoms, and having 1 to 5 double bonds and preferably 1 double bond. Examples of alkenyl groups include, but are not limited to are ethenyl, propenyl, isopropenyl, butenyl, bicycle[2.2.1]heptene and the like.

"Alkynyl", alone or in combination with any other term means a straight or branched hydrocarbon containing 2 to 10 carbon atoms containing 1 to 3 carbon to carbon triple bonds and at least one carbon to carbon triple bond. Examples of alkynyl groups include but are not limited to ethynyl, propynyl, butynyl and the like.

"Halo" or "Halogen", alone or in combination with any other term means halogens such as chloro (Cl), fluoro (F), bromo (Br) and iodo (I).

Common substitution or common substituents are defined as halo, straight chain or branched chain alkyl, alkenyl, alkynyl, cycloalkyl, aryl, heteroaryl, heterocycle, alkylsulfonyl, nitro, cyano, —COOR$^6$, —C(O)NR$^6$R$^7$, —OR$^6$, —SR$^6$, —NR$^6$R$^7$, oxo.

The compounds of the present disclosure may have the ability to crystallize in more than one form, a characteristic known as polymorphism, and all such polymorphic forms ("polymorphs") are encompassed within the scope of the disclosure. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

The compounds described herein may contain one or more chiral centers and/or double bonds and therefore, may exist as stereoisomers, such as geometric isomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

Compounds may exist in unsolvated forms as well as solvated forms, including hydrated forms. In general, compounds may be hydrated, solvated or N-oxides. Certain compounds may exist in multiple crystalline or amorphous forms. Also contemplated within the scope of the disclosure are congeners, analogs, hydrolysis products, metabolites and precursor or prodrugs of the compound. In general, unless otherwise indicated, all physical forms are equivalent for the uses contemplated herein and are intended to be within the scope of the present disclosure.

"Prodrug" refers to a derivative of a drug molecule as, for example, esters, carbonates, carbamates, ureas, amides or phosphates that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

The present disclosure relates to a series of acetamide derivatives described in formula (I), their stereoisomers, tautomers, prodrugs, pharmaceutically acceptable salts, polymorphs, solvates and formulations thereof as glucokinase activators

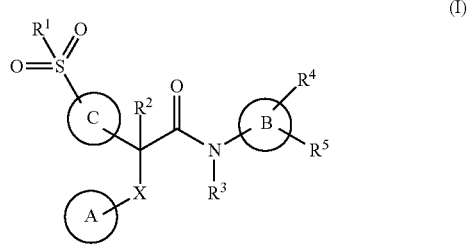

(I)

wherein
ring A and ring C are monocyclic ring independently selected from aryl, heteroaryl or heterocyclyl;
wherein rings A and C are optionally substituted with 1 to 4 substituents independently selected from halogen, monohaloalkyl, dihaloalkyl or perhaloalkyl, monohaloalkoxy, dihaloalkoxy or perhaloalkoxy, cyano, nitro, alkyl, alkenyl, alkynyl, methylenedioxy, amidino —$NR^6R^7$, —$OR^6$, —$NR^6C(O)R^7$, —$(CR^8R^9)_nC(O)OR^6$, —$(CR^8R^9)_nC(O)NR^6R^7$, —$(CR^8R^9)_nC(O)R^6$, cycloalkyl, heterocyclyl, aryl or heteroaryl groups;
n=0-4;
$R^6$ and $R^7$ are independently selected from the group consisting of hydrogen, alkyl, alkenyl, alkynyl, aryl, arylalkyl, heteroaryl, heteroarylalkyl, cycloalkyl, cycloalkylalkyl, heterocyclyl and heterocyclylalkyl; wherein $R^6$ and $R^7$ is each optionally substituted with one or more substituents selected from halo, straight chain or branched chain alkyl, cycloalkyl, aryl, heteroaryl, heterocycle, alkylsulfonyl, oxo, nitro, cyano, —$(CR^8R^9)_nCOOR^6$, —$(CR^8R^9)_nC(O)NR^6R^7$, —$OR^6$, —$SR^6$ or —$NR^6R^7$; or
$R^6$ and $R^7$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, nito, cyano, —$OR^6$, —$SR^6$, —$NR^6R^7$, oxo, alkylsulfonyl, —$COOR^6$, —$C(O)NR^6R^7$, cycloalkyl, aryl, heterocyclyl or heteroaryl; wherein $R^6$ and $R^7$ are as described above;
$R^8$ and $R^9$ are independently selected from the group consisting of hydrogen, fluorine, $OR^6$, alkyl and perfluoroalkyl; or
$R^8$ and $R^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, nitro, cyano, oxo, —$OR^6$, —$SR^6$, —$NR^6R^7$, alkylsulfonyl, —$COOR^6$, —$C(O)NR^6R^7$, cycloalkyl, aryl, heterocyclyl or heteroaryl;
wherein $R^6$ and $R^7$ are as described above;
ring-B is an optionally substituted 4-12 membered mono or bicyclic ring containing 1-4 hetero atoms selected from N, O, S with at least one nitrogen in the ring;
X represents 0 or $NR^6$;
wherein
$R^6$ is as described above;
$R^1$ is selected from cycloalkyl or heterocyclyl;
$R^2$ is hydrogen;
$R^3$ is selected from the group consisting of hydrogen, alkyl and perfluoroalkyl;
$R^4$ and $R^5$ are independently selected from the group consisting of hydrogen, halogen, alkyl, alkenyl, alkynyl, cycloalkyl, cycloalkylalkyl, heterocyclyl, heterocycloalkyl, aryl, arylalkyl, heteroaryl, heteroarylalkyl, mono, di or tri substituted haloalkyl, nitrile, nitro, oxo, —$NR^6R^7$, —$OR^6$, —$S(O)_pR^6$, —$S(O)_pNR^6R^7$, —$NR^6S(O)_pR^7$, —$NR^6C(O)R^2$, —$OS(O)_pR^7$, —$NR^6C(O)OR^7$, —$(CR^8R^9)_nC(O)OR^6$, —$(CR^8R^9)_n(CO)NR^6R^7$, —$(CR^8R^9)_nS(O)_pNR^6R^7$, —$(CR^8R^9)_nN(R^6)C(O)R^6$, —$(CR^8R^9)_nOR^6$, —$C(R^8R^9)_nNR^6R^7$, —$C(R^8R^9)_nCO(R^6)$ and —$S(O)_pC(R^8R^9)_nC(O)OR^6$, wherein $R^4$ and $R^5$ is each optionally substituted with one or more substituents selected from halo, straight chain or branched chain alkyl, alkenyl, alkynyl, cycloalkyl, aryl, heteroaryl, heterocycle, alkylsulfonyl, oxo, nitro, cyano, —$(CR^8R^9)$—$COOR^6$, —$(CR^8R^9)_nC(O)NR^6R^7$, —$OR^6$, —$SR^6$ or —$NR^6R^7$;

wherein n=0-4;
$R^6$, 1e, $R^8$ and $R^9$ are as described above;
in addition to $R^4$ and $R^5$, ring-B is further optionally substituted with one or more substituents selected from halo, straight chain or branched chain alkyl, alkenyl, alkynyl, cycloalkyl, aryl, heteroaryl, heterocyclyl, alkylsulfonyl, oxo, nitro, cyano, —$COOR^6$, —$C(O)NR^6R^7$, —$OR^6$, —$SR^6$ or —$NR^6R^2$.

According to another embodiment, the present disclosure relates to compounds of formula (I), or its stereoisomers, tautomers, prodrugs, pharmaceutically acceptable salts, polymorphs, solvates and formulations thereof wherein ring-A is selected from ring-B is selected from ring-C is ring A is optionally substituted with 1 to 4 substituents independently selected from alkyl, halogen, monohaloalkyl, dihaloalkyl or perhaloalkyl, nitrile, nitro, —$NR^6R^7$, —$OR^6$, —$NR^6C(O)R^7$, —$NR^6C(O)OR^7$, —$(CR^8R^9)_nC(O)OR^6$, —$(CR^8R^9)_nC(O)NR^6R^7$, —$(CR^8R^9)_nC(O)R^6$, cycloalkyl or cycloalkylalkyl;
ring C is optionally substituted with 1 to 4 substituents independently selected from alkyl, halogen, mono, di or perhaloalkyl, nitrile, nitro, —$NR^6R^7$, —$OR^6$, —$NR^6C(O)R^7$, —$NR^6C(O)OR^7$, —$(CR^8R^9)_nC(O)OR^6$, —$(CR^8R^9)_nC(O)NR^6R^7$, —$(CR^8R^9)_nC(O)R^6$, cycloalkyl, cycloalkylalkyl;
wherein n=0-4;
X represents O or $NR^6$;
$R^1$ is selected from $C_3$-$C_6$ cycloalkyl or heterocyclyl;
$R^2$ and $R^3$ are hydrogen,
$R^4$ and $R^5$ are independently selected from the group consisting of hydrogen, halogen, alkyl, cycloalkyl, cycloalkylalkyl, aryl, arylalkyl, heterocyclyl, heterocyclylalkyl, heteroaryl, heteroarylalkyl, —$OR^6$, —$S(O)_pR^6$, —$NR^6C(O)R^7$, —$(CR^8R^9)_nC(O)OR^6$, —$(CR^8R^9)_nOR^6$, and —$C(R^8R^9)_nCO(R^6)$, wherein n=0-4; wherein each of $R^4$ and $R^5$ is optionally substituted with one or more substituents selected from halo, straight chain or branched chain alkyl, alkenyl, alkynyl, cycloalkyl, aryl, heteroaryl, heterocycle, alkylsulfonyl, oxo, nitro, cyano, —$(CR^8R^9)_n COOR^6$, —$(CR^8R^9)_n C(O)NR^6R^7$, —$OR^6$, —$SR^6$ or —$NR^6R^7$;

$R^6$ and $R^7$ are independently selected from the group consisting of hydrogen, alkyl, cycloalkyl, aryl, heterocyclyl and heteroaryl; wherein $R^6$ and $R^7$ is each optionally substituted with one or more substituents selected from halo, straight chain or branched chain alkyl, cycloalkyl, aryl, heteroaryl, heterocycle, alkylsulfonyl, oxo, nitro, cyano, —$(CR^8R^9)_n COOR^6$, —$(CR^8R^9)_n C(O)NR^6R^7$, —$OR^6$, —$SR^6$ or —$NR^6R^7$; or $R^6$ and $R^7$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, cyano, —$OR^6$, —$SR^6$, —$NR^6R^7$, —$COOR^6$, —$C(O)NR^6R^7$, cycloalkyl, aryl, arylalkyl, heterocyclyl or heteroaryl;

$R^8$ and $R^9$ are independently selected from the group consisting of hydrogen, fluorine, $OR^6$, alkyl and perfluoroalkyl.

According to another embodiment, the present disclosure relates to compounds of formula (Ia), their tautomers, prodrugs, pharmaceutically acceptable salts, polymorphs, solvates and formulations thereof

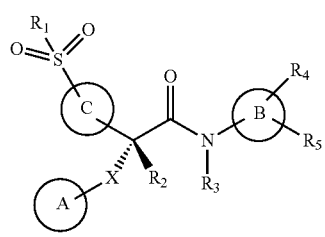
(Ia)

wherein ring-A is selected from

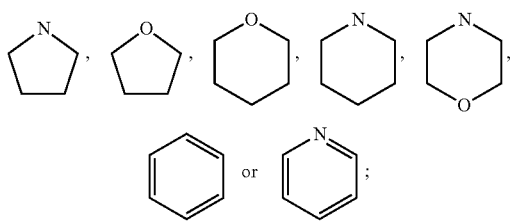

ring-B is selected from

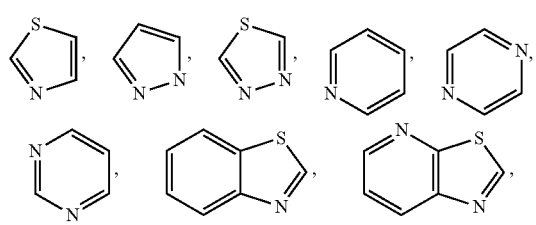

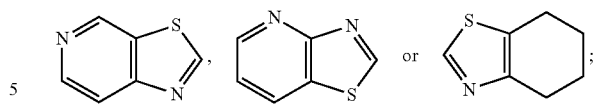
-continued ring-C is

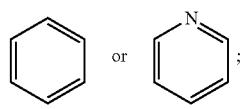 [SMILES: c1ccccc1 ; c1ccncc1]

ring A is optionally substituted with 1 to 4 substituents independently selected from alkyl, halogen, monohaloalkyl, dihaloalkyl or perhaloalkyl, nitrile, nitro, —$NR^6R^7$, —$OR^6$, —$(CR^8R^9)_n C(O)OR^6$, —$(CR^8R^9)_n C(O)NR^6R^7$, or —$(CR^8R^9)_n C(O)R^6$;

wherein n=0-4;

ring C is optionally substituted with 1 to 4 substituents independently selected from alkyl, halogen, mono, di or perhaloalkyl;

X represents O or $NR^6$;

$R^1$ is selected from cyclopropyl, cyclopentyl, cyclohexyl, pyrrolidinyl, tetrahydrofurnyl, piperidinyl, piperazinyl, tetrahydropyranyl or morpholinyl;

$R^2$ and $R^3$ are hydrogen;

$R^4$ and $R^5$ are independently selected from the group consisting of hydrogen, halogen, alkyl, cycloalkyl, cycloalkylalkyl, aryl, arylalkyl, heterocyclyl, heterocyclylalkyl, heteroaryl, heteroarylalkyl, —$OR^6$, —$S(O)_p R^6$, —$NR^6C(O)R^7$, —$(CR^8R^9)_n C(O)OR^6$, —$(CR^8R^9)_n OR^6$, and —$C(R^8R^9)_n CO(R^6)$, wherein n=0-4; wherein each of $R^4$ and $R^5$ is optionally substituted with one or more substituents selected from halo, straight chain or branched chain alkyl, alkenyl, alkynyl, cycloalkyl, aryl, heteroaryl, heterocycle, alkylsulfonyl, oxo, nitro, cyano, —$(CR^8R^9)_n COOR^6$, —$(CR^8R^9)_n C(O)NR^6R^7$, —$OR^6$, —$SR^6$ or —$NR^6R^7$;

$R^6$ and $R^7$ are independently selected from the group consisting of hydrogen, alkyl, cycloalkyl, aryl, heterocyclyl and heteroaryl; wherein $R^6$ and $R^7$ is each optionally substituted with one or more substituents selected from halo, straight chain or branched chain alkyl, cycloalkyl, aryl, heteroaryl, heterocycle, alkylsulfonyl, oxo, nitro, cyano, —$(CR^8R^9)_n COOR^6$, —$(CR^8R^9)_n C(O)NR^6R^7$, —$OR^6$, —$SR^6$ or —$NR^6R^7$; or $R^6$ and $R^7$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, cyano, —$OR^6$, —$SR^6$, —$NR^6R^7$, —$COOR^6$, —$C(O)NR^6R^7$, cycloalkyl, aryl, arylalkyl, heterocyclyl or heteroaryl;

$R^8$ and $R^9$ are independently selected from the group consisting of hydrogen, fluorine, $OR^6$, alkyl and perfluoroalkyl.

According to another embodiment, the present disclosure relates to compounds of formula (Ib), their tautomers, prodrugs, pharmaceutically acceptable salts, polymorphs, solvates and formulations thereof

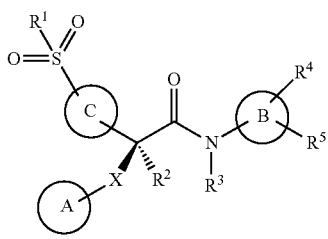

(Ib)

wherein ring-A is selected from

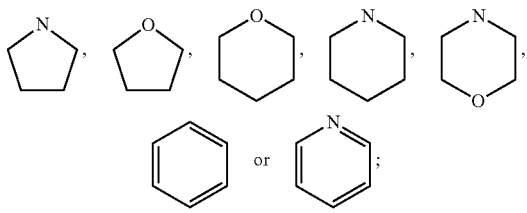

ring-B is selected from

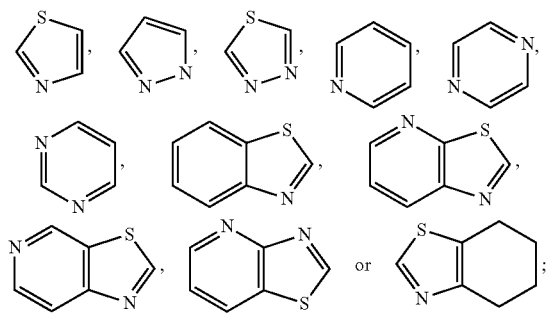

ring-C is

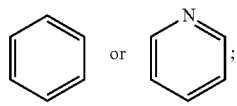 [SMILES: c1ccccc1 ; c1ccncc1]

ring A is optionally substituted with 1 to 4 substituents independently selected from alkyl, halogen, monohaloalkyl, dihaloalkyl or perhaloalkyl, nitrile, nitro, —$NR^6R^7$, —$OR^6$, —$(CR^8R^9)_nC(O)OR^6$, —$(CR^8R^9)_nC(O)NR^6R^7$, or —$(CR^8R^9)_nC(O)R^6$;
wherein n=0-4;
ring C is optionally substituted with 1 to 4 substituents independently selected from alkyl, halogen, mono, di or perhaloalkyl;
X represents O or $NR^6$;
$R^1$ is selected from cyclopropyl, cyclopentyl, cyclohexyl, pyrrolidinyl, tetrahydrofurnyl, piperidinyl, piperazinyl, tetrahydropyranyl or morpholinyl;
$R^2$ and $R^3$ are hydrogen;
$R^4$ and $R^5$ are independently selected from the group consisting of hydrogen, halogen, alkyl, cycloalkyl, cycloalkylalkyl, aryl, arylalkyl, heterocyclyl, heterocyclylalkyl, heteroaryl, heteroarylalkyl, —$OR^6$, —$S(O)_pR^6$, —$NR^6C(O)R^7$, —$(CR^8R^9)_nC(O)OR^6$, —$(CR^8R^9)_nOR^6$, and —$C(R^8R^9)_nCO(R^6)$, wherein n=0-4; wherein each of $R^4$ and $R^5$ is optionally substituted with one or more substituents selected from halo, straight chain or branched chain alkyl, alkenyl, alkynyl, cycloalkyl, aryl, heteroaryl, heterocycle, alkylsulfonyl, oxo, nitro, cyano, —$(CR^8R^9)_nCOOR^6$, —$(CR^8R^9)_nC(O)NR^6R^7$, —$OR^6$, —$SR^6$ or —$NR^6R^7$;
$R^6$ and $R^7$ are independently selected from the group consisting of hydrogen, alkyl, cycloalkyl, aryl, heterocyclyl and heteroaryl; wherein $R^6$ and $R^7$ is each optionally substituted with one or more substituents selected from halo, straight chain or branched chain alkyl, cycloalkyl, aryl, heteroaryl, heterocycle, alkylsulfonyl, oxo, nitro, cyano, —$(CR^8R^9)_nCOOR^6$, —$(CR^8R^9)_nC(O)NR^6R^7$, —$OR^6$, —$SR^6$ or —$NR^6R^7$; or
$R^6$ and $R^7$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, cyano, —$OR^6$, —$SR^6$, —$NR^6R^7$, —$COOR^6$, —$C(O)NR^6R^7$, cycloalkyl, aryl, arylalkyl, heterocyclyl or heteroaryl;
$R^8$ and $R^9$ are independently selected from the group consisting of hydrogen, fluorine, $OR^6$, alkyl and perfluoroalkyl.

According to an embodiment, the present disclosure relates to a process for the preparation of a compound of formula (I), their stereoisomers, tautomers, prodrugs, pharmaceutically acceptable salts, polymorphs, solvates, said process comprising:
reacting an acid of formula (II)

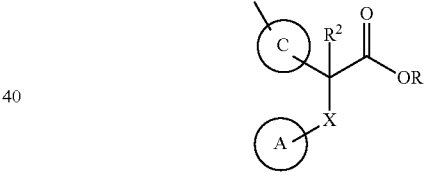

(II)

wherein R is hydrogen, alkyl or arylalkyl, with a compound of formula (III)

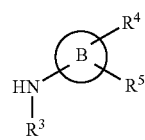

(III)

in presence of a suitable amide coupling reagent, optionally hydrolyzing and optionally further coupling with an amine of formula $NHR^6R^7$ to obtain compound of formula (I).

Compounds of formula I may be prepared as shown in the following reaction schemes and the description thereof, as well as relevant literature procedures that may be used by one skilled in the art. Exemplary reagents and procedures for these reactions appear hereinafter and in the working examples. Protection and deprotection in the schemes below may be carried out by procedures generally known in the art (see, for example, Greene, T. W. and Wuts, P. G. M., Protecting Groups in Organic Synthesis, 3$^{rd}$ Edition, 1999 [Wiley]).

The compounds of formula (I) may be prepared following independent general synthetic routes as outlined in the Schemes 1-6:

Scheme 1: General route for the synthesis of compounds of formula (I). Compounds of formula (II) wherein R is hydrogen, alkyl or arylalkyl, may be reacted with compounds of formula (III) following amide coupling reaction conditions to obtain compounds of formula (I), as shown herein below.

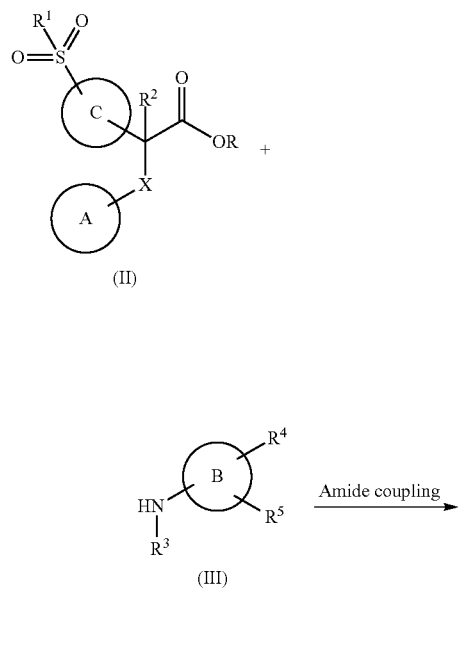

Scheme 2: Alternate route for the synthesis of compounds of formula (I). Compounds of formula (IV) wherein R is hydrogen, alkyl or arylalkyl, obtained according to WO2004072031, may be reduced to compounds of formula (V) which may be reacted with compounds of formula (III) under amide coupling conditions to provide compounds of formula (VI). Compounds of formula (VI) may be reacted with compounds of formula (VIIa) under Mitsunobu conditions to provide compounds of formula (I).

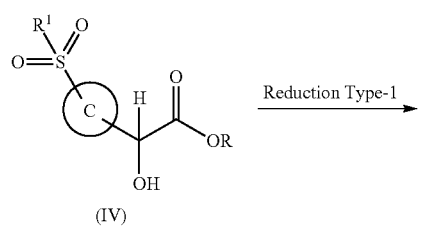

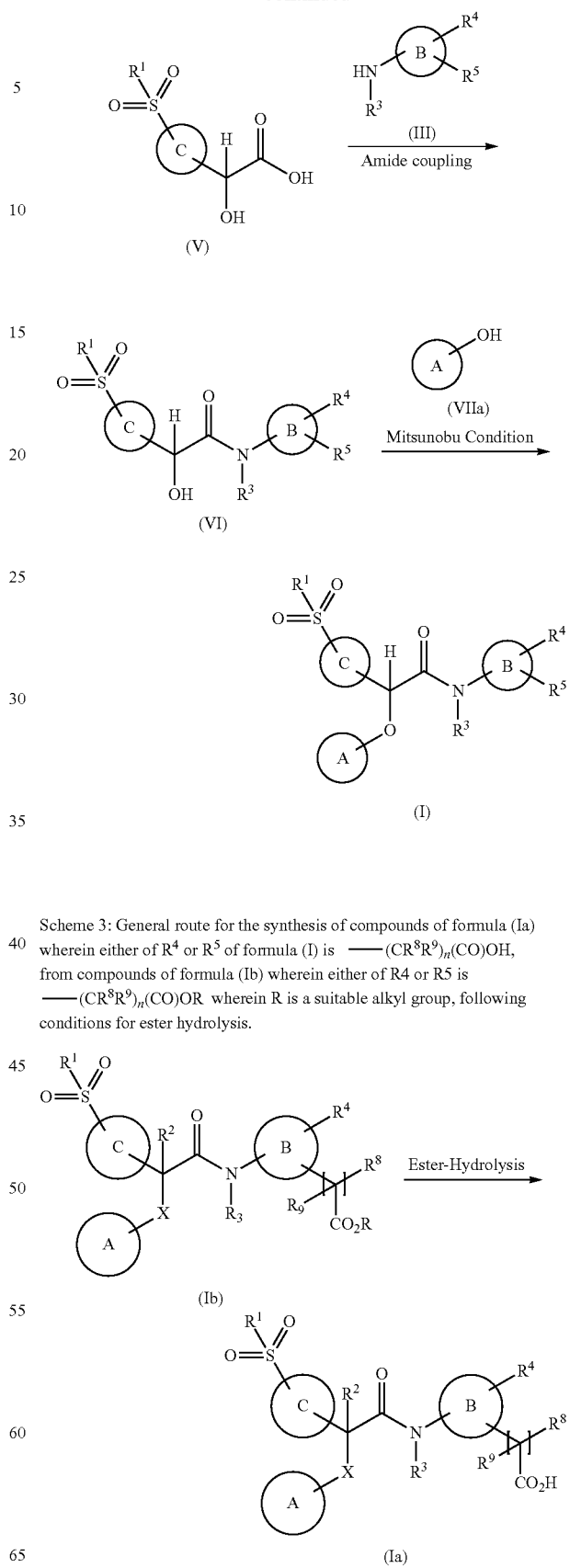

Scheme 3: General route for the synthesis of compounds of formula (Ia) wherein either of $R^4$ or $R^5$ of formula (I) is ——$(CR^8R^9)_n(CO)OH$, from compounds of formula (Ib) wherein either of R4 or R5 is ——$(CR^8R^9)_n(CO)OR$ wherein R is a suitable alkyl group, following conditions for ester hydrolysis.

Scheme 4: General route for the synthesis of compounds of formula (Ic) wherein either of $R^4$ or $R^5$ of formula (I) is —$(CR^8R^9)_nC(O)NR^6R^7$, from compounds of formula (Ia) wherein either of $R^4$ or $R^5$ is —$(CR^8R^9)_n(CO)OH$ following conditions for amide coupling.

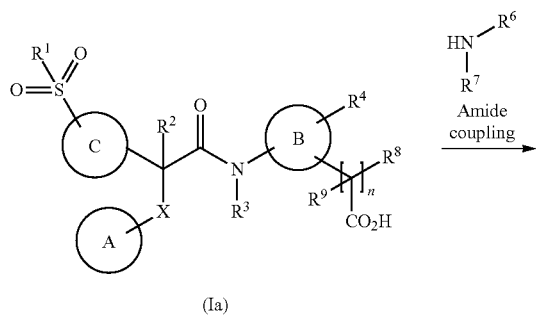

(Ia)

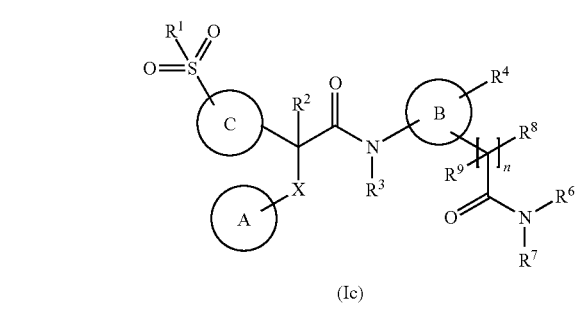

(Ic)

Scheme 5: General route for synthesis of compounds of formula (Id) wherein either of $R^4$ or $R^5$ is $OR^6$ and $R^6$ is aryl, heteroaryl described as ring D in the following scheme.
Compounds of formula (II) wherein R is hydrogen, alkyl or arylalkyl, may be reacted with compounds of formula (IIIa) wherein R' is alkyl following amide coupling reaction conditions to obtain compounds of formula (Id). Compounds of formula (Id) may further be hydrolysed to obtain the corresponding carboxylic acid which may further be derivatised.

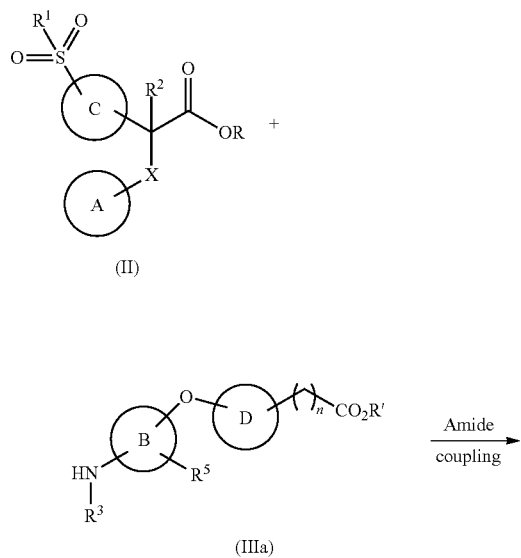

(IIIa)

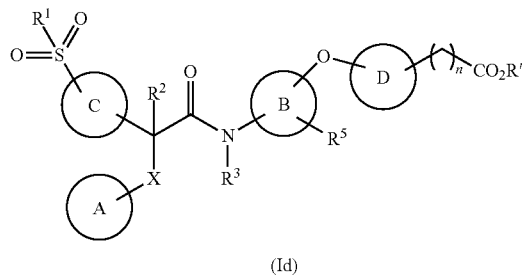

(Id)

Scheme 6: General route for synthesis of compounds of formula (Ie) wherein either of $R^4$ or $R^5$ is heterocycle as described in the following scheme. Compounds of formula (II) wherein R is hydrogen, alkyl or arylalkyl, may be reacted with compounds of formula (IIIb) wherein R' is alkyl following amide coupling reaction conditions to obtain compounds of formula (Ie). Compounds of formula (Ie) may further be hydrolysed to obtain the corresponding carboxylic acid which may further be derivatised.

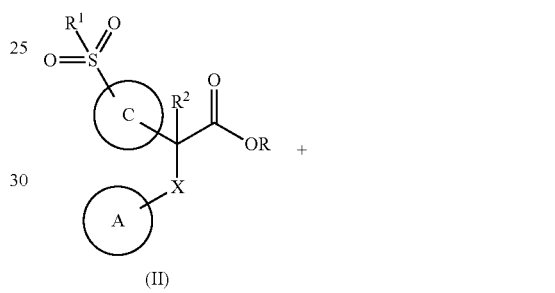

(II)

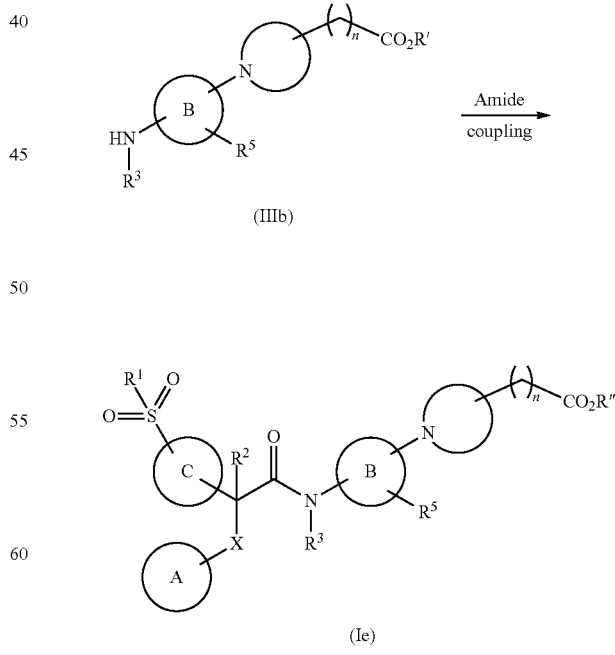

(Ie)

The compounds of formula (II) may be prepared following independent synthetic routes as outlined in Schemes 7-11.

Scheme 7: General route for the synthesis of compounds of formula (IIa). Compounds of formula (IVa) may be reduced to compounds of formula (VIIIa) followed by esterification to obtain compounds of formula (VIII), which may be halogenated to obtain compounds of formula (IX). Compounds of formula (IX) may be reacted with compounds of formula (VII) under nucleophilic substitution conditions to obtain compounds of formula (IIb) wherein R is alkyl or arylalkyl, which may be hydrolysed to obtain intermediates of formula (IIa).

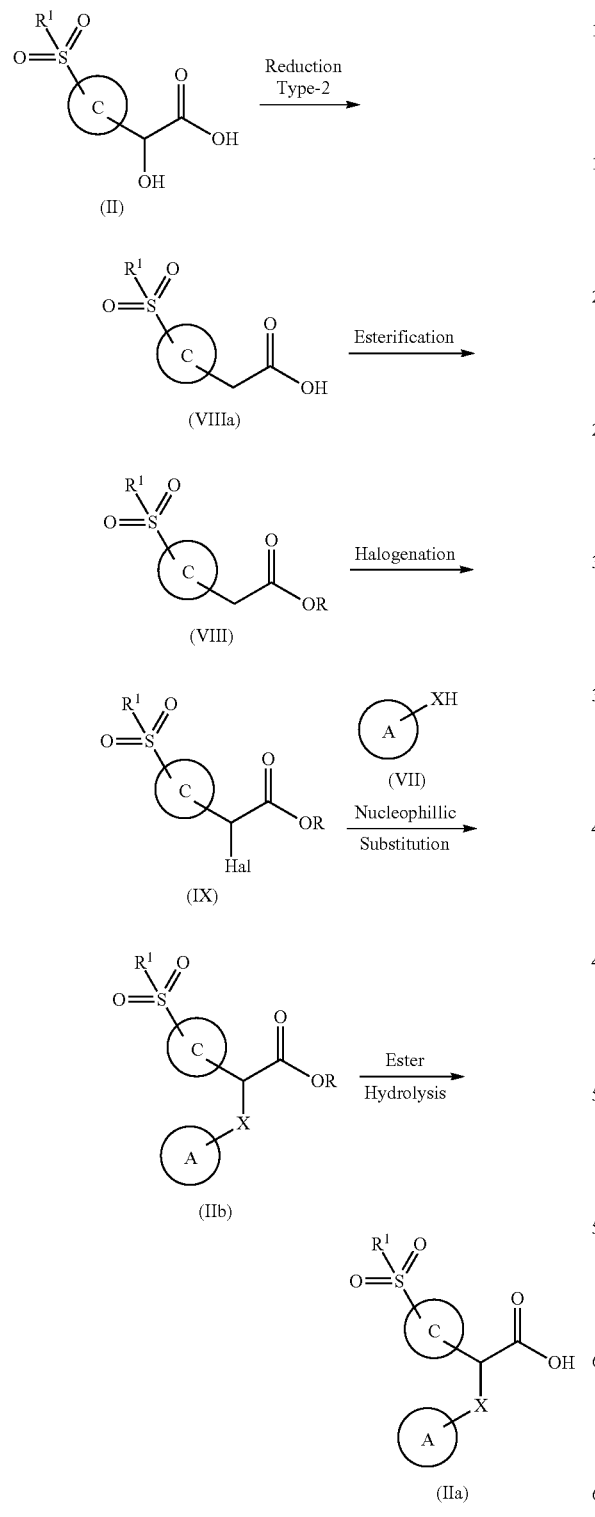

Scheme 8: General route for synthesis of compounds of formula (IIc). Compounds of formula (V) wherein R is hydrogen, alkyl or arylalkyl, may be reacted with compounds of formula (VIIa) under Mitsunobu conditions to obtain compounds of formula (IIc) (which is formula (II) wherein X is O).

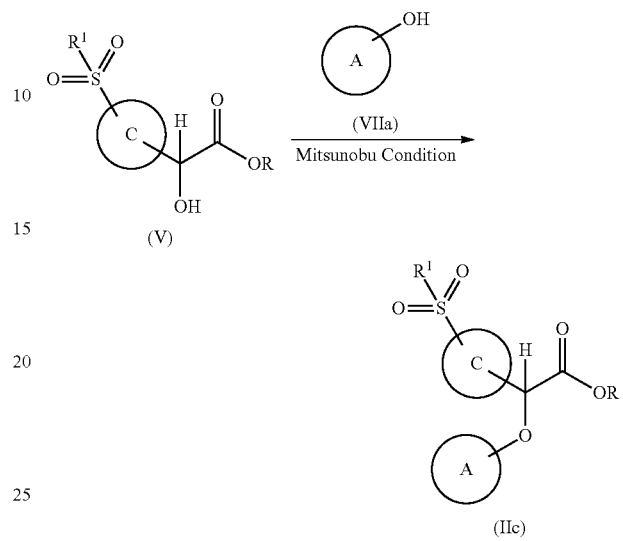

The compounds of formula (II), may be prepared following independent synthetic routes as outlined in Schemes 8-11.

Scheme 9: General route for synthesis of compounds of formula (IId) wherein $R^1$ is heterocycle forming sulfonamide linkage and ring A is aryl or heteroaryl: Compounds of formula (X) on oxidative chlorination provide compounds of formula (XI) (following procedure described in *J. Org. Chem.* 2007, 72(15), 5847-5850). Compounds of formula (XI) may be halogenated to obtain compounds of formula (XII), which may then be subjected to coupling reaction with an heterocyclyl amine to form sulfonamide linkage, in presence of organic or inorganic bases to obtain compounds of formula (XIII). Compounds of formula (XIII) may be reacted with compounds of formula (VII) under nucleophilic substitution conditions to obtain the compounds of formula (IIe) wherein R is alkyl or arylalkyl, which may be hydrolysed to obtain intermediates of formula (IId).

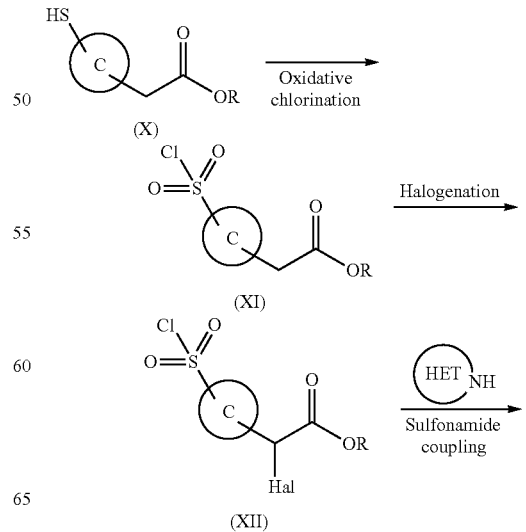

-continued

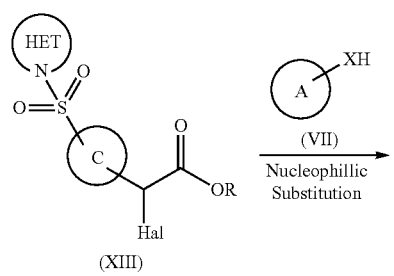

(XIII)

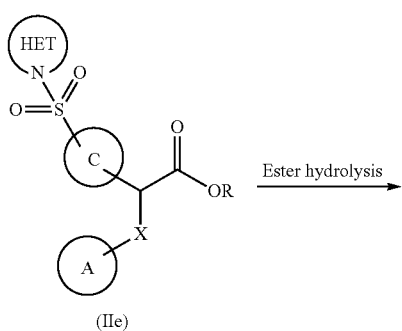

(IIe)

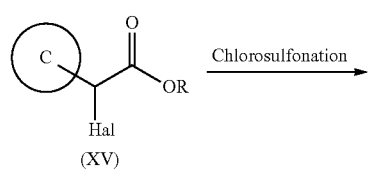

(IId)

Scheme 10: General route for synthesis of compounds of formula (IId) wherein R¹ is heterocycle forming sulfonamide linkage: Compounds of formula (XIV) on halogenation provide compounds of formula (XV), which on chlorosulfonation may provide compounds of formula (XII) as a mixture of meta & para regioisomers. The compound of formula (XII) may be converted to compounds of formula (IId) following the route as described in scheme 9 as a mixture of regioisomers.

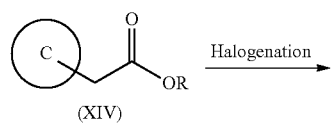

(XIV)

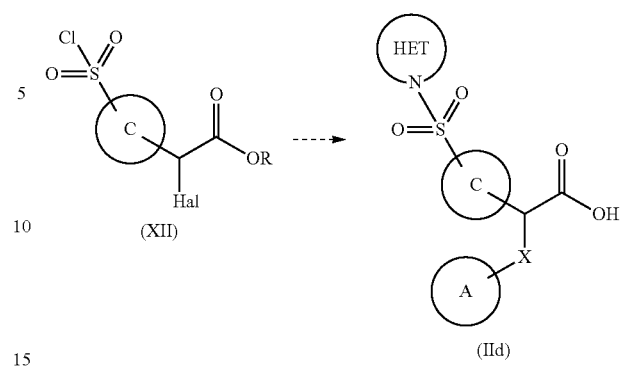

(XII)

(IId)

Scheme 11: General route for the synthesis of (IIf) wherein ring A is heterocycle. Compounds of formula (IV) wherein R is alkyl may be condensed with tosyl hydrazine to obtain compounds of formula (XVI) which may be oxidized in the presence of a base like TEA, DBU to provide compounds of formula (XVII). Alternatively, compounds of formula (XVII) may also be obtained by reacting compounds of formula (VIII) with tosylazide in presence of base. The compounds of formula (XVII) may be reacted with compounds of formula (VII) in the presence of a Rhodium catalyst to provide compounds of formula (IIe) (following procedure as described in WO2002008209), which may be hydrolyzed to obtain intermediates of formula (IIf).

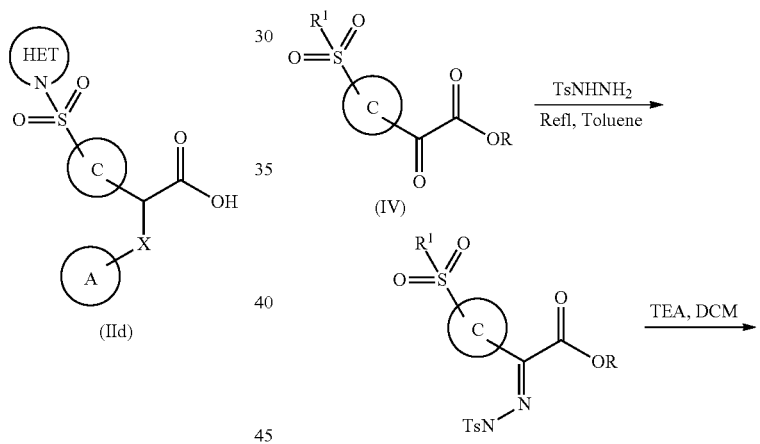

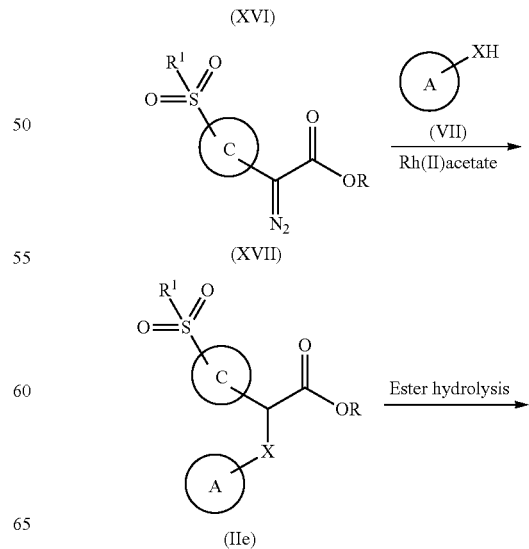

(IIe)

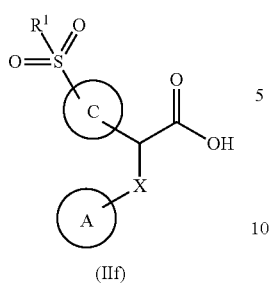

(IIf)

The compounds of formula (VIII) may be prepared following independent synthetic routes as outlined in Schemes 12-13.

Scheme 12: General route for synthesis of compounds of formula (IIh) wherein $R^1$ is heterocycle forming sulfonamide linkage and ring A is also heterocylyl: Compounds of formula (XI) subjected to coupling reaction with heterocyclyl amine to form sulfonamide linkage, in presence of organic or inorganic bases to obtain compounds of formula (XVIII). Compounds of formula (XVIII) may be reacted with tosyl azide in presence of base to obtain compounds of formula (XIX). The compounds of formula (XIX) may be reacted with compounds of formula (VII) in the presence of a Rhodium catalyst to provide compounds of formula (IIg) (following procedure as described in WO2002008209), which may be hydrolyzed to obtain intermediates of formula (IIh).

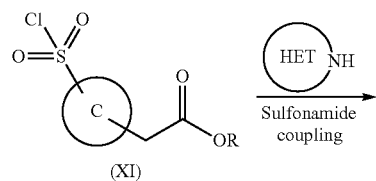

(XI)

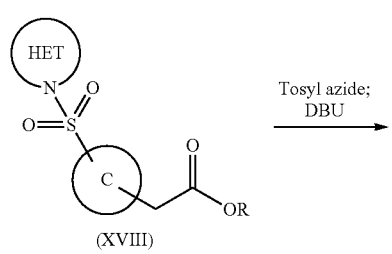

(XVIII)

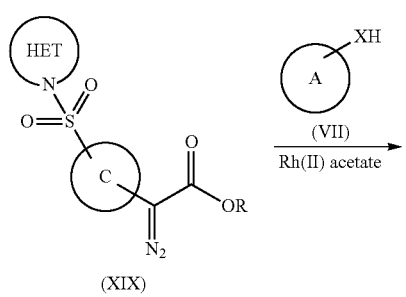

(XIX)

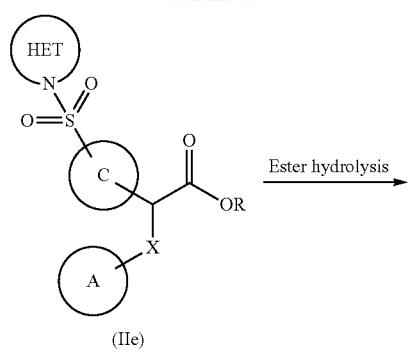

(IIe)

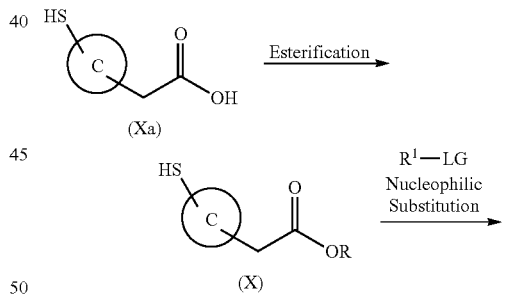
(Provided)

(IId)

Scheme 13: General route for the synthesis of compounds of formula (VIII): Compounds of formula (X), which are available commercially, may be reacted with $R^1$—LG, where LG is a suitable leaving group, using reaction conditions for nucleophilic substitution to obtain S-alkylated compounds of formula (XX). The compounds of formula (XX) may be oxidized (sulfur to sulfone) to obtain compounds of formula (VIII).

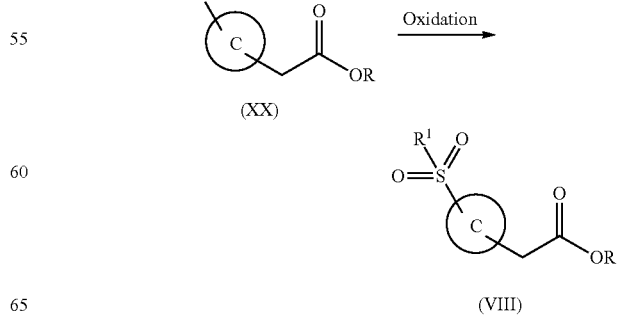

Scheme 14: General route for the synthesis of compounds of formula (VIII) wherein R¹ is cycloalkanon-3-yl: Compounds of formula (X) may be treated with cycloalk-2-enone such as cyclohex-2-enone or cyclopent-2-enone, under Michael addition conditions to provide compounds of formula (XI) which are then oxidized to obtain compounds of formula (VIII).

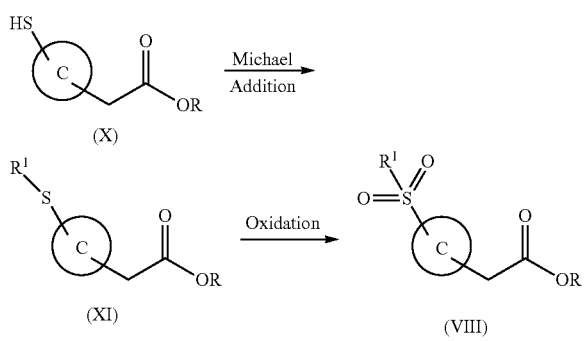

Amide Coupling Conditions:

Condition-I: When R=H, the amide coupling may be carried out using any suitable amide coupling regents such as oxallyl chloride, thionyl chloride, BOP-Cl, DCC, HOBt, HOAt, HATU, EDCl, alkylchloroformate and the like in the presence of organic non-nucleophillic bases such as triethyl amine, di-isopropylethyl amine, pyridine, N-methyl pyrrolidine, N,N-dimethylaminopyridine, DBU, DABCO, other hindered amines and pyridines. The amide coupling reaction may be carried out in the presence of solvents such as dichloromethane, dichloroethane, DMF, dimethylacetamide, THF, acetonitrile or mixture of them may be used at a temperature ranging from −5 to 150° C. The reaction may be carried out optionally in presence of catalytic amount of DMF. Condition-II: When R is not H, the amide coupling may be carried out by heating ester and amine either in the absence of solvent or in presence of high boiling solvent like toluene, xylene, DMSO. Amide coupling may be carried out in presence of trialkyl aluminium (Chem. Commun., 2008, 1100-1102).

Halogenation Conditions:

Halogenation reaction may be carried out using reagents such as N-halosuccinimide, dihalogens and the like, in presence of radical generating reagents like peroxides such as benzoylperoxide. Solvents used for this reaction include, but are not limited to, carbontetrachloride and ethers or mixtures thereof. The reaction may be carried out at a temperature ranging from −5 to 80° C.

Conditions for Nucleophilic Substitution:

Nucleophilic substitution reaction, may be carried out using any suitable organic or inorganic bases. Organic bases may be selected from a group consisting of mono, di or trialkyl amines particularly methylamine, ethylamine, dimethylamine, diethylamine or triethylamine. Inorganic bases may be selected from a group consisting of alkali and alkaline earth metal hydrides, hyroxides, carbonates and bicarbonates or mixtures thereof. Solvents used for this reaction may be selected from a group consisting of lower alcohols, acetone, acetonitrile, DMSO, DMF, dimethylacetamide, THF and toluene, or mixtures thereof. The reaction may be carried out at a temperature in the range of 0 to 150° C.

Conditions for Ester Hydrolysis:

Ester hydrolysis of carboxylic acids may be carried out using general saponification conditions employing inorganic bases such as alkali and alkaline earth metal hyroxides, carbonates and bicarbonates, for example lithium hydroxide, sodium hydride, sodium carbonate, potassium carbonate, cesium carbonate and the like; in the presence of solvents such as water, methanol, ethanol, THF and diethyl ether or mixtures thereof. These reactions may be done at 0° C. to refluxing temperature.

Conditions for Esterification:

Ester formation, from the above mentioned carboxylic acids, may be carried out using general esterification conditions employing appropriate alcohol like methanol, ethanol and a suitable inorganic acid selected from HCl, $H_2SO_4$, or thionyl chloride, or base catalysed ester formation using alkyl halide and suitable base like sodium hydride, sodium hydroxide, sodium carbonate, potassium carbonate, sodium bicarbonate, potassium bicarbonate, cesium carbonate and the like in presence of solvents such as acetone, acetonitrile, DMF, DMSO, THF and diethyl ether or mixtures thereof.

Conditions for Oxidation:

Oxidation of sulfanyls to sulfonyls, may be carried out using appropriate oxidizing reagent such as $H_2O_2$, perbenzoic acid, mCPBA, Oxone, dioxirane and the like in the presence of a solvent such as DCM, DCE, DMF, DMSO, THF and diethyl ether or mixtures thereof. Reagents like $OsO_4$, $KMnO_4$, PCC can also be used for such oxidation process.

Conditions for Reduction Type-1:

Reduction Type-1, may be carried out using appropriate reduction conditions for transforming carbonyls to sec-alcohols employing reducing agents like hydrogenation in presence of catalysts such as Pd/C, Pt/C, $PtO_2$ and the like. Such reduction by hydrogenation can also be done using organometallic complexes as catalyst from metals like Iron, Rhodium, Ruthenium, and phosphorus-based organic ligands like triphenylphosphine, bidentate phosphine ligands such as bis(diphenylphosphino)ethane. Such hydrogenation based reductions can also be done under asymmetric reduction conditions to yield chiral products (in individual enantiomers and in enantiometically enriched form) if employed appropriate chiral phosphine ligands such as chiral 2,2'-bis(diphenylphosphino)-1,1'-binaphthyl (BINAP) to form the organometallic complex. Such reductions can also be done using metal hydrides such as sodium borohydride, lithium aluminiumhydride, borane reagents and like. Such metal hydride or borane reagent based reductions can also be done in asymmetric way to yield chiral products (in individual enantiomers and in enantiometically enriched form) by using appropriate chiral ligands like tartarate (EP 0320096), chiral 1,1'-bi-2-napthol (BINOL), oxazaborolidines.

Conditions for Reduction Type-2:

Reduction Type-2, may be carried out using specific conditions known for transformation of arylic carbonyl group to corresponding arylalkyl functionality. Such reductions may be done using known Wolf Krishner (KOH, $NH_2$—$NH_2$) or Clemmensen (Zn/HCl) reduction conditions.

Conditions for Mitsunobu Reaction:

The Mitsunobu reaction between alcohol and phenol, to obtain the corresponding ether, may be carried out in THF using triphenylphosphine (TPP) and diethyl azodicarboxylate (DEAD) or diisopropyl azodicarboxylate (DIAD) as reagents.

Sulfonamide Coupling Condition:

Sulfonamide may be prepared by reacting any appropriate amine with sulfonylhalide in the presence of base such as pyridine, triethylamine & diisopropylethylamine. The reaction may be carried out in suitable solvent like pyridine, dichloromethane or tetrahydrofuran.

Oxidative Chlorination:

Thiols can be converted to sulfonyl chlorides under mild condition of oxidative chlorination. Here thiols are treated with combination of oxidant and chlorinating agent such as $KNO_3$-TMSCl, $H_2O_2$—$SOCl_2$, Oxone-$SOCl_2$ in appropriate solvent such as DCM, acetonitrile, DMF or combination of acetonitrile-AcOH. The reaction may be carried out at a temperature in the range of 5 to 100° C.

Chlorosulfonation:

Aryl or hetroaryl sulfonyl chloride synthesis may be carried out by elecrophilic substitution reaction using reagent like chlorosulfonic acid, $SO_2Cl_2$ in appropriate solvent which are not limited to halogenated like DCM, DCE, $CHCl_3$, $CCl_4$, but also nonpolar solvents like Benzene, Tolune, Dioxane or mixture thereof. The reaction may be carried out at a temperature in the range of 0° C. to 60° C.

Above mentioned conditions, for the respective functional group transformations, are only to illustrated the type of synthesis. More specific conditions for above transformations are well documented and referred in the literature (R. C. Larock in Comprehensive Organic Transformations, Wiley-VCH Publication; B. M. Trost and I. Fleming Ed. Comprehensive Organic Synthesis, Elsevier Publication)

Wherever desired or necessary, in any of the above mentioned processes, any of the compounds of formula (I) may be converted into a pharmaceutically acceptable salt or vice versa or converting one salt form into another pharmaceutically acceptable salt form.

According to an embodiment, the present disclosure relates to compounds of formula (I) their stereoisomers, tautomers, prodrugs, pharmaceutically acceptable salts, polymorphs, solvates and formulations thereof, which are glucokinase activators, and are beneficial for the prophylaxis, management, treatment, control of progression, or adjunct treatment of diseases and/or medical conditions where the activation of glucokinase would be beneficial, such as diabetes, dyslipidemia, metabolic syndrome, and/or diabetes-related complications including retinopathy, nephropathy, neuropathy, ischemic heart disease, arteriosclerosis, β-cell dysfunction, and as therapeutic and/or prophylactic agents for obesity.

According to yet another embodiment, the present disclosure relates to compounds of formula (I) their stereoisomers, tautomers, prodrugs, pharmaceutically acceptable salts, polymorphs, solvates and formulations thereof, which are liver selective Glucokinase activators, useful for the treatment of hyperglycemia, diabetes, obesity, dyslipidemia, metabolic syndrome and like, in mammals and have minimum hypoglycemic potential.

A further embodiment of the disclosure includes a method of treatment of glucokinase activator mediated disease by administering a therapeutically effective amount of a compound of formula (I) to a mammal in need of such treatment.

By "pharmaceutically acceptable salts" as used herein, it covers salts of compounds of formula (I) prepared from pharmaceutically acceptable non-toxic bases or acids including inorganic or organic bases and inorganic or organic acids. Inorganic bases salts include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, poly amine resins, procaine, purines, theobromine, triethylamine, trimethylamine, tripropylamine, tromethamine, and the like. Salts in the solid form may exist in more than one crystal structure, and may also be in the form of hydrates. When the compound of the present disclosure is basic, salts may be prepared from pharmaceutically acceptable non-toxic acids, including inorganic and organic acids, such as acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are hydrochloric, maleic, phosphoric, citric, hydrobromic, sulfuric, fumaric, and tartaric acids.

By "therapeutically effective amount" in this disclosure, it means an amount of compound of formula (I), its polymorphs, stereoisomers, pharmaceutically acceptable salt, solvate or pro-drug thereof, that is sufficient for effective treatment of obesity and/or type II diabetes. The therapeutically effective amount or dosage of a compound according to this disclosure can vary within wide limits. The dosage will depend on individual requirements in each particular case including the specific compound(s) being administered, the manner of administration, the severity of condition being treated, as well as the patient being treated, which is readily determinable by a person skilled in the art.

In using a compound of formula (I), its polymorphs, stereoisomers, pharmaceutically acceptable salt, solvate or pro-drug thereof, for therapeutic or prophylactic purposes it will generally be administered so that a daily dose in the range, for example, about 0.01 mg to 100 mg per kg body weight is received, given if required in divided doses. In general lower doses will be administered when a parenteral route is employed. Thus, for example, for intravenous administration, a dose in the range, for example, about 0.01 mg to 30 mg per kg body weight will generally be used. Similarly, for administration by inhalation, a dose in the range, for example, about 0.01 mg to 30 mg per kg body weight will be used.

The disclosure also relates to compound of formula (I), or its polymorph, stereoisomer, prodrug, solvate or a pharmaceutically acceptable salt thereof, for treating a disease through Glucokinase activation.

The disclosure also relates to compounds of formula (I), or its polymorph, stereoisomer, prodrug, solvate or a pharmaceutically acceptable salt thereof, for treating a disease through Glucokinase modulation or regulation.

The disclosure also relates to compounds of formula (I), or its polymorph, stereoisomer, prodrug, solvate or a pharmaceutically acceptable salt thereof, for treating a disease through Glucokinase deinhibition.

The disclosure also relates to compounds of formula (I), or its polymorph, stereoisomer, prodrug, solvate or a pharmaceutically acceptable salt thereof, for prophylactic or therapeutic treatment of hyperglycemia or diabetes, particularly type II diabetes.

The disclosure also relates to compounds of formula (I), or its polymorph, stereoisomer, prodrug, solvate or a pharmaceutically acceptable salt thereof, for preventing diabetes, particularly type II diabetes, in a human demonstrating prediabetic hyperglycemia or impaired glucose tolerance.

The disclosure also relates to compounds of formula (I), or its polymorph, stereoisomer, prodrug, solvate or a pharmaceutically acceptable salt thereof, for combined treatment or preventing diabetes and obesity.

The disclosure also relates to compounds of formula (I), or its polymorph, stereoisomer, prodrug, solvate or a pharmaceutically acceptable salt thereof, for treating or preventing obesity.

The disclosure also relates to compounds of formula (I), or its polymorph, stereoisomer, prodrug, solvate or a pharmaceutically acceptable salt thereof, for enhancing the secretion of enteroincretins, like GLP-1 and GIP, thereby managing diseases or disorders associated with modulation of secretions of enteroincretins, such as hyperglycemia, insulin resistance, impaired glucose tolerance, obesity, gastric emptying, gastroparesis, satiety, leptin resistance, dyslipidemia, wound healing, diabetic complications, such as nephropathy, retinopathy, neuropathy and cataracts.

The disclosure also relates to the use of compounds of formula (I), or its polymorphs, stereoisomers, pharmaceutically acceptable salt, solvate or pro-drug thereof, in the prophylactic or therapeutic treatment of dyslipidemia.

The disclosure also relates to compound of formula (I), or its stereoisomers, tautomers, prodrugs, pharmaceutically acceptable salts, polymorphs, solvates and formulations thereof, for treating hyperglycemia, IGT, Syndrome X, type 2 diabetes, type 1 diabetes, dyslipidemia or hyperlipidemia, hypertension, for the treatment or prophylaxis of obesity, for lowering of food intake, for appetite regulation, for regulating feeding behaviour.

The disclosure also relates to identifying the compounds of formula (I), its polymorphs, stereoisomers, pharmaceutically acceptable salt, solvate or pro-drug thereof, which are beneficial for the prophylaxis, management, treatment, control of progression, or adjunct treatment of diseases and/or medical conditions where the activation of glucokinase would be beneficial, such as diabetes (both Type-I and Type-II), obesity, dyslipidemia, metabolic syndrome X, and/or diabetes-related complications and as therapeutic and/or prophylactic agents for obesity, metabolic syndrome X incluses Type-II diabetes, obesity, dyslipidemia, hypertension, and atherosclerosis and like.

The disclosure further relates to compounds of formula (I), its polymorphs, stereoisomers, pharmaceutically acceptable salt, solvate or pro-drug thereof, for use in the manufacture of medicament for the treatment of diabetes, obesity, metabolic syndrome X, insulin resistance, impaired glucose tolerance and dyslipidemia.

The disclosure also relates to the use of a compounds of formula (I), its polymorphs, stereoisomers, pharmaceutically acceptable salt, solvate or pro-drug thereof, in the manufacture of a medicament for the activation of Glucokinase.

The disclosure also relates to the use of a compounds of formula (I), its polymorphs, stereoisomers, pharmaceutically acceptable salt, solvate or pro-drug thereof, in the manufacture of a medicament for the prevention of diabetes, particularly type II diabetes, in a human demonstrating pre-diabetic hyperglycemia or impaired glucose tolerance.

The disclosure also relates to a method of prophylactic or therapeutic treatment of hyperglycemia or diabetes, particularly type II diabetes, comprising a step of administering an effective amount of a compound of formula (I), its polymorphs, stereoisomers, pharmaceutically acceptable salt, solvate or pro-drug thereof.

The disclosure also relates to a method for the prevention of diabetes, particularly type II diabetes, in a human demonstrating pre-diabetic hyperglycemia or impaired glucose tolerance comprising a step of administering an effective prophylactic amount of a compound of formula (I), its polymorphs, stereoisomers, pharmaceutically acceptable salt, solvate or pro-drug thereof.

The disclosure also relates to a method of combined treatment of diabetes and obesity by administering an effective amount of a compound of formula (I), its polymorph, stereoisomer, prodrug, solvate or a pharmaceutically acceptable salt thereof, to a mammal in need of such treatment.

The disclosure also relates to the use of a compound of formula (I), its polymorphs, stereoisomers, pharmaceutically acceptable salt, solvate or pro-drug thereof, for the prevention of diabetes, particularly type II diabetes, in a human demonstrating pre-diabetic hyperglycemia or impaired glucose tolerance.

The disclosure also relates to the use of a compound of formula (I), its polymorphs, stereoisomers, pharmaceutically acceptable salt, solvate or pro-drug thereof, for use as medicament, for the prophylactic or therapeutic treatment of hyperglycemia or diabetes, particularly type II diabetes.

The disclosure also relates to the use of a compound of formula (I), its polymorphs, stereoisomers, pharmaceutically acceptable salt, solvate or pro-drug thereof, in the manufacture of a medicament for the prophylactic or therapeutic treatment of hyperglycemia or diabetes, particularly type II diabetes.

The disclosure also relates to the use of a compound of formula (I), their stereoisomers, tautomers, prodrugs, pharmaceutically acceptable salts, polymorphs, and solvates, in the manufacture of a medicament for use in combined treatment or prevention of diabetes and obesity.

The disclosure also relates to the use of a compound of formula (I), their stereoisomers, tautomers, prodrugs, pharmaceutically acceptable salts, polymorphs, solvates and formulations thereof for prophylactic or therapeutic treatment of a disease selected from a group consisting of a disease needing Glucokinase activation, a disease needing Glucokinase deinhibition, hyperglycemia, IGT, Syndrome X, type 2 diabetes, type 1 diabetes, dyslipidemia, hyperlipidemia, hypertension, insulin resistance, impaired glucose tolerance, obesity, gastric emptying, gastroparesis, satiety, leptin resistance, dyslipidemia, wound healing, nephropathy, retinopathy, neuropathy and cataracts.

The disclosure also relates to the use of a compound of formula (I), their stereoisomers, tautomers, prodrugs, pharmaceutically acceptable salts, polymorphs, solvates and formulations thereof for lowering of food intake, for appetite regulation, for regulating feeding behaviour, for enhancing the secretion of enteroincretins like GLP-1 and GIP.

The disclosure also relates to the use of a compound of formula (I), their stereoisomers, tautomers, prodrugs, pharmaceutically acceptable salts, polymorphs, solvates and formulations thereof for preventing diabetes, particularly type II diabetes, in a human demonstrating pre-diabetic hyperglycemia or impaired glucose tolerance, preventing obesity and preventing dyslipidemia.

The disclosure also relates to the use of a compound of formula (I), their stereoisomers, tautomers, prodrugs, pharmaceutically acceptable salts, polymorphs, solvates and formulations thereof for combined treatment or prevention of diabetes and obesity.

The disclosure also relates to pharmaceutical composition comprising, as an active ingredient, at least one compound of formula (I), or its stereoisomers, tautomers, prodrugs, pharmaceutically acceptable salts, polymorphs, and solvates thereof, together with one or more pharmaceutically acceptable carriers or excipients.

The compounds and compositions of the present disclosure may be optionally employed in combination with one or more, from current or future therapy, other anti-diabetic agents or anti-hyperglycemic agents, which include, for example, (a) insulin secretagogues such as sulfonylureas (e.g. Amaryl, glyburide, glimepiride, glipyride, glipizide, etc.); (b) Insulinotropic sulfonyl urea receptor ligands such as meglitinides (e.g. nateglinide, rapaglinide); (c) biguanides (e.g. metformin, phenformin, buformin, etc.); (d) glucagon antagonists (e.g. a peptide or non-peptide glucagon antagonist); (e) glucosidase inhibitors (e.g. acarbose, miglitol, etc.); (f) glucose sensitive insulinotropic agents (e.g. GLP-1, GLP-1 mimetics e.g Exendin-4); (g) insulin sensitizers (e.g. troglitazone, rosiglitazone, pioglitazone, etc.); (h) Dipeptidyl peptidase-IV inhibitors (e.g. sitagliptin, vildagliptin); and the like. The said additional therapeutic agent is added in a dose range of about 0.01 mg to 100 mg per kg body weight.

The compounds and compositions of the present disclosure may also be optionally employed in combination with one or more, from current or future therapy, anti-obesity agents (e.g. sibutramine, orlistat, rimonabant etc.) and the like.

The compounds and compositions of the present disclosure may also be optionally employed in combination with one or more, from current or future therapy, dyslipidemic agents which include, for example: (a) fibrates (e.g. gemfibrozil, fenofibrate); (b) Niacin; (c) Statins (e.g. rosuvatatin, atorvastatin, simvastatin); (d) cholesterol absorption inhibitors (e.g. Ezetimibe); (e) bile acid sequestrants (e.g. cholestyramine) and the likes.

The compounds and compositions of the present disclosure may also be optionally employed in combination with one or more, from current or future therapy, antihypertensive agents such as: (a) diuretics (e.g hydrochlorothiazides, mannitol, indapamide, furosemide); (b) angiotensin converting enzyme (ACE) inhibitors (e.g. captopril, enalapril); (c) Angiotensin-II receptor type-I blockers (ARB) (e.g. losartan, irbesartan); (d) rennin inhibitors (e.g aliskerin); (e) ☐he compounds and compositions of theatenolol, metoprolol); (f) calcium channel blockers (e.g. amlodipine, nifedipine); (g) aldosterone receptor antagonist (e.g. spironolactone); (h) aldosterone synthase inhibitors (e.g. FAD286). The said additional therapeutic agent is added in a dose range of about 0.01 mg to 100 mg per kg body weight.

The compounds and compositions of the present disclosure and the other therapeutic agents such as described above may be administered simultaneously, sequentially or separately.

The pharmaceutical compositions of the present disclosure comprise a compound of formula (I), polymorphs, stereoisomers, pharmaceutically acceptable salt, solvate or pro-drug thereof, as an active ingredient, a pharmaceutically acceptable carrier and optionally other therapeutic active agent in any suitable ratios.

The disclosure also relates to pharmaceutical composition comprising, as an active ingredient, at least one compound of formula (I), or its stereoisomers, tautomers, prodrugs, pharmaceutically acceptable salts, polymorphs, and solvates thereof, wherein the pharmaceutically acceptable therapeutically active agent is selected from anti-diabetic agents, anti-hyperglycemic agents, anti-obesity agents, anti-hypertensive agents or anti-dyslipidemic agents.

The pharmaceutical compositions of the present disclosure comprising compounds of formula (I), polymorphs, stereoisomers, pharmaceutically acceptable salt, solvate or prodrugs thereof, may be manufactured in a manner that is known in the art, e.g. by means of conventional mixing, encapsulating, dissolving, granulating, emulsifying, entrapping, dragee making, or lyophilizing processes. These pharmaceutical preparations can be formulated with therapeutically inert, inorganic or organic carriers such as lactose, corn starch or derivatives thereof, talc, steric acid or its salts as carriers for tablets, coated tablets, dragées and hard gelatin capsules. For soft gelatin capsules suitable carriers include vegetable oils, waxes and fats. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semiliquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula (I), its polymorphs, stereoisomers, pharmaceutically acceptable salt, solvate or prodrugs thereof.

The pharmaceutical compositions containing the active ingredient of compound of formula (I), its polymorphs, stereoisomers, pharmaceutically acceptable salt, solvate or prodrugs thereof, maybe in a form suitable for oral use, for example, as tablets, troches, lozenges, aqueous or oily suspensions, dispersible powders or granules, emulsions, hard or soft capsules, or syrups or elixirs; sterile injectable aqueous or oleaginous suspension; suppositories; topical use, for example creams, ointments, jellies, solutions or suspension etc including mouth washes and gargles. These compositions can be manufactured by any method known in the art with the active ingredient combined with non-toxic pharmaceutically acceptable excipients.

While the disclosure has been described and illustrated with reference to certain preferred embodiments thereof, those skilled in the art will appreciate that various changes, modifications and substitutions can be made therein without departing from the spirit and scope of the present disclosure. For example, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present disclosure.

ABBREVIATIONS

The following abbreviations are employed in the examples and elsewhere herein:
DMF: Dimethyl formamide
DMSO: Dimethyl sulfoxide
DCM: Dichloromethane
DCE: Dichloroethane
THF: Tetrahydrofuran
mCPBA: meta chloro perbenzoic acid
BOP-Cl: Bis(2-oxo-3-oxazolidinyl)phosphinic chloride
DABCO: 1,4-Diazabicyclo[2.2.2]octane
DBU: 1,8-Diazabicyclo[5.4.0]undec-7-ene
DCC: N,N-Dicyclohexyl carbodiimide
EDCl: 1-Ethyl-3-(3-dimetylaminopropyl)carbodiimide
HOBT: 1-Hydroxybenzotriazole
HOAT: 1-Hydroxy-7-azabenzotriazole
HBTU: O-(benzotriazol-1-yl)-tetramethyluronium hexafluorophosphate
HATU: O-(7-azabenzotriazol-1-yl)-tetramethyluronium hexafluorophosphate
TPP: triphenylphosphine
DEAD: diethyl azodicarboxylate
DIAD: diisopropyl azodicarboxylate
MTBE: methyltert-butyl ether

EXAMPLES

The disclosure is further illustrated by the following examples which in no way should be construed as being further limiting. One skilled in the art will readily appreciate that the specific methods and results described are merely illustrative. All stereoisomers of the compounds of the instant disclosure are contemplated, either in admixture or in pure or substantially pure form. The compounds of the present disclosure can have asymmetric centers at any of the carbon atoms, consequently, compounds of formula (I) can exist in enantiomeric, or diastereomeric forms, or in mixtures thereof. The processes for preparation can utilize racemates, enantiomers, or diastereomers as starting materials. When diastereomeric or enantiomeric products are obtained as mixtures, they can be separated by conventional methods for example, chromatographic separation or fractional crystallization or through diasteriomeric salt formation. When intended, a desired enantiomer or diasteriomer can also be obtained by following appropriate enantioselective or diastereoselective reactions.

Structures of the intermediates as well as the final compounds were confirmed by nuclear magnetic resonance spectra for proton ($^1$H NMR) and LCMS.

Preparation 1

2-(4-cyclopropanesulfonylphenyl)-2-(2,4-difluorophenoxy)acetic acid

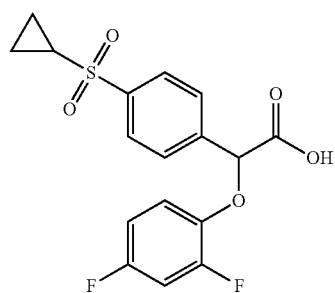 [SMILES: O=C(O)C(Oc1ccc(F)cc1F)c1ccc(S(=O)(=O)C2CC2)cc1]

2-(4-cyclopropanesulfonylphenyl)-2-(2,4-difluorophenoxy) acetic acid was obtained according to WO2009/047798 A2 (Example A1).

Preparation 2

2-(2,4-difluorophenoxy)-2-(4-morpholinosulfonylphenyl)acetic acid

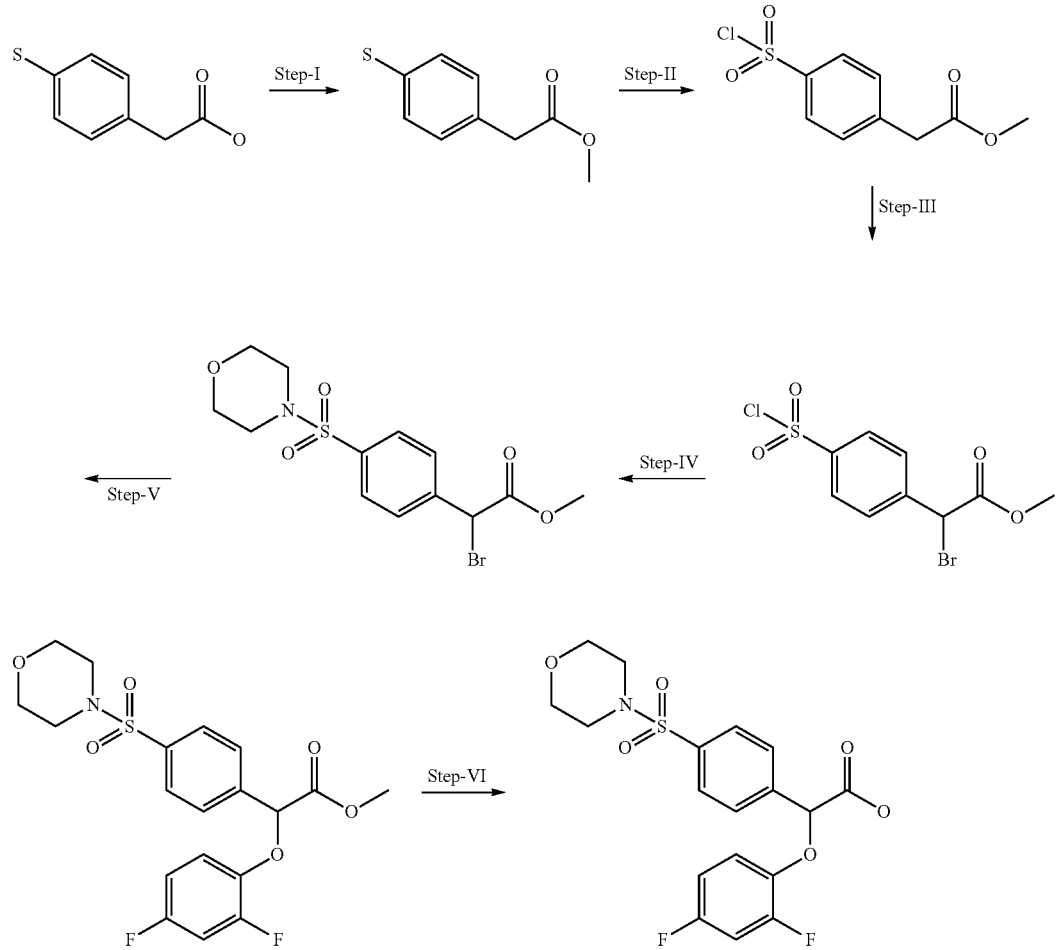

Step I (4-Mercapto-phenyl)-acetic acid methyl ester

To a solution of 4-mercapto-phenyl acetic acid (30 g, 178.34 mmol) in methanol (60 ml) was added sulfuric acid (9.5 mL, 178.34 mmol) dropwise. Reaction mixture was then heated at 60° C. for 3 hr, concentrated to remove methanol. The residue was neutralized with satd. aq. NaHCO$_3$ solution and extracted with ethyl acetate (3×30 mL) washed with brine, dried over anhydrous sodium sulfate, filtered and concentrated. Product was purified using column chromatography in 1% ethyl acetatae:hexane as eluent which afforded (4-mercapto-phenyl)-acetic acid methyl ester (27 g).

$^1$H NMR (400 MHz, CDCl$_3$): δ 3.43 (s, 1H), 3.57 (s, 2H), 3.68 (s, 3H), 7.15 (d, J=7.6 Hz, 2H), 7.23 (d, J=8.0 Hz, 2H), MS (EI) m/z: 183.1 (M+1), 200.1 (M+18).

Step II (4-Chlorosulfonyl-phenyl)-acetic acid methyl ester (4-Mercapto-phenyl)-acetic acid methyl ester (2 g, 10.98 mmole) was taken in a seal tube. To it DCM (30 mL) was added followed by KNO$_3$ (2.60 g, 24.16 mmole) and TMSCl (3.0 mL, 24.16 mmole). Mixture was heated at 50° C. for 24 hr, cooled to room temperature and filtered to remove solids, residue was washed with DCM (2×10 mL), combined filtrate was washed with water followed by brine solution, dried over anhydrous sodium sulfate, filtered and concentrated under reduced pressure to provide (4-chlorosulfonyl-phenyl)-acetic acid methyl ester (1.6 g) [reaction was repeated several times on 2 g scale]

$^1$H NMR (400 MHz, CDCl$_3$): δ 3.70 (s, 3H) 3.75 (s, 2H), 7.53 (d, J=8.8 Hz, 2H), 7.98 (d, J=8.8 Hz, 2H).

Step III

Bromo-(4-chlorosulfonyl-phenyl)-acetic acid methyl ester (4-Chlorosulfonyl-phenyl)-acetic acid methyl ester (13 g, 52.41 mmol) was taken in carbon tetrachloride (262 mL). N-Bromosuccinimide (10.26 g, 57.66 mmol) was added in one lot followed by benzoyl peroxide (1.39 g, 5.766 mmol). The reaction mixture was refluxed for 2 days. The reaction mixture was cooled to room temperature and filtered; filtrate was washed with water followed by brine solution, dried over anhydrous sodium sulfate and concentrated. Product was purified using column chromatography in 3% ethyl acetate: hexane which yielded bromo-(4-chlorosulfonyl-phenyl)-acetic acid methyl ester (2.8 g) as a gummy mass.

$^1$H NMR (400 MHz, CDCl$_3$): δ 3.82 (s, 3H), 5.38 (s, 1H), 7.80 (d, J=8.6 Hz, 2H), 8.04 (d, J=8.3 Hz, 2H).

Step IV

Bromo-[4-(Morpholine-1-sulfonyl)-phenyl]-acetic acid methyl ester

Bromo-(4-chlorosulfonyl-phenyl)-acetic acid methyl ester (2.0 g, 6.11 mmol) and triethyl amine (0.88 mL. 6.72 mmol) were taken in DCM (30 mL) under argon atmosphere and cooled to 0-5° C. A solution of morpholine (0.48 mL, 5.50 mmol) in DCM (31 mL) was added dropwise to the mixture at 0-5° C. Reaction mixture was then stirred at room temperature for 2 hours. Reaction mixture was washed with water followed by brine, dried over anhydrous sodium sulfate and concentrated under reduced pressure to give the crude product bromo-[4-(morpholine-1-sulfonyl)-phenyl]acetic acid methyl ester (2.02 g).

$^1$H NMR (400 MHz, CDCl$_3$): δ 2.95 (t, J=4.6 Hz, 4H), 3.68 (d, J=3.6 Hz, 4H), 3.75 (s, 3H), 5.31 (s, 1H), 7.67 (s, 4H).

Step V (2,4-Difluoro-phenoxy)-[4-(morpholine-1-sulfonyl)-phenyl]-acetic acid methyl ester 2,4-Difluorophenol (0.56 mL, 5.87 mmol) and cesium carbonate (1.14 g, 3.52 mmol) were taken in acetonitrile (10 mL) under argon atmosphere and was stirred for 30 minutes. Bromo-[4-(morpholine-1-sulfonyl)-phenyl]acetic acid methyl ester (2.02 g, 5.33 mmol) in acetonitrile (10 mL) was added to the mixture and stirred at 25° C. for 3 hours. Reaction mixture was diluted with water (30 mL), extracted with ethyl acetate (3×30 mL), organic layer was washed with cold 1N NaOH, brine, dried over anhydrous sodium sulfate and concentrated under reduced pressure to give a gummy mass. (2,4-difluoro-phenoxy)-[4-(morpholine-1-sulfonyl)-phenyl]-acetic acid methyl ester (1.90 g).

$^1$H NMR (400 MHz, CDCl$_3$): δ 3.01 (t, J=4.6 Hz, 4H), 3.73 (t, J=4.6 Hz, 4H), 3.76 (s, 3H), 5.65 (s, 1H), 6.74-6.80 (m, 1H), 6.86-6.91 (m, 1H), 6.94-7.00 (m, 1H), 7.75-7.80 (m, 4H).

MS (EI) m/z: 428.0 (M+1)

Step VI (2,4-Difluoro-phenoxy)-[4-(morpholine-1-sulfonyl)-phenyl]-acetic acid (2,4-Difluoro-phenoxy)-[4-(morpholine-1-sulfonyl)-phenyl]-acetic acid methyl ester(1.9 g, 4.44 mmol) was dissolved in THF (6 mL) and methanol (0.5 mL). To this was added a solution of lithium hydroxide (0.930 g, 22.24 mmol) in water (12 mL) and stirred for 18 hours at room temperature. Organic solvents were evaporated from the reaction mixture and aqueous layer was washed with DCM acidified with 1N HCl, extracted with ethyl acetate (3×50 mL), organic layer was washed with brine, dried over anhydrous sodium sulphate and concentrated to give gummy solid product as (2,4-difluoro-phenoxy)-[4-(morpholine-1-sulfonyl)-phenyl]-acetic acid (1.6 g).

$^1$H NMR (400 MHz, DMSO-d$_6$): δ 2.87 (t, J=4.1 Hz, 4H), 3.62 (t, J=4.6 Hz, 4H), 6.14 (s, 1H), 7.01-7.06 (m, 1H), 7.17-7.23 (m, 1H), 7.32-7.38 (m, 1H), 7.78-7.83 (m, 4H), 13.6 (bs, 1H).

MS (EI) m/z: 413.9 (M+1).

Preparations 3

2-(4-cyclopropylsulfonylphenyl)-2-(2,4-difluoroanilino)acetic acid

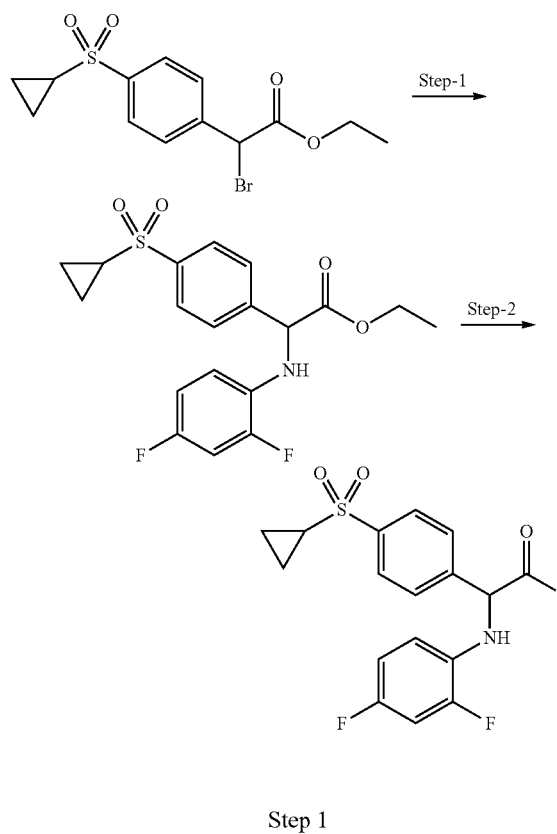

Step 1 ethyl 2-(4-cyclopropylsulfonylphenyl)-2-(2,4-difluoroanilino)acetate

Ethyl 2-bromo-2-(4-cyclopropylsulfonylphenyl)acetate (0.8 g, 2.30 mmol) [obtained as described in WO2009/047798 A2; Example A1] and 2,4-difluoroaniline (3.0 mL) mixed together and heated at 150° C. in a seal tube for 12 hrs. Reaction mixture was cooled to rt and purified by column chromatography using 20% ethyl acetate in hexane as eluent to provide ethyl 2-(4-cyclopropylsulfonylphenyl)-2-(2,4-difluoroanilino)acetate (0.65 g).

$^1$H NMR (400 MHz, CDCl$_3$): δ 1.04-1.06 (m, 2H), 1.23 (t, J=7.3 Hz, 3H), 1.36-1.37 (m, 2H), 2.43-2.50 (m, 1H), 4.11-4.23 (m, 1H), 4.25-4.29 (m, 1H), 5.10 (app. d, 1H), 5.16 (br. s, 1H), 6.22-6.28 (m, 1H), 6.58-6.63 (m, 1H), 6.79-6.84 (m, 1H), 7.70 (d, J=8.3 Hz, 2H), 7.90 (d, J=8.3 Hz, 2H). MS (EI) m/z: 396.1 (M+1).

Step 2

2-(4-cyclopropylsulfonylphenyl)-2-(2,4-difluoroanilino)acetic acid

To ethyl 2-(4-cyclopropylsulfonylphenyl)-2-(2,4-difluoroanilino)acetate (0.6 g, 1.51 mmol) was added a solution of lithium hydroxide (0.317 g, 7.22 mmol) in water (4 mL) followed by THF (4 mL) and methanol (0.5 mL) and stirred for 12 hours at 25° C. Organic solvents were evaporated from the reaction mixture and aqueous layer was acidified 1N HCl, extracted with ethyl acetate (3×15 mL), organic layer was washed with brine solution, dried over anhydrous sodium sulfate, and washed concentrated under reduced pressure to provide 2-(4-cyclopropylsulfonylphenyl)-2-(2,4-difluoroanilino)acetic acid (0.5 g).

$^1$H NMR (400 MHz, CDCl$_3$): δ1.00-1.05 (m, 2H), 1.30-1.34 (m, 2H), 2.41-2.45 (m, 1H), 5.07 (s, 1H), 6.22-6.27 (m, 1H), 6.58-6.62 (m, 1H), 6.77-6.82 (m, 1H), 7.67 (d, J=8.3 Hz, 2H), 7.83 (d, J=8.0 Hz, 2H). MS (EI) m/z: 368.1 (M+1).

Preparation 4

(4-(Cyclopropanesulfonyl)phenyl)-[(tetrahydro-pyran-4-yloxy)]-acetic acid

Two routes used for synthesis of 4

Route 1

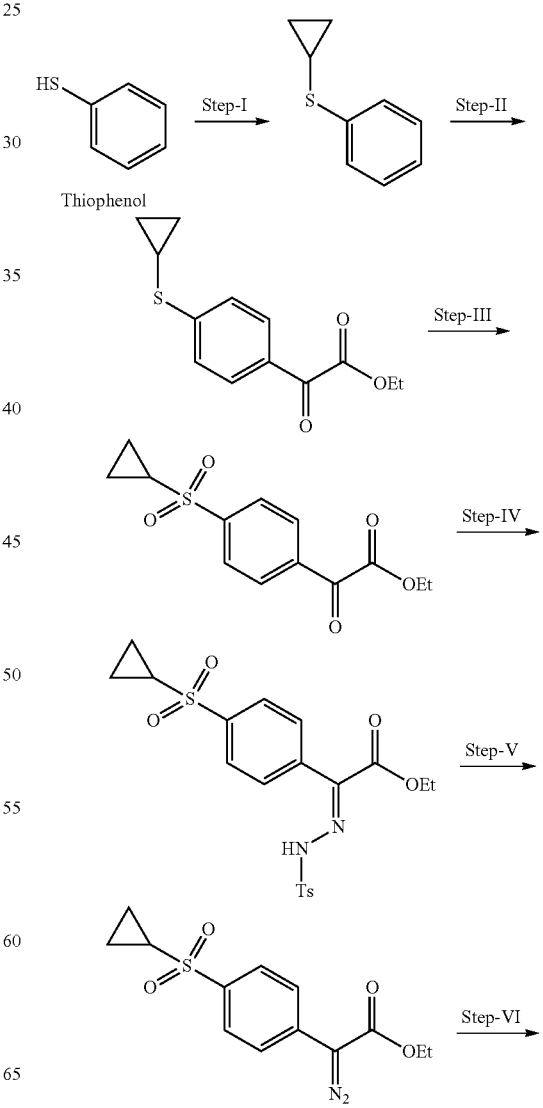

-continued

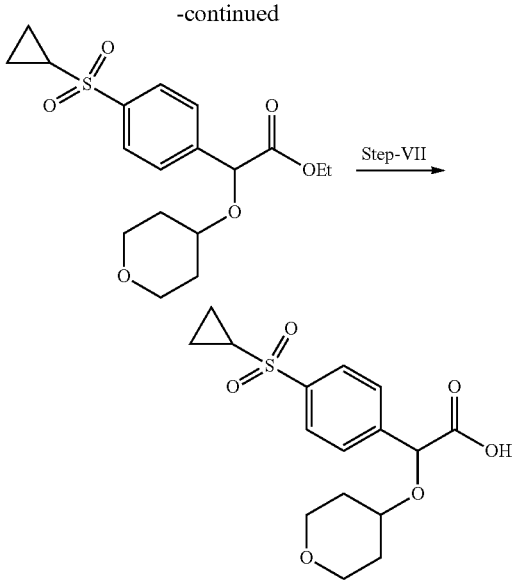

Step I

Synthesis of Cyclopropylsulfanylbenzene

To a stirred suspension of potassium tert-butoxide (52.4 g, 467 mmol) in DMSO (200 mL) was added thiophenol (42.9 g, 389 mmol) at 0° C. and stirred for 30 minutes at 20-25° C., followed by addition of bromocyclopropane (37.3 mL, 467 mmol). The reaction mixture was heated to 60° C. and continued to stir for 24 hours at the same temperature (with cold water circulation in the condenser). Reaction monitoring was done by TLC showed completion of reaction. The reaction mixture was then cooled to 20-25° C., added water (800 mL) then extracted with diethyl ether (3×400 mL). Diethyl ether layer was washed with water (500 mL) then with brine (150 mL) and dried over anhydrous sodium sulfate (75 g). Sodium sulfate was filtered and wash with diethyl ether (50 mL), solvent was removed under reduced pressure using rotavapour (bath temperature 30-35° C.) to get the required oily product which was dried under vacuum for 30 minutes. The crude material was used for the next step with out any purification.

$^1$H NMR (CDCl$_3$, 400 MHz): δ 0.65-0.72 (m, 2H), 1.02-1.12 (m, 2H), 2.15-2.23 (m, 1H), 7.13 (t, J=7.3 Hz, 1H), 7.28 (t, J=7.8 Hz, 2H), 7.37 (d, J=7.8 Hz, 2H).

Step II

Synthesis of 2-[4-(Cyclopropylsulfanyl)phenyl]-2-oxo-acetic acid, ethyl ester A stirred solution of Aluminum chloride (48.4 g, 363 mmol) in DCM (480 mL) was cooled to 0° C. using an ice-salt bath under inert atmosphere. At the same temperature ethyl oxalyl chloride (31.9 mL, 285 mmol) was added slowly. Reaction mixture was stirred for 60 min. at 0° C. To this stirred suspension, solution of cyclopropylsulfanylbenzene (39 g, 259 mmol) in DCM (100 mL) was added drop wise at 0° C. Reaction mixture was slowly brought to 20-25° C. and stirred for 2 hours. Completion of reaction was confirmed by TLC. Reaction mixture was slowly poured in ice-cold water (500 mL). Organic layer was separated and aqueous layer was extracted with of DCM (3×100 mL). Combined organic layer was washed with water (200 mL) and then with aqueous saturated sodium bicarbonate solution (300 mL) followed by brine (100 mL). Organic layer was dried over anhydrous sodium sulfate, sodium sulfate was filtered and washed with DCM (100 mL) and solvent was evaporated under reduced pressure using rotavapour to get required oily product which was dried under vacuum for 1 hour. The obtained residue was purified by column chromatography using 0-5% ethyl acetate in hexanes as solvent system to get a pure product $^1$H NMR (CDCl$_3$, 400 MHz): δ 0.70-0.78 (m, 2H), 1.12-1.21 (m, 2H), 1.42 (t, J=7.3 Hz, 3H), 2.16-2.25 (m, 1H), 4.44 (q, J=7.3 Hz, 2H), 7.45 (d, J=8.8 Hz, 2H) 7.92 (d, J=8.4 Hz, 2H).; LCMS (EI) m/z: 251 (M+1)

Step III

Synthesis of ethyl 2-[4-(cyclopropylsulfonyl)phenyl]-2-oxo-acetate

A stirred solution of 2-(4-cyclopropylsulfanylphenyl)-2-oxoacetic acid, ethyl ester (19 g, 76 mmol) in DCM (500 mL) was cooled to 0° C. using an ice-salt bath. At the same temperature m-CPBA (32.7 g, 19 mmol) was added portion wise. Reaction mixture was slowly brought to 20-25° C. and stirred for 4 h. The reaction mixture was filtered through Buchner funnel and filtrate washed with aqueous sat. sodium thiosulfate solution (100 mL) and then with aqueous saturated sodium bicarbonate solution (100 mL) followed by brine (100 mL). Organic layer was dried over anhydrous sodium sulfate, sodium sulfate was filtered and washed with DCM (100 mL) and solvent was evaporated under reduced pressure using rotavapour to get required product which was dried under vacuum for 1 hour. The crude material was used for the next step with out any further purification.

$^1$H NMR (CDCl$_3$, 400 MHz): δ 1.05-1.15 (m, 2H), 1.32-1.44 (m, 2H), 1.45 (t, J=7.3 Hz, 3H), 2.43-2.54 (m, 1H), 4.48 (q, J=7.3 Hz, 2H), 8.05 (d, J=8.3 Hz, 2H), 8.23 (d, J=8.3 Hz, 2H); LCMS (EI) m/z: 282.9 (M+1)

Step IV

Synthesis of 2-[p-(Toluene sulfonyl)hydrazone]-2-[4 (cyclopropylsulfonyl)phenyl]acetic acid ethyl ester A mixture of ethyl 2-(4-cyclopropylsulfonyl)phenyl-2-oxo-acetate (21 g, 74 mmol), p-toluenesulfonyl hydrazide (18 g, 96 mmol) and toluene (350 mL) was placed in 2-necked RBF equipped with dean-stark apparatus. The reaction mixture was refluxed for 3 h. Completion of reaction was confirmed by TLC. Reaction was cooled to room temperature and solvent was evaporated under reduced pressure using rotavapour to get crude product which was dried under vacuum. The obtained residue was purified by column chromatography using 20-40% ethyl acetate in hexanes as solvent system to get a pure solid product.

$^1$H NMR (CDCl$_3$, 400 MHz): δ 1.04-1.10 (m, 2H), 1.34 (t, J=7.4 Hz, 3H), 1.35-1.41 (m, 2H), 2.43 (s, 3H), 2.44-2.51 (m 1H), 4.38 (q, J=7.4 Hz, 2H), 7.34 (d, J=7.8 Hz, 2H), 7.69 (d, J=8.3 Hz, 2H), 7.80 (d, J=8.3 Hz, 2H), 7.87 (d, J=8.3 Hz, 2H); LCMS (EI) m/z: 450.8 (M+1)

Step V

Synthesis of 2-[4-(Cyclopropanesulfonyl)phenyl]-2-diazo acetic acid ethyl ester To a stirred solution of 2-[p-(Toluene sulfonyl)hydrazone]-2-[4(cyclopropylsulfonyl)phenyl]acetic acid ethyl ester (27.5 g, 61 mmol) in DCM (200 mL) at 25° C. under inert atmosphere was added triethyl amine (9.3 mL, 67 mmol) slowly. Reaction mixture was stirred for 1 h at 25° C. Completion of reaction was confirmed by TLC. Solvent was evaporated under reduced pressure using rotavapour to get crude product which was dried under vacuum. The obtained residue was purified by column chromatography using 5-20% ethyl acetate in hexanes as solvent system to get a pure solid product.

$^1$H NMR (CDCl$_3$, 400 MHz): δ 1.0-1.06 (m, 2H), 1.32-1.39 (m, 5H), 2.41-2.49 (m, 1H), 4.37 (q, J=7.4 Hz, 2H), 7.68 (d, J=8.8 Hz, 2H), 7.88 (d, J=8.8 Hz, 2H); MS (EI) m/z: 294.9 (M+1)

Step VI

Synthesis of 2-[4-(Cyclopropanesulfonyl)phenyl]-2-(tetrahydro-pyran-4-yloxy)acetic acid ethyl ester To a stirred solution of compound 2-[4-(Cyclopropanesulfonyl)phenyl]-2-diazo acetic acid ethyl ester (11.3 g, 38 mmol) in DCM (110 mL) under argon atmosphere, 4-hydroxy tetrahydropyran (4.36 mL, 45 mmol) was added followed by portion wise addition of rhodium(II)acetate dimer (0.354 g, 0.8 mmol). Reaction proceeds with evolution of N$_2$ gas. Reaction mixture was stirred at 25° C. for 0.5 h. Completion of reaction was confirmed by TLC and reaction mixture was poured into water (100 mL). Organic layer was separated; aqueous layer was again extracted with of DCM (250 mL). Combined organic layer was washed with water (100 mL) and then with aqueous saturated sodium bicarbonate (300 mL) followed by brine (75 mL). Organic layer was dried over anhydrous sodium sulfate, sodium sulfate was filtered and washed with DCM (100 mL) and solvent was evaporated under reduced pressure using rotavapour to get required crude product. The crude product was purified by column chromatography using silica gel 100-200 mesh, mobile phase hexanes to 35% ethyl acetate in hexanes. Removal of solvent from appropriate fractions under reduced pressure in rotavapour gave pure product.

$^1$H NMR (400 MHz, CDCl$_3$): δ 1.01-1.09 (m, 2H), 1.24 (t, J=7.2 Hz, 3H), 1.34-1.40 (m, 2H), 1.62-1.82 (m, 2H), 1.86-1.94 (m, 1H), 1.95-2.03 (m, 1H), 2.42-2.50 (m, 1H), 3.38-3.50 (m, 2H), 3.62-3.70 (m, 1H), 3.90-4.03 (m, 2H) 4.12-4.24 (m, 2H), 5.11 (s, 1H), 7.68 (d, J=7.9 Hz, 2H), 7.90 (d, J=7.8 Hz, 2H); MS (EI) m/z: 369.2 (M+1).

Step VII

2-[4-(Cyclopropanesulfonyl)phenyl]-2-(tetrahydro-pyran-4-yloxy)acetic acid

To a stirred solution of intermediate 2-[4-(Cyclopropanesulfonyl)phenyl]-2-(tetrahydro-pyran-4-yloxy)acetic acid ethyl ester (8.0 g, 21 mmol) in tetrahydrofuran (80 mL) was added a solution of LiOH (2.27 g in 40 mL of water, 54 mmol) at 25° C. and stirred for 2 h. Completion of reaction was confirmed by TLC. Organic solvent was removed under reduced pressure. The aqueous layer was acidified to pH 2-3 using 1 N HCl. White solid obtained was filtered through Buchner funnel dried under vacuum to afford pure product.

$^1$H NMR (400 MHz, DMSO-d$_6$): δ 1.0-1.08 (m, 2H), 1.10-1.16 (m, 2H) 1.36-1.58 (m, 2H), 1.82-1.96 (m, 2H), 2.82-2.90 (m, 1H), 3.26-3.36 (m, 2H), 3.58-3.66 (m, 1H), 3.73-3.86 (m, 2H) 5.24 (s, 1H), 7.67 (d, J=8.3 Hz, 2H), 7.89 (d, J=7.8 Hz, 2H), 13.08 (bs, 1H); MS (EI) m/z: 341.1 (M+1), 358.1 (M+18).

Route 2

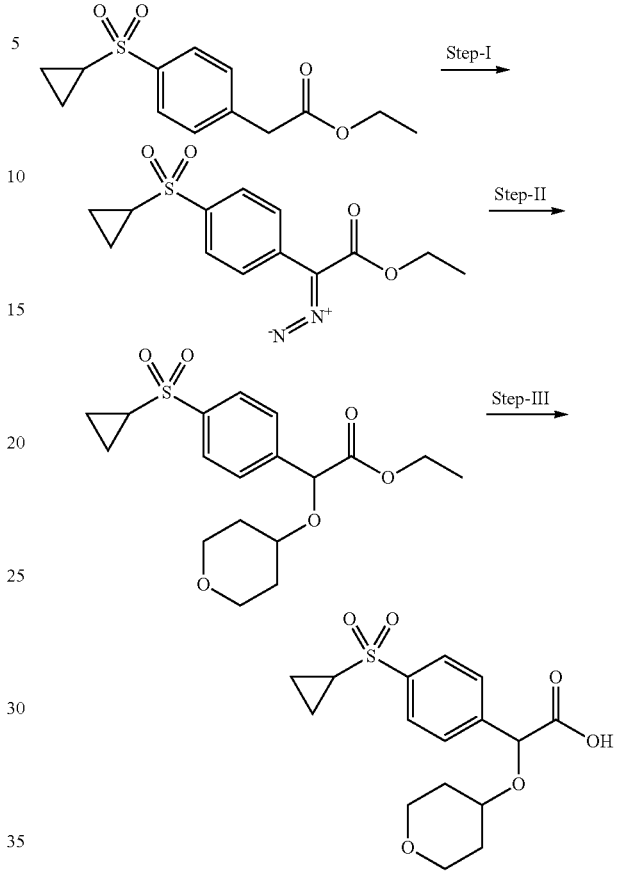

Step I

Ethyl 2-(4-cyclopropylsulfonylphenyl)-2-diazo-acetate

Ethyl 2-(4-cyclopropylsulfonylphenyl)acetate [obtained as described in WO2004/072031 (40 g, 149.07 mmol)] was dissolved in dry acetonitrile (745 mL) under argon atmosphere. To the above solution para toluene sulfonyl azide (32.33 g, 163.97 mmol) was added, followed by DBU (33.40 mL, 223.6 mmol) in dropwise manner, and stirred for 30 min. Reaction mixture was poured in ice cold water (500 mL), solid obtained was filtered through buchner funnel and dried under vaccum which yielded ethyl 2-(4-cyclopropylsulfonylphenyl)-2-diazo-acetate (40 g).

$^1$H NMR (400 MHz, CDCl$_3$): δ 0.99-1.04 (m, 2H), 1.32-1.40 (m, 5H), 2.41-2.47 (m, 1H), 4.36 (q, J=7.0 Hz, 2H), 7.67 (d, J=8.3 Hz, 2H), 7.88 (d, J=8.8 Hz, 2H). MS (EI) m/z: 295 (M+1).

Step II (4-Cyclopropanesulfonyl-phenyl)-[(tetrahydro-pyran-4-yloxy)]-acetic acid ethyl ester Ethyl 2-(4-cyclopropylsulfonylphenyl)-2-diazo-acetate (36 g, 121.62 mmol) was dissolved in DCM (608 mL) under argon atmosphere. To this solution, 4-hydroxy tetrahydropyran (12.75 mL, 133.78 mmol) was added followed by rhodium(II)acetate dimer (1.12 g, 0.021 mmol). Mixture was stirred at 25° C. for 1 hr. Reaction mixture was diluted with DCM (500 mL), organic layer was washed with water followed by brine solution, dried over anhydrous sodium sulfate, filtered and concentrated under reduced pressure to give a product (4-cyclopropanesulfonyl-phenyl)-[(tetrahydro-pyran-4-yloxy)]-acetic acid ethyl ester (50 g).

$^1$H NMR (400 MHz, CDCl$_3$): δ 1.02-1.07 (m, 2H), 1.24 (t, 3H), 1.34-1.37 (m, 2H), 1.65-1.81 (m, 2H), 1.87-1.92 (m, 1H), 1.95-2.01 (m, 1H), 2.43-2.49 (m, 1H), 3.39-3.48 (m, 2H), 3.62-3.68 (m, 1H), 3.91-4.02 (m, 2H) 4.15-4.23 (m, 2H), 5.11 (s, 1H), 7.68–(d, J=8.0 Hz, 2H), 7.90 (d, J=8.0 Hz 2H). MS (EI) m/z: 369 (M+1), 386.1 (M+18).

Step III (4-Cyclopropanesulfonyl-phenyl)-[(tetrahydro-pyran-4-yloxy)]-acetic acid To (4-cyclopropanesulfonyl-phenyl)-[(tetrahydro-pyran-4-yloxy)]-acetic acid ethyl ester (23.2 g, 62.87 mmol) was added a solution of lithium hydroxide (13.0 g, 314.36 mmol) in water (150 mL) followed by THF (200 mL) and methanol (10 mL) and stirred for 2 hours at 25° C. Organic solvents were evaporated from the reaction mixture and aqueous layer was acidified 1N HCl, extracted with ethyl acetate (3×200 mL), organic layer was washed with brine solution, dried over anhydrous sodium sulfate, and washed concentrated under reduced pressure to provide (4-cyclopropanesulfonyl-phenyl)-[(tetrahydro-pyran-4-yloxy)]-acetic acid (18.49 g)

$^1$H NMR (400 MHz, CDCl$_3$): δ 1.02-1.06 (m, 2H), 1.07-1.15 (m, 2H) 1.23-1.56 (m, 2H), 1.83-1.94 (m, 2H), 2.83-2.89 (m, 1H), 3.28-3.35 (m, 2H), 3.69-3.65 (m, 1H), 3.74-3.85 (m, 2H) 5.26 (s, 1H), 7.69 (d, J=8.0 Hz, 2H), 7.90 (d, J=8.0 Hz, 2H).

MS (EI) m/z: 341.0 (M+1), 358.2 (M+18).

Preparations 5 to 10 were prepared in analogous manner of preparation 4.

| Prep. No. | IUPAC Name |
| --- | --- |
| 5 | (4-Cyclopropanesulfonyl-phenyl)-[(R)-(tetrahydro-furan-3-yl)oxy]-acetic acid |
| 6 | (4-Cyclopropanesulfonyl-phenyl)-[(S)-(tetrahydro-furan-3-yl)oxy]-acetic acid |
| 7 | (4-Cyclopentanesulfonyl-phenyl)-[(tetrahydro-pyran-4-yloxy)]-acetic acid |
| 8 | (4-Cyclopropanesulfonyl-phenyl)-(tetrahydro-pyran-3-yloxy)]-acetic acid |
| 9 | 2-(4-Cyclopropylsulfonylphenyl)-2-[(2R,3S,4R)-3-hydroxy-2-(hydroxymethyl) tetrahydropyran-4-yl]oxy-acetic acid |
| 10 | 2-[(1-tert-Butoxycarbonyl-4-piperidyl)oxy]-2-(4-cyclopropylsulfonylphenyl) acetic acid |

Preparation 11

[4-(morpholine-1-sulfonyl)-phenyl]-[(tetrahydro-pyran-4-yloxy)]-acetic acid

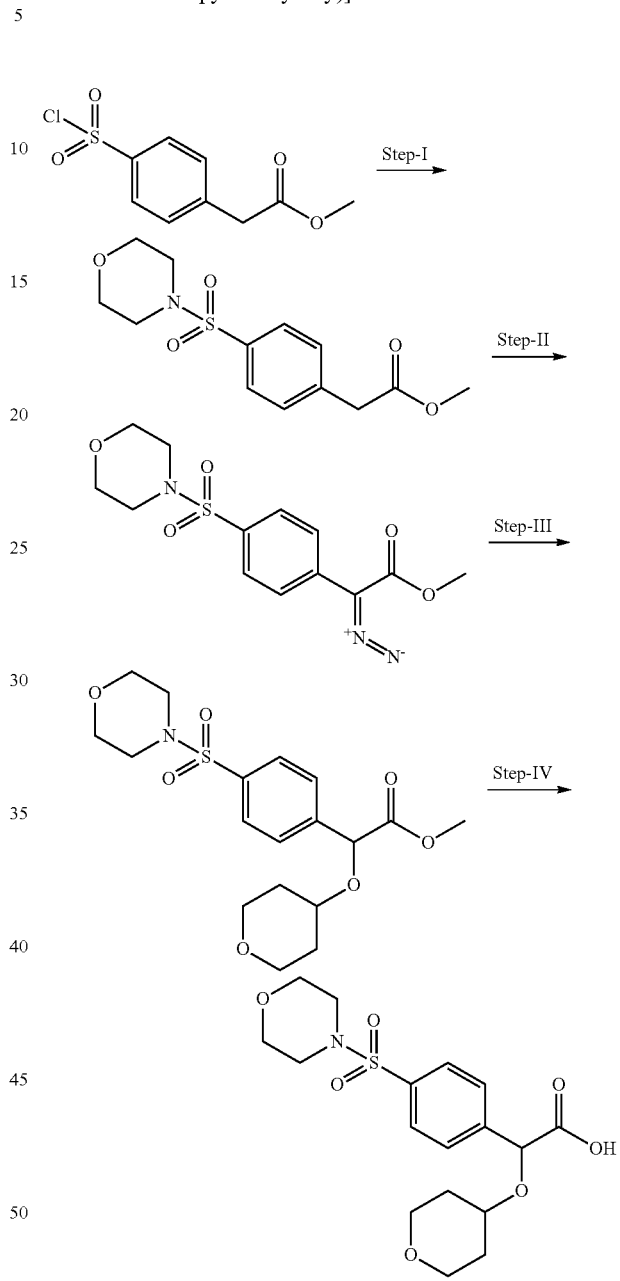

Step I

Methyl 2-(4-morpholinosulfonylphenyl)acetate

Methyl 2-(4-chlorosulfonylphenyl)acetate (2.0 g, 8.04 mmol) was taken in dry DCM (50 mL) under argon atmosphere and cooled to 0-5° C., morpholine (0.77 mL, 8.84 mmol) followed by triethylamine (1.16 mL, 8.84 mmol) was added dropwise to the mixture at 0-5° C. Reaction mixture was then brought to room temperature and stirred for additional 2 hours. Reaction mixture was washed with water followed by brine solution, dried over anhydrous sodium sulfate and concentrated under reduced pressure to give the crude product, which was purified by column chromatography using 14-20% ethyl acetate in hexane as eluent to give Methyl 2-(4-morpholinosulfonylphenyl)acetate (1.5 g).

$^1$H NMR (400 MHz, CDCl$_3$): δ 2.98-3.05 (m, 4H), 3.70-3.78 (m, 9H), 7.48 (d, J=8.0 Hz, 2H), 7.72 (d, J=8.1 Hz, 2H). MS (EI) m/z: 300.1 (M+1).

Step II

Diazo-[4-(Morpholine-1-sulfonyl)-phenyl]acetic acid methyl ester

[4-(Morpholine-1-sulfonyl)-phenyl]-acetic acid methyl ester (1.4 g, 4.67 mmol) was dissolved in dry acetonitrile (23 mL) under argon atmosphere. To the above solution para toluene sulfonyl azide (1.01 g, 5.14 mmol) was added, followed by DBU (1.0 mL, 7.00 mmol) in dropwise manner, and stirred for 30 min. Reaction mixture was poured in ice cold water (40 mL), solid obtained was filtered through buchner funnel and dried under vaccum which yielded Diazo-[4-(piperidine-1-sulfonyl)-phenyl]-acetic acid methyl ester (1.1 g).

$^1$H NMR (400 MHz, CDCl$_3$): δ 2.98-3.01 (m, 4H), 3.73-3.75 (m, 4H), 3.90 (s, 3H), 7.68 (d, J=8.8 Hz, 2H), 7.74 (d, J=8.6 Hz, 2H). MS (EI) m/z: 326.1 (M+1).

Step III

[4-(Morpholine-1-sulfonyl)-phenyl]-[(tetrahydro-pyran-4-yloxy)]-acetic acid methyl ester Diazo-[4-(morpholine-1-sulfonyl)-phenyl]-acetic acid methyl ester (1.1 g, 3.36 mmol) was dissolved in DCM (17 mL) under argon atmosphere. To this solution, 4-hydroxy tetrahydropyran (0.4 mL, 4.036 mmol) was added followed by rhodium (II) acetate dimer (0.031 g, 0.070 mmol). Mixture was stirred at 25° C. for 30 min. Reaction mixture was diluted with DCM (10 mL), organic layer was washed with water followed by brine solution, dried over anhydrous sodium sulfate, filtered and concentrated under reduced pressure to give a crude product as [4-(Piperidine-1-sulfonyl)-phenyl]-[(tetrahydro-pyran-4-yloxy)]-acetic acid methyl ester (1.3 g). MS (EI) m/z: 400.1 (M+1).

Step IV

[4-(Morpholine-1-sulfonyl)-phenyl]-[(tetrahydro-pyran-4-yloxy)]-acetic acid

To [4-(morpholine-1-sulfonyl)-phenyl]-[(tetrahydro-pyran-4-yloxy)]-acetic acid methyl ester (1.3 g, 3.25 mmol) was added a solution of lithium hydroxide (0.68 g, 16.27 mmol) in water (5 mL) followed by THF (5 mL) and methanol (0.3 mL) and stirred for 2 hours at 25° C. Organic solvents were evaporated from the reaction mixture and aqueous layer was acidified by using 1N HCl, extracted with ethyl acetate (3×20 mL), organic layer was washed with brine solution, dried over anhydrous sodium sulfate, and concentrated under reduced pressure to provide [4-(morpholine-1-sulfonyl)-phenyl]-[(tetrahydro-pyran-4-yloxy)]-acetic acid (1.0 g).

$^1$H NMR (400 MHz, DMSO-d$_6$): δ 1.64-1.78 (m, 2H), 1.88-1.99 (m, 2H), 3.00-3.02 (m, 4H) 3.39-3.49 (m, 2H), 3.65-3.72 (m, 1H), 3.75-3.77 (m, 4H), 3.92-4.03 (m, 2H), 5.14 (s, 1H), 7.69 (d, J=8.0 Hz, 2H), 7.77 (d, J=8.0 Hz, 2H). MS (EI) m/z: 386.0 (M+1).

Preparation 12 was prepared in analogous manner of preparation 11.

| Preparation No. | IUPAC Name |
|---|---|
| 12 | [4-(Piperidine-1-sulfonyl)-phenyl]-[(tetrahydro-pyran-4-yloxy)]-acetic acid: |

Preparation 13

2-tetrahydropyran-4-yloxy-2-(4-tetrahydropyran-4-ylsulfonylphenyl) acetic acid

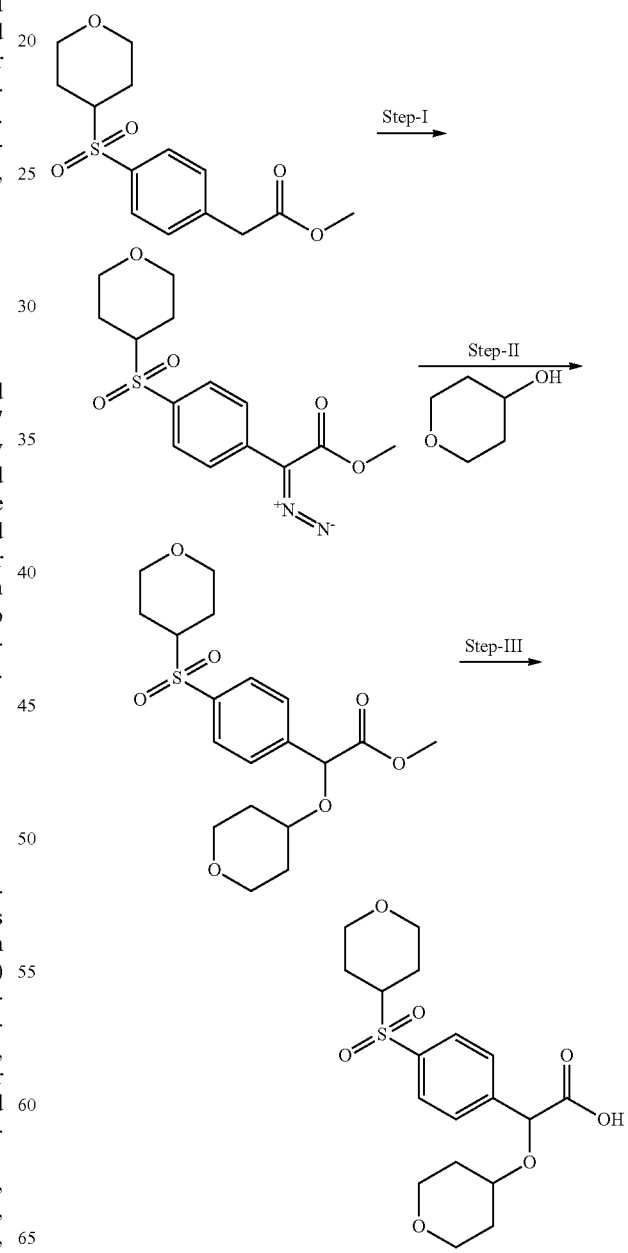

Step I

Methyl 2-diazo-2-(4-tetrahydropyran-4-ylsulfonylphenyl)acetate

Methyl 2-(4-tetrahydropyran-4-ylsulfonylphenyl)acetate (Obtained as per Preparation 1 described in US2010/0310493 A1) (6.0 g, 20.13 mmol) was dissolved in dry acetonitrile (85 mL) under argon atmosphere. To the above solution para toluene sulfonyl azide (3.95 g, 20.13 mmol) was added, followed by DBU (4.5 mL, 30.2 mmol) in dropwise manner, and stirred for 30 min. Reaction mixture was poured in ice cold water (160 mL), solid obtained was filtered through buchner funnel and dried under vaccum which yielded methyl 2-diazo-2-(4-tetrahydropyran-4-ylsulfonylphenyl)acetate (5.5 g).

$^1$H NMR (400 MHz, CDCl$_3$): δ 1.71-1.84 (m, 2H), 1.87-1.95 (m, 2H), 3.08-3.18 (m, 1H), 3.32 (dt, J=12 Hz, 2.2 Hz, 2H), 3.90 (s, 3H), 4.05 (dd, J=11 Hz, 3.6 Hz, 2H), 7.70 (d, J=8.8 Hz, 2H), 7.85 (d, J=8.8 Hz, 2H). MS (EI) m/z: 325.1 (M+1).

Step III

Methyl 2-tetrahydropyran-4-yloxy-2-(4-tetrahydropyran-4-ylsulfonylphenyl)acetate Methyl 2-diazo-2-(4-tetrahydropyran-4-ylsulfonylphenyl)acetate (4.0 g, 12.34 mmol) was dissolved in DCM (40 mL) under argon atmosphere. To this solution, 4-hydroxy tetrahydropyran (1.5 g, 14.8 mmol) was added followed by rhodium (II) acetate dimer (0.109 g, 0.24 mmol). Mixture was stirred at 25° C. for 30 min. Reaction mixture was diluted with DCM (10 mL), organic layer was washed with water followed by brine solution, dried over anhydrous sodium sulfate, filtered and concentrated under reduced pressure to give a crude product as methyl 2-tetrahydropyran-4-yloxy-2-(4-tetrahydropyran-4-ylsulfonylphenyl)acetate (4.1 g).

MS (EI) m/z: 399.2 (M+1).

Step IV

2-tetrahydropyran-4-yloxy-2-(4-tetrahydropyran-4-lsulfonylphenyl) acetic acid To a solution of methyl 2-tetrahydropyran-4-yloxy-2-(4-tetrahydropyran-4-ylsulfonylphenyl)acetate (3.4 g, 8.54 mmol) in THF (30 mL) and methanol (10 mL) was added a solution of lithium hydroxide (1.07 g, 25.62 mmol) in water (10 mL) and stirred for 16 h at 25° C. Organic solvents were evaporated from the reaction mixture and aqueous layer was acidified by using 1N HCl, extracted with ethyl acetate (3×100 mL), organic layer was washed with brine solution, dried over anhydrous sodium sulfate, and concentrated under reduced pressure to provide 2-tetrahydropyran-4-yloxy-2-(4-tetrahydropyran-4-lsulfonylphenyl) acetic acid (2.2 g).

$^1$H NMR (400 MHz, CDCl$_3$): δ 1.62-1.84 (m, 4H), 1.85-2.06 (m, 4H), 3.11-3.21 (m, 1H) 3.33 (t, J=11.5 Hz, 2H), 3.38-3.50 (m, 2H), 3.64-3.72 (m, 1H), 3.91-4.10 (m, 4H), 5.15 (s, 1H), 7.72 (d, J=8.3 Hz, 2H), 7.88 (d, J=7.8 Hz, 2H). MS (EI) m/z: 385.0 (M+1).

Preparation 14

2-(6-cyclopentylsulfonyl-3-pyridyl)-2-tetrahydropyran-4-yloxy-acetic acid

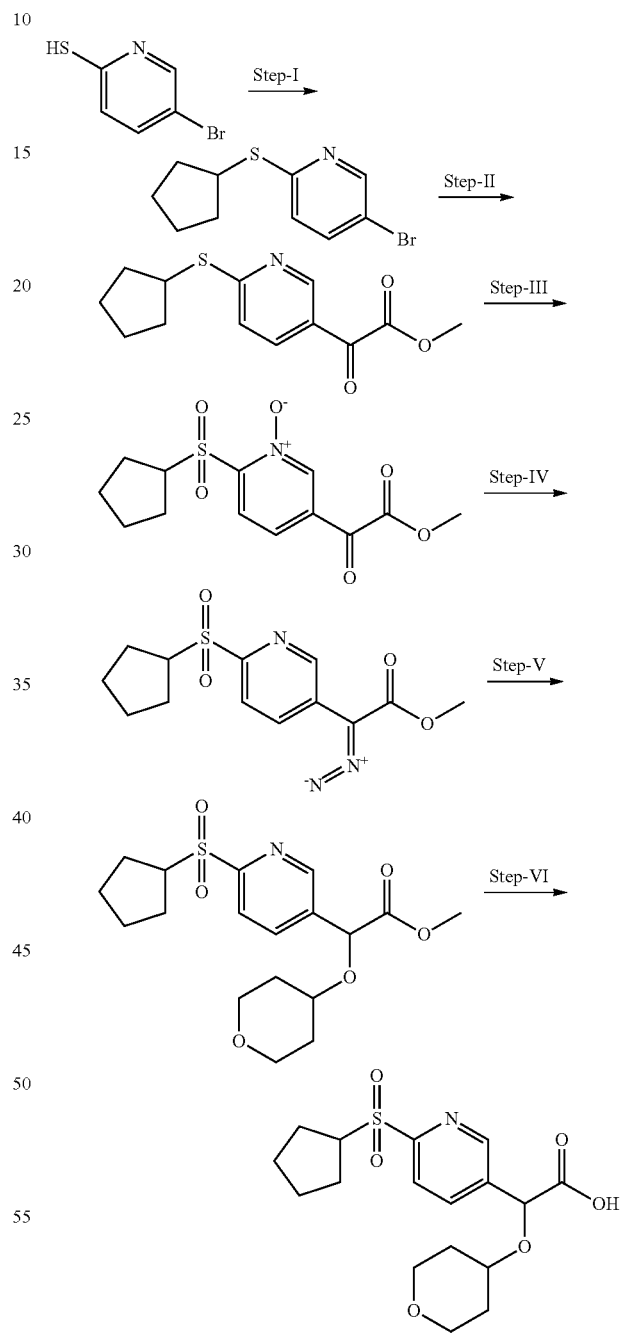

Step-I

5-bromo-2-cyclopentylsulfanyl-pyridine 5-bromopyridine-2-thiol (0.5 g, 3.44 mmol) was dissolved in anhydrous DMSO (10 mL). CS$_2$CO$_3$ (2.23 g, 6.89 mmol)

was added and stirred for 5 minutes followed by addition of bromocyclopentane (0.73 mL, 6.89 mmol). The reaction mixture was stirred for 30 min. at room temperature. The reaction mixture was poured on ice cold water (25 mL) and extracted with MTBE (2×25 mL) washed with water and brine dried over anhydrous sodium sulfate, filtered and concentrated to obtain a crude product which was purified by column chromatography over silica gel using 2-5% ethyl acetate in hexanes as eluent to provide 5-bromo-2-cyclopentylsulfanyl-pyridine (0.7 g).

$^{1}$HNMR (CDCl$_3$, 400 MHz):—δ 1.55-1.65 (m, 4H), 1.68-1.76 (m, 2H), 2.12-2.60 (m, 2H), 3.93-3.99 (m, 1H), 7.09 (d, J=8.6 Hz, 1H), 7.42 (dd, J=2.2, 8.6 Hz, 1H), 8.36 (d, J=2.2 Hz, 1H). MS (EI) m/z: 258.0 [M($^{79}$Br)+1], 260 [M($^{81}$Br)+1].

Step-II

Methyl 2-(6-cyclopentylsulfanyl-3-pyridyl)-2-oxo-acetate

Under anhydrous condition n-BuLi (1.6 M solution in hexane, 5.08 mL, 8.13 mmol) was added to stirred solution of 5-bromo-2-cyclopentylsulfanyl-pyridine (2.0 g, 8.13 mmol) in 15 mL dry diethyl ether at −78° C. and stirred for 20 minutes. A solution of dimethyl oxalate (1.09 g, 9.30 mmol) in 15 mL of dry diethyl ether was added dropwise with the help of syringe and resulted reaction mixture was allowed to warm slowly to 0° C. within 1 hr. Reaction mixture was poured on aq. saturated solution of NH$_4$Cl (25 mL), mixture was then extracted with (3×50 mL) diethyl ether; organic layer was washed with brine, dried over anhydrous sodium sulfate, sodium sulfate was filtered and washed with diethyl ether and solvent was removed under reduced pressure. The crude material was purified by silica-gel column chromatography (3 to 5% ethyl acetate in hexane) to afford pure compound (0.5 g).

$^{1}$HNMR (CDCl$_3$, 400 MHz):—δ 1.62-1.72 (m, 4H), 1.75-1.87 (m, 2H), 2.20-2.26 (m, 2H), 3.98 (s, 3H), 4.11-4.14 (m, 1H), 7.24 (d, J=8.8 Hz, 1H), 8.08 (dd, J=2.2, 8.8 Hz, 1H), 9.05 (d, J=2.2 Hz, 1H). MS (EI) m/z: 266.2 (M+1)

Step-III

Methyl 2-(6-cyclopentylsulfonyl-1-oxido-pyridin-1-ium-3-yl)-2-oxo-acetate

Methyl 2-(6-cyclopentylsulfanyl-3-pyridyl)-2-oxo-acetate (0.5 g, 1.88 mmol) was taken in dichloromethane (20 mL) at 0° C. mCPBA (1.00 g, 3.77 mmol) was added portion wise and stirred for 3 hrs at room temperature. Reaction mixture was diluted with dichloromethane (20 mL), solid was filtered, filtrate was washed with saturated solution of sodium thiosulphate (150 mL), organic layer was washed with saturated solution of sodium bicarbonate, water and brine (25 mL each), dried over anhydrous sodium sulfate, filtered and concentrated to afford crude methyl 2-(6-cyclopentylsulfonyl-1-oxido-pyridin-1-ium-3-yl)-2-oxo-acetate (0.6 g).

MS (EI) m/z: 314.2 (M+1)

Step-IV

Methyl 2-(6-cyclopentylsulfonyl-3-pyridyl)-2-diazo-acetate

To a mixture of methyl 2-(6-cyclopentylsulfonyl-1-oxido-pyridin-1-ium-3-yl)-2-oxo-acetate (0.6 g, 2.02 mmol) and para-tolune sulfonyl hydrazide (0.37 g, 2.02 mmol) in toluene (20 mL) and refluxed using Dean-Stark apparatus 12 hrs. Reaction mixture was cooled to rt and concentrated under reduced pressure. The crude material was purified by silica-gel column chromatography (15 to 20% ethyl acetate in hexane) to afford pure compound (0.25 g).

$^{1}$HNMR (CDCl$_3$, 400 MHz):—δ 1.62-1.75 (m, 2H), 1.78-1.84 (m, 2H), 1.85-1.95 (m, 2H), 2.06-2.13 (m, 2H), 3.92 (s, 3H), 3.99-4.03 (m, 1H), 8.05 (dd, J=0.7 Hz, 2.2 Hz, 1H), 8.10 (dd, J=2.2, 8.3 Hz, 1H), 8.83 (dd, J=0.7, 8.3 Hz, 1H). MS (EI) m/z: 310.1 (M+1)

Step-V

Methyl 2-(6-cyclopentylsulfonyl-3-pyridyl)-2-tetrahydropyran-4-yloxy-acetate

Methyl 2-(6-cyclopentylsulfonyl-3-pyridyl)-2-diazo-acetate (0.25 g, 0.80 mmol) was dissolved in DCM (5 mL) under argon atmosphere. To this solution, 4-hydroxy tetrahydropyran (0.11 mL, 1.21 mmol) was added followed by rhodium (II) acetate dimer (9 mg, 0.021 mmol). Mixture was stirred at 25° C. for 60 min. Reaction mixture was diluted with DCM (10 mL), organic layer was washed with water followed by brine solution, dried over anhydrous sodium sulfate, filtered and concentrated under reduced pressure to give a crude product (280 mg).

MS (EI) m/z: 384.1 (M+1).

Step-VI 2-(6-cyclopentylsulfonyl-3-pyridyl)-2-tetrahydropyran-4-yloxy-acetic acid To methyl 2-(6-cyclopentylsulfonyl-3-pyridyl)-2-tetrahydropyran-4-yloxy-acetate (0.25 g, 0.65 mmol) was added a solution of lithium hydroxide (0.082 g, 1.95 mmol) in water (3 mL) followed by THF (3 mL) and methanol (0.1 mL) and stirred for 12 hours at 25° C. Organic solvents were evaporated from the reaction mixture and aqueous layer was acidified 1N HCl, extracted with ethyl acetate (3×20 mL), organic layer was washed with brine solution, dried over anhydrous sodium sulfate, and washed concentrated under reduced pressure to provide (4-cyclopropanesulfonyl-phenyl)-[(tetrahydro-pyran-4-yloxy)]-acetic acid (0.21 g)

MS (EI) m/z: 370.1 (M+1).

Intermediates 15-19 were either obtained from commercial source or prepared as per literature method.

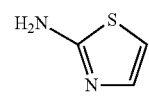

15-1

Commercial Source

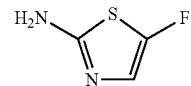

15-2

Commercial Source 15-3
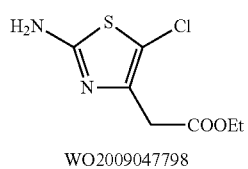
WO2009047798
15-4
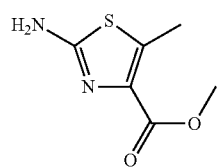
Commercial Source
16-1
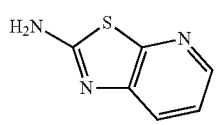
J. Het. Chem. 1977, 14, 129
16-2
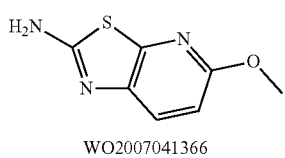
WO2007041366
16-3
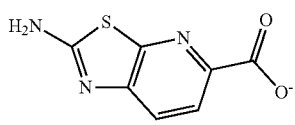
16-4
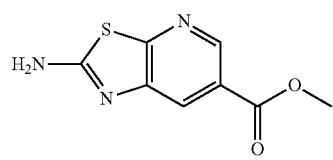
16-5
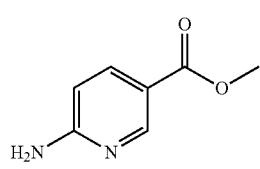
Commercial Source
17-1
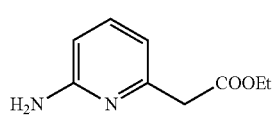
Commercial Source
17-2
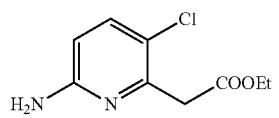
US 2003/0158218 A1
17-3
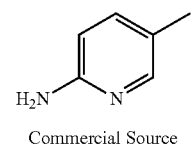
US 2003/0158218 A1
17-4
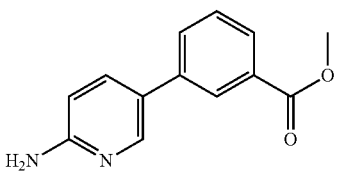
Commercial Source
17-5
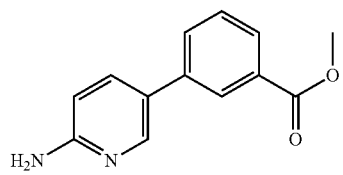
Commercial Source
17-6
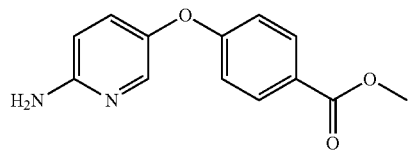
J. Med. Chem. 2007, 50(8), 4464
17-7
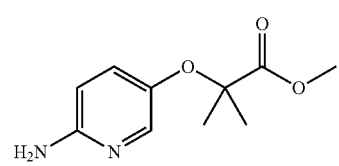
J. Med Chem. 2007, 50(4), 685-695
18-1
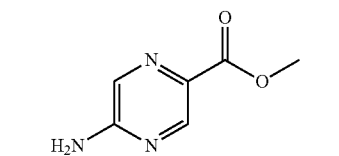
Commercial Source
18-2
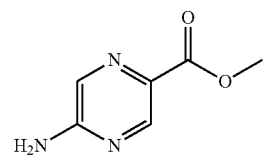
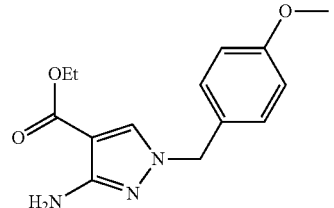
US20020133008 A1
19
Aq. NH₄OH

Preparation 20

Ethyl 3-(2-aminothiazol-5-yl)oxybenzoate

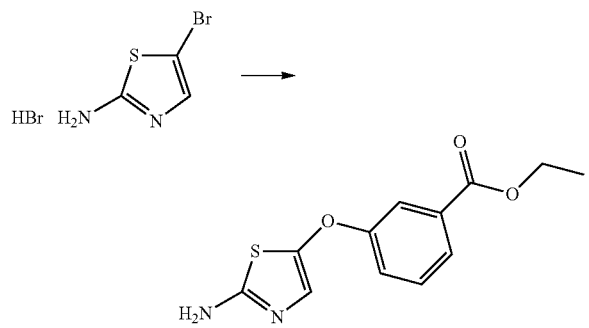

A 1 L round bottom flask was charged with sodium hydride (8.6 g, 215 mmol, washed with dry hexanes to remove the oil) in dry THF and maintained under inert atmosphere at 0° C. To above suspension the solution of ethyl 3-hydroxy benzoate (32.45 g, 195 mmol) in dry THF (400 mL) was added in a dropwise manner. After complete addition reaction was continued to stir for additional half an hour at 25° C. followed by addition of 2-amino-5-bromothiazole (34.9 g, 195 mmol) in dry THF (300 mL). After complete addition the reaction mixture was stirred for 3 hours at 25° C. and completion of reaction was confirmed by TLC. The reaction was quenched with water (500 mL) and extracted with ethyl acetate (3×500 mL). The combined organic layer was washed with brine and dried over anhydrous sodium sulphate (50 g). The solvent was removed under reduced pressure and the residue was purified by column chromatography using 10-30% ethyl acetate in hexane. Removal of solvent from appropriate fractions under reduced pressure using rotavapour gave pure product.

$^1$H NMR (400 MHz, CDCl$_3$): δ 1.38 (t, J=7.1 Hz, 3H), 4.37 (q, J=7.1 Hz, 2H), 4.77 (bs, 2H), 6.79 (s, 1H), 7.28 (dd, J=8.1, 1.2 Hz, 1H), 7.37 (t, J=8.1 Hz, 1H), 7.73 (d, J=1.4 Hz, 1H), 7.78 (d, J=7.8 Hz, 1H); MS (EI) m/z: 265.0 (M+1).

Preparation 21

4-(2-Amino-thiazol-5-yloxy)-3-fluoro-benzoic acid ethyl ester

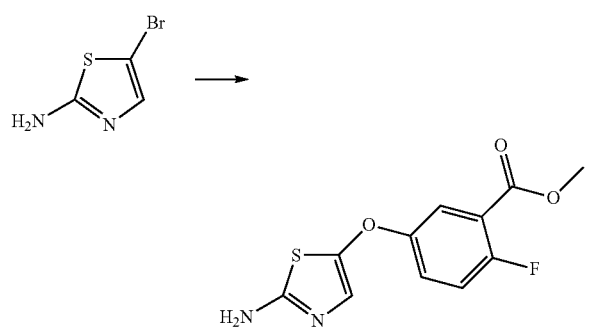

To a solution of sodium hydride (1.7 g, 44.11 mmol) in tetrahydrofuran (50 mL) was added solution of 2-fluoro-5-hydroxy benzoic acid methyl ester (5 g, 29.41 mmol) in tetrahydrofuran (50 mL) under argon atmosphere and stirred for 15 minutes. A solution of 2-amino-5-bromothiazole (5.2 g, 29.41 mmol) in tetrahydrofuran (47 mL) was added dropwise over a period of 30 min and stirred at room temperature for 4 hrs. Reaction mixture was poured into ice cold water (300 mL) extracted with ethyl acetate (3×200 mL), combined organic layers were washed with brine and dried over anhydrous sodium sulfate, filtered and concentrated under reduced pressure. Crude compound was purified by silica gel column chromatography using 40% ethyl acetate in hexane as eluent to afford pure 5-[(2-amino-5H-thiazol-5-yl)oxy]-2-fluorobenzoic acid methyl ester. (2.5 g).

$^1$H NMR (400 MHz, CDCl$_3$): δ 3.84 (s, 3H), 6.79 (s, 1H), 6.95 (br. s, 2H), 7.36-7.47 (aromatics, 3H). MS (EI) m/z: 269.1 (M+1).

Preparation 22 tert-Butyl 3-[(6-amino-3-pyridyl)oxy]benzoate

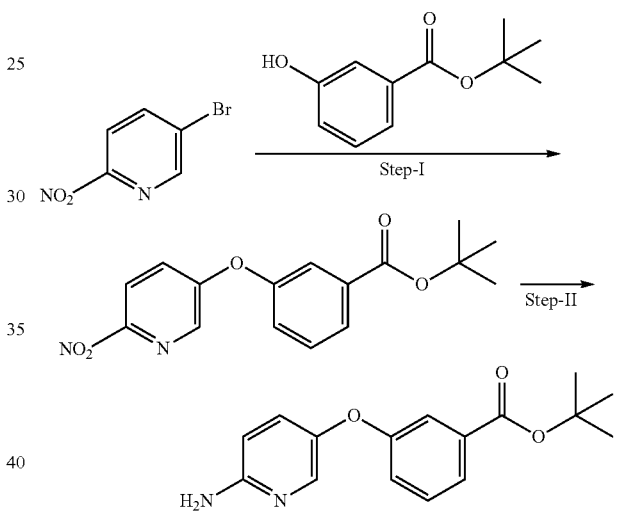

Step-I tert-butyl 3-[(6-nitro-3-pyridyl)oxy]benzoate

A solution of tert-butyl 3-hydroxybenzoate (1.14 g, 5.91 mmol), and cesium carbonate (3.85 g, 11.82 mmol) in DMF (10 mL) was stirred for 20 min. A solution of 5-bromo-2-nitro-pyridine (1.0 g, 4.92 mmol) in DMF (10 mL) was added slowly and reaction mixture was stirred at room temperature for 1 h. Completion of reaction was confirmed by TLC. Reaction mixture was poured in water (100 mL), extracted with ethylacetate (3×50 mL), washed with brine solution, dried over anhydrous sodium sulfate, filtered and concentrated under reduced pressure. Crude compound was purified by silica gel column chromatography using 2-10% ethyl acetate in hexane to get pure product (1.1 g).

$^1$H NMR (400 MHz, CDCl$_3$): δ 1.58 (s, 9H), 7.26-7.3 (ddd, J=1.2, 2.4, 8.4 Hz, 1H), 7.4-7.43 (dd, J=2.8, 8.8 Hz, 1H), 7.53 (t, J=8.0 Hz, 1H), 7.72 (t, J=2.0 Hz, 1H), 7.92-7.94 (dt, J=1.2, 8.0 Hz, 1H), 8.6 (d, J=8.8 Hz, 1H), 8.34 (d, J=3.2 Hz, 1H).

MS (EI) m/z: 317.1 (M+1).

Step II tert-butyl 3-[(6-amino-3-pyridyl)oxy]benzoate

To a solution of tert-butyl 3-[(6-nitro-3-pyridyl)oxy]benzoate (1.0 g, 3.161 mmol), in ethyl acetate (20 mL) was added 10% Pd on carbon (0.2 g, 20% w/w), and reaction mixture was stirred under H$_2$ gas balloon for 6 h. Completion of reaction was confirmed by TLC. Reaction mixture was filtered through celite pad washed with ethyl acetate, filtrate was concentrated under reduced pressure to afford pure product (0.9 g).

$^1$H NMR (400 MHz, CDCl$_3$): δ 1.57 (s, 9H), 4.39 (s, 2H), 6.53 (d, J=8.8 Hz, 1H), 7.07-7.1 (ddd, J=0.8, 2.4, 8.0 Hz, 1H), 7.18-7.21 (dd, J=3.2, 8.8 Hz, 1H), 7.33 (t, J=8.0 Hz, 1H), 7.53 (t, J=2.8 Hz, 1H), 7.65-7.67 (dd, J=1.2, 8.0 Hz, 1H), 7.91 (d, J=2.8 Hz, 1H); MS (EI) m/z: 287.2 (M+1).

Preparations 23 to 39 were prepared in analogous manner of preparation 20 to 22.

| Prep. No. | IUPAC Name |
|---|---|
| 23 | Ethyl 2-(2-aminothiazol-5-yl)oxybenzoate |
| 24 | Methyl 4-(2-aminothiazol-5-yl)oxy-2-methoxy-benzoate |
| 25 | Methyl 4-(2-aminothiazol-5-yl)oxy-2-methyl-benzoate |
| 26 | Methyl 5-(2-aminothiazol-5-yl)oxy-2-methyl-benzoate |
| 27 | Methyl 4-(2-aminothiazol-5-yl)oxy-2-chloro-benzoate |
| 28 | Methyl 5-(2-aminothiazol-5-yl)oxy-2-chloro-benzoate |
| 29 | Methyl 5-(2-aminothiazol-5-yl)oxy-2-fluoro-benzoate |
| 30 | Methyl 3-(2-aminothiazol-5-yl)oxy-5-isopropoxy-benzoate |
| 31 | Ethyl 3-(2-aminothiazol-5-yl)oxybenzoate |
| 32 | Ethyl 3-[(5-amino-1,3,4-thiadiazol-2-yl)oxy]benzoate |
| 33 | Methyl 4-(2-amino-4-methyl-thiazol-5-yl)oxy-2-methyl-benzoate |
| 34 | Methyl 4-(2-aminothiazol-5-yl)oxypyridine-2-carboxylate |
| 35 | Methyl 5-(2-aminothiazol-5-yl)oxypyridine-3-carboxylate |
| 36 | tert-Butyl 4-[(6-amino-3-pyridyl)oxy]-2-methyl-benzoate |
| 37 | 3-(2-Amino-6-methyl-pyrimidin-4-yl)oxybenzoic acid |
| 38 | Methyl 2-amino-5-(4-fluorophenoxy)thiazole-4-carboxylate |

Preparation 39 tert-butyl 6-(3-aminopyrazol-1-yl)pyridine-3-carboxylate

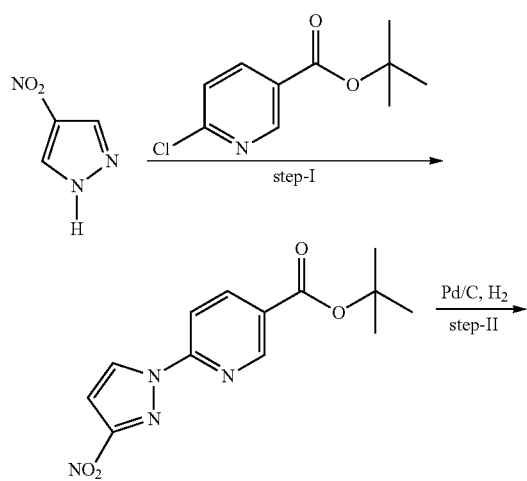

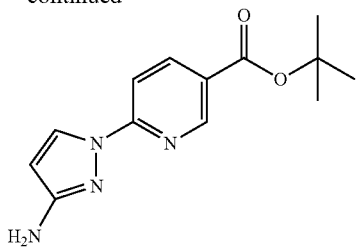

Step-I tert-butyl 6-(3-nitropyrazol-1-yl)pyridine-3-carboxylate

A mixture of 3-Nitro-1H-pyrazole (0.265 gm, 2.34 mmol), tert-butyl 6-chloropyridine-3-carboxylate (0.500 gm, 2.34 mmol) was dissolved in anhydrous DMF (10 mL). Cesium carbonate (1.90 gm, 5.86 mmol) was added and reaction mixture was heated at 100° C. for 6 h. The reaction mixture was cooled to room temperature and poured into ice water, a white precipitate formed was filtered and dried under vacuum to give tert-butyl 6-(3-nitropyrazol-1-yl)pyridine-3-carboxylate (0.505 gm).

$^1$H NMR (400 MHz, CDCl$_3$): δ 1.63 (s, 9H), 7.11 (d, J=2.7 Hz, 1H), 8.14 (d, J=8.6 Hz, 1H), 8.43 (dd, J=8.6, 2.2 Hz, 1H), 8.71 (d, J=2.7 Hz, 1H), 9.02 (d, J=2.0 Hz, 1H).

MS (EI) m/z: 291.1 (M+1).

Step-II tert-butyl 6-(3-aminopyrazol-1-yl)pyridine-3-carboxylate

To a solution of tert-butyl 6-(3-nitropyrazol-1-yl)pyridine-3-carboxylate (0.505 gm, 1.74 mmol) in ethyl acetate (15 mL), 10% Pd/C (0.100 g, 20% w/w) was added under argon atmosphere. Argon gas was removed under vacuum and reaction flask was filled with hydrogen gas at 40 psi pressure. Reaction mixture was stirred for 1 hr on parr-apparatus. Reaction mixture was filtered through celite pad and concentrated under reduced pressure to give tert-butyl 6-(3-aminopyrazol-1-yl)pyridine-3-carboxylate (0.450 gm.)

$^1$H NMR (400 MHz, CDCl$_3$): δ 1.56 (s, 9H), 5.50 (br. s, 2H), 7.74 (d, J=8.6 Hz, 1H), 8.32 (dd, J=8.6, 2.0 Hz, 1H), 8.46 (d, J=2.7 Hz, 1H), 8.59 (d, J=2.7 Hz, 1H), 8.83 (d, J=2.0 Hz, 1H).

MS (EI) m/z: 261.1 (M+1)

Preparation 40

5-Pyrazol-1-yl-thiazol-2-ylamine

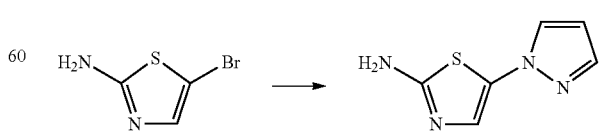

A solution of 2-amino-5-bromothiazole (2.6 g, 14.68 mmol), pyrazole (1 g, 14.68 mmol) and cesium carbonate (11.92 g, 36.7 mmol) in DMF (29 mL) was heated at 55° C.

for 1 hr under argon argon atmosphere. After 1 hr, 2-amino-5-bromothiazole (2.6 g, 14.68 mmol) was added and continued for next 1 hr. Reaction mixture was cooled to rt and poured over ice cold water (200 mL), extracted with ethylacetate (4×100 mL), washed with brine solution, dried over anhydrous sodium sulfate, filtered and concentrated under reduced pressure. Crude compound was purified by silica gel column chromatography using 60% ethyl acetate in hexane as eluent to afford pure 5-pyrazol-1-yl-5H-thiazol-2-amine (0.2 g).

$^1$H NMR (400 MHz, DMSO-d6): δ6.44 (t, J=1.9 Hz, 1H), 7.08 (br. s, 2H), 7.17 (s, 1H), 7.62 (d, J=1.2 Hz, 1H), 8.15 (d, J=2.2 Hz, 1H). MS (EI) m/z: 167.1 (M+1).

Preparation 41 was prepared in analogous manner of preparation 40.

| Preparation No. | IUPAC Name |
| --- | --- |
| 41 | Ethyl 1-(2-aminothiazol-5-yl)pyrazole-4-carboxylate |

Preparation 42

5-Vinyl-thiazol-2-ylamine

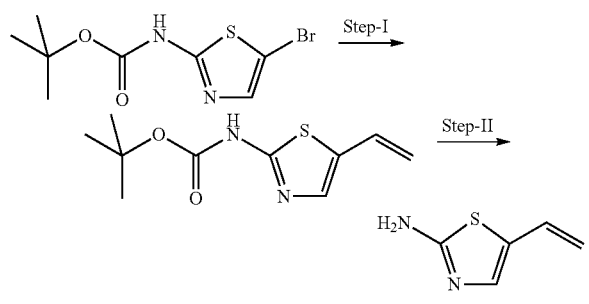

Step I

(5-Vinyl-thiazol-2-yl)-carbamic acid tert-butyl ester (5-Bromo-thiazol-2-yl)-carbamic acid tert-butyl ester (0.200 g, 0.71 mmol), tetrakis(triphenylphospine)palladium (0.042 g, 0.036 mmol), lithium chloride (0.91 g, 2.14 mmol), and tributyl (vinyl)stannate (0.68 g, 2.14 mmol) were taken in 8 mL of THF and 8 mL of DMF and reflux for 2 hrs. After completion of reaction THF was removed under reduced pressure on ratavapour and the residue was partioned between ethyl acetate (20 mL) and water (20 mL). The layers were separated. Aq. Layer was extracted with ethyl acetate (2×20 mL). The combined organic layer was washed with brine and dried over anhydrous sodium sulfate filtered and concentrated under reduced pressure to get the crude product which was purified by preparative TLC to get the pure product (5-Vinyl-thiazol-2-yl)-carbamic acid tert-butyl ester (0.137 g).

$^1$H NMR—(CDCl$_3$, 400 MHz): δ 1.57 (s, 9H), 5.12 (d, J=10.8 Hz, 1H), 5.41 (d, J=17.2 Hz, 1H), 6.71 (dd, J=17.6, 11 Hz, 1H), 7.19 (s, 1H), 11.55 (bs, 1H).

MS (EI) m/z: 227.1 (M+1).

Step II

5-Vinyl-thiazol-2-ylamine (5-Vinyl-thiazol-2-yl)-carbamic acid tert-butyl ester (0.130 g, 0.574 mmol) was taken in 15 mL of DCM, to it trifluoroacetic acid (1 mL, 13.46 mmol) was added and the reaction was stirred for room temperature for over night. Solvent was removed under reduced pressure and the residue was partioned between aq. saturated NaHCO$_3$ (20 mL) and ethyl acetate (20 mL). The layers were separated. Aq. layer was extracted with ethyl acetate (2×20 mL). The combined organic layer was washed with brine and dried over anhydrous sodium sulfate filtered and concentrated under reduced pressure to get the 5-Vinyl-thiazol-2-ylamine (0.054 g).

$^1$H NMR—(CDCl$_3$, 400 MHz): δ 4.98 (bs, 2H), 5.02 (d, J=11 Hz, 1H), 5.16 (d, J=17.4 Hz, 1H), 6.65 (dd, J=16.8 & 10.8 Hz, 1H), 6.95 (s, 1H).

Preparation 43 was prepared in analogous manner of preparation 42.

| Prep. No. | IUPAC Name |
| --- | --- |
| 43 | 4-Vinyl-thiazol-2-ylamine |

Preparation 44

2-(2-Amino-5-chloro-thiazol-4-yl)-2-methyl-propionic acid ethyl ester

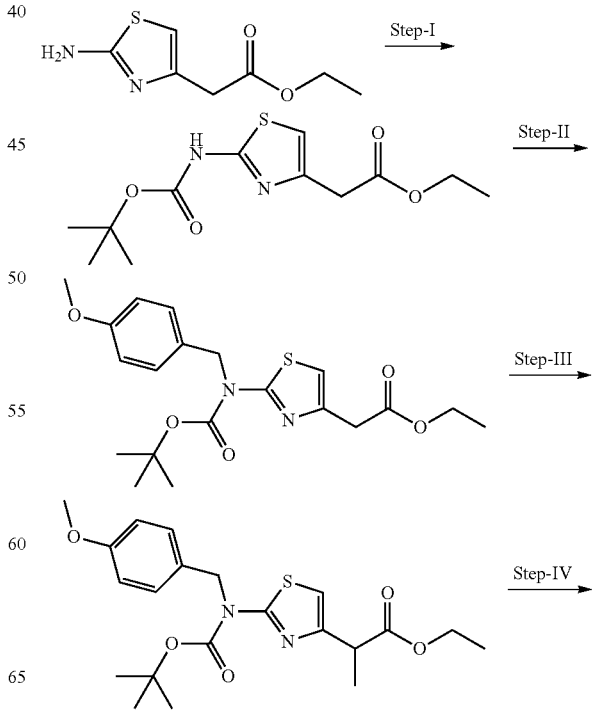

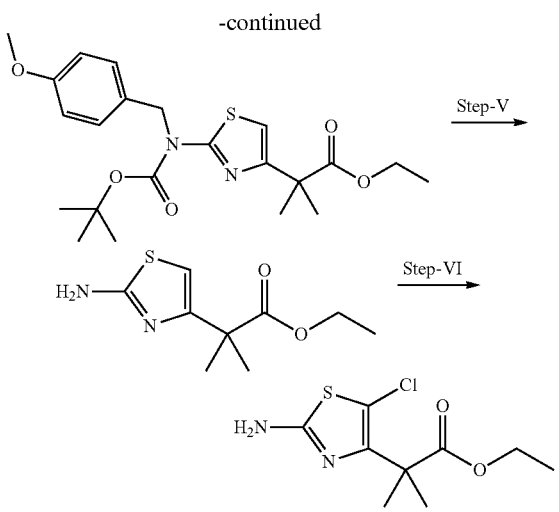

Step I

(2-tert-Butoxycarbonylamino-thiazol-4-yl)-acetic acid ethyl ester

A mixture of (2-Amino-thiazol-4-yl)-acetic acid ethyl ester (5 g, 26.85 mmol) and di-tert-butoxydicarbonate (8.2 g, 37.59 mmol) was heated at 80° C. in toluene for 24 hrs. Toluene was removed under vacuo and the residue was partitioned between water (100 mL) and ethyl acetate (100 mL). The layers were separated and the aqueous layer was extracted with ethyl acetate (2×50 mL). The combined organic layer was washed with brine and dried over anhydrous sodium sulphate and the solvent was removed in vacuo to get the oily product (7.5 g).
$^1$H NMR (CDCl$_3$, 400 MHz):—δ 1.22 (t, J=7.2 Hz, 3H), 1.55 (s, 9H), 3.73 (s, 2H), 4.17 (q, J=7.2 Hz, 2H), 6.75 (s, 1H), 9.6 (br. s, 1H). MS (EI) m/z: 287.1 (M+1).

Step II

{2-[tert-Butoxycarbonyl-(4-methoxy-benzyl)-amino]-thiazol-4-yl}-acetic acid ethyl ester To a solution of (2-tert-Butoxycarbonylamino-thiazol-4-yl)-acetic acid ethyl ester (7.5 g, 26.11 mmol) in 100 mL of dry dichloromethane was added DBU (11.96 g, 78.56 mmol) followed by para-methoxybenzyl chloride (6.15 g, 39.28 mmol) and the reaction mixture was stirred for 18 hrs at room temperature. The reaction was quenched with water and the layers were separated. The organic layer was washed with brine and dried over anhydrous sodium sulphate and the solvent was removed in vacuo. The residue was purified by column chromatography (silica gel 60-120 mesh and 2-10% ethyl acetate in hexanes as eluent) to get the pure compound (8.0 g).
$^1$H NMR (CDCl$_3$, 400 MHz):—δ 1.26 (t, J=7.2 Hz, 3H), 1.52 (s, 9H), 3.69 (s, 2H), 3.78 (s, 3H), 4.18 (q, J=7.6 Hz, 2H), 5.23 (s, 2H), 6.75 (s, 1H), 6.81 (d, J=7.2 Hz, 2H), 7.34 (d, J=7.2 Hz, 2H). MS (EI) m/z: 407.2 (M+1).

Step III

2-{2-[tert-Butoxycarbonyl-(4-methoxy-benzyl)-amino]-thiazol-4-yl}-propionic acid ethyl ester To a solution of lithium diisopropylamide (prepared in situ) (4.24 g, 39.6 mmol) in dry THF (40 mL) was added the solution of {2-[tert-butoxycarbonyl-(4-methoxy-benzyl)-amino]-thiazol-4-yl}-acetic acid ethyl ester (8.0 g, 19.68 mmol) in 20 mL of dry THF in a dropwise fashion at −78° C. The reaction mixture was continued to stir at −78° C. for 1 hour followed by the addition of methyl iodide (4.19 g, 29.52 mmol) at the same temperature. The reaction mixture was kept on stirring and slowly allowed to come to room temperature. The reaction mixture was quenched with saturated ammonium chloride solution and diluted with ethyl acetate. The aqueous layer was extracted with ethyl acetate (2×50 mL). The combined organic layer was washed with brine and dried over anhydrous sodium sulphate and the solvent was removed in vacuo to get the sticky compound (8.2 g). The compound was used for the next reaction without any purification.
$^1$H NMR (CDCl$_3$, 400 MHz):—δ 1.22 (t, J=7.2 Hz, 3H), 1.45-1.65 (m, 12H), 3.78 (s, 3H), 3.83 (q, J=7.6 Hz, 1H), 4.15 (q, J=7.6 Hz, 2H), 5.21 (s, 2H), 6.68 (s, 1H), 6.80 (d, J=8.4 Hz, 2H), 7.36 (d, J=8.0 Hz, 2H). MS (EI) m/z: 421.3 (M+1).

Step IV

2-{2-[tert-Butoxycarbonyl-(4-methoxy-benzyl)-amino]-thiazol-4-yl}-2-methyl-propionic acid ethyl ester The reaction was done by the same way as mentioned in the step III. The crude product was purified by column chromatography (Silica gel 60-120 mesh, and 2-4% ethyl acetate in hexanes as eluent) to afford pure solid compound.
$^1$HNMR (CDCl$_3$, 400 MHz):—δ 1.15 (t, J=7.2 Hz, 3H), 1.51-1.59 (m, 15H), 3.77 (s, 3H), 4.09 (q, J=7.2 Hz, 2H), 5.19 (s, 2H), 6.63 (s, 1H), 6.80 (d, J=8.4 Hz, 2H), 7.36 (d, J=8.4 Hz, 2H). MS (EI) m/z: 435.3 (M+1).

Step V

2-(2-Amino-thiazol-4-yl)-2-methyl-propionic acid ethyl ester

2-{2-[tert-Butoxycarbonyl-(4-methoxy-benzyl)-amino]-thiazol-4-yl}-2-methyl-propionic acid ethyl ester (1.5 g, 3.45 mmol) was refluxed in 15 mL of trifluoroacetic acid for 18 hrs. Trifluoroacetic acid was removed in vacuo and the residue was partitioned between water (50 mL) and ethyl acetate (50 mL). The layers were separated and the aqueous layer was extracted with ethyl acetate (2×50 mL). The combined organic layer was washed with brine and dried over anhydrous sodium sulphate and the solvent was removed in vacuo to get the solid product (0.7 g).
$^1$H NMR (CDCl$_3$, 400 MHz):—δ 1.21 (t, J=7.2 Hz, 3H), 1.52 (s, 6H), 4.14 (q, J=7.2 Hz, 2H), 6.25 (s, 1H). MS (EI) m/z: 215.1 (M+1).

Step VI

2-(2-Amino-5-chloro-thiazol-4-yl)-2-methyl-propionic acid ethyl ester 2-(2-Amino-thiazol-4-yl)-2-methyl-propionic acid ethyl ester (0.3 g, 1.40 mmol) was taken in 10 mL of acetonitrile and N-Chlorosuccinamide (0.224 g, 1.68 mmol) was added the reaction was stirred for 1 hr. at room temperature. After completion of reaction acetonitrile was evaporated under reduced pressure and the residue was partitioned between water (25 mL) and ethyl acetate (25 mL). The layers were separated and the aqueous layer was extracted with ethyl acetate (2×25 mL). The combined organic layer was washed with brine and dried over anhydrous sodium sulphate and the solvent was removed in vacuo. The residue was purified by preparative TLC plate (mobile phase 40% ethyl acetate in hexane) to afford pure compound (0.3 g).

¹HNMR (CDCl₃, 400 MHz):—δ 1.25 (t, J=7.2 Hz, 3H), 1.55 (s, 6H), 4.18 (q, J=7.2 Hz, 2H), 4.82 (br. s, 2H). MS (EI) m/z: 249.1 (M+1).

Preparation 45

2-(2-Amino-5-fluoro-thiazol-4-yl)-2-methyl-propionic acid ethyl ester

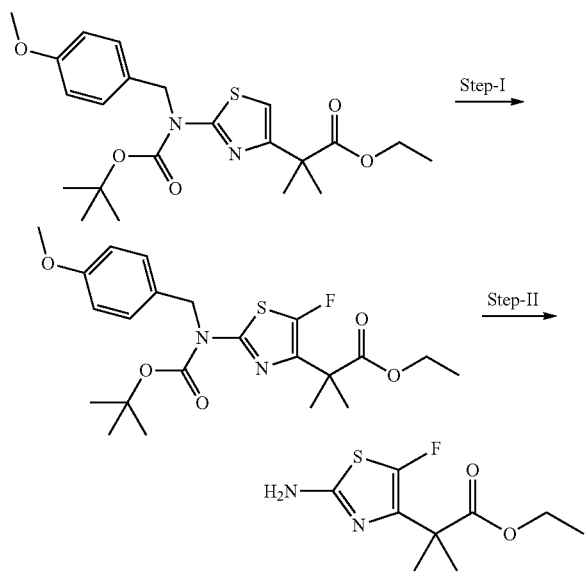

Step I

2-{2-[tert-Butoxycarbonyl-(4-methoxy-benzyl)-amino]-5-fluoro-thiazol-4-yl}-2-methyl-propionic acid ethyl ester Under anhydrous condition n-BuLi (3.6 M solution in hexane, 2.55 mL, 9.20 mmol) was added to stirred solution of N,N-Diisopropyl amine (1.29 mL, 9.20 mmol) in 10 mL dry THF at −78° C. and reaction mixture was stirred for 1 hr. A solution of 2-{2-[tert-Butoxycarbonyl-(4-methoxy-benzyl)-amino]-thiazol-4-yl}-2-methyl-propionic acid ethyl ester (synthesized as per preparation 44; 2.0 g, 4.60 mmol) in 10 mL of dry THF was added dropwise to above reaction mixture and continued to stir for an additional 1 hr at −78° C. N-Fluorobenzenesulfonimide (2.17 g, 6.90 mmol) dissolved in 10 mL dry THF was added to reaction mixture dropwise and resulted reaction mixture was allowed to warm 0° C. within 3 hrs. Reaction mixture was poured on aq. saturated solution of NH₄Cl (50 mL), mixture was then extracted with (3×50 mL) ethyl acetate; organic layer was washed with brine, dried over anhydrous sodium sulfate, filtered and washed with ethyl acetate and solvent was removed under reduced pressure. The crude material was purified by silica-gel column chromatography (4% ethyl acetate in hexane) to afford pure compound (0.5 g).

¹H NMR (CDCl₃, 400 MHz):—δ 1.19 (t, J=7.3 Hz, 3H), 1.52 (s, 9H), 1.57-1.60 (m, 6H), 3.78 (s, 3H), 4.12 (q, J=7.3 Hz, 2H), 5.08 (s, 2H), 6.81 (d, J=8.3 Hz, 2H), 7.33 (d, J=7.8 Hz, 2H). MS (EI) m/z: 453.3 (M+1).

Step II 2-(2-Amino-5-fluoro-thiazol-4-yl)-2-methyl-propionic acid ethyl ester

The reaction was done by the same way as mentioned in the preparation 45, step-V using 2-{2-[tert-Butoxycarbonyl-(4-methoxy-benzyl)-amino]-5-fluoro-thiazol-4-yl}-2-methyl-propionic acid ethyl ester (0.5 g, 1.1 mmol) and TFA (5 mL) to afford 2-(2-Amino-5-fluoro-thiazol-4-yl)-2-methyl-propionic acid ethyl ester (0.25 g).

¹H NMR (CDCl₃, 400 MHz):—δ 1.23 (t, J=7.3 Hz, 3H), 1.53-1.54 (m, 6H), 4.16 (q, J=6.9 Hz, 2H). MS (EI) m/z: 233.1 (M+1).

Preparation 46

Ethyl 2-[4-(2-aminothiazol-5-yl)oxyphenyl]-2-methyl-propanoate

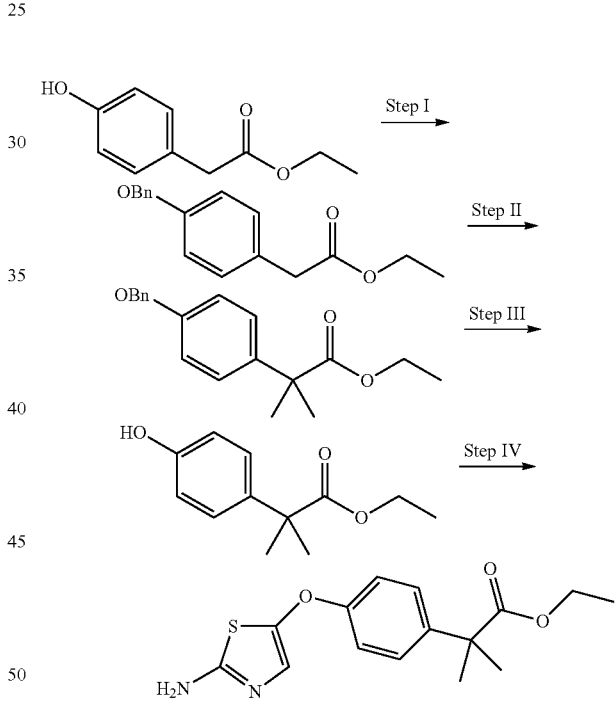

Step I

Ethyl 2-(4-benzyloxyphenyl)acetate

A solution of ethyl-4-hydroxy phenyl acetate (10 g, 55.49 mmol) in 50 mL of dry acetonitrile was added in a drop wise manner to a suspension of cesium carbonate (36 g, 110.98 mmol) in 50 mL of dry acetonitrile. Reaction mixture was allowed to stir at rt for 10 min then benzyl bromide (7.25 mL, 61.03 mmol) was added drop wise and continued to stir overnight at rt. Reaction was quenched with water and solid was filtered through Buchner funnel, filtrate obtained was diluted with ethyl acetate, and organic layer was washed with water, brine and dried over anhydrous sodium sulphate. Solvent was removed under reduced pressure to obtain crude product which was purified using column chromatography using 5-10% ethyl acetate in hexane to afford 8.0 g of liquid.

¹H NMR (400 MHz, CDCl₃): δ 1.27 (t, J=7.1 Hz, 3H), 3.57 (s, 2H), 4.16 (q, J=7.1 Hz, 2H), 5.07 (s, 2H), 6.95 (d, J=7.3 Hz, 2H), 7.22 (d, J=7.6 Hz, 2H), 7.34-7.46 (m, 5H). MS (EI) m/z: 271.2 (M+1).

Step II

Ethyl 2-(4-benzyloxyphenyl)-2-methyl-propanoate

Under N₂ atmosphere n-Buli (47.78 mL, 172.01 mmol) was added drop wise to a solution of N,N-diisopropyl amine (24.3 mL, 172.01 mmol) in 60 mL of anhydrous THF at −78° C. Reaction mixture was stirred for 45 min. Followed by addition of ethyl 2-(4-benzyloxyphenyl)acetate (15 g, 55.48 mmol) in 50 mL of anhydrous THF in drop wise manner and continued to stir at −78° C. for additional 45 min. To above reaction mixture methyl iodide (12.09 mL, 194.18 mmol) was added dropwise and allowed reaction mixture to warm slowly to room temperature and stirred overnight. The reaction mixture was quenched by aq. saturated NH₄Cl solution and extracted with diethyl ether (3×100 mL). Combined organic layer was washed with water, brine and dried over anhydrous Na₂SO4. The organic solvent was removed under reduced pressure to afford 18 g of crude monomethylated product. The monomethylated crude product was subjected once again to above mentioned reaction condition to afford 15 g of dimethylated product as oil.

MS (EI) m/z: 299.3 (M+1).

Step III

Ethyl 2-(4-hydroxyphenyl)-2-methyl-propanoate

Under inert atmosphere, a round bottom flask was charged with ethyl 2-(4-benzyloxyphenyl)-2-methyl-propanoate (15 g, mmol) and ethyl acetate (200 mL). To above reaction mixture 2-3 drops of water was added followed by Pd/C. Reaction mixture allowed to stir and evacuated the flask until solvent begins to bubble and then carefully backfill with nitrogen gas (repeated twice). Nitrogen balloon was replaced by hydrogen bladder and flask was again evacuated and refilled with hydrogen (repeated twice). The reaction mixture thus maintained under hydrogen atmosphere was allowed to stir overnight at room temperature. The reaction mixture was filtered through cellite pad and the filtrate was concentrated under reduced pressure to afford 6.5 g of product.

¹H NMR (400 MHz, CDCl₃): δ 1.19 (t, J=7.1 Hz, 3H), 1.55 (s, 6H), 4.12 (q, J=6.8 Hz, 2H), 5.36 (bs, 1H), 6.78 (d, J=8.5 Hz, 2H), 7.21 (d, J=8.6 Hz, 2H). MS (EI) m/z: 209.2 (M+1).

Step IV

Ethyl 2-[4-(2-aminothiazol-5-yl)oxyphenyl]-2-methyl-propanoate

Synthesized in analogues manner to preparation 20
MS (EI) m/z: 307.1 (M+1).

Preparation 47

Ethyl 2-[2-[tert-butoxycarbonyl-[(4-methoxyphenyl)methyl]amino]thiazol-4-yl]acetate

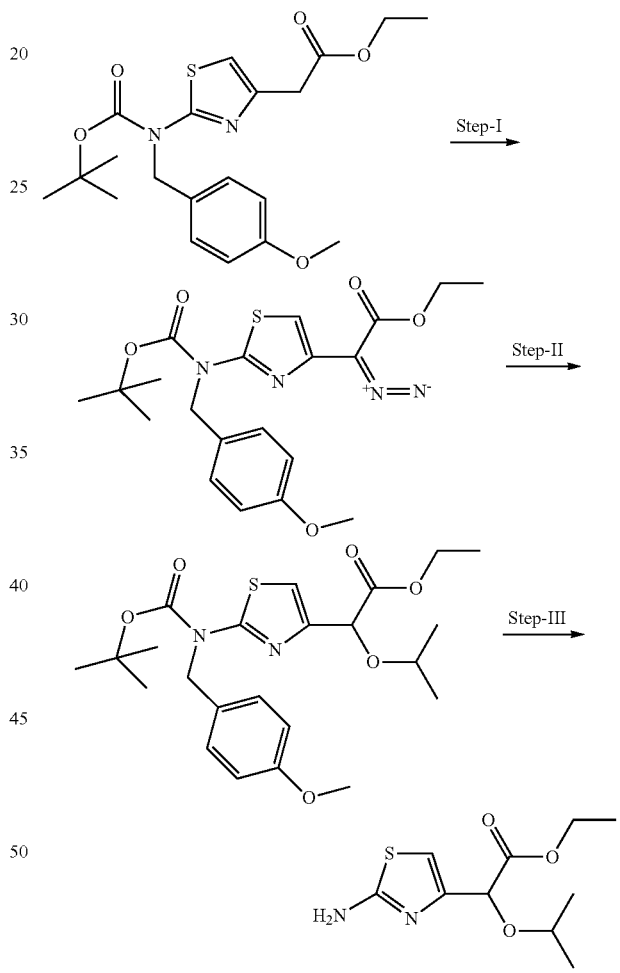

Step I

Ethyl 2-[2-[tert-butoxycarbonyl-[(4-methoxyphenyl)methyl]amino]thiazol-4-yl]-2-diazo-acetate To a solution of ethyl 2-[2-[tert-butoxycarbonyl-[(4-methoxyphenyl)methyl]amino]thiazol-4-yl]acetate (synthesized as per preparation 44; 3.8 g, 9.35 mmol) in dry acetonitrile was added para-toluene sulfonyl azide (2.04 g, 10.3 mmol)

followed by DBU (2.09 mL, 14.0 mmol) in dropwise manner. The reaction stirred for 30 min. then poured in ice cold water (20 mL) extracted with ethyl acetate (3×20 mL). The organic layer was washed with brine, dried over anhydrous sodium sulfate, and concentrated under reduced pressure to provide crude product, which was purified by column chromatography using 5-7% ethyl acetate in hexane to afford Ethyl 2-[2-[tert-butoxycarbonyl-[(4-methoxyphenyl)methyl]amino] thiazol-4-yl]-2-diazo-acetate (3.3 g).

$^1$H NMR (400 MHz, CDCl$_3$): δ 1.26 (t, J=6.8 Hz, 3H), 1.52 (s. 9H), 3.78 (s. 3H), 4.18 (q, J=6.8 Hz, 2H), 5.22 (s, 2H), 7.13 (s, 1H), 6.81 (d, J=8.3 Hz, 2H), 7.33 (d, J=8.3 Hz, 2H). MS (EI) m/z: 433.2 (M+1).

Step II

Ethyl 2-[2-[tert-butoxycarbonyl-[(4-methoxyphenyl) methyl]amino]thiazol-4-yl]-2-isopropoxy-acetate Ethyl 2-[2-[tert-butoxycarbonyl-[(4-methoxyphenyl)methyl]amino]thiazol-4-yl]-2-diazo-acetate (0.6 g, 1.38 mmol) was dissolved in DCM (10 mL) under argon atmosphere. To this solution, iso-propanol (0.12 mL, 1.66 mmol) was added followed by rhodium (II) acetate dimer (12 mg, 0.028 mmol). Mixture was stirred at room temperature for 30 min. then diluted with DCM (10 mL). Organic layer was washed with water, brine, dried over anhydrous sodium sulfate and concentrated under reduced pressure to give a crude product which was purified by silica gel column chromatography using 20% ethyl acetate in hexane to provide ethyl 2-[2-[tert-butoxycarbonyl-[(4-methoxyphenyl)methyl]amino]thiazol-4-yl]-2-isopropoxy-acetate (0.55 g).

MS (EI) m/z: 465.3 (M+1).

Step III

Ethyl 2-(2-aminothiazol-4-yl)-2-isopropoxy-acetate

Ethyl 2-[2-[tert-butoxycarbonyl-[(4-methoxyphenyl)methyl]amino]thiazol-4-yl]-2-isopropoxy-acetate (0.55 g, 1.2 mmol) was dissolved in TFA (7 mL). The reaction mixture was refluxed for 5 hours. TFA was removed under reduced pressure. The residue was diluted with water (10 mL) and ethyl acetate (15 mL) and basified with sodium bicarbonate. The organic layer was separated and aqueous layer was again extracted with ethyl acetate (15 mL). The combined organic layer was washed with brine, dried over sodium sulphate and concentrated under reduced pressure to obtain crude product which was purified by silica gel column chromatography using 20% ethyl acetate in hexane to provide ethyl 2-(2-aminothiazol-4-yl)-2-isopropoxy-acetate (0.22 g).

MS (EI) m/z: 245.1 (M+1).

Preparation 48: was synthesized in analogous manner of preparation 47.

| Prep. No. | IUPAC Name |
|---|---|
| 48 | Ethyl 2-(2-aminothiazol-4-yl)-2-hydroxy-acetate |

Preparation 49

2-Amino-4,5,6,7-tetrahydro-benzothiazole-6-carboxylic acid ethyl ester

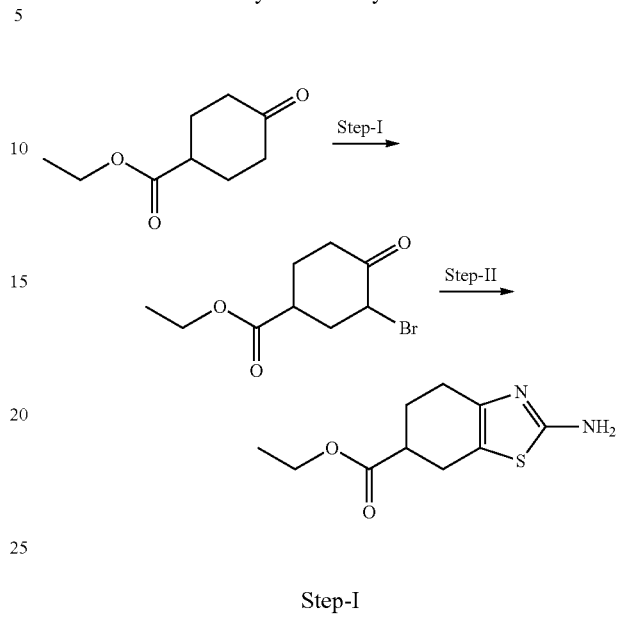

Step-I

3-Bromo-4-oxo-cyclohexanecarboxylic acid ethyl ester

To a stirred solution of N-bromosuccinimide (1.11 g, 6.274 mmol), PTSA (0.108 g, 0.627 mmol) in toluene (15 mL) was added 4-oxocyclohexanecarboxylic acid ethyl ester (1.068 g, 6.274 mmol) under nitrogen atmosphere and the reaction was refluxed for 2 hrs. Toluene was evaporated under reduced pressure and the residue was partitioned between water (50 mL) and ethyl acetate (50 mL). The layers were separated; the organic layer was washed with sat. sodium bicarbonate solution followed by brine, dried over anhydrous sodium sulfate, filtered and concentrated under reduced pressure to get title the compound (2.2 g) which was carried without purification for the next step.

Step-II

-2-amino-4,5,6,7-tetrahydro-benzothiazole-6-carboxylic acid ethyl ester

Thiourea (0.672 g, 8.835 mmol) was taken in ethanol (30 mL). To this stirred solution was added 3-Bromo-4-oxo-cyclohexane carboxylic acid ethyl ester (2.2 g, 8.835 mmol). The reaction was refluxed for 2 hrs. The reaction mixture was allowed to cool to room temperature and ethanol was evaporated under reduced pressure, the residue was partitioned between water and ethyl acetate. The water layer was collected and basified using sat. sodium bicarbonate solution, extracted with ethyl acetate, the organic layer was washed with brine, dried over anhydrous sodium sulfate filtered and concentrated under reduced pressure to afford 2-Amino-4,5,6,7-tetrahydro-benzothiazole-6-carboxylic acid ethyl ester (1.6 g)

$^1$H NMR (400 MHZ, CDCl$_3$): δ 1.27 (t, J=6.8 Hz, 3H), 1.87-1.97 (m, 1H), 2.17-2.23 (m, 1H), 2.54-2.68 (m, 2H), 2.68-2.79 (m, 1H), 2.80-2.85 (m, 2H), 4.172 (q, J=6.9, 2H), 4.74 (bs, 2H). MS (EI) m/z: 227.1 (M+1)

Preparation 50 and 51 were synthesized in analogous manner of preparation 49.

| Prep. No. | IUPAC Name |
|---|---|
| 50 | (2-Amino-4,5,6,7-tetrahydro-benzothiazol-4-yl)-acetic acid ethyl ester. |
| 51 | Ethyl 2-amino-4,5,6,7-tetrahydro-1,3-benzothiazole-4-carboxylate |

Preparation 52

Ethyl 3-[4-(2-aminothiazol-5-yl)oxyphenyl]isoxazole-5-carboxylate

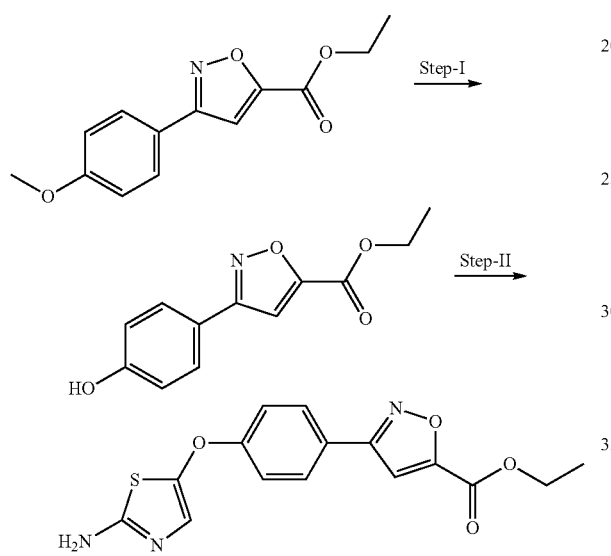

Step-I

Ethyl 3-(4-hydroxyphenyl)isoxazole-5-carboxylate

To a stirred solution of ethyl 3-(4-methoxyphenyl)isoxazole-5-carboxylate (1 g, 4.04 mmol, prepared according to literature method *Tet. Lett* 2009, 50(27), 3948-3951) in 8 mL DCM, Boron tribromide 1 M solution in DCM (8.0 mL, 8.08 mmol) was added dropwise at −78° C. After complete addition reaction mixture was allowed to warm slowly and further stirred for 16 hrs at RT. After completion of the reaction, solvent was removed under reduced pressure. The reaction mixture was diluted with ice cold water (20 mL) and extracted with ethyl acetate (3×50 mL). The combined organic layer was washed with water, brine and dried over sodium sulfate, filtered and concentrated under reduced pressure to get ethyl 3-(4-hydroxyphenyl)isoxazole-5-carboxylate (0.7 g).
LC-MS (m/z): 234.1 [M+1].

Step-2

Ethyl 3-[4-(2-aminothiazol-5-yl)oxyphenyl]isoxazole-5-carboxylate

To a stirred solution of ethyl 3-(4-hydroxyphenyl)isoxazole-5-carboxylate (0.97 g, 4.16 mmol) in dry THF, sodium hydride (60%, 0.25 g, 6.09 mmol) was added at room temperature and stirred for 10 min. 5-bromothiazol-2-amine (0.5 g, 2.77 mmol) dissolved in 10 mL dry THF was added and continued to stir for additional 1 hr. Reaction mixture was poured on ice cold water and extracted with ethyl acetate (50 mL×3). The combined organic layer was washed with water, brine and dried over sodium sulfate, filtered and concentrated under reduced pressure to get crude material which was purified by silica gel column chromatography using 40-50% ethyl acetate in hexane to provide the title compound (0.19 g).
LC-MS (m/z): 332.1 [M+1].

Preparation 53

Synthesis of 5-[3-[[tert-butyl(dimethyl)silyl]oxymethyl]phenoxy]thiazol-2-amine

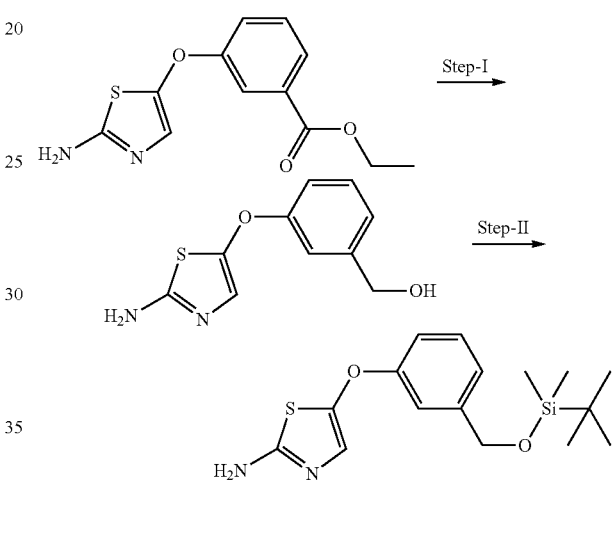

Step I

[3-(2-aminothiazol-5-yl)oxyphenyl]methanol

Ethyl 3-(2-aminothiazol-5-yl)oxybenzoate (Preparation 20; 2.0 g, 7,575 mmol) in 20 mL of dry THF was added slowly to stirring suspension of lithium aluminium hydride (0.287 g, 7.575 mmol) in 20 mL of dry THF in inert atmosphere and at 0° C. After complete addition the reaction was allowed to stir at room temperature for 3 hrs. TLC showed complete consumption of ethyl 3-(2-aminothiazol-5-yl)oxybenzoate. To the reaction mixture saturated $NH_4Cl$ solution was added and the layers were separated. The aqueous layer was extracted with ethyl acetate. The combined organic layer was washed with brine and dried over anhydrous sodium sulfate. The solvent was removed under reduced pressure to get the crude product which was taken as it was for next reaction without purification (1.74 g).
MS (EI) m/z: 223.1 (M+1).

Step II

5-[3-[[tert-butyl(dimethyl)silyl]oxymethyl]phenoxy]thiazol-2-amine

[3-(2-aminothiazol-5-yl)oxyphenyl]methanol (1.70 g, 7.575 mmol), tert-butyldimethylchlorosilane (1.38 g, 9.189 mmol), and imidazole (0.625 g, 9.189 mmol) was taken in 20 mL of dry DMF and heated at 60° C. for overnight. TLC showed consumption of starting material. The reaction mixture was cooled to room temperature and poured into water and extracted with ethyl acetate. The combined organic layer was washed with brine and dried over anhydrous sodium sulfate. The solvent was removed under reduced pressure to get the crude product which was purified by column chromatography using 5-30% ethyl acetate in hexanes to get pure title compound (0.998 g).

¹H NMR (400 MHz, DMSO-d₆): δ 0.085 (s, 6H), 0.93 (s, 9H), 4.7 (s, 2H), 4.89 (bs, 2H) 6.74 (s, 1H), 6.90-6.98 (m, 1H), 7.02 (d, J=7.6 Hz, 1H), 7.07 (s, 1H), 7.21-7.30 (m, 1H); MS (EI) m/z: 337.1 (M+1).

Preparation 54

Synthesis of tert-butyl 6-aminopyridine-3-carboxylate

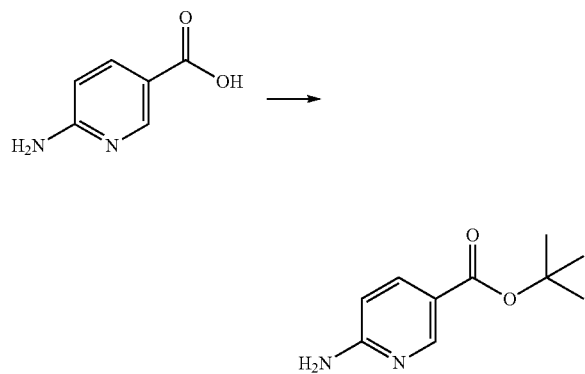

A mixture of 6-amino pyridine 3-carboxylic acid (2.0 g, 14.48 mmol) and thionyl chloride (10 mL) was reflux for 3.5 h under anhydrous atmosphere. Acid chloride formation was confirmed by TLC. Excess of thionyl chloride was removed under reduced pressure on rotavapour. Triethyl amine (5 mL, 36.2 mmol) and tert-butanol (5 mL) was added to acid chloride at 0° C. under inner atmosphere and reaction mixture was heated at 80° C. for 2 h. completion of reaction was confirmed by TLC. The reaction mixture was diluted with dichloromethane (50 mL) and water (50 mL), layers were separated and aqueous layer was extracted with DCM (2×30 mL) combined organic layers were washed with water (50 mL), brine (50 mL) and dried over anhydrous sodium sulphate (50 g). The solvent was removed under reduced pressure and the residue was purified by column chromatography using 20-30% ethyl acetate in hexane. Removal of solvent from appropriate fractions under reduced pressure using rotavapour gave pure product (0.7 g).

¹H NMR (400 MHz, DMSO-d₆): δ 1.50 (s, 9H), 6.42 (d, J=8.8 Hz, 1H), 6.75 (s, 2H), 7.75 (dd, J=8.8 Hz, 2.4 Hz, 1H), 8.43 (d, J=2.4 Hz, 1H); MS (EI) m/z: 195.1 (M+1).

Example A1

2-(4-Cyclopropylsulfonylphenyl)-2-tetrahydropyran-4-yloxy-N-thiazol-2-yl-acetamide

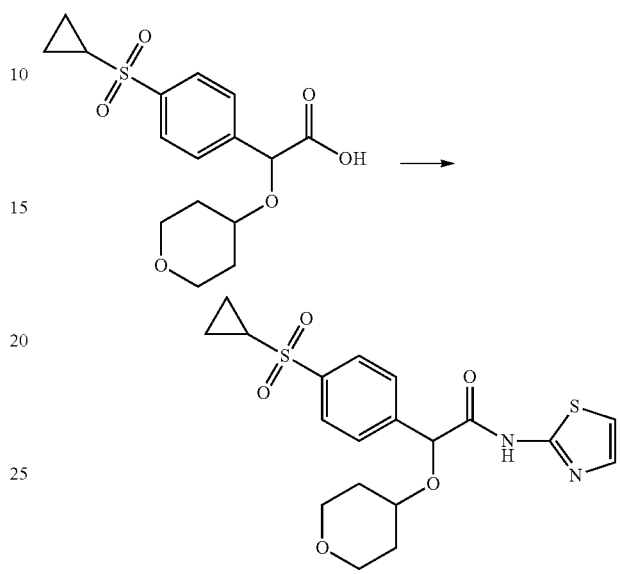

Procedure-A:

To a mixture of 2-(4-cyclopropylsulfonylphenyl)-2-tetrahydropyran-4-yloxy-acetic acid (preparation 4; 0.2 g, 0.58 mmol), 2-aminothiazole (0.070 g, 0.70 mmol), HOBt (0.095 g), and EDCl (0.134 g, 0.70 mmol) in methylene chloride (6 mL), was added N-methyl morpholine (0.08 mL, 0.70 mmol). The resulting mixture was stirred at room temperature overnight followed by dilution with methylene chloride. The reaction mixture was poured into water; organic layer was washed with water, brine, dried over sodium sulfate, and the organic solvent evaporated to get a residue which was purified by preparative TLC to obtain a title compound (0.118 g)

Compound (A 1) can also be prepared using procedure-B or procedure-C

Procedure-B:

2-(4-Cyclopropylsulfonylphenyl)-2-tetrahydropyran-4-yloxy-acetic acid (preparation 4) was dissolved in DCM. To this solution was added DMF and cooled to 0° C., followed by the addition of oxalyl chloride under stirring. To this mixture, a solution of 2-aminothiazole and pyridine in DCM was added drop wise at 0° C. and was stirred further for 4 h. at room temperature. The reaction mixture was poured into 1N aqueous HCl under stirring, organic layer was again washed with 1N HCl, followed by 5% brine, dried over anhydrous sodium sulfate, solvent was removed under reduced pressure to get the crude compound which was purified by flash chromatography to get the title product.

Procedure-C:

2-(4-Cyclopropylsulfonylphenyl)-2-tetrahydropyran-4-yloxy-acetic acid (preparation 4; (1 equi.) and HATU (1.5 equi) was dissolved in DCM. To this solution was added D1PEA (2 equi.) and stirred for 15 minutes followed by addition of 2-aminothiazole (1 equi.) and continued to stir over night at room temperature. Reaction mixture was diluted with dichloromethane, washed with water, brine, dried over anhydrous sodium sulfate, solvent was removed under reduced pressure to get the crude compound which was purified by flash chromatography to get the title product.

¹H NMR (400 MHz, CDCl₃): δ 1.01-1.07 (m, 2H), 1.25-1.39 (m, 2H), 1.64-1.79 (m, 2H), 1.85-1.89 (m, 1H), 2.00-2.05 (m, 1H), 2.41-2.48 (m, 1H), 3.35-3.43 (m, 2H), 3.64-3.71 (m, 1H), 3.93-4.03 (m, 2H), 5.24 (s, 1H), 7.01 (d, J=3.7 Hz, 1H), 7.58 (d, J=3.6 Hz, 1H), 7.70 (d, J=8.3 Hz, 2H), 7.93 (d, J=8.6 Hz, 2H), 9.94 (br. s, 1H). HPLC-MS (EI) m/z: 422.6 (M+1).

Example A2

Ethyl 3-[2-[[2-(4-cyclopropylsulfonylphenyl)-2-tetrahydropyran-4-yloxy-acetyl]amino]thiazol-5-yl]oxybenzoate

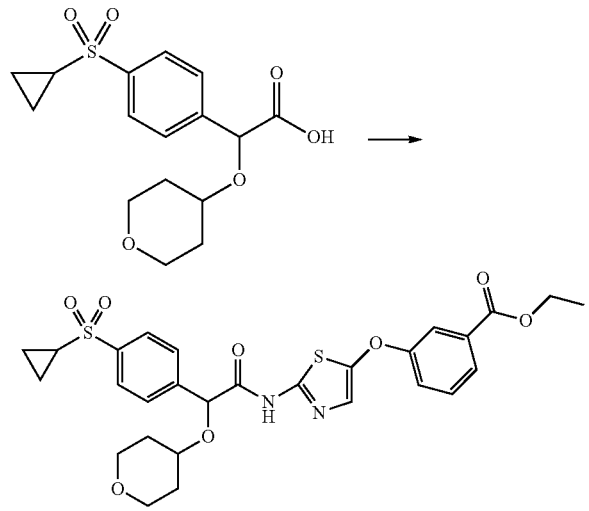

A 1 L two necked round bottom flask maintained under inert atmosphere was charged with 2-(4-cyclopropylsulfonylphenyl)-2-tetrahydropyran-4-yloxy-acetic acid (16 g, 47 mmol; preparation 4), ethyl 3-(2-aminothiazol-5-yl)oxybenzoate (13.6 g, 51 mmol; preparation 20), HOBt (7.6 g, 56 mmol) and EDCl (10.8 g, 56 mmol) in Dichloromethane (500 mL). The reaction mixture was stirred at 25° C. and added triethylamine (15.8 mL, 113 mmol). The resulting mixture was continued to stir for 16 hours at 25° C. Completion of reaction was confirmed by TLC. The reaction mixture was diluted with water (400 mL) and DCM (250 mL). The layers were separated. The aqueous layer was again extracted with DCM (2×200 mL). The combined organic layer was washed with 1N HCl (300 mL), brine and dried over anhydrous sodium sulphate and concentrated under reduced pressure. The obtained residue was purified by column chromatography using 5-40% ethyl acetate in hexanes as solvent system to get a pure product (16 g).

¹H NMR (400 MHz, CDCl₃): δ 1.0-1.08 (m, 2H), 1.34-1.40 (m, 5H), 1.70-1.82 (m, 2H), 1.84-1.92 (m, 1H), 1.98-2.20 (m, 1H), 2.42-2.69 (m, 1H), 3.34-3.46 (m, 2H), 3.62-3.74 (m, 1H), 3.92-4.04 (m, 2H), 4.34 (q, J=6.9 Hz, 2H), 5.21 (s, 1H), 7.13 (s, 1H), 7.25-7.30 (m, 1H), 7.39 (t, J=7.9 Hz, 1H), 7.65-7.75 (m, 3H), 7.79 (d, J=7.8 Hz, 1H), 7.93 (d, J=8.3 Hz, 2H), 9.74 (bs, 1H); MS (EI) m/z: 587.2 (M+1).

Example A3

Methyl 5-[2-[[2-(4-cyclopropylsulfonylphenyl)-2-[(3R)-tetrahydrofuran-3-yl]oxy-acetyl]amino]thiazol-5-yl]oxy-2-methyl-benzoate

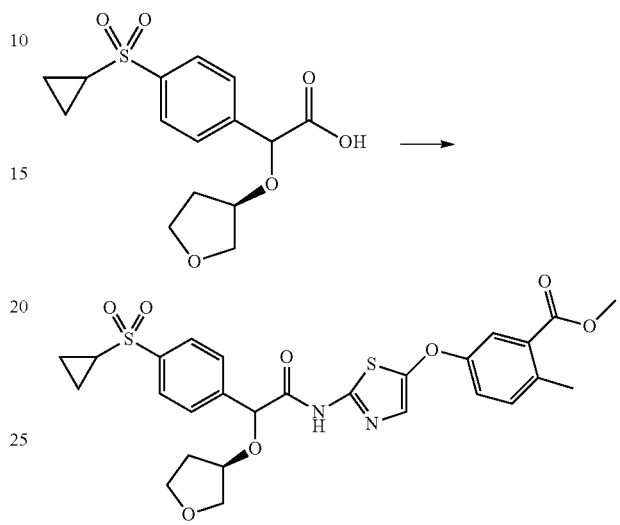

The compound of example A3 was obtained by similar method described in example A2 using 2-(4-Cyclopropanesulfonyl-phenyl)-2-[(R)-(tetrahydro-furan-3-yl)oxy]-acetic acid (preparation 5, 0.200 g, 0.613 mmol), methyl 5-(2-aminothiazol-5-yl)oxy-2-methyl-benzoate (preparation 26; 0.194 g, 0.736 mmol), HOBt (0.099 g, 0.736 mmol), and EDCl (0.140 g, 0.736 mmol), N-methyl morpholine (0.0154 g, 1.53 mmol) in DCM (8 mL) to provide the title compound (0.3 g).

¹H NMR (CDCl₃, 400 MHz): δ 1.04-1.06 (m, 2H), 1.33-1.38 (m, 2H), 2.05-2.13 (m, 2H), 2.40-2.45 (m, 1H), 2.54 (s, 3H), 3.73-3.76 (m, 1H), 3.86 (s, 3H), 3.92-3.94 (m, 1H), 4.04-4.08 (m, 2H), 4.28-4.31 (m, 1H), 5.01 (s, 1H), 7.09 (s, 1H), 7.12 (d, J=8.3 Hz, 1H), 7.18 (d, J=8.3 Hz, 1H), 7.59 (s, 1H), 7.66-7.69 (aromatics, 2H), 7.93 (d, J=8.0 Hz, 2H), 9.85 (br. s, 1H). MS (EI) m/z: 573.2.

Example A4

2-(4-Morpholinosulfonylphenyl)-2-tetrahydropyran-4-yloxy-N-thiazolo[5,4-b]pyridin-2-yl-acetamide

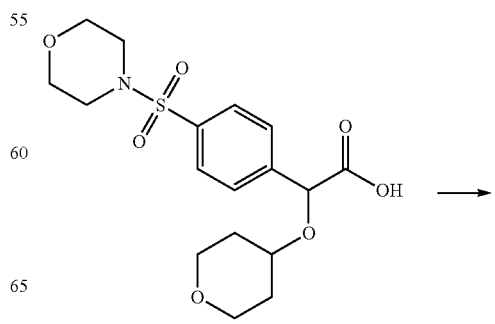

-continued

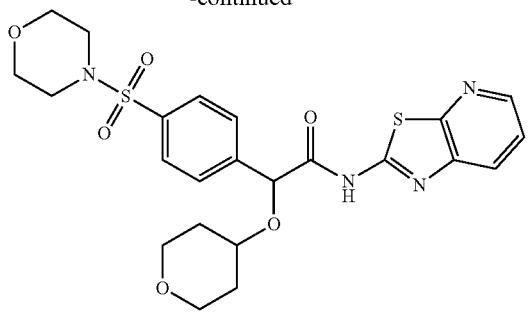

The compound of example A4 was obtained by similar method described in example A2 using 2-(4-morpholinosulfonylphenyl)-2-tetrahydropyran-4-yloxy-acetic acid (Preparation 11, 0.1 g, 0.25 mmol), thiazolo[5,4-b]pyridin-2-ylamine (0.050 g, 0.31 mmol), HOBt (0.042 g, 0.31 mmol), and EDCl (0.060 g, 0.31 mmol), N-methyl morpholine (0.065 g, 0.64 mmol) in DMF (5 mL) to provide the title compound (0.028 g).

$^1$H NMR (400 MHz, CDCl$_3$):—δ 1.73-1.83 (m, 2H), 1.89-1.93 (m, 1H), 2.01-2.18 (m, 1H), 3.02 (t, J=4.4 Hz, 4H), 3.38-3.45 (m, 2H), 3.74 (m, 5H), 3.97-4.05 (m, 2H), 5.28 (s, 1H), 7.26-7.42 (m, 1H), 7.72 (d, J=8.5 Hz, 2H), 7.80 (d, J=8.5 Hz, 2H), 8.03 (dd, J=1.5 Hz & 8.3 Hz 1H), 8.52 (dd, J=1.5 & 4.4 Hz, 1H), 9.95 (br. s, 1H). HPLC-MS (EI) m/z: 519.2 (M+1).

Example A5

Ethyl 1-[2-[[2-(4-cyclopropylsulfonylphenyl)-2-tetrahydropyran-4-yloxy-acetyl]amino]thiazol-5-yl]pyrazole-4-carboxylate

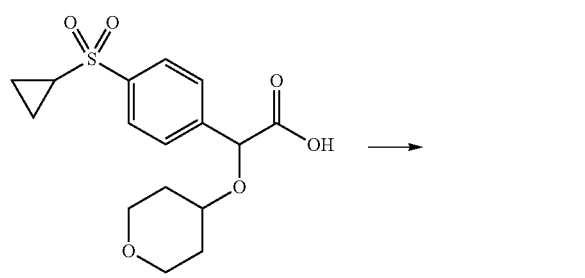

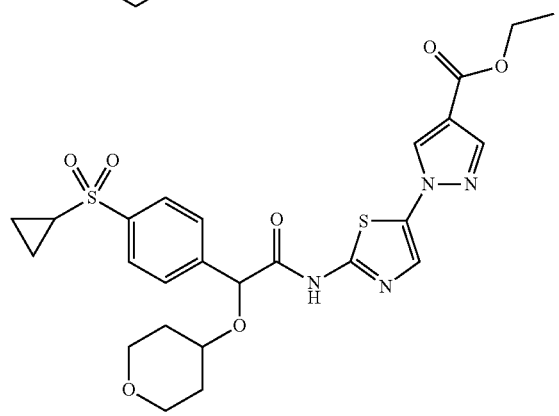

The compound of example A5 was obtained by similar method described in example A1 using 2-(4-cyclopropanesulfonyl-phenyl)-2-[(tetrahydro-pyran-4-yloxy)]-acetic acid (Preparation 4; 1.1 g, 3.23 mmol), ethyl 1-(2-aminothiazol-5-yl)pyrazole-4-carboxylate (Preparation 41; 0.924 g, 3.88 mmol), HOBt (0.524 g, 3.88 mmol), and EDCl (0.741 g, 3.88 mmol), N-methyl morpholine (0.815 g, 0.88 mmol) in DCM (20 mL) to provide the title compound (0.9 g).

$^1$H NMR (400 MHz, CDCl$_3$):—Δ 1.02-1.07 (M, 2H), 1.33-1.37 (M, 5H), 1.69-1.79 (M, 2H), 1.84-1.89 (M, 1H), 2.00-2.04 (M, 1H), 2.42-2.46 (M, 1H), 3.34-3.42 (M, 2H), 3.66-3.69 (M, 1H), 3.39-4.01 (M, 2H), 4.31 (Q, J=6.9 HZ, 2H), 5.62 (S, 1H), 7.57 (S, 1H), 7.69 (D, J=8.3 HZ, 2H), 7.93 (D, J=8.4 HZ, 2H), 8.05 (D, J=6.0 HZ, 1H), 8.21 (S, 1H), 10.01 (BR. S, 1H). MS (EI) M/Z: 561.3 (M+1).

Example A6

Methyl 2-[[2-(4-cyclopropylsulfonylphenyl)-2-tetrahydropyran-4-yloxy-acetyl]amino]-4,5,6,7-tetrahydro-1,3-benzothiazole-6-carboxylate

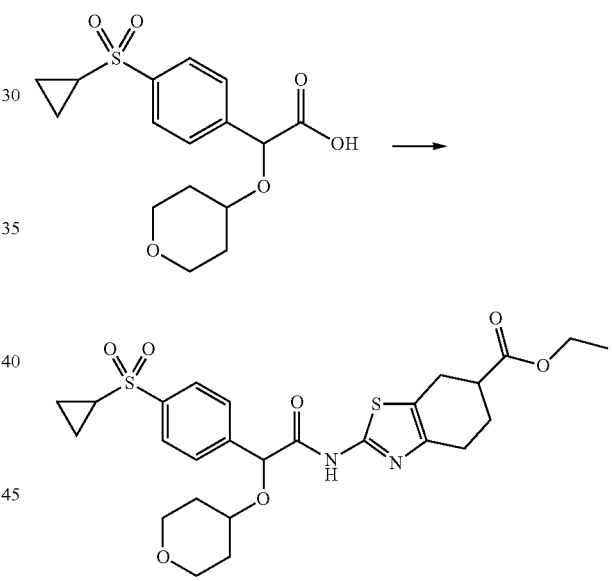

The compound of example A6 was obtained by similar method described in example A1 using 2-(4-cyclopropanesulfonyl-phenyl)-2-[(tetrahydro-pyran-4-yloxy)]-acetic acid (Preparation 4, 0.340 g, 1.0 mmol), 2-Amino-4,5,6,7-tetrahydro-benzothiazole-6-carboxylic acid ethyl ester (Preparation 49; 0.286 g, 1.0 mmol), HOBt (0.162 g, 1.2 mmol), and EDCl (0.229 g, 1.2 mmol), N-methyl morpholine (0.36 g, 3.58 mmol) in DMF (6 mL) to provide the title compound (0.22 g).

$^1$H NMR (400 MHz, DMSO-d$_6$):—δ $^1$H NMR (400 MHz, CDCl$_3$): δ 1.02-1.06 (m, 2H), 1.24-1.30 (m, 3H), 1.34-1.38 (m, 2H), 1.64-1.80 (m, 2H), 1.81-1.88 (m, 1H), 1.92-2.08 (m, 2H), 2.22-2.23 (m, 1H), 2.4-2.48 (m, 1H), 2.64-2.84 (m, 3H), 2.92-2.98 (m, 2H), 3.32-3.42 (m, 2H), 3.62-3.7 (m, 1H), 3.92-4.02 (m, 2H), 4.14-4.22 (m, 2H), 5.21 (s, 1H), 7.67 (d, J=8.4 Hz, 2H), 7.91 (d, J=8.4 Hz, 2H), 9.8 (bs, 1H).

MS (EI) m/z: 549.3 (M+1).

Example A7 tert-butyl 6-[[2-(4-cyclopropylsulfonylphenyl)-2-(2, 4-difluorophenoxy)acetyl]amino]pyridine-3-carboxylate

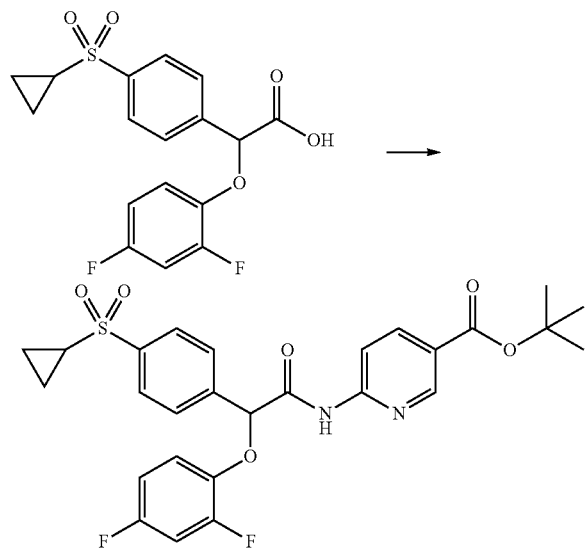

2-(4-cyclopropylsulfonylphenyl)-2-(2,4-difluorophenoxy)acetic acid (Preparation 1; 2.0 g, 5.42 mmol) was dissolved in DCM (20 mL). To this solution was added DMF (0.41 mL, 5.42 mmol) and cooled to 0° C., followed by the addition of oxalyl chloride (0.77 mL, 8.14 mmol) and further stirred for 1 hr at room temp. To this mixture, a solution of tert-butyl 6-aminopyridine-3-carboxylate (preparation 54, 1.26 g, 6.51 mmol) and pyridine (2.19 mL, 2.71 mmol) in DCM 20 (mL) was added drop wise at 0° C. and was stirred further for 1 hr at room temperature. The reaction mixture was diluted with DCM (50 mL), organic layer was washed with water, followed by brine, dried over anhydrous sodium sulfate, solvent was removed under reduced pressure to get the crude compound which was purified by silica gel column chromatography to get the title product (1.6 g).

$^1$H NMR (400 MHz, DMSO-d$_6$):—δ $^1$H NMR (400 MHz, CDCl$_3$): δ 1.02-1.07 (m, 2H), 1.35-1.37 (m, 2H), 1.60 (s, 9H), 2.42-2.46 (m, 1H), 5.66 (s, 1H), 6.72-6.78 (m, 1H), 6.84-6.96 (m, 2H), 7.78 (d, J=8.1 Hz, 2H), 7.95 (d, J=8.3 Hz, 2H), 8.21-8.27 (m, 2H), 8.90 (dd, J=1.9 Hz, 1H), 9.41 (s, 1H); MS (EI) m/z: 545.2 (M+1).

Example A8 tert-Butyl 6-[[2-(4-cyclopropylsulfonylphenyl)-2-(2, 4-difluoroanilino)acetyl]amino]pyridine-3-carboxylate

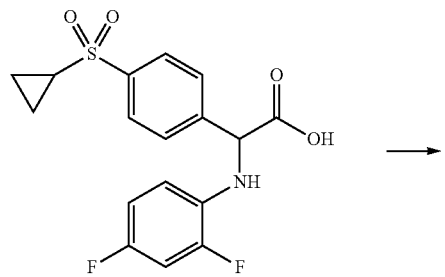

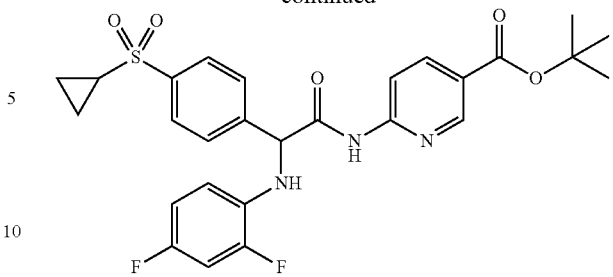

The compound of example A8 was obtained by similar method described in example A1 using 2-(4-cyclopropylsulfonylphenyl)-2-(2,4-difluoroanilino)acetic acid (Preparation 3, 0.150 g, 0.408 mmol), 6-aminopyridine-3-carboxylic acid tert-butyl ester (preparation 54, 0.095 g, 0.49 mmol), HOBT (0.082 g, 0.612 mmol), and EDCl (0.116 g, 0.612 mmol), N-methyl morpholine (0.103 g, 1.02 mmom) in DCM (4 mL) to provide the title compound (0.031 g).

$^1$H NMR (400 MHz, CDCl$_3$):—1.04-1.10 (m, 2H), 1.24-1.42 (m, 2H), 1.57 (s, 9H), 2.43-2.48 (m, 1H), 4.73 (s, 1H), 4.96 (d, J=3 Hz, 1H), 6.55-6.59 (m, 1H), 6.72-6.77 (m, 1H), 6.84-6.89 (m, 1H), 7.72 (d, J=8.3 Hz, 2H), 7.96 (d, J=8.3 Hz, 2H), 8.05-8.10 (aromatics, 2H), 8.25 (d, J=1.2 Hz, 1H), 9.20 (s, 1H). MS (EI) m/z: 543.9 (M+1).

Example A9

Ethyl 2-[6-[[2-(4-cyclopropylsulfonylphenyl)-2-tetrahydropyran-4-yloxy-acetyl]amino]-2-pyridyl]acetate

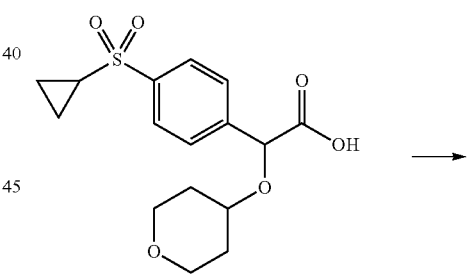

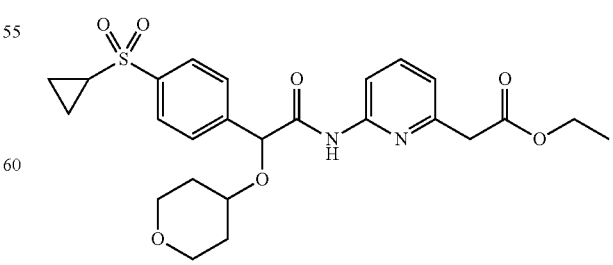

The compound of example A9 was obtained by similar method described in example A1 using 2-(4-cyclopropane sulfonyl-phenyl)-2-[(tetrahydro-pyran-4-yloxy)]-acetic acid (Preparation 4; 0.990 g, 2.91 mmol), ethyl 2-(6-amino-2-pyridyl)acetate (0.35 g, 1.94 mmol), HOBt (0.65 g, 4.81 mmol), and EDCl (0.92 g, 4.81 mmol), N-methyl morpholine (0.64 mL, 5.83 mmol) in DMF (25 mL) to provide the title compound (0.45 g).

¹H NMR (400 MHz, CDCl₃):—δ 1.00-1.06 (m, 2H), 1.28 (t, J=6.9 Hz 3H), 1.33-1.37 (m, 2H), 1.72-1.83 (m, 2H), 1.86-1.92 (m, 1H), 2.01-2.07 (m, 1H), 2.41-2.47 (m, 1H), 3.36-3.46 (m, 2H), 3.66-3.72 (m, 1H), 3.75 (s, 2H), 3.94-4.03 (m, 2H), 4.20 (q, J=7.3 Hz, 2H), 5.12 (s, 1H), 7.06 (d, J=7.4 Hz, 1H), 7.66 (t, J=8.3 Hz, 1H), 7.73 (d, J=8.4 Hz, 2H), 7.91 (d, J=8.3 Hz 2H), 8.06 (d, J=8.3 Hz, 1H), 9.05 (bs, 1H); MS (EI) m/z: 503.2 (M+1).

Example A10

Methyl 3[2-[[2-(6-cyclopentylsulfonyl-3-pyridyl)-2-tetrahydropyran-4-yloxy-acetyl]amino]thiazol-5-yl] oxybenzoate

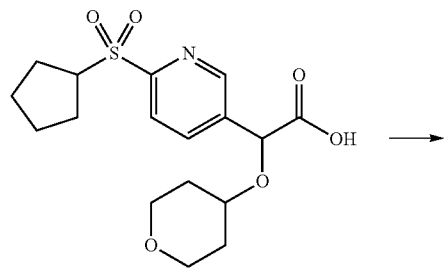

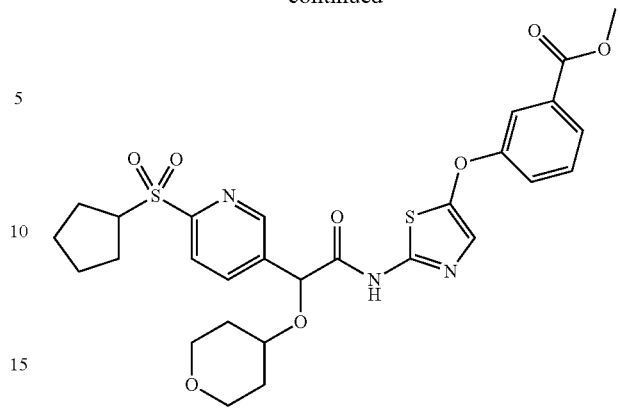

The compound of example A10 was obtained by similar method described in example A1 using 2-(6-cyclopentylsulfonyl-3-pyridyl)-2-tetrahydropyran-4-yloxy-acetic acid (Preparation 14; 0.200 g, 0.542 mmol), methyl 3-(2-aminothiazol-5-yl)oxybenzoate (Preparation 20, 0.162 g, 0.650 mmol), HOBt (0.087 g, 0.650 mmol), and EDCl (0.124 g, 0.650 mmol), N-methyl morpholine (0.136 g, 1.35 mmol) in DCM (8 mL) to provide the title compound (0.140 g).

¹H NMR (400 MHz, CDCl₃): δ 1.65-1.82 (m, 5H), 1.88-1.90 (m, 4H), 2.05-2.11 (m, 3H), 3.37-3.44 (m, 2H), 3.70-3.72 (m, 1H), 3.89 (s, 3H), 3.97-4.07 (m, 3H), 5.26 (s, 1H), 7.14 (s, 1H), 7.29 (s, 1H), 7.40 (app.t, J=8.1 Hz, 1H), 7.69 (s, 1H), 7.79 (d, J 7.8 Hz, 1H), 8.10 (d, J=8.0 Hz, 2H), 8.88 (s, 1H), 9.80 (br. s, 1H). MS (EI) m/z: 602.2 (M+1).

Examples A11 to A74 were prepared in analogues manner of examples A1-A10 from the appropriate intermediate that are available commercially or synthesized as above.

| Example No. | Structure | MS (EI)m/z: (M + 1). | IUPAC Name |
|---|---|---|---|
| A11 | 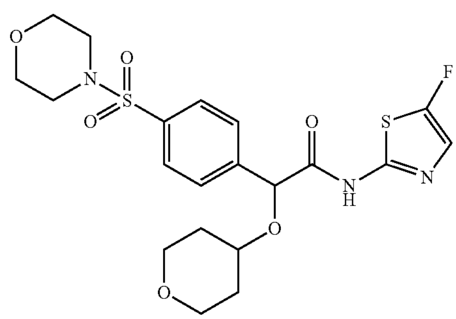 [SMILES: O=C(Nc1ncc(F)s1)C(OC1CCOCC1)c1ccc(S(=O)(=O)N2CCOCC2)cc1] | 486.3 | N-(5-fluorothiazol-2-yl)-2-(4-morpholinosulfonylphenyl)-2-tetrahydropyran-4-yloxy-acetamide |
| A12 | 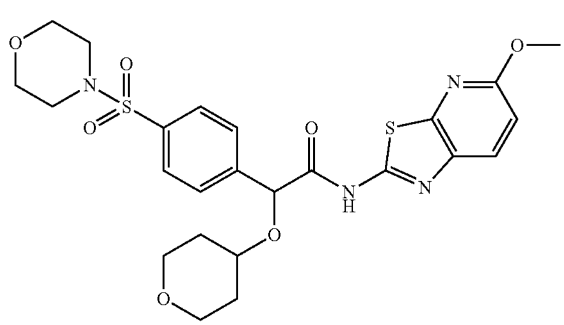 [SMILES: COc1ccc2nc(NC(=O)C(OC3CCOCC3)c3ccc(S(=O)(=O)N4CCOCC4)cc3)sc2n1] | 549.2 | N-(5-methoxythiazolo[5,4-b]pyridin-2-yl)-2-(4-morpholinosulfonylphenyl)-2-tetrahydropyran-4-yloxy-acetamide |

| Example No. | Structure | MS (EI)m/z: (M + 1). | IUPAC Name |
|---|---|---|---|
| A13 | 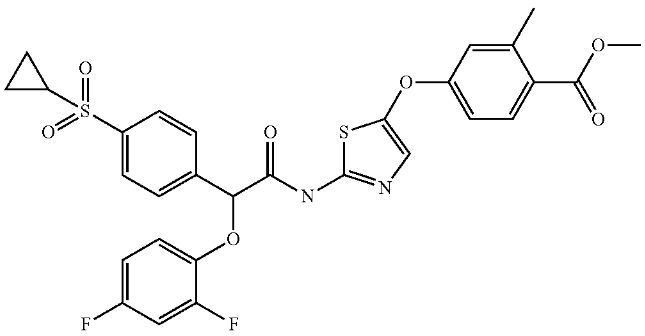 [SMILES: COC(=O)c1ccc(Oc2cnc(NC(=O)C(Oc3ccc(F)cc3F)c3ccc(S(=O)(=O)C4CC4)cc3)s2)cc1C] | 615.2 | Methyl 4-[2-[[2-(4-cyclopropylsulfonylphenyl)-2-(2,4-difluorophenoxy)acetyl]amino]thiazol-5-yl]oxy-2-methyl-benzoate |
| A14 | 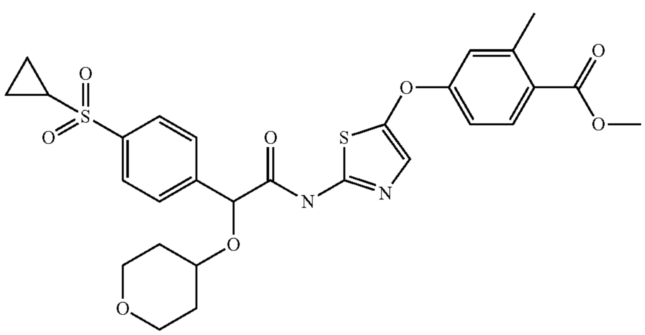 [SMILES: COC(=O)c1ccc(Oc2cnc(NC(=O)C(OC3CCOCC3)c3ccc(S(=O)(=O)C4CC4)cc3)s2)cc1C] | 587.2 | Methyl 4-[2-[[2-(4-cyclopropylsulfonylphenyl)-2-tetrahydropyran-4-yloxy-acetyl]amino]thiazol-5-yl]oxy-2-methyl-benzoate |
| A15 | 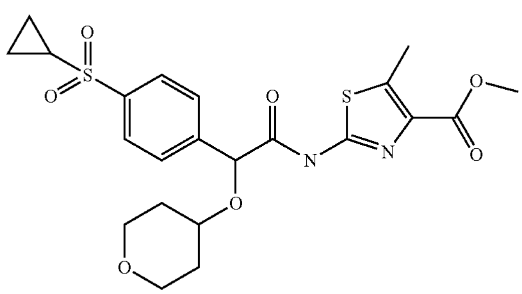 [SMILES: COC(=O)c1nc(NC(=O)C(OC2CCOCC2)c2ccc(S(=O)(=O)C3CC3)cc2)sc1C] | 495.2 | Methyl 2-[[2-(4-cyclopropylsulfonylphenyl)-2-tetrahydropyran-4-yloxy-acetyl]amino]-5-methyl-thiazole-4-carboxylate |
| A16 | Chiral | 520.2 | 2-(4-cyclopropylsulfonylphenyl)-2-[(2R,3S,4R)-3-hydroxy-2-(hydroxymethyl)tetrahydropyran-4-yl]oxy-N-thiazolo[5,4-b]pyridin-2-yl-acetamide |

-continued

| Example No. | Structure | MS (EI)m/z: (M + 1). | IUPAC Name |
|---|---|---|---|
| A17 | 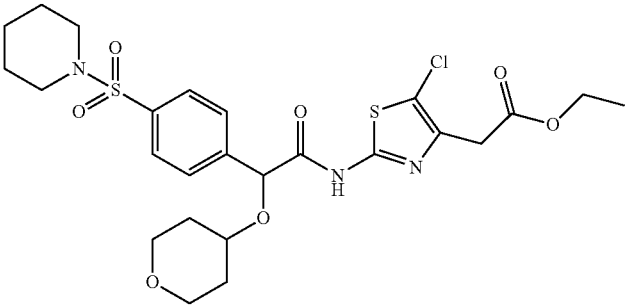 [SMILES: CCOC(=O)Cc1nc(NC(=O)C(OC2CCOCC2)c2ccc(S(=O)(=O)N3CCCCC3)cc2)sc1Cl] | 586.2 ($^{35}$Cl) | Ethyl 2-[5-chloro-2-[[2-[4-(1-piperidylsulfonyl)phenyl]-2-tetrahydropyran-4-yloxy-acetyl]amino]thiazol-4-yl]acetate |
| A18 | 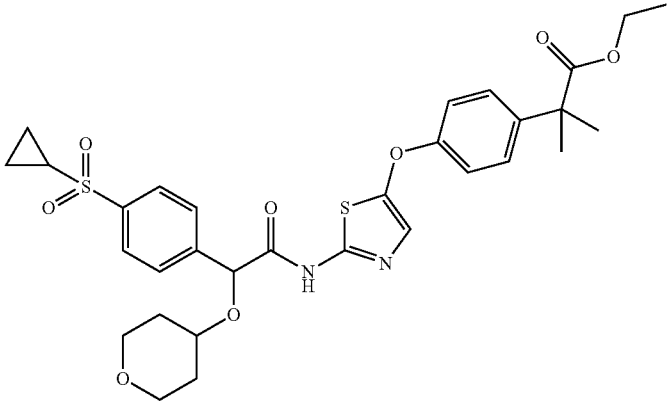 [SMILES: CCOC(=O)C(C)(C)c1ccc(Oc2cnc(NC(=O)C(OC3CCOCC3)c3ccc(S(=O)(=O)C4CC4)cc3)s2)cc1] | 629.3 | Ethyl 2-[4-[2-[[2-(4-cyclopropylsulfonylphenyl)-2-tetrahydropyran-4-yloxy-acetyl]amino]thiazol-5-yl]oxyphenyl]-2-methyl-propanoate |
| A19 | 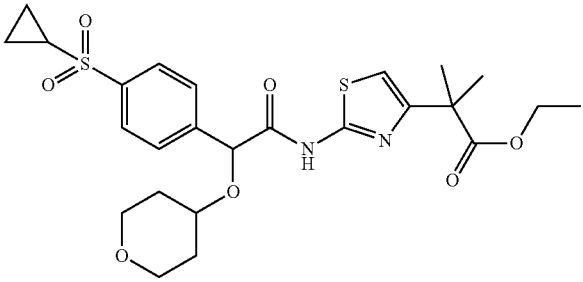 [SMILES: CCOC(=O)C(C)(C)c1csc(NC(=O)C(OC2CCOCC2)c2ccc(S(=O)(=O)C3CC3)cc2)n1] | 537.3 | Ethyl 2-[2-[[2-(4-cyclopropylsulfonylphenyl)-2-tetrahydropyran-4-yloxy-acetyl]amino]thiazol-4-yl]-2-methyl-propanoate |
| A20 | 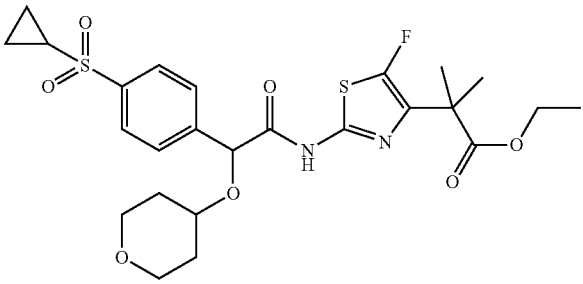 [SMILES: CCOC(=O)C(C)(C)c1nc(NC(=O)C(OC2CCOCC2)c2ccc(S(=O)(=O)C3CC3)cc2)sc1F] | 555.3 | Ethyl 2-[2-[[2-(4-cyclopropylsulfonylphenyl)-2-tetrahydropyran-4-yloxy-acetyl]amino]-5-fluoro-thiazol-4-yl]-2-methyl-propanoate |

-continued

| Example No. | Structure | MS (EI)m/z: (M + 1). | IUPAC Name |
|---|---|---|---|
| A21 | 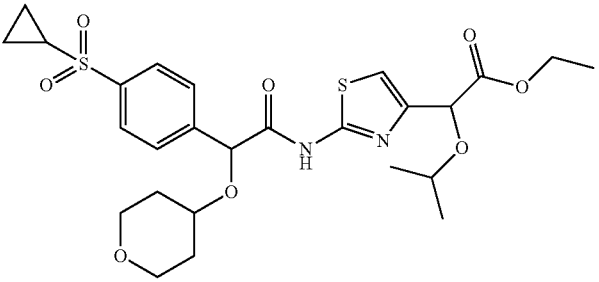 [SMILES: CCOC(=O)C(OC(C)C)c1csc(NC(=O)C(OC2CCOCC2)c2ccc(S(=O)(=O)C3CC3)cc2)n1] | 567.2 | Ethyl 2-[2-[[2-(4-cyclopropylsulfonylphenyl)-2-tetrahydropyran-4-yloxy-acetyl]amino]thiazol-4-yl]-2-isopropoxy-acetate |
| A22 | 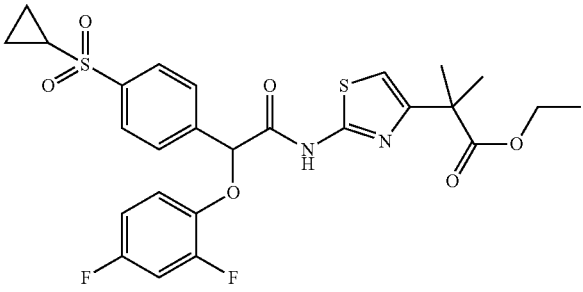 [SMILES: CCOC(=O)C(C)(C)c1csc(NC(=O)C(Oc2ccc(F)cc2F)c2ccc(S(=O)(=O)C3CC3)cc2)n1] | 565.2 | Ethyl 2-[2-[[2-(4-cyclopropylsulfonylphenyl)-2-(2,4-difluorophenoxy)acetyl]amino]thiazol-4-yl]-2-methyl-propanoate |
| A23 | 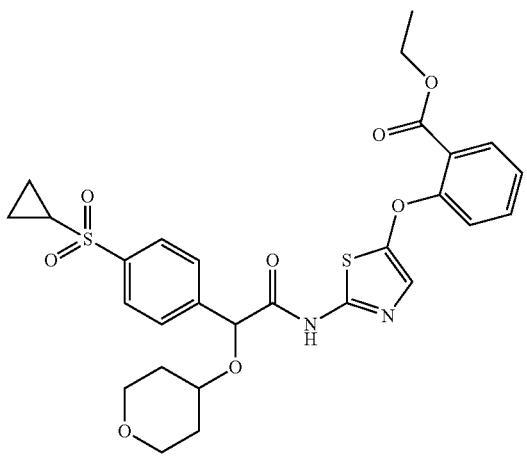 [SMILES: CCOC(=O)c1ccccc1Oc1cnc(NC(=O)C(OC2CCOCC2)c2ccc(S(=O)(=O)C3CC3)cc2)s1] | 587.2 | Ethyl 2-[2-[[2-(4-cyclopropylsulfonylphenyl)-2-tetrahydropyran-4-yloxy-acetyl]amino]thiazol-5-yl]oxybenzoate |
| A24 | 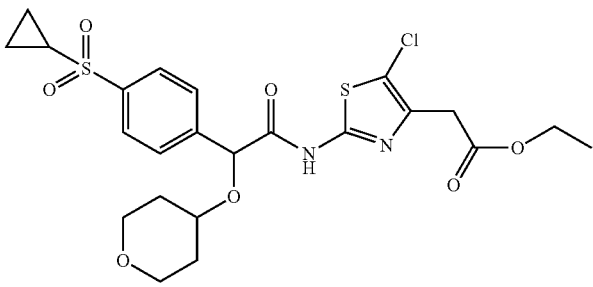 [SMILES: CCOC(=O)Cc1nc(NC(=O)C(OC2CCOCC2)c2ccc(S(=O)(=O)C3CC3)cc2)sc1Cl] | 543.2 ($^{35}$Cl) | Ethyl 2-[5-chloro-2-[[2-(4-cyclopropylsulfonylphenyl)-2-tetrahydropyran-4-yloxy-acetyl]amino]thiazol-4-yl]acetate |

-continued

| Example No. | Structure | MS (EI)m/z: (M + 1). | IUPAC Name |
|---|---|---|---|
| A25 | 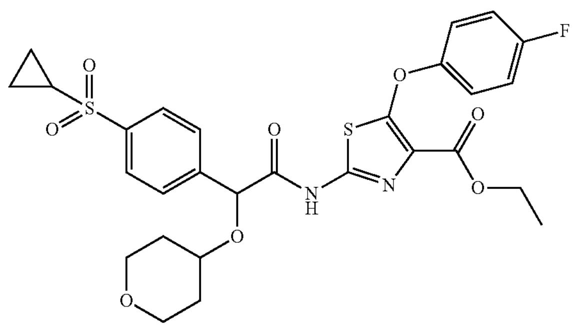 [SMILES: CCOC(=O)c1nc(NC(=O)C(OC2CCOCC2)c2ccc(S(=O)(=O)C3CC3)cc2)sc1Oc1ccc(F)cc1] | 605.1 | Ethyl 2-[[2-(4-cyclopropylsulfonylphenyl)-2-tetrahydropyran-4-yloxy-acetyl]amino]-5-(4-fluorophenoxy)thiazole-4-carboxylate |
| A26 | 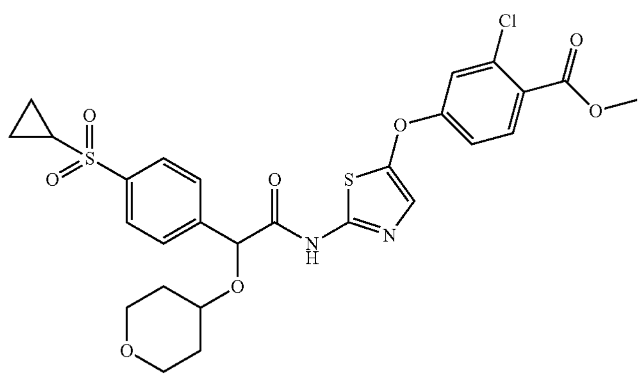 [SMILES: COC(=O)c1ccc(Oc2cnc(NC(=O)C(OC3CCOCC3)c3ccc(S(=O)(=O)C4CC4)cc3)s2)cc1Cl] | 607.2 ($^{35}$Cl) | Methyl 2-chloro-4-[2-[[2-(4-cyclopropylsulfonylphenyl)-2-tetrahydropyran-4-yloxy-acetyl]amino]thiazol-5-yl]oxy-benzoate |
| A27 | 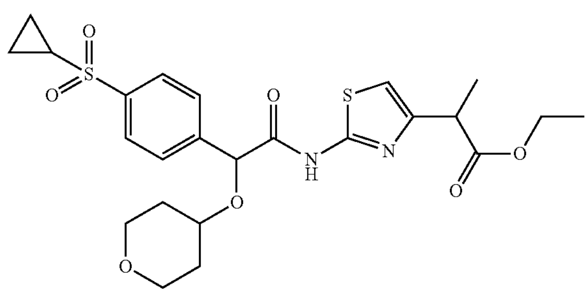 [SMILES: CCOC(=O)C(C)c1csc(NC(=O)C(OC2CCOCC2)c2ccc(S(=O)(=O)C3CC3)cc2)n1] | 523.2 | Ethyl 2-[2-[[2-(4-cyclopropylsulfonylphenyl)-tetrahydropyran-4-yloxy-acetyl]amino]thiazol-4-yl]propanoate |
| A28 | 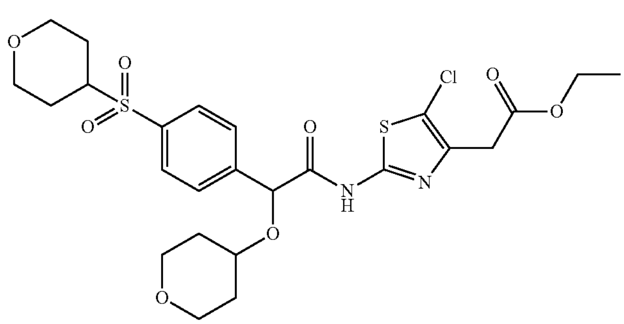 [SMILES: CCOC(=O)Cc1nc(NC(=O)C(OC2CCOCC2)c2ccc(S(=O)(=O)C3CCOCC3)cc2)sc1Cl] | 587.1 ($^{35}$Cl) | Ethyl 2-[5-chloro-2-[[2-tetrahydropyran-4-yloxy-2-(4-tetrahydropyran-4-ylsulfonylphenyl)acetyl]amino]thiazol-4-yl]acetate |

-continued

| Example No. | Structure | MS (EI)m/z: (M + 1). | IUPAC Name |
|---|---|---|---|
| A29 | 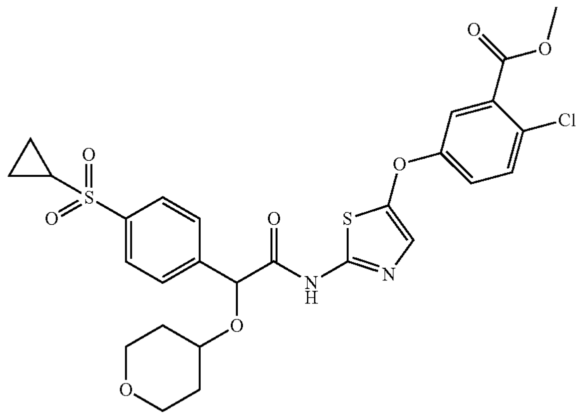 [SMILES: COC(=O)c1cc(Oc2cnc(NC(=O)C(OC3CCOCC3)c3ccc(S(=O)(=O)C4CC4)cc3)s2)ccc1Cl] | 607.1 ($^{35}$Cl) | Methyl 2-chloro-5-[2-[[2-(4-cyclopropylsulfonylphenyl)-2-tetrahydropyran-4-yloxy-acetyl]amino]thiazol-5-yl]oxy-benzoate |
| A30 | 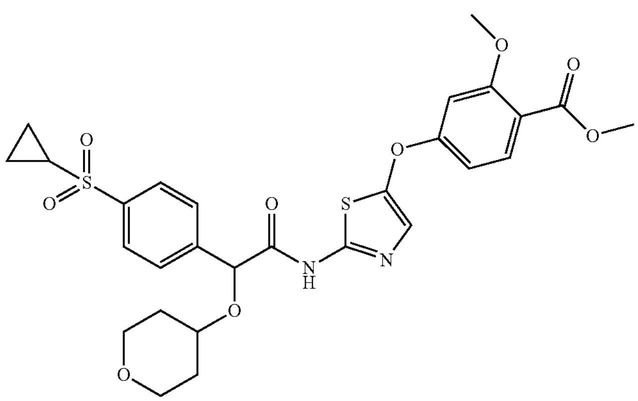 [SMILES: COC(=O)c1ccc(Oc2cnc(NC(=O)C(OC3CCOCC3)c3ccc(S(=O)(=O)C4CC4)cc3)s2)cc1OC] | 603.2 | Methyl 4-[2-[[2-(4-cyclopropylsulfonylphenyl)-2-tetrahydropyran-4-yloxy-acetyl]amino]thiazol-5-yl]oxy-2-methoxy-benzoate |
| A31 | 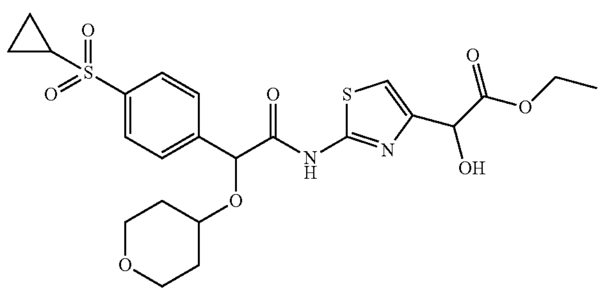 [SMILES: CCOC(=O)C(O)c1csc(NC(=O)C(OC2CCOCC2)c2ccc(S(=O)(=O)C3CC3)cc2)n1] | 525.2 | Ethyl 2-[2-[[2-(4-cyclopropylsulfonylphenyl)-2-tetrahydropyran-4-yloxy-acetyl]amino]thiazol-4-yl]-2-hydroxy-acetate |
| A32 | 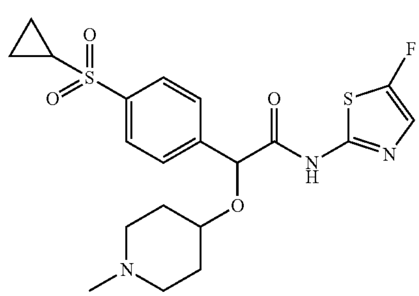 [SMILES: CN1CCC(OC(C(=O)Nc2ncc(F)s2)c2ccc(S(=O)(=O)C3CC3)cc2)CC1] | 454.2 | 2-(4-Cyclopropylsulfonylphenyl)-N-(5-fluorothiazol-2-yl)-2-[(1-methyl-4-piperidyl)oxy]acetamide |

| Example No. | Structure | MS (EI)m/z: (M + 1). | IUPAC Name |
|---|---|---|---|
| A33 | 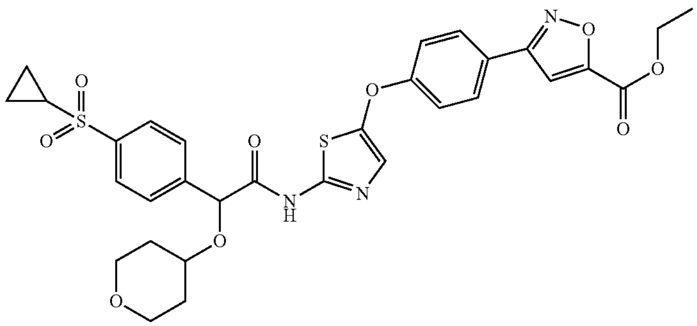 [SMILES: CCOC(=O)c1cc(-c2ccc(Oc3cnc(NC(=O)C(OC4CCOCC4)c4ccc(S(=O)(=O)C5CC5)cc4)s3)cc2)no1] | 654.2 | Ethyl 3-[4-[2-[[2-(4-cyclopropylsulfonylphenyl)-2-tetrahydropyran-4-yloxy-acetyl]amino]thiazol-5-yl]oxyphenyl]isoxazole-5-carboxylate |
| A34 | 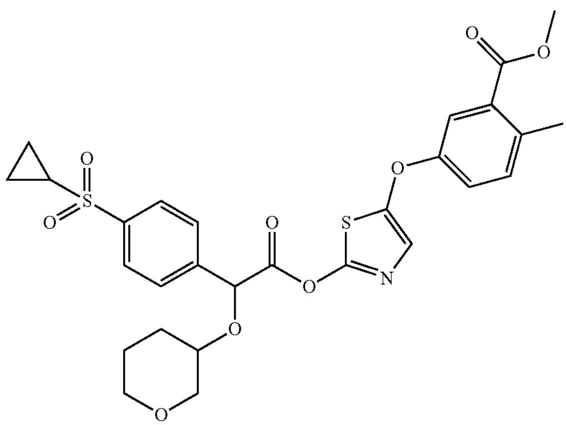 [SMILES: COC(=O)c1cc(Oc2cnc(OC(=O)C(OC3CCCOC3)c3ccc(S(=O)(=O)C4CC4)cc3)s2)ccc1C] | 587.3 | Methyl 5-[2-[2-(4-cyclopropylsulfonylphenyl)-2-tetrahydropyran-3-yloxy-acetyl]oxythiazol-5-yl]oxy-2-methyl-benzoate |
| A35 | 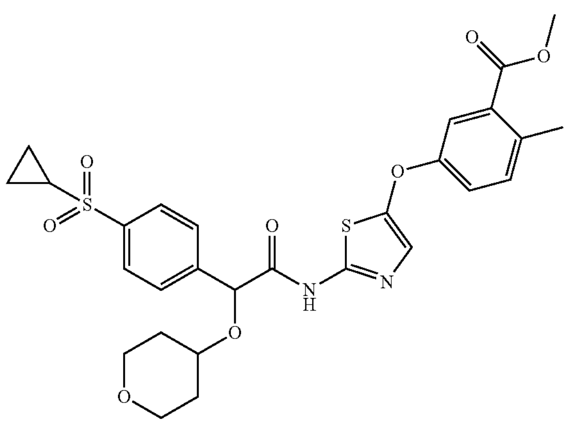 [SMILES: COC(=O)c1cc(Oc2cnc(NC(=O)C(OC3CCOCC3)c3ccc(S(=O)(=O)C4CC4)cc3)s2)ccc1C] | 587.3 | Methyl 5-[2-[[2-(4-cyclopropylsulfonylphenyl)-2-tetrahydropyran-4-yloxy-acetyl]amino]thiazol-5-yl]oxy-methyl-benzoate |
| A36 | 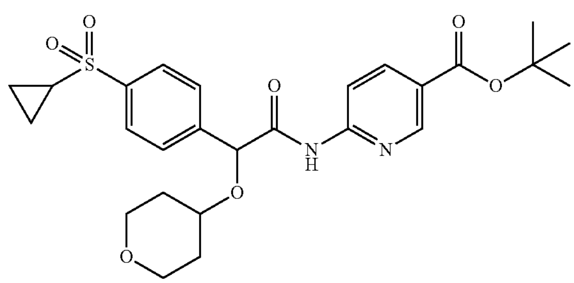 [SMILES: CC(C)(C)OC(=O)c1ccc(NC(=O)C(OC2CCOCC2)c2ccc(S(=O)(=O)C3CC3)cc2)nc1] | 517.3 | tert-Butyl 6-[[2-(4-cyclopropylsulfonylphenyl)-2-tetrahydropyran-4-yloxy-acetyl]amino]pyridine-3-carboxyl |

-continued

| Example No. | Structure | MS (EI)m/z: (M + 1). | IUPAC Name |
|---|---|---|---|
| A37 | Chiral | 573.2 | Methyl 4-[2-[[2-(4-cyclopropylsulfonylphenyl)-2-[(3R)-tetrahydrofuran-3-yl]oxy-acetyl]amino]thiazol-5-yl]oxy-2-methyl-benzoate |
| A38 | 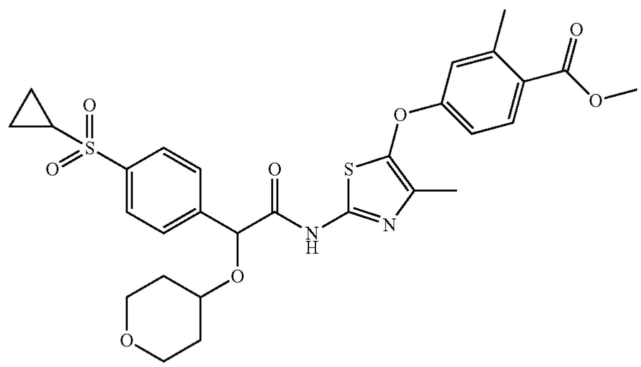 [SMILES: COC(=O)c1ccc(Oc2sc(NC(=O)C(OC3CCOCC3)c3ccc(S(=O)(=O)C4CC4)cc3)nc2C)cc1C] | 601.3 | Methyl 4-[2-[[2-(4-cyclopropylsulfonylphenyl)-2-tetrahydropyran-4-yloxy-acetyl]amino]-4-methyl-thiazol-5-yl]oxy-2-methyl-benzoate |
| A39 | 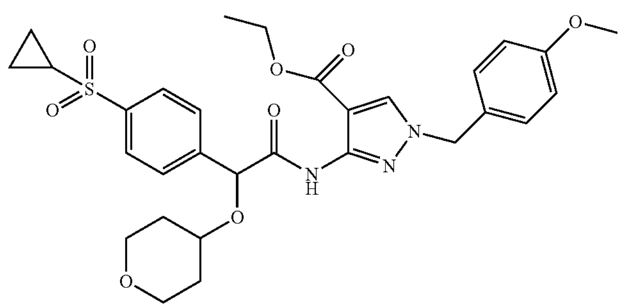 [SMILES: CCOC(=O)c1cn(Cc2ccc(OC)cc2)nc1NC(=O)C(OC1CCOCC1)c1ccc(S(=O)(=O)C2CC2)cc1] | 598.3 | Ethyl 3-[[2-(4-cyclopropylsulfonylphenyl)-2-tetrahydropyran-4-yloxy-acetyl]amino]-1-[(4-methoxyphenyl)methyl]pyrazole-4-carboxylate |
| A40 | 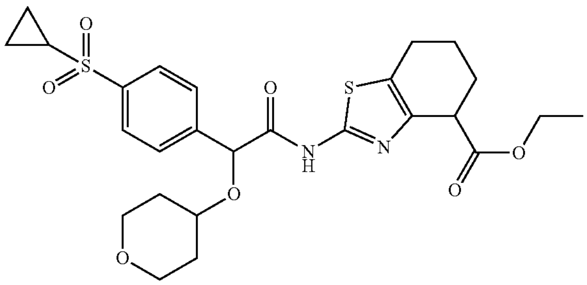 [SMILES: CCOC(=O)C1CCCc2sc(NC(=O)C(OC3CCOCC3)c3ccc(S(=O)(=O)C4CC4)cc3)nc21] | 549.2 | Ethyl 2-[[2-(4-cyclopropylsulfonylphenyl)-2-tetrahydropyran-4-yloxy-acetyl]amino]-4,5,6,7-tetrahydro-1,3-benzothiazole-4-carboxylate |

-continued

| Example No. | Structure | MS (EI)m/z: (M + 1). | IUPAC Name |
|---|---|---|---|
| A41 | 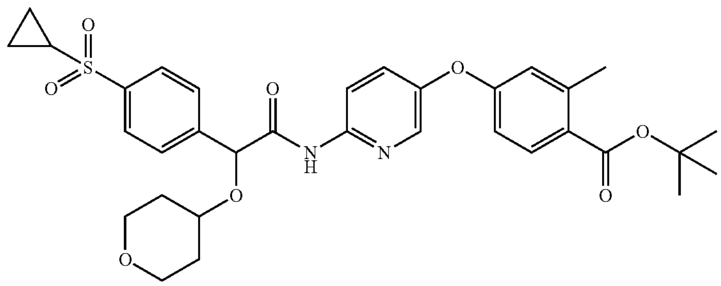 [SMILES: Cc1cc(Oc2ccc(NC(=O)C(OC3CCOCC3)c3ccc(S(=O)(=O)C4CC4)cc3)nc2)ccc1C(=O)OC(C)(C)C] | 623.3 | tert-Butyl 4-[[6-[[2-(4-cyclopropylsulfonylphenyl)-2-tetrahydropyran-4-yloxy-acetyl]amino]-3-pyridyl]oxy]-2-methyl-benzoate |
| A42 | 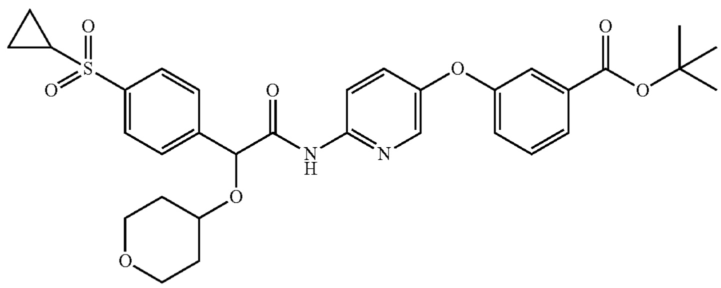 [SMILES: CC(C)(C)OC(=O)c1cccc(Oc2ccc(NC(=O)C(OC3CCOCC3)c3ccc(S(=O)(=O)C4CC4)cc3)nc2)c1] | 609.3 | tert-Butyl 3-[[6-[[2-(4-cyclopropylsulfonylphenyl)-2-tetrahydropyran-4-yloxy-acetyl]amino]-3-pyridyl]oxy]benzoate |
| A43 | 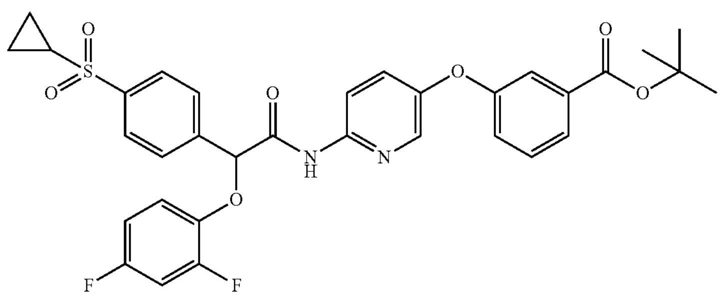 [SMILES: CC(C)(C)OC(=O)c1cccc(Oc2ccc(NC(=O)C(Oc3ccc(F)cc3F)c3ccc(S(=O)(=O)C4CC4)cc3)nc2)c1] | 637.3 | tert-Butyl 3-[[6-[[2-(4-cyclopropylsulfonylphenyl)-2-(2,4-difluorophenoxy)acetyl]amino]-3-pyridyl]oxy]benzoate |
| A44 | 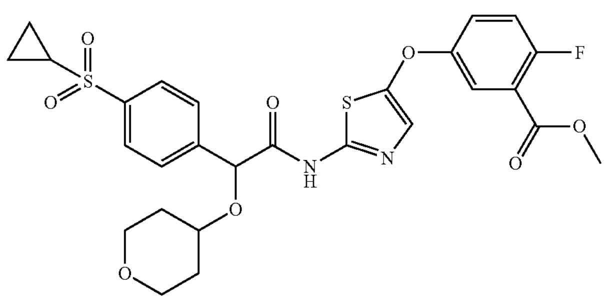 [SMILES: COC(=O)c1cc(Oc2cnc(NC(=O)C(OC3CCOCC3)c3ccc(S(=O)(=O)C4CC4)cc3)s2)ccc1F] | 591.2 | Methyl 5-[2-[[2-(4-cyclopropylsulfonylphenyl)-2-tetrahydropyran-4-yloxy-acetyl]amino]thiazol-5-yl]oxy-2-fluoro-benzoate |
| A45 | 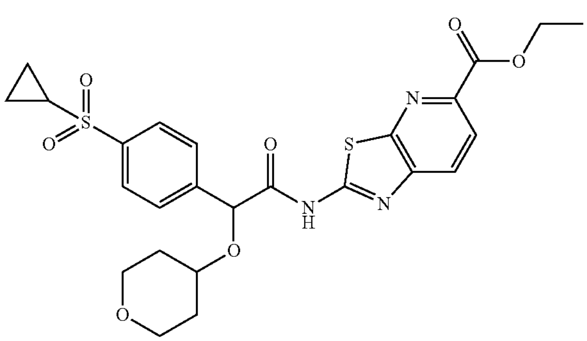 [SMILES: CCOC(=O)c1ccc2nc(NC(=O)C(OC3CCOCC3)c3ccc(S(=O)(=O)C4CC4)cc3)sc2n1] | 546.2 | Ethyl 2-[[2-(4-cyclopropylsulfonylphenyl)-2-tetrahydropyran-4-yloxy-acetyl]amino]thiazolo[5,4-b]pyridine-5-carboxylate |

-continued

| Example No. | Structure | MS (EI)m/z: (M + 1). | IUPAC Name |
|---|---|---|---|
| A46 | 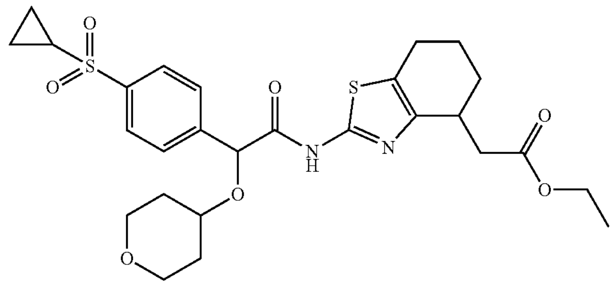 [SMILES: CCOC(=O)CC1CCCc2sc(NC(=O)C(OC3CCOCC3)c3ccc(S(=O)(=O)C4CC4)cc3)nc21] | 563.2 | Ethyl 2-[2-[[2-(4-cyclopropylsulfonylphenyl)-2-tetrahydropyran-4-yloxy-acetyl]amino]-4,5,6,7-tetrahydro-1,3-benzothiazol-4-yl]acetate |
| A47 | 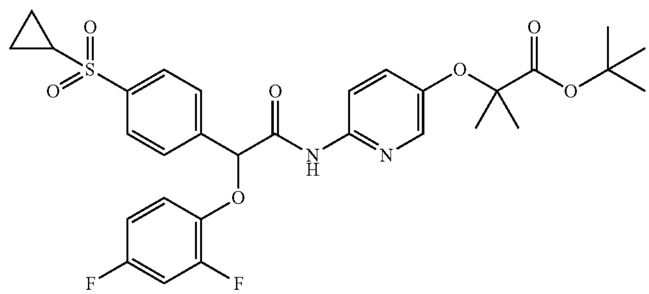 [SMILES: CC(C)(C)OC(=O)C(C)(C)Oc1ccc(NC(=O)C(Oc2ccc(F)cc2F)c2ccc(S(=O)(=O)C3CC3)cc2)nc1] | 603.2 | tert-Butyl 2-[[6-[[2-(4-cyclopropylsulfonylphenyl)-2-(2,4-difluorophenoxy)acetyl]amino]-3-pyridyl]oxy]-2-methyl-propanoate |
| A48 | 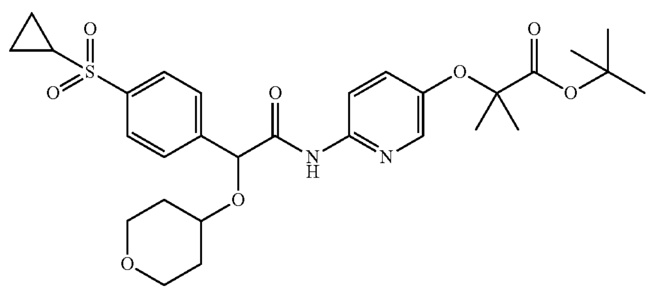 [SMILES: CC(C)(C)OC(=O)C(C)(C)Oc1ccc(NC(=O)C(OC2CCOCC2)c2ccc(S(=O)(=O)C3CC3)cc2)nc1] | 575.2 | tert-Butyl 2-[[6-[[2-(4-cyclopropylsulfonylphenyl)-2-tetrahydropyran-4-yloxy-acetyl]amino]-3-pyridyl]oxy]-2-methyl-propanoate |
| A49 | 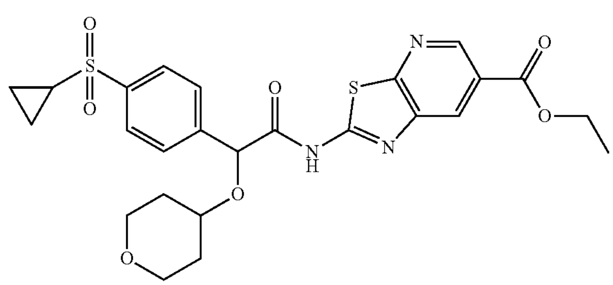 [SMILES: CCOC(=O)c1cnc2sc(NC(=O)C(OC3CCOCC3)c3ccc(S(=O)(=O)C4CC4)cc3)nc2c1] | 546.2 | Ethyl 2-[[2-(4-cyclopropylsulfonylphenyl)-tetrahydropyran-4-yloxy-acetyl]amino]thiazolo[5,4-b]pyridine-6-carboxylate |
| A50 | 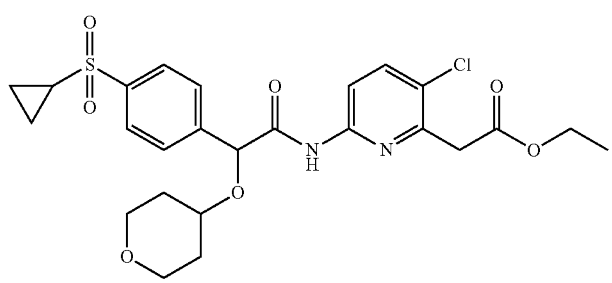 [SMILES: CCOC(=O)Cc1nc(NC(=O)C(OC2CCOCC2)c2ccc(S(=O)(=O)C3CC3)cc2)ccc1Cl] | 536.8 ($^{35}$Cl) | Ethyl 2-[3-chloro-6-[[2-(4-cyclopropylsulfonylphenyl)-2-tetrahydropyran-4-yloxy-acetyl]amino]-2-pyridyl]acetate |

| Example No. | Structure | MS (EI)m/z: (M + 1) | IUPAC Name |
|---|---|---|---|
| A51 | 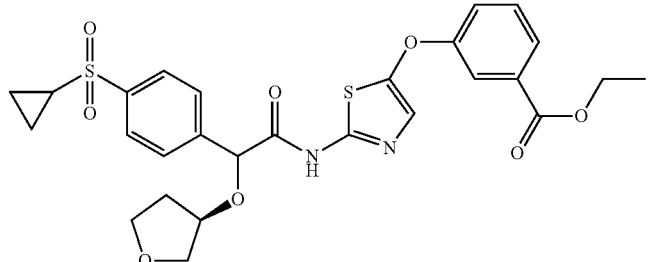 Chiral | 573.1 | Ethyl 3-[2-[[2-(4-cyclopropylsulfonylphenyl)-2-[(3R)-tetrahydrofuran-3-yl]oxy-acetyl]amino]thiazol-5-yl]oxybenzoate |
| A52 | 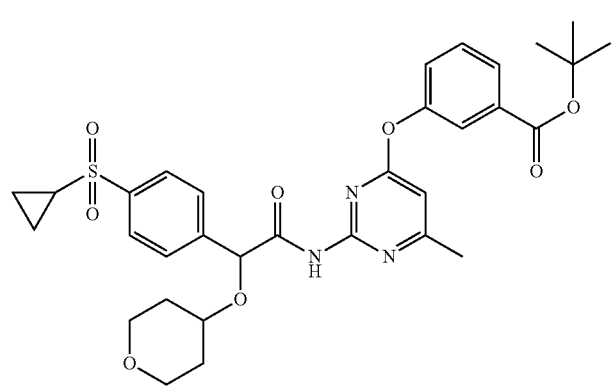 [SMILES: Cc1cc(Oc2cccc(C(=O)OC(C)(C)C)c2)nc(NC(=O)C(OC2CCOCC2)c2ccc(S(=O)(=O)C3CC3)cc2)n1] | 624.2 | tert-Butyl 3-[2-[[2-(4-cyclopropylsulfonylphenyl)-2-tetrahydropyran-4-yloxy-acetyl]amino]-6-methyl-pyrimidin 4-yl]oxybenzoate |
| A53 | 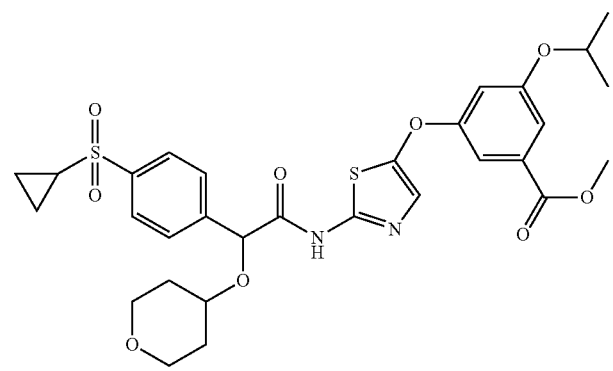 [SMILES: COC(=O)c1cc(Oc2cnc(NC(=O)C(OC3CCOCC3)c3ccc(S(=O)(=O)C4CC4)cc3)s2)cc(OC(C)C)c1] | 631.2 | Methyl 3-[2-[[2-(4-cyclopropylsulfonylphenyl)-2-tetrahydropyran-4-yloxy-acetyl]amino]thiazol-5-yl]oxy-5-isopropoxy-benzoate |
| A54 | 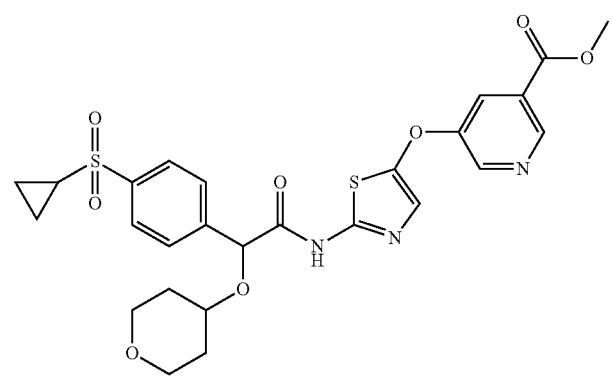 [SMILES: COC(=O)c1cncc(Oc2cnc(NC(=O)C(OC3CCOCC3)c3ccc(S(=O)(=O)C4CC4)cc3)s2)c1] | 574.1 | Methyl 5-[2-[[2-(4-cyclopropylsulfonylphenyl)-2-tetrahydropyran-4-yloxy-acetyl]amino]thiazol-5-yl]oxypyridine-3-carboxylate |

| Example No. | Structure | MS (EI)m/z: (M + 1) | IUPAC Name |
|---|---|---|---|
| A55 | 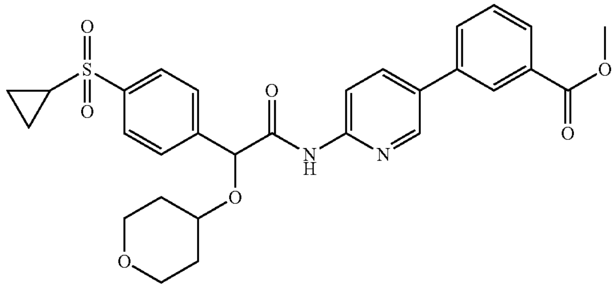 [SMILES: COC(=O)c1cccc(-c2ccc(NC(=O)C(OC3CCOCC3)c3ccc(S(=O)(=O)C4CC4)cc3)nc2)c1] | 551.2 | Methyl 3-[6-[[2-(4-cyclopropylsulfonylphenyl)-2-tetrahydropyran-4-yloxy-acetyl]amino]-3-pyridyl]benzoate |
| A56 | 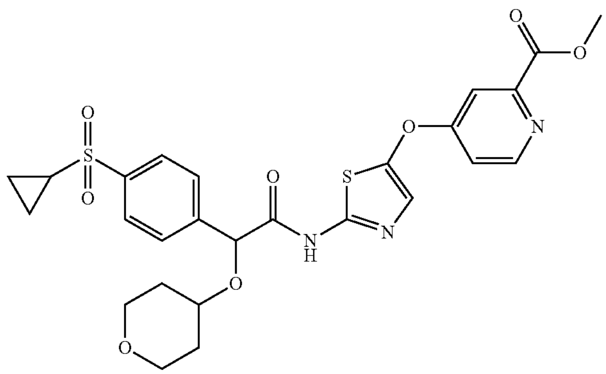 | 574.1 | Methyl 4-[2-[[2-(4-cyclopropylsulfonylphenyl)-2-tetrahydropyran-4-yloxy-acetyl]amino]thiazol-5-yl]oxypyridine-2-carboxylate |
| A57 | 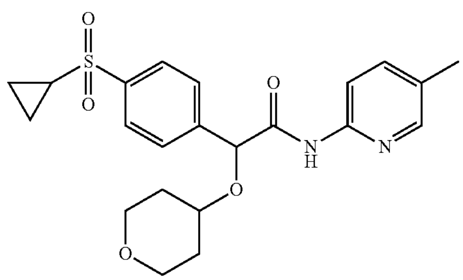 [SMILES: Cc1ccc(NC(=O)C(OC2CCOCC2)c2ccc(S(=O)(=O)C3CC3)cc2)nc1] | 431.2 | 2-(4-Cyclopropylsulfonylphenyl)-N-(5-methyl-2-pyridyl)-2-tetrahydropyran-4-yloxy-acetamide |
| A58 | 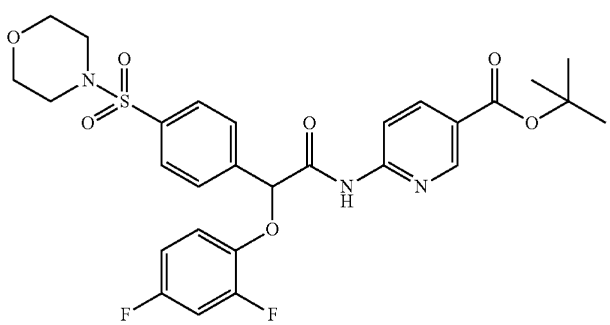 [SMILES: CC(C)(C)OC(=O)c1ccc(NC(=O)C(Oc2ccc(F)cc2F)c2ccc(S(=O)(=O)N3CCOCC3)cc2)nc1] | 590.5 | tert-Butyl 6-[[2-(2,4-difluorophenoxy)-2-(4-morpholinosulfonylphenyl)acetyl]amino]pyridine-3-carboxylate |
| A59 | 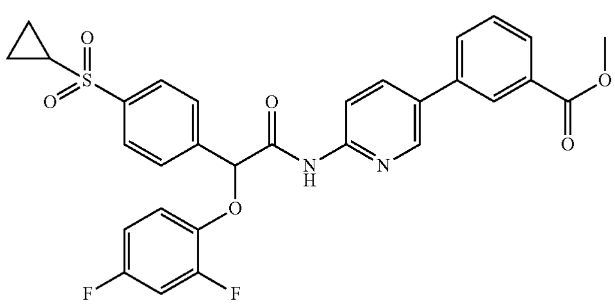 [SMILES: COC(=O)c1cccc(-c2ccc(NC(=O)C(Oc3ccc(F)cc3F)c3ccc(S(=O)(=O)C4CC4)cc3)nc2)c1] | 578.5 | Methyl 3-[6-[[2-(4-cyclopropylsulfonylphenyl)-2-(2,4-difluorophenoxy)acetyl]amino]-3-pyridyl]benzoate |

-continued

| Example No. | Structure | MS (EI)m/z: (M + 1). | IUPAC Name |
|---|---|---|---|
| A60 | 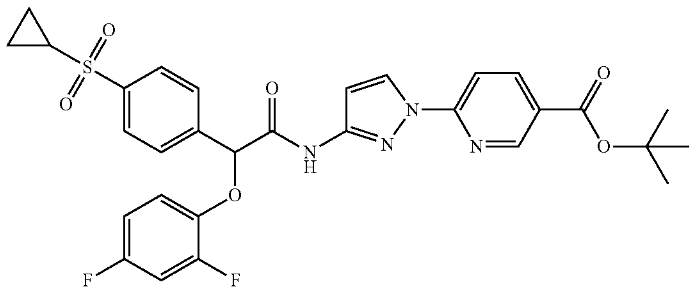 [SMILES: CC(C)(C)OC(=O)c1ccc(-n2ccc(NC(=O)C(Oc3ccc(F)cc3F)c3ccc(S(=O)(=O)C4CC4)cc3)n2)nc1] | 611.2 | tert-Butyl 6-[3-[[2-(4-cyclopropylsulfonylphenyl)-2-(2,4-difluorophenoxy)acetyl]amino]pyrazol-1-yl]pyridine-3-carboxylate |
| A61 | 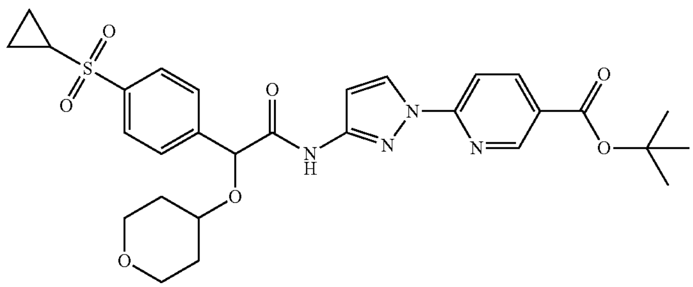 [SMILES: CC(C)(C)OC(=O)c1ccc(-n2ccc(NC(=O)C(OC3CCOCC3)c3ccc(S(=O)(=O)C4CC4)cc3)n2)nc1] | 583.2 | tert-Butyl 6-[3-[[2-(4-cyclopropylsulfonylphenyl)-2-tetrahydropyran-4-yloxy-acetyl]amino]pyrazol-1-yl]pyridine-3-carboxylate |
| A62 | 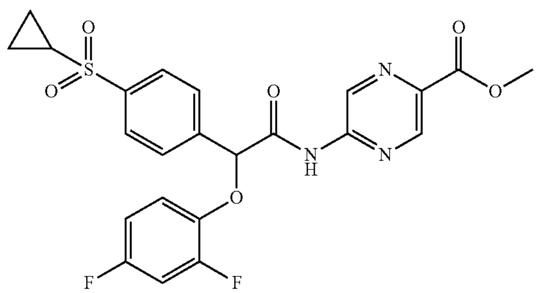 [SMILES: COC(=O)c1cnc(NC(=O)C(Oc2ccc(F)cc2F)c2ccc(S(=O)(=O)C3CC3)cc2)cn1] | 504.1 | Methyl 5-[[2-(4-cyclopropylsulfonylphenyl)-2-(2,4-difluorophenoxy)acetyl]amino]pyrazine-2-carboxylate |
| A63 | 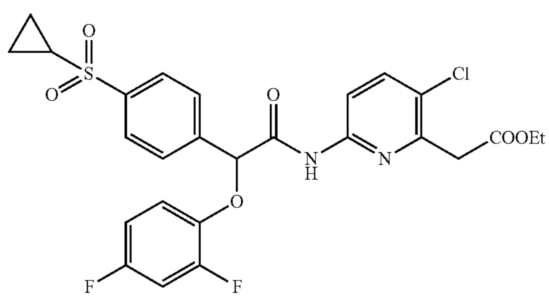 [SMILES: CCOC(=O)Cc1nc(NC(=O)C(Oc2ccc(F)cc2F)c2ccc(S(=O)(=O)C3CC3)cc2)ccc1Cl] | 565.2 ($^{35}$Cl) | Ethyl 2-[3-chloro-6-[[2-(4-cyclopropylsulfonylphenyl)-2-(2,4-difluorophenoxy)acetyl]amino]-2-pyridyl]acetate |
| A64 | 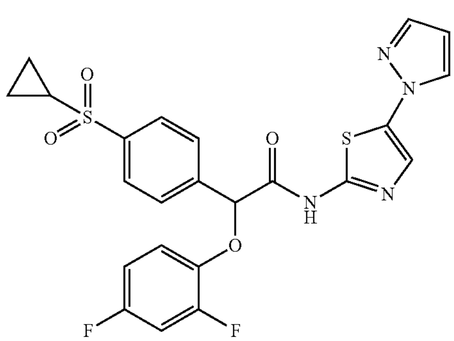 [SMILES: O=C(Nc1ncc(-n2cccn2)s1)C(Oc1ccc(F)cc1F)c1ccc(S(=O)(=O)C2CC2)cc1] | 517.1 | 2-(4-cyclopropylsulfonylphenyl)-2-(2,4-difluorophenoxy)-N-(5-pyrazol-1-ylthiazol-2-yl)acetamide |

-continued

| Example No. | Structure | MS (EI)m/z: (M + 1). | IUPAC Name |
|---|---|---|---|
| A65 | Chiral | 573.3 | 5-[2-[[2-(4-cyclopropylsulfonylphenyl)-2-[(3R)-tetrahydrofuran-3-yl]oxy-acetyl]amino]thiazol-5-yl]oxy-2-methyl-benzoic acid |
| A66 | 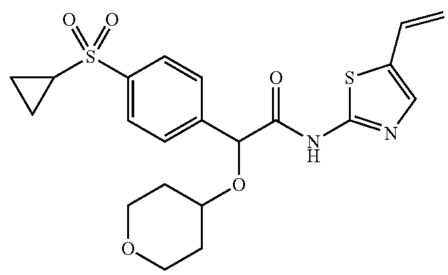 [SMILES: C=Cc1cnc(NC(=O)C(OC2CCOCC2)c2ccc(S(=O)(=O)C3CC3)cc2)s1] | NA | 2-(4-cyclopropylsulfonylphenyl)-2-tetrahydropyran-4-yloxy-N-(5-vinylthiazol-2-yl)acetamide |
| A67 | 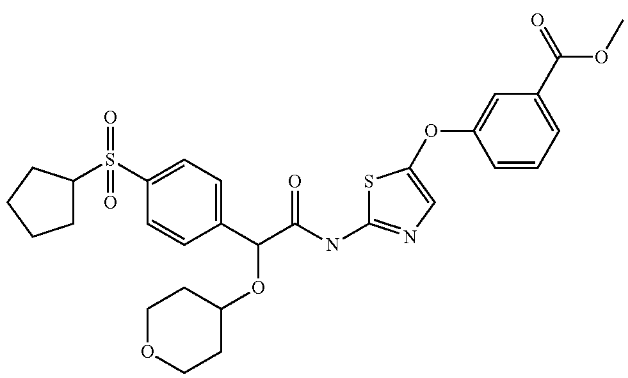 [SMILES: COC(=O)c1cccc(Oc2cnc(NC(=O)C(OC3CCOCC3)c3ccc(S(=O)(=O)C4CCCC4)cc3)s2)c1] | 601.1 | Methyl 3-[2-[[2-(4-cyclopentylsulfonylphenyl)-2-tetrahydropyran-4-yloxy-acetyl]amino]thiazol-5-yl]oxybenzoate |
| A68 | Chiral | 573.3 | Ethyl 3-[2-[[2-(4-cyclopropylsulfonylphenyl)-2-[(3S)-tetrahydrofuran-3-yl]oxy-acetyl]amino]thiazol-5-yl]oxybenzoate |

-continued

| Example No. | Structure | MS (EI)m/z: (M + 1). | IUPAC Name |
|---|---|---|---|
| A69 | 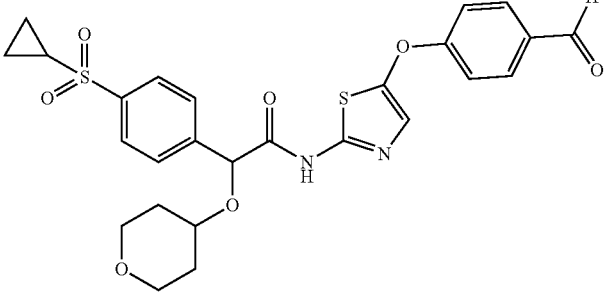 | NA | 2-(4-cyclopropylsulfonylphenyl)-N-[5-(4-formylphenoxy)thiazol-2-yl]-2-tetrahydropyran-4-yloxy-acetamide |
| A70 | 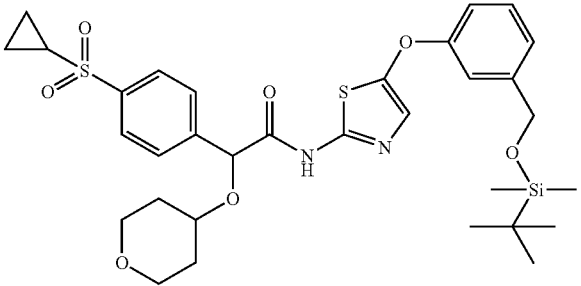 [SMILES: CC(C)(C)[Si](C)(C)OCc1cccc(Oc2cnc(NC(=O)C(OC3CCOCC3)c3ccc(S(=O)(=O)C4CC4)cc3)s2)c1] | 659.2 | N-[5-[3-[[tert-butyl(dimethyl)silyl]oxymethyl]phenoxy]thiazol-2-yl]-2-(4-cyclopropylsulfonylphenyl)-2-tetrahydropyran-4-yloxy-acetamide |
| A71 | 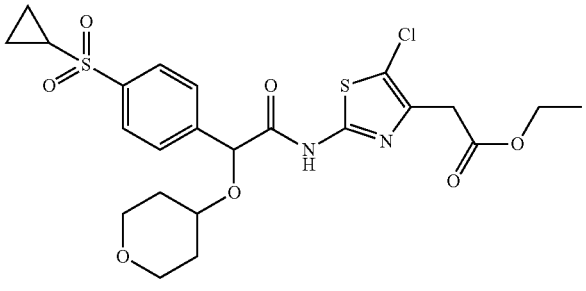 [SMILES: CCOC(=O)Cc1nc(NC(=O)C(OC2CCOCC2)c2ccc(S(=O)(=O)C3CC3)cc2)sc1Cl] | NA | ethyl 2-[5-chloro-2-[[2-(4-cyclopropylsulfonylphenyl)-2-tetrahydropyran-4-yloxy-acetyl]amino]thiazol-4-yl]acetate |
| A72 | 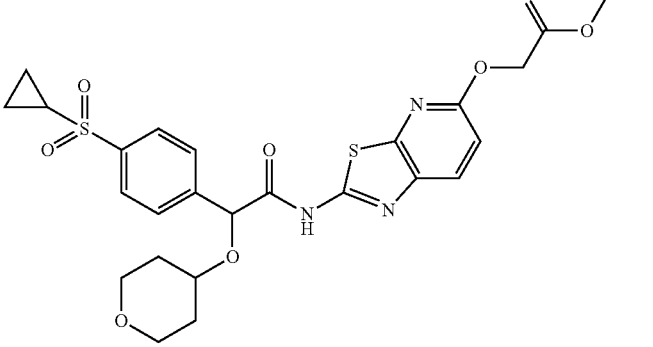 | NA | ethyl 2-[2-[[2-(4-cyclopropylsulfonylphenyl)-2-tetrahydropyran-4-yloxy-acetyl]amino]thiazolo[5,4-b]pyridin-5-yl]oxyacetate |
| A73 | 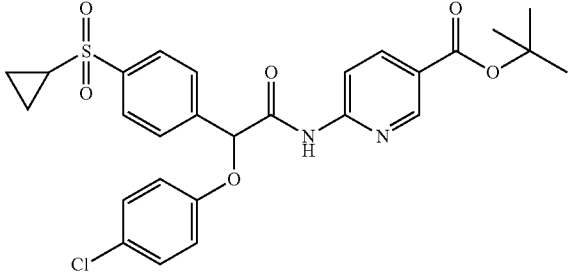 [SMILES: CC(C)(C)OC(=O)c1ccc(NC(=O)C(Oc2ccc(Cl)cc2)c2ccc(S(=O)(=O)C3CC3)cc2)nc1] | 542.6 ($^{35}$Cl) | tert-butyl 6-[[2-(4-chlorophenoxy)-2-(4-cyclopropylsulfonylphenyl)acetyl]amino]pyridine-3-carboxylate |

| Example No. | Structure | MS (EI)m/z: (M + 1). | IUPAC Name |
|---|---|---|---|
| A74 | 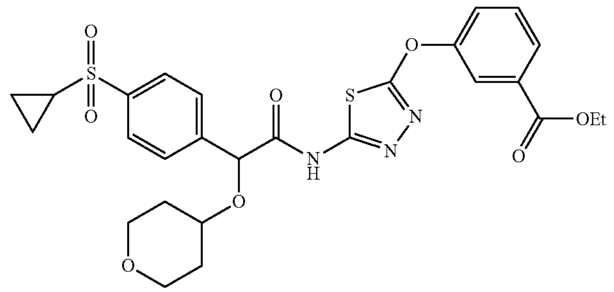 [SMILES: CCOC(=O)c1cccc(Oc2nnc(NC(=O)C(OC3CCOCC3)c3ccc(S(=O)(=O)C4CC4)cc3)s2)c1] | 588.2 | ethyl 3-[[5-[[2-(4-cyclopropylsulfonylphenyl)-2 tetrahydropyran-4-yloxy-acetyl]amino]-1,3,4-thiadiazol-2-yl]oxy]benzoate |

Example B1

3-[2-[[2-(4-Cyclopropylsulfonylphenyl)-2-tetrahydropyran-4-yloxy-acetyl]amino]thiazol-5-yl]oxybenzoic acid

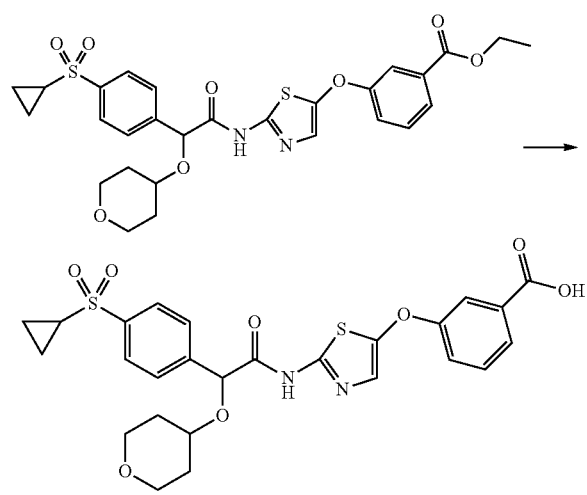

Ethyl3-[2-[[2-(4-cyclopropylsulfonylphenyl)-2-tetrahydropyran-4-yloxy-acetyl]amino]thiazol-5-yl]oxybenzoate (Example A2; 16 g, 27 mmol) was taken in THF (200 mL) and Methanol (100 mL) in a 1 L single necked round bottom flask at 20-25° C. To it was added solution of LiOH (11.44 g in 200 mL water, 272 mmol) slowly under vigorous stirring for 15 minutes and further continued to stir for 16 hours. Completion of reaction was confirmed by TLC. Organic solvent was removed under reduced pressure. The obtained residue was diluted with water (200 mL) and washed with ethyl acetate (2×150 mL). The aqueous layer was acidified with 1N HCl to pH 1-2 and extracted with Ethyl acetate (3×150 mL). The combined organic layer was washed with brine (150 mL) dried over anhydrous sodium sulphate and the solvent was removed under vacuum to get the pure product.

$^1$H NMR (400 MHz, DMSO-$d_6$): δ 1.0-1.08 (m, 2H), 1.10-1.15 (m, 2H), 1.44-1.61 (m, 2H), 1.83-1.96 (m, 2H), 2.82-2.91 (m, 1H), 3.27-3.37 (m, 2H), 3.62-3.70 (m, 1H), 3.75-3.86 (m, 2H), 5.49 (s, 1H), 7.30-7.36 (m, 2H), 7.46 (t, J=7.8 Hz, 1H), 7.50-7.53 (m, 1H), 7.69 (d, J=7.8 Hz, 1H), 7.77 (d, J=8.4 Hz, 2H), 7.92 (d, J=8.3 Hz, 2H), 12.60 (bs, 1H); MS (EI) m/z: 559.2 (M+1).

Example B2

4 5-[2-[[2-(4-cyclopropylsulfonylphenyl)-2-[(3R)-tetrahydrofuran-3-yl]oxy-acetyl]amino]thiazol-5-yl]oxy-2-methyl-benzoic acid

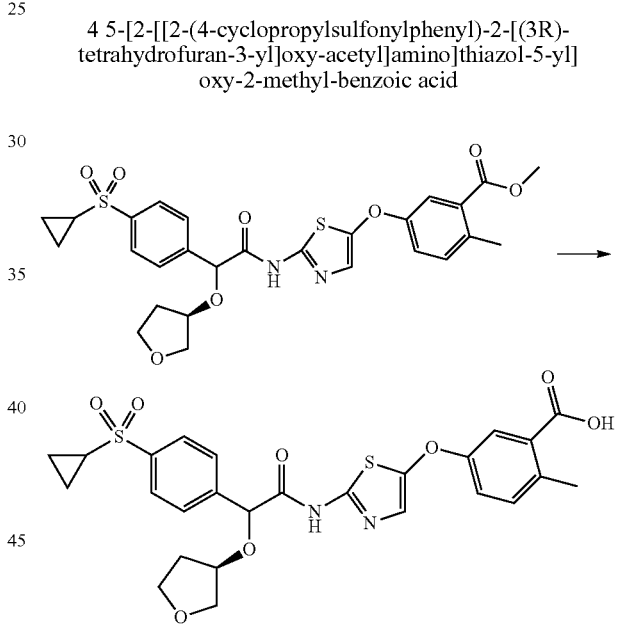

5-[2-[[2-(4-cyclopropylsulfonylphenyl)-2-[(3R)-tetrahydrofuran-3-yl]oxy-acetyl]amino]thiazol-5-yl]oxy-2-methyl-benzoic acid methyl ester (Example A3; 0.300 g, 0.524 mmol) was taken in THF(4 mL) and MeOH (0.1 mL), to it was added aqueous solution of LiOH (0.110 g, 2.62 mmol in 7 mL water) and stirred for 1-4 h at room temperature. After completion of the reaction, organic solvent was removed under reduced pressure. The aqueous layer was washed with diisopropyl ether then acidified with 1 N HCl to pH 2. The solid formed was filtered, washed with water, followed by washing with diisopropyl ether & dried under vacuum to get the title compound (0.260 g).

$^1$H NMR (400 MHz, DMSO-$d_6$): δ 1.03-1.04 (m, 2H), 1.07-1.11 (m, 2H), 1.96-1.99 (m, 2H), 2.50 (s, 3H), 2.86 (m, 1H), 3.61-3.81 (m, 4H), 4.25 (m, 1H), 5.37 (s, 1H), 7.23 (m, J=7.6 Hz, 1H), 7.31 (m, 2H), 7.46 (s, 1H), 7.75 (d, J=7.6 Hz, 2H), 7.93 (d, J=8.0 Hz, 2H), 12.6 (bs, 1H), 13.1 (bs, 1H); HPLC-MS (EI) m/z: 559.2 (M+1).

Example B3

1-[2-[[2-(4-cyclopropylsulfonylphenyl)-2-tetrahydropyran-4-yloxy-acetyl]amino]thiazol-5-yl]pyrazole-4-carboxylic acid

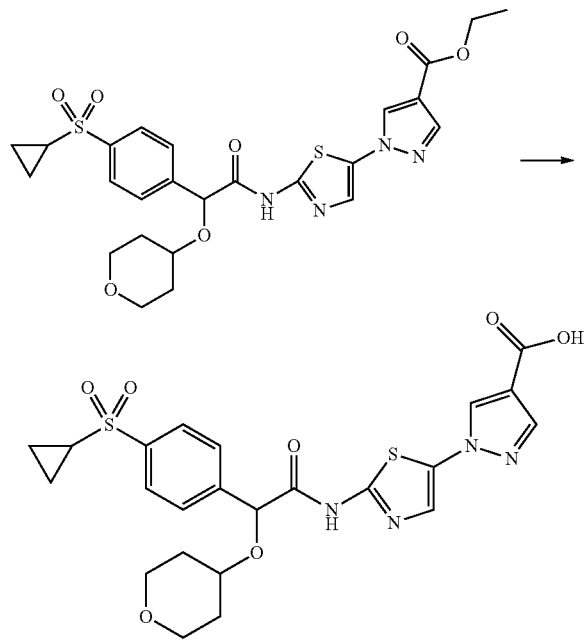

The compound of example B3 was obtained by similar method described in example B1 using 1-[2-[[2-(4-cyclopropylsulfonylphenyl)-2-tetrahydropyran-4-yloxyacetyl]amino]thiazol-5-yl]pyrazole-4-carboxylic acid ethyl ester. (Example A5; 0.90 g, 1.607 mmol), LiOH (0.337 g, 8.03 mmol) in Water:THF:MeOH (2:1:0.2 20 mL) to provide the title compound (0.575 g).

$^1$H NMR (400 MHz, DMSO-d$_6$): δ 1.02-1.04 (m, 2H), 1.05-1.11 (m, 2H), 1.49-1.58 (m, 2H), 1.85-1.92 (m, 2H), 2.86 (m, 1H), 3.34-3.36 (m, 2H), 3.64-3.69 (m, 1H), 3.78-3.85 (m, 2H), 5.52 (s, 1H), 7.79 (d, J=8.0 Hz, 2H), 7.93 (d, aromatics, 3H), 8.03 (s, 1H), 8.89 (bs 1H), 12.7 (bs, 2H); HPLC-MS (EI) m/z: 533.3 (M+1).

Example B4

2-[[2-(4-cyclopropylsulfonylphenyl)-2-tetrahydropyran-4-yloxy-acetyl]amino]-4,5,6,7-tetrahydro-1,3-benzothiazole-6-carboxylic acid

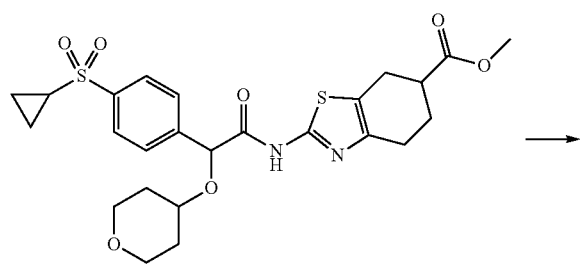

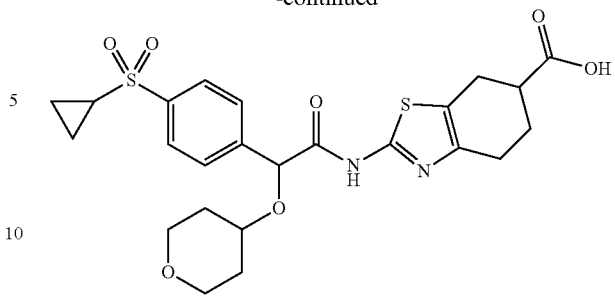

The compound of example B4 was obtained by similar method described in example B1 using ethyl 2-[[2-(4-cyclopropylsulfonylphenyl)-2-tetrahydropyran-4-yloxy-acetyl]amino]-4,5,6,7-tetrahydro-1,3-benzothiazole-6-carboxylate (ExampleA6; 0.200 g, 0.401 mmol); LiOH (0.034 g, 0.81 mmol) in Water:THF (3:10 mL) to provide the title compound (0.160 g).

$^1$H NMR (400 MHz, DMSO-d$_6$): δ 0.99-1.07 (m, 2H), 1.07-1.12 (m, 2H), 1.45-1.61 (m, 2H), 1.75-1.96 (m, 3H), 2.05-2.15 (m, 1H), 2.57-2.66 (m, 2H), 2.68-2.92 (m, 4H), 3.27-3.34 (m, 2H), 3.58-3.68 (m, 1H), 3.75-3.85 (m, 2H), 5.40 (s, 1H), 7.76 (d, J=8.4 Hz, 2H), 7.92 (d, J=8.4 Hz, 2H), 12.3 (bs, 1H), 12.4 (bs, 1H); MS (EI) m/z: 521.2 (M+1).

Example B5

6-[[2-(4-cyclopropylsulfonylphenyl)-2-(2,4-difluorophenoxy)acetyl]amino]pyridine-3-carboxylic acid

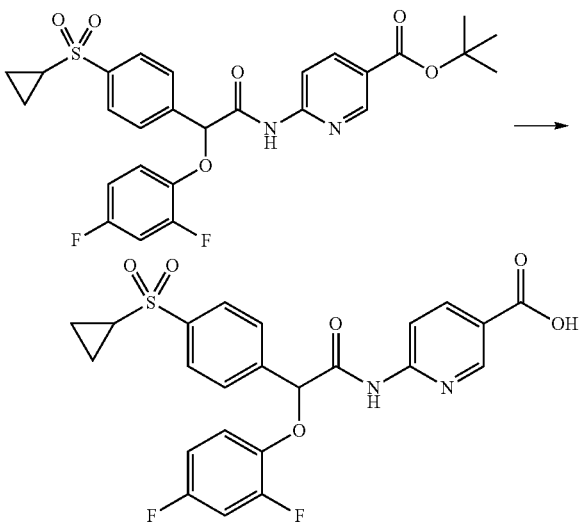

To a solution of tert-butyl 6-[[2-(4-cyclopropylsulfonylphenyl)-2-(2,4-difluorophenoxy)acetyl]amino]pyridine-3-carboxylate (Example A7; 1.6 g, 2.94 mmole) in DCM (5 mL) was added TFA (7 mL) dropwise at 0° C. Reaction mixture was stirred at rt for 3 hr. TFA was removed invaccuo, residue was neutralised using sat.NaHCO$_3$ solution, extracted with ethyl acetate (3×25 mL) washed with brine, dried over anhydrous sodium sulfate and concentrated. Crude solid was triturated in diisopropyl ether and filtered washed with diisopropyl ether to afford pure product (1.2 g).

$^1$H NMR (400 MHz, DMSO d$_6$): δ 1.02-1.08 (m, 2H), 1.09-1.14 (m, 2H), 2.83-2.90 (m, 1H), 6.26 (s, 1H), 7.03-7.08

(m, 1H), 7.11-7.17 (m, 1H), 7.36-7.42 (m, 1H), 7.92 (d, J=8.4 Hz, 2H), 7.99 (d, J=8.4 Hz, 2H), 8.25 (dd, J=2.2 Hz, 1H), 8.84 (d, J=2.4 Hz, 1H), 11.53 (br. s, 1H), 13.26 (br.s, 1H).

MS (EI) m/z: 489.2 (M+1).

Example B6

6-[[2-(4-cyclopropylsulfonylphenyl)-2-(2,4-difluoroanilino)acetyl]amino]pyridine-3-carboxylic acid

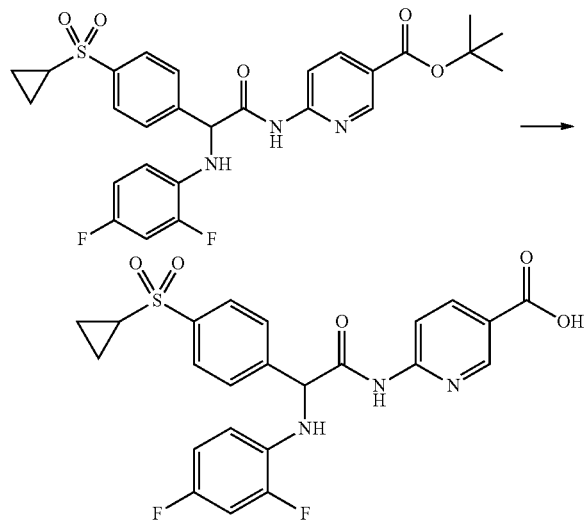

To a solution of tert-butyl 6-[[2-(4-cyclopropylsulfonylphenyl)-2-(2,4-difluoroanilino)acetyl]amino]pyridine-3-carboxylate (Example A8; 31 mg, 0.057 mmole) in DCM (1 mL) was added TFA at 0° C. Reaction mixture was stirred at rt for 1 hr. TFA was removed invaccuo, residue was neutralised using sat.NaHCO₃ solution, extracted with ethyl acetate (3×10 mL) washed with brine, dried over anhydrous sodium sulfate and concentrated. Product was purified using preparative TLC, provided title compound (0.005 g).

¹H NMR (400 MHz, DMSO-d₆): δ 0.99-1.01 (m, 2H), 1.07-1.10 (m, 2H), 2.79-2.85 (m, 1H), 5.60 (d, J=8.6 Hz, 1H), 5.91 (d, J=9.0 Hz, 1H), 6.62-6.68 (m, 1H), 6.83-6.87 (m, 1H), 7.12-7.18 (m, 1H), 7.87 (app. q, J=8.5 Hz, 4H), 8.03 (d, J=8.6 Hz, 1H), 8.18 (dd, J=8.6.2 Hz, 1H), 8.76 (s, 1H), 11.26 (bs, 1H). HPLC-MS (EI) m/z: 488.1 (M+1),

Example B7

2-[6-[[2-(4-cyclopropylsulfonylphenyl)-2-tetrahydropyran-4-yloxy-acetyl]amino]-2-pyridyl]acetic acid

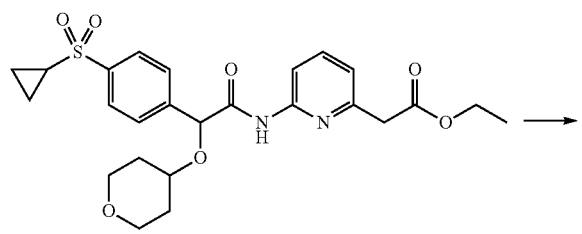

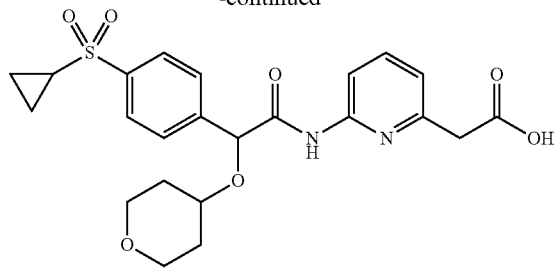

Ethyl 2-[6-[[2-(4-cyclopropylsulfonylphenyl)-2-tetrahydropyran-4-yloxy-acetyl]amino]-2-pyridyl]acetate (Example A9; 0.4 g, 0.796 mmol) was taken in THF(12 mL) and EtOH (4 mL), to it was added aqueous solution of LiOH (0.033 g, 0.796 mmol in 4 mL water) and stirred for 1 h at room temperature. Completion of reaction was confirmed by TLC. Organic solvent was removed under reduced pressure. The obtained residue was diluted with water (50 mL) and washed with ethyl acetate (2×20 mL). The aqueous layer was acidified with 1N HCl to pH 1-2 and extracted with Ethyl acetate (3×50 mL). The combined organic layer was washed with brine (50 mL) dried over anhydrous sodium sulphate and the solvent was removed under vacuum to get the pure product (0.320 g).

¹H NMR (400 MHz, DMSO-d₆): δ 1.0-1.07 (m, 2H), 1.08-1.13 (m, 2H), 1.45-1.61 (m, 2H), 1.85-1.98 (m, 2H), 2.80-2.88 (m, 1H), 3.3-3.39 (m, 2H), 3.61-3.68 (m, 1H), 3.69 (s, 2H), 3.76-3.87 (m, 2H), 5.53 (s, 1H), 7.10 (d, J=7.4 Hz, 1H), 7.74 (t, J=7.9 Hz, 1H), 7.79 (d, J=8.3 Hz, 2H), 7.91 (d, J=8.3 Hz, 3H), 10.56 (s, 1H), 12.46 (bs, 1H).

HPLC-MS (EI) m/z: 475.2 (M+1).

Example B8

3-[2-[[2-(6-cyclopentylsulfonyl-3-pyridyl)-2-tetrahydropyran-4-yloxy-acetyl]amino]thiazol-5-yl]oxybenzoic acid

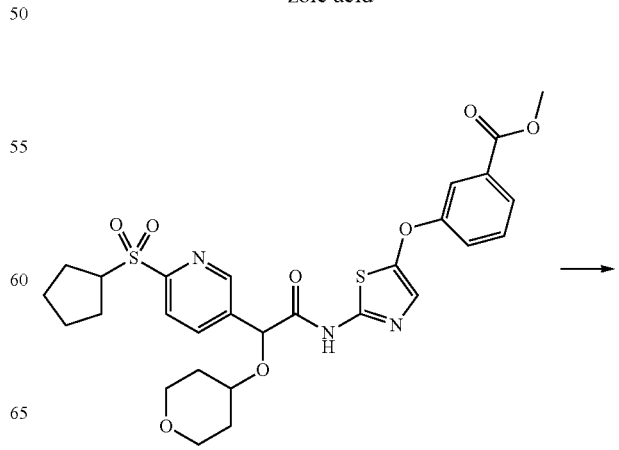

-continued

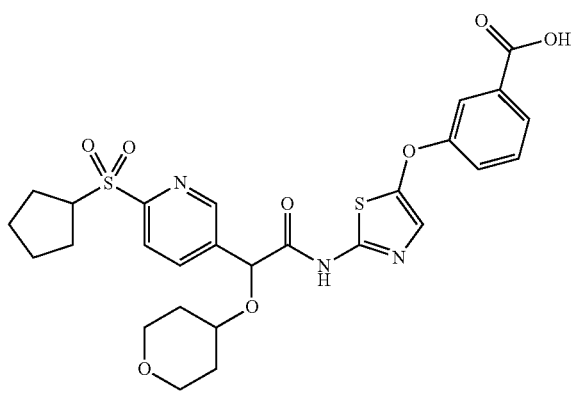

The compound of example B8 was obtained by similar method described in example B1 using 3-[2-[[2-(6-cyclopentylsulfonyl-3-pyridyl)-2-tetrahydropyran-4-yloxy-acetyl]amino]thiazol-5-yl]oxybenzoic acid methyl ester (Example A10; 0.140 g, 0.232 mmol), LiOH (0.049 g, 1.16 mmol) in Water:THF:MeOH (2:1:0.2 8 mL) to provide the title compound (0.100 g).

$^1$H NMR (400 MHz, DMSO-$d_6$): δ 1.46-1.62 (m, 6H), 1.84-1.94 (m, 6H), 3.27-3.33 (m, 2H), 3.67-3.70 (m, 1H), 3.76-3.83 (m, 2H), 4.02-4.06 (m, 1H), 5.56 (s, 1H), 7.37-(s, 1H), 7.38-7.40 (m, 1H), 7.48-7.52 (m, 2H), 7.70 (d, J=7.6 Hz, 1H), 8.09 (d, J=8.0 Hz, 1H), 8.21 (d, J=8.0 Hz, 1H) 8.88 (s, 1H), 12.5 (bs, 1H), 13.20 (bs, 1H); HPLC-MS (EI) m/z: 588.3 (M+1).

Examples B9 to B61 were prepared in analogues manner of examples B1-B8 from the appropriate intermediate that are available commercially or synthesized as above.

| Example No. | Structure | MS (EI) m/z: (M + 1). | IUPAC Name |
|---|---|---|---|
| B9 | 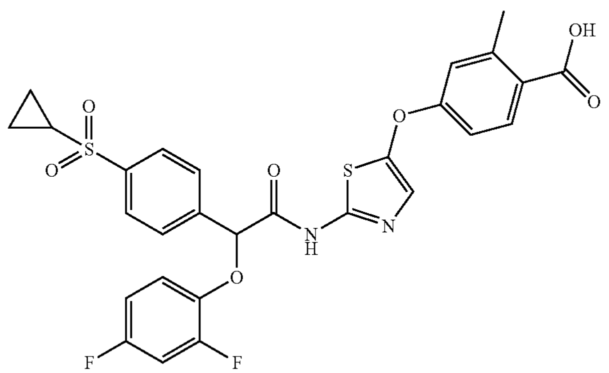 [SMILES: Cc1cc(Oc2cnc(NC(=O)C(Oc3ccc(F)cc3F)c3ccc(S(=O)(=O)C4CC4)cc3)s2)ccc1C(=O)O] | 601.1 | 4-[2-[[2-(4-cyclopropylsulfonylphenyl)-2-(2,4-difluorophenoxy)acetyl]amino]thiazol-5-yl]oxy-2-methyl-benzoic acid |
| B10 | 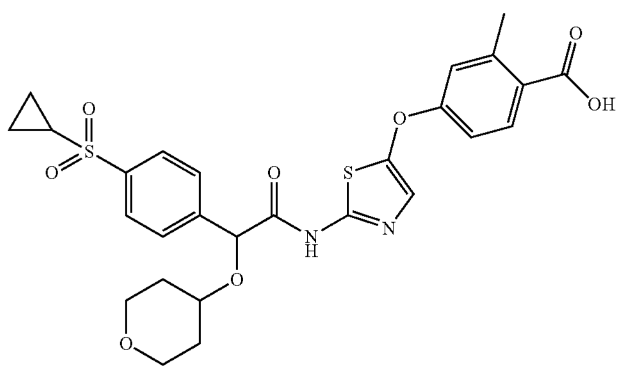 [SMILES: Cc1cc(Oc2cnc(NC(=O)C(OC3CCOCC3)c3ccc(S(=O)(=O)C4CC4)cc3)s2)ccc1C(=O)O] | 573.2 | 4-[2-[[2-(4-cyclopropylsulfonylphenyl)-2-tetrahydropyran-4-yloxy-acetyl]amino]thiazol-5-yl]oxy-2-methyl-benzoic acid |
| B11 | 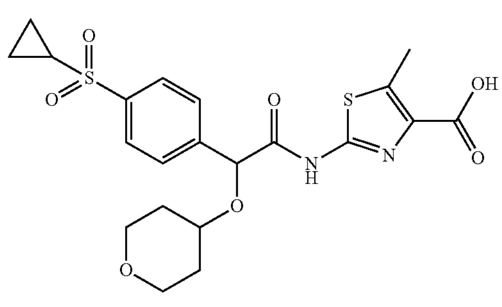 [SMILES: Cc1sc(NC(=O)C(OC2CCOCC2)c2ccc(S(=O)(=O)C3CC3)cc2)nc1C(=O)O] | 481.2 | 2-[[2-(4-cyclopropylsulfonylphenyl)-2-tetrahydropyran-4-yloxy-acetyl]amino]-5-methyl-thiazole-4-carboxylic acid |

-continued

| Example No. | Structure | MS (EI) m/z: (M + 1). | IUPAC Name |
|---|---|---|---|
| B12 | 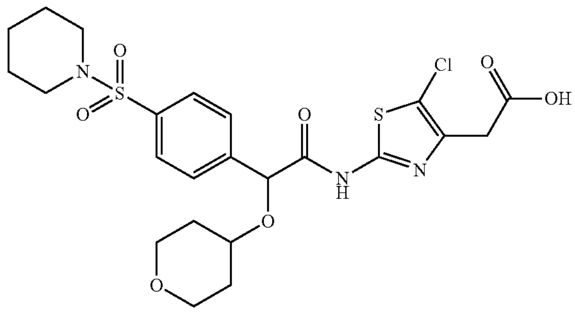 [SMILES: O=C(O)Cc1nc(NC(=O)C(OC2CCOCC2)c2ccc(S(=O)(=O)N3CCCCC3)cc2)sc1Cl] | 558.2 | 2-[5-chloro-2-[[2-[4-(1-piperidylsulfonyl)phenyl]-2-tetrahydropyran-4-yloxy-acetyl]amino]thiazol-4-yl]acetic acid |
| B13 | 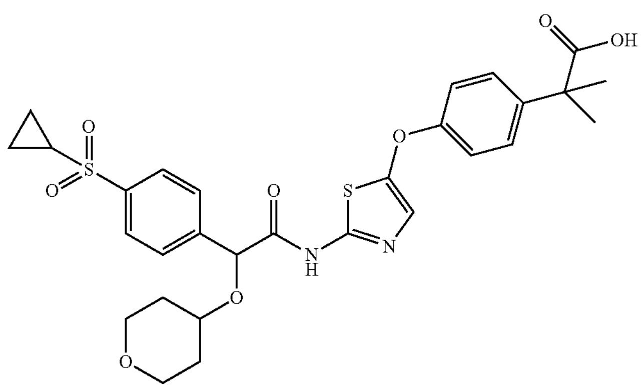 [SMILES: CC(C)(C(=O)O)c1ccc(Oc2cnc(NC(=O)C(OC3CCOCC3)c3ccc(S(=O)(=O)C4CC4)cc3)s2)cc1] | 601.3 | 2-[4-[2-[[2-(4-cyclopropylsulfonylphenyl)-2-tetrahydropyran-4-yloxy-acetyl]amino]thiazol-5-yl]oxyphenyl]-2-methyl-propanoic acid |
| B14 | 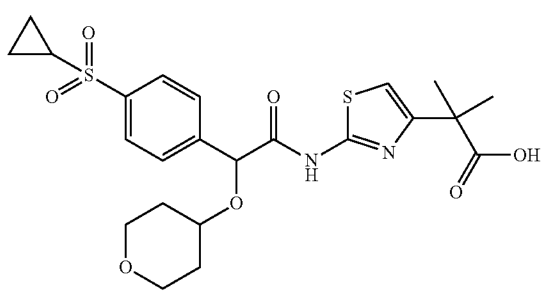 [SMILES: CC(C)(C(=O)O)c1csc(NC(=O)C(OC2CCOCC2)c2ccc(S(=O)(=O)C3CC3)cc2)n1] | 509.2 | 2-[2-[[2-(4-cyclopropylsulfonylphenyl)-2-tetrahydropyran-4-yloxy-acetyl]amino]thiazol-4-yl]-2-methyl-propanoic acid |
| B15 | 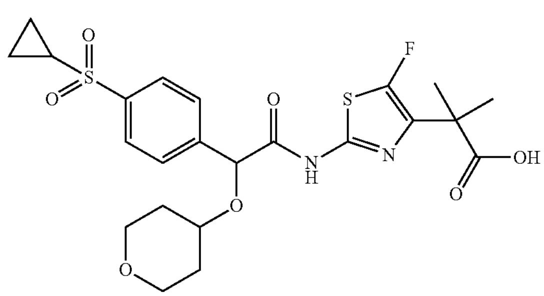 [SMILES: CC(C)(C(=O)O)c1nc(NC(=O)C(OC2CCOCC2)c2ccc(S(=O)(=O)C3CC3)cc2)sc1F] | 527.2 | 2-[2-[[2-(4-cyclopropylsulfonylphenyl)-2-tetrahydropyran-4-yloxy-acetyl]amino]-5-fluoro-thiazol-4-yl]-2-methyl-propanoic acid |

| Example No. | Structure | MS (EI) m/z: (M + 1) | IUPAC Name |
|---|---|---|---|
| B16 | 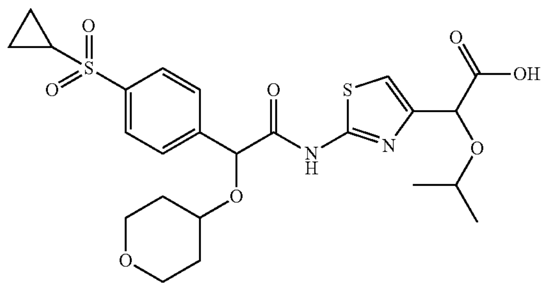 [SMILES: CC(C)OC(C(=O)O)c1csc(NC(=O)C(OC2CCOCC2)c2ccc(S(=O)(=O)C3CC3)cc2)n1] | 539.2 | 2-[2-[[2-(4-cyclopropylsulfonylphenyl)-2-tetrahydropyran-4-yloxy-acetyl]amino]thiazol-4-yl]-2-isopropoxy-acetic acid |
| B17 | 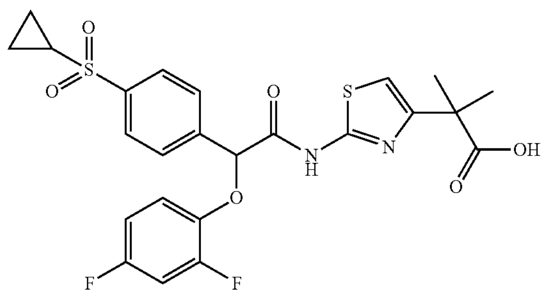 [SMILES: CC(C)(C(=O)O)c1csc(NC(=O)C(Oc2ccc(F)cc2F)c2ccc(S(=O)(=O)C3CC3)cc2)n1] | 537.2 | 2-[2-[[2-(4-cyclopropylsulfonylphenyl)-2-(2,4-difluorophenoxy)acetyl]amino]thiazol-4-yl]-2-methyl-propanoic acid |
| B18 | 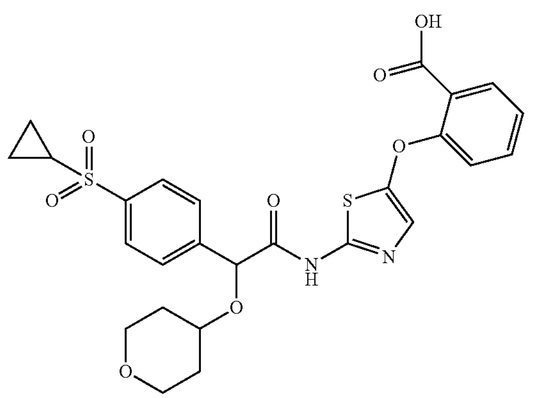 [SMILES: O=C(O)c1ccccc1Oc1cnc(NC(=O)C(OC2CCOCC2)c2ccc(S(=O)(=O)C3CC3)cc2)s1] | 559.2 | 2-[2-[[2-(4-cyclopropylsulfonylphenyl)-2-tetrahydropyran-4-yloxy-acetyl]amino]thiazol-5-yl]oxybenzoic acid |
| B19 | 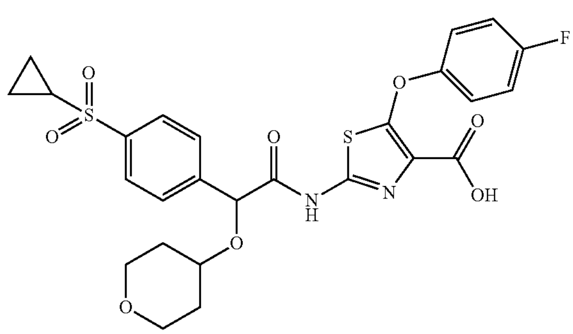 [SMILES: O=C(O)c1nc(NC(=O)C(OC2CCOCC2)c2ccc(S(=O)(=O)C3CC3)cc2)sc1Oc1ccc(F)cc1] | 577.0 | 2-[[2-(4-cyclopropylsulfonylphenyl)-2-tetrahydropyran-4-yloxy-acetyl]amino]-5-(4-fluorophenoxy)thiazole-4-carboxylic acid |

-continued

| Example No. | Structure | MS (EI) m/z: (M + 1). | IUPAC Name |
|---|---|---|---|
| B20 | 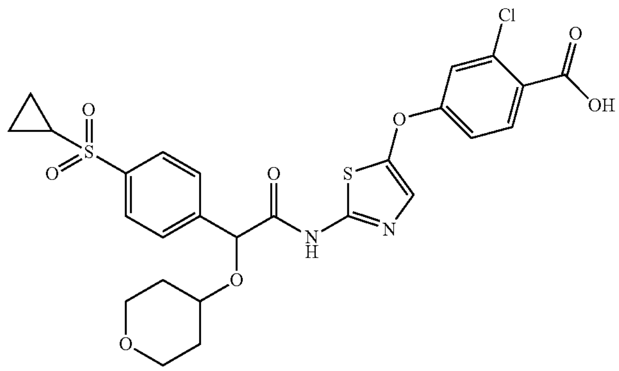 [SMILES: O=C(O)c1ccc(Oc2cnc(NC(=O)C(OC3CCOCC3)c3ccc(S(=O)(=O)C4CC4)cc3)s2)cc1Cl] | 593.2 ($^{35}$Cl) | 2-chloro-4-[2-[[2-(4-cyclopropylsulfonylphenyl)-2-tetrahydropyran-4-yloxy-acetyl]amino]thiazol-5-yl]oxy-benzoic acid |
| B21 | 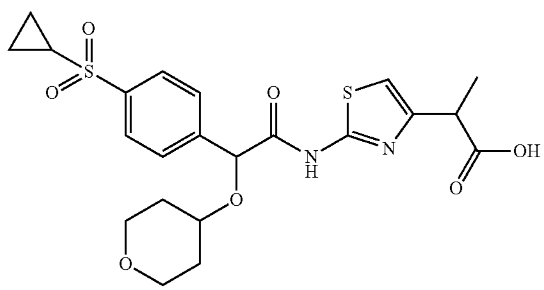 [SMILES: CC(C(=O)O)c1csc(NC(=O)C(OC2CCOCC2)c2ccc(S(=O)(=O)C3CC3)cc2)n1] | 495.1 | 2-[2-[[2-(4-cyclopropylsulfonylphenyl)-2-tetrahydropyran-4-yloxy-acetyl]amino]thiazol-4-yl]propanoic acid |
| B22 | 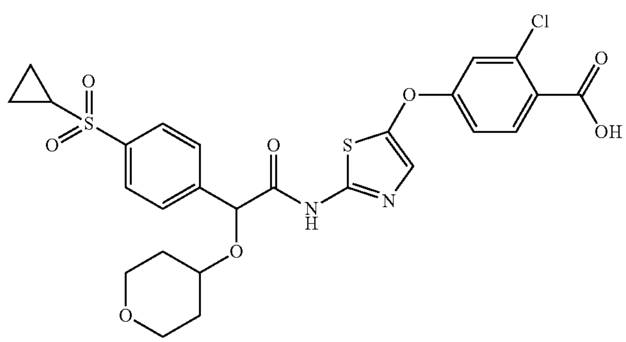 [SMILES: O=C(O)c1ccc(Oc2cnc(NC(=O)C(OC3CCOCC3)c3ccc(S(=O)(=O)C4CC4)cc3)s2)cc1Cl] | 559.1 ($^{35}$Cl) | 2-[5-chloro-2-[[2-tetrahydropyran-4-yloxy-2-(4-tetrahydropyran-4-ylsulfonylphenyl)acetyl]amino]thiazol-4-yl]acetic acid |
| B23 | 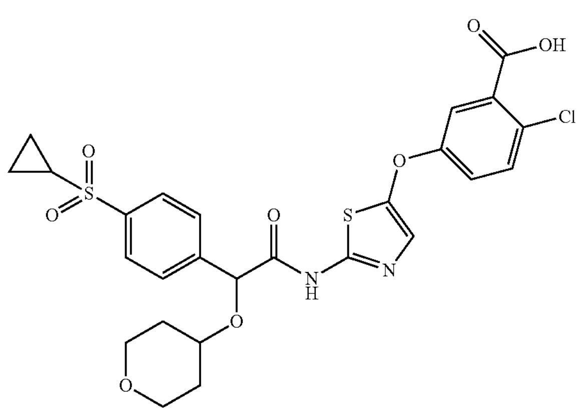 [SMILES: O=C(O)c1cc(Oc2cnc(NC(=O)C(OC3CCOCC3)c3ccc(S(=O)(=O)C4CC4)cc3)s2)ccc1Cl] | 593.1 ($^{35}$Cl) | 2-chloro-5-[2-[[2-(4-cyclopropylsulfonylphenyl)-2-tetrahydropyran-4-yloxy-acetyl]amino]thiazol-5-yl]oxy-benzoic acid |

| Example No. | Structure | MS (EI) m/z: (M + 1). | IUPAC Name |
|---|---|---|---|
| B24 | 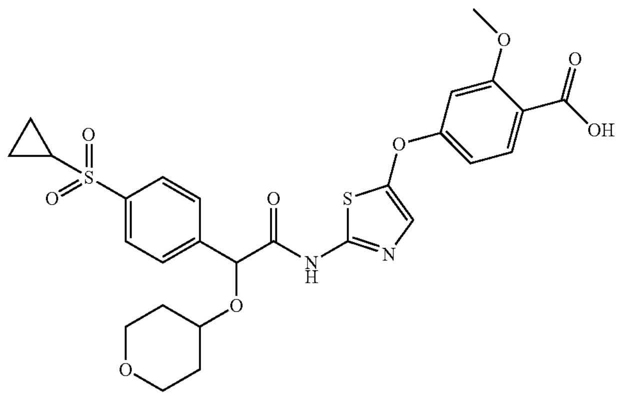 [SMILES: COc1cc(Oc2cnc(NC(=O)C(OC3CCOCC3)c3ccc(S(=O)(=O)C4CC4)cc3)s2)ccc1C(=O)O] | 589.2 | 4-[2-[[2-(4-cyclopropylsulfonylphenyl)-2-tetrahydropyran-4-yloxy-acetyl]amino]thiazol-5-yl]oxy-2-methoxy-benzoic acid |
| B25 | 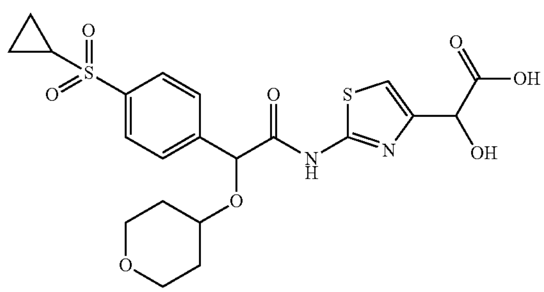 [SMILES: O=C(O)C(O)c1csc(NC(=O)C(OC2CCOCC2)c2ccc(S(=O)(=O)C3CC3)cc2)n1] | 497.2 | 2-[2-[[2-(4-cyclopropylsulfonylphenyl)-2-tetrahydropyran-4-yloxy-acetyl]amino]thiazol-4-yl]-2-hydroxy-acetic acid |
| B26 | 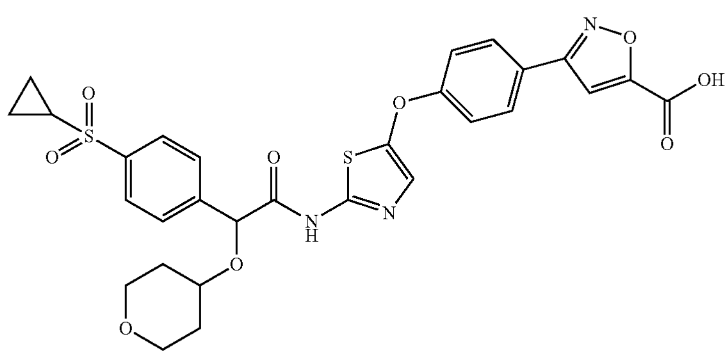 [SMILES: O=C(O)c1cc(-c2ccc(Oc3cnc(NC(=O)C(OC4CCOCC4)c4ccc(S(=O)(=O)C5CC5)cc4)s3)cc2)no1] | 626.2 | 3-[4-[2-[[2-(4-cyclopropylsulfonylphenyl)-2-tetrahydropyran-4-yloxy-acetyl]amino]thiazol-5-yl]oxyphenyl]isoxazole-5-carboxylic acid |
| B27 | 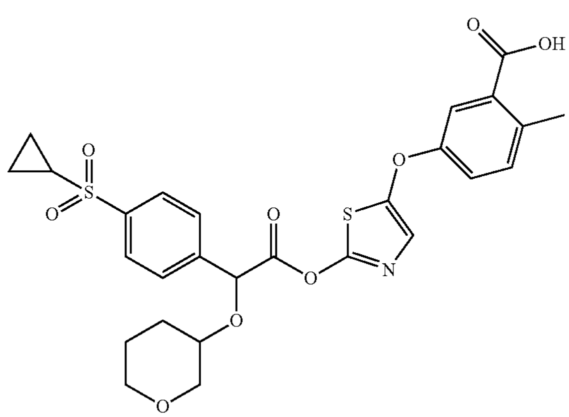 [SMILES: Cc1ccc(Oc2cnc(OC(=O)C(OC3CCCOC3)c3ccc(S(=O)(=O)C4CC4)cc3)s2)cc1C(=O)O] | 573.3 | 5-[2-[2-(4-cyclopropylsulfonylphenyl)-2-tetrahydropyran-3-yloxy-acetyl]oxythiazol-5-yl]oxy-2-methyl-benzoic acid |

-continued

| Example No. | Structure | MS (EI) m/z: (M+1) | IUPAC Name |
|---|---|---|---|
| B28 | 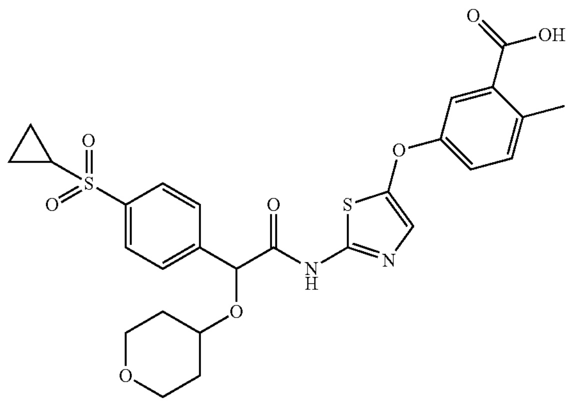 [SMILES: Cc1ccc(Oc2cnc(NC(=O)C(OC3CCOCC3)c3ccc(S(=O)(=O)C4CC4)cc3)s2)cc1C(=O)O] | 573.2 | 5-[2-[[2-(4-cyclopropylsulfonylphenyl)-2-tetrahydropyran-4-yloxy-acetyl]amino]thiazol-5-yl]oxy-2-methyl-benzoic acid |
| B29 | 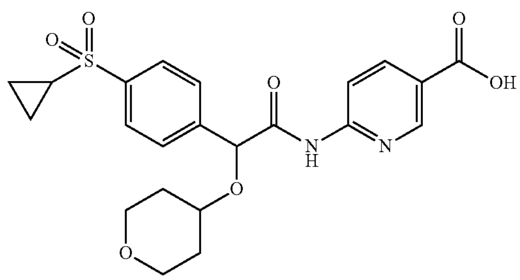 [SMILES: O=C(O)c1ccc(NC(=O)C(OC2CCOCC2)c2ccc(S(=O)(=O)C3CC3)cc2)nc1] | 461.2 | 6-[[2-(4-cyclopropylsulfonylphenyl)-2-tetrahydropyran-4-yloxy-acetyl]amino]pyridine-3-carboxylic acid |
| B30 | 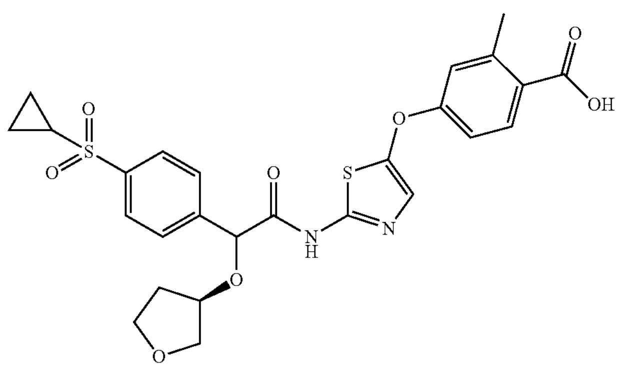 [SMILES: Cc1cc(Oc2cnc(NC(=O)C(O[C@@H]3CCOC3)c3ccc(S(=O)(=O)C4CC4)cc3)s2)ccc1C(=O)O] | 559.2 | 4-[2-[[2-(4-cyclopropylsulfonylphenyl)-2-[(3R)-tetrahydrofuran-3-yl]oxy-acetyl]amino]thiazol-5-yl]oxy-2-methyl-benzoic acid |
| B31 | 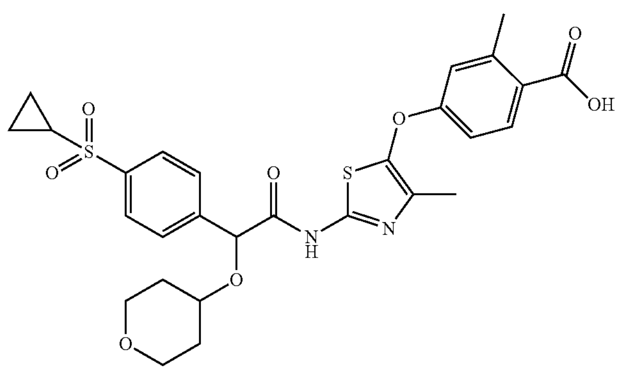 [SMILES: Cc1cc(Oc2sc(NC(=O)C(OC3CCOCC3)c3ccc(S(=O)(=O)C4CC4)cc3)nc2C)ccc1C(=O)O] | 587.2 | 4-[2-[[2-(4-cyclopropylsulfonylphenyl)-2-tetrahydropyran-4-yloxy-acetyl]amino]-4-methyl-thiazol-5-yl]oxy-2-methyl-benzoic acid |

-continued

| Example No. | Structure | MS (EI) m/z: (M+1). | IUPAC Name |
|---|---|---|---|
| B32 | 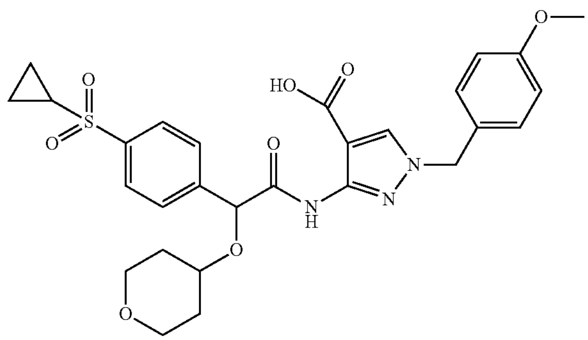 [SMILES: COc1ccc(Cn2cc(C(=O)O)c(NC(=O)C(OC3CCOCC3)c3ccc(S(=O)(=O)C4CC4)cc3)n2)cc1] | 570.2 | 3-[[2-(4-cyclopropylsulfonylphenyl)-2-tetrahydropyran-4-yloxy-acetyl]amino]-1-[(4-methoxyphenyl)methyl]pyrazole-4-carboxylic acid |
| B33 | 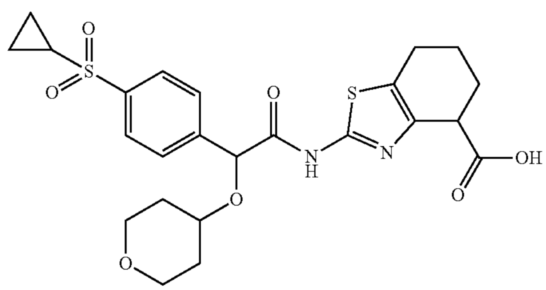 [SMILES: O=C(O)C1CCCc2sc(NC(=O)C(OC3CCOCC3)c3ccc(S(=O)(=O)C4CC4)cc3)nc21] | 521.2 | 2-[[2-(4-cyclopropylsulfonylphenyl)-2-tetrahydropyran-4-yloxy-acetyl]amino]-4,5,6,7-tetrahydro-1,3-benzothiazole-4-carboxylic acid |
| B34 | 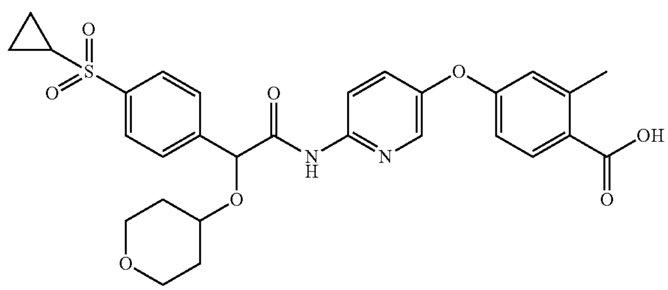 [SMILES: Cc1cc(Oc2ccc(NC(=O)C(OC3CCOCC3)c3ccc(S(=O)(=O)C4CC4)cc3)nc2)ccc1C(=O)O] | 567.2 | 4-[[6-[[2-(4-cyclopropylsulfonylphenyl)-2-tetrahydropyran-4-yloxy-acetyl]amino]-3-pyridyl]oxy]-2-methyl-benzoic acid |
| B35 | 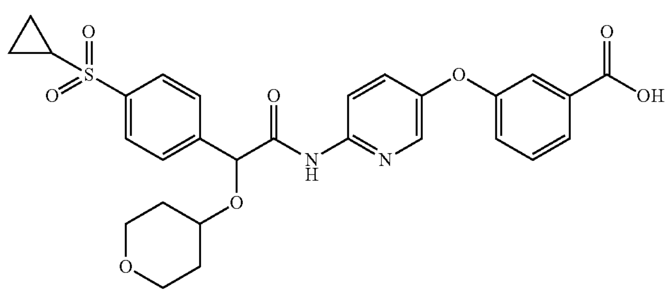 [SMILES: O=C(O)c1cccc(Oc2ccc(NC(=O)C(OC3CCOCC3)c3ccc(S(=O)(=O)C4CC4)cc3)nc2)c1] | 553.2 | 3-[[6-[[2-(4-cyclopropylsulfonylphenyl)-2-tetrahydropyran-4-yloxy-acetyl]amino]-3-pyridyl]oxy]benzoic acid |
| B36 | 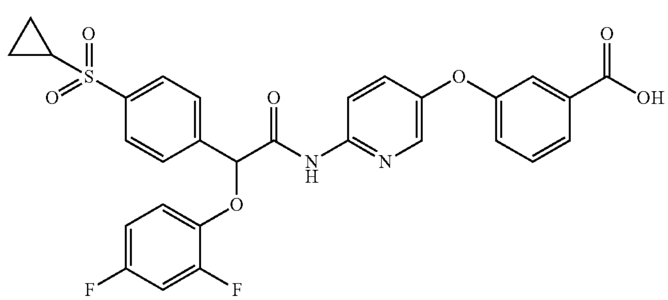 [SMILES: O=C(O)c1cccc(Oc2ccc(NC(=O)C(Oc3ccc(F)cc3F)c3ccc(S(=O)(=O)C4CC4)cc3)nc2)c1] | 581.2 | 3-[[6-[[2-(4-cyclopropylsulfonylphenyl)-2-(2,4-difluorophenoxy)acetyl]amino]-3-pyridyl]oxy]benzoic acid |

| Example No. | Structure | MS (EI) m/z: (M + 1). | IUPAC Name |
|---|---|---|---|
| B37 | 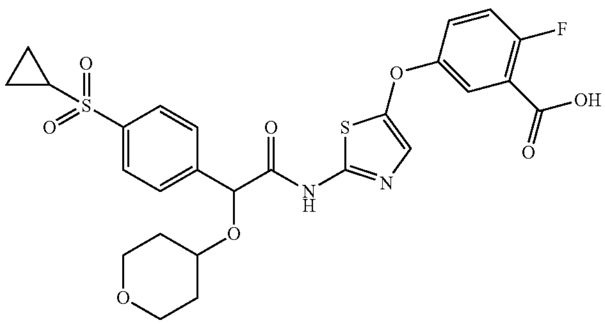 [SMILES: O=C(O)c1cc(Oc2cnc(NC(=O)C(OC3CCOCC3)c3ccc(S(=O)(=O)C4CC4)cc3)s2)ccc1F] | 577.2 | 5-[2-[[2-(4-cyclopropylsulfonylphenyl)-2-tetrahydropyran-4-yloxy-acetyl]amino]thiazol-5-yl]oxy-2-fluoro-benzoic acid |
| B38 | 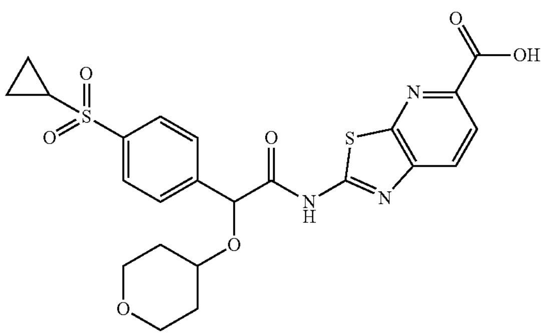 [SMILES: O=C(O)c1ccc2nc(NC(=O)C(OC3CCOCC3)c3ccc(S(=O)(=O)C4CC4)cc3)sc2n1] | 518.1 | 2-[[2-(4-cyclopropylsulfonylphenyl)-2-tetrahydropyran-4-yloxy-acetyl]amino]thiazolo[5,4-b]pyridine-5-carboxylic acid |
| B39 | 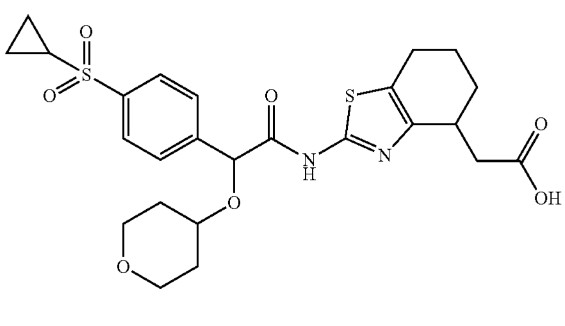 [SMILES: O=C(O)CC1CCCc2sc(NC(=O)C(OC3CCOCC3)c3ccc(S(=O)(=O)C4CC4)cc3)nc21] | 535.2 | 2-[2-[[2-(4-Cyclopropylsulfonylphenyl)-2-tetrahydropyran-4-yloxy-acetyl]amino]-4,5,6,7-tetrahydro-1,3-benzothiazol-4-yl]acetic acid |
| B40 | 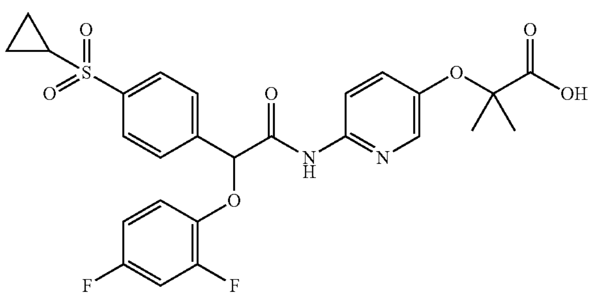 [SMILES: CC(C)(Oc1ccc(NC(=O)C(Oc2ccc(F)cc2F)c2ccc(S(=O)(=O)C3CC3)cc2)nc1)C(=O)O] | 547.2 | 2-[[6-[[2-(4-cyclopropylsulfonylphenyl)-2-(2,4-difluorophenoxy)acetyl]amino]-3-pyridyl]oxy]-2-methyl-propanoic acid |

| Example No. | Structure | MS (EI) m/z: (M + 1) | IUPAC Name |
|---|---|---|---|
| B41 | 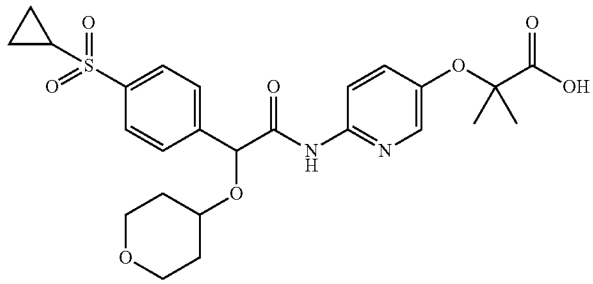 [SMILES: CC(C)(Oc1ccc(NC(=O)C(OC2CCOCC2)c2ccc(S(=O)(=O)C3CC3)cc2)nc1)C(=O)O] | 519.2 | 2-[[6-[[2-(4-cyclopropylsulfonylphenyl)-2-tetrahydropyran-4-yloxy-acetyl]amino]-3-pyridyl]oxy]-2-methyl-propanoic acid |
| B42 | 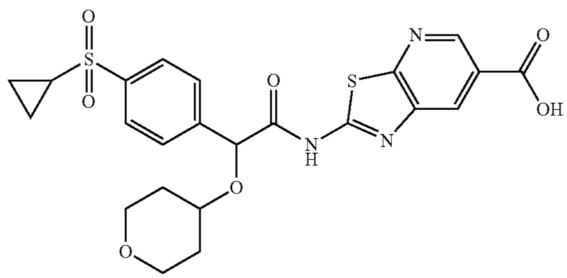 [SMILES: O=C(O)c1cnc2sc(NC(=O)C(OC3CCOCC3)c3ccc(S(=O)(=O)C4CC4)cc3)nc2c1] | 518.2 | 2-[[2-(4-cyclopropylsulfonylphenyl)-2-tetrahydropyran-4-yloxy-acetyl]amino]thiazolo[5,4-b]pyridine-6-carboxylic acid |
| B43 | 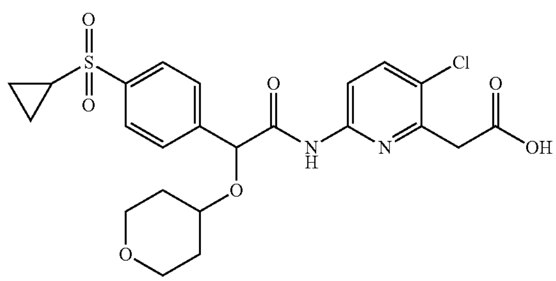 [SMILES: O=C(O)Cc1nc(NC(=O)C(OC2CCOCC2)c2ccc(S(=O)(=O)C3CC3)cc2)ccc1Cl] | 509.1 | 2-[3-chloro-6-[[2-(4-($^{35}$Cl)cyclopropylsulfonylphenyl)-2-tetrahydropyran-4-yloxy-acetyl]amino]-2-pyridyl]acetic acid |
| B44 | Chiral | 545.2 | 3-[2-[[2-(4-cyclopropylsulfonylphenyl)-2-[(3R)-tetrahydrofuran-3-yl]oxy-acetyl]amino]thiazol-5-yl]oxybenzoic acid |
| B45 | 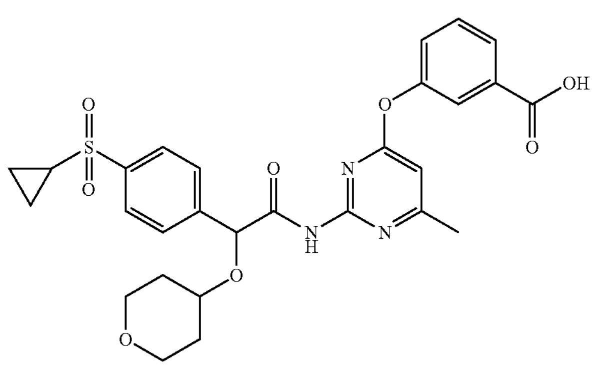 [SMILES: Cc1cc(Oc2cccc(C(=O)O)c2)nc(NC(=O)C(OC2CCOCC2)c2ccc(S(=O)(=O)C3CC3)cc2)n1] | 568.2 | 3-[2-[[2-(4-cyclopropylsulfonylphenyl)-2-tetrahydropyran-4-yloxy-acetyl]amino]-6-methyl-pyrimidin-4-yl]oxybenzoic acid |

-continued

| Example No. | Structure | MS (EI) m/z: (M + 1). | IUPAC Name |
|---|---|---|---|
| B46 | 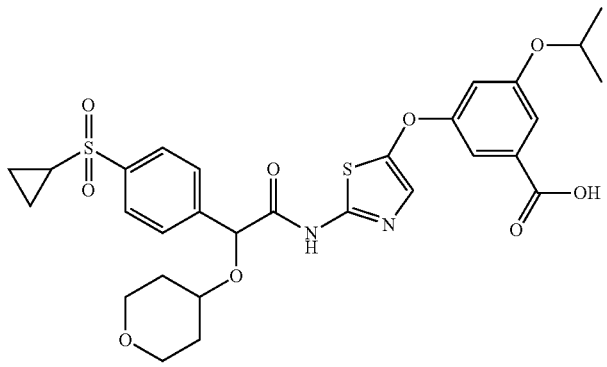 [SMILES: CC(C)Oc1cc(Oc2cnc(NC(=O)C(OC3CCOCC3)c3ccc(S(=O)(=O)C4CC4)cc3)s2)cc(C(=O)O)c1] | 617.1 | 3-[2-[[2-(4-cyclopropylsulfonylphenyl)-2-tetrahydropyran-4-yloxy-acetyl]amino]thiazol-5-yl]oxy-5-isopropoxy-benzoic acid |
| B47 | 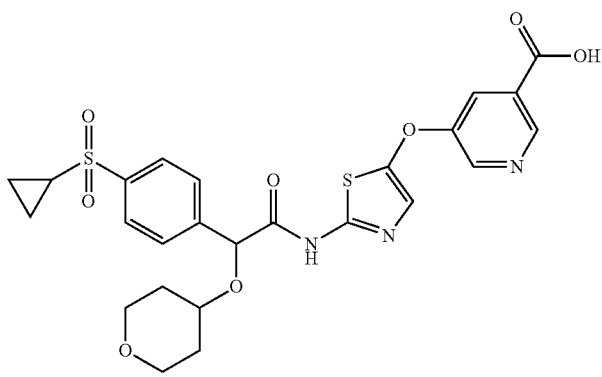 [SMILES: O=C(O)c1cncc(Oc2cnc(NC(=O)C(OC3CCOCC3)c3ccc(S(=O)(=O)C4CC4)cc3)s2)c1] | 560.1 | 5-[2-[[2-(4-cyclopropylsulfonylphenyl)-2-tetrahydropyran-4-yloxy-acetyl]amino]thiazol-5-yl]oxypyridine-3-carboxylic acid |
| B48 | 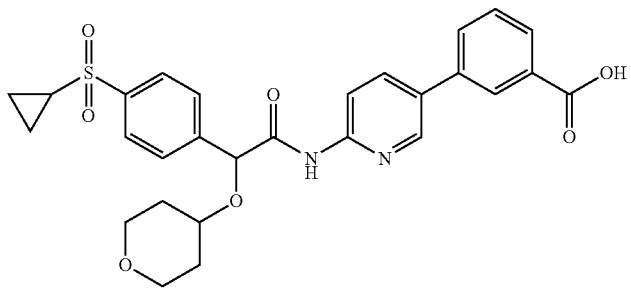 [SMILES: O=C(O)c1cccc(-c2ccc(NC(=O)C(OC3CCOCC3)c3ccc(S(=O)(=O)C4CC4)cc3)nc2)c1] | 537.2 | 3-[6-[[2-(4-cyclopropylsulfonylphenyl)-2-tetrahydropyran-4-yloxy-acetyl]amino]-3-pyridyl]benzoic acid |
| B49 | 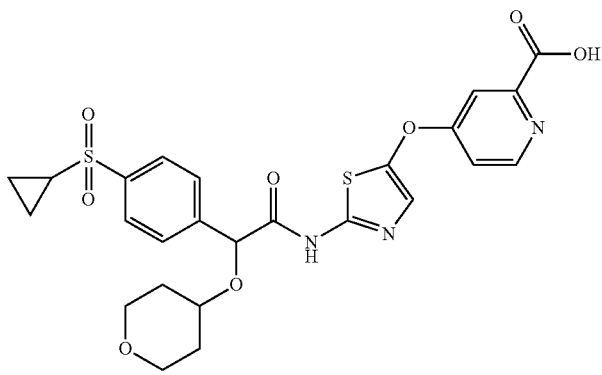 [SMILES: O=C(O)c1cc(Oc2cnc(NC(=O)C(OC3CCOCC3)c3ccc(S(=O)(=O)C4CC4)cc3)s2)ccn1] | 560.1 | 4-[2-[[2-(4-cyclopropylsulfonylphenyl)-2-tetrahydropyran-4-yloxy-acetyl]amino]thiazol-5-yl]oxypyridine-2-carboxylic acid |

-continued

| Example No. | Structure | MS (EI) m/z: (M + 1) | IUPAC Name |
|---|---|---|---|
| B50 | 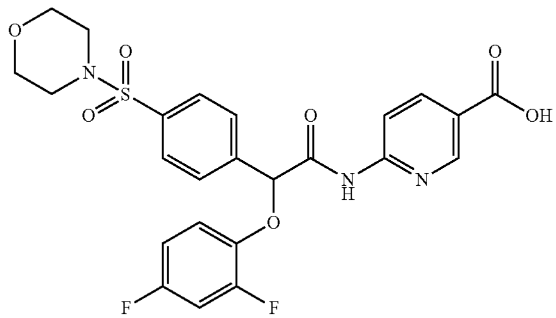 [SMILES: O=C(O)c1ccc(NC(=O)C(Oc2ccc(F)cc2F)c2ccc(S(=O)(=O)N3CCOCC3)cc2)nc1] | 534.2 | 6-[[2-(2,4-difluorophenoxy)-2-(4-morpholinosulfonylphenyl)acetyl]amino]pyridine-3-carboxylic acid |
| B51 | 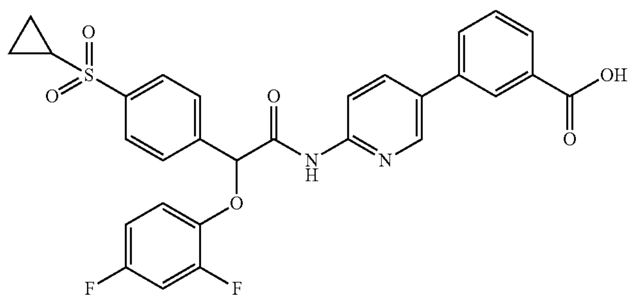 [SMILES: O=C(O)c1cccc(-c2ccc(NC(=O)C(Oc3ccc(F)cc3F)c3ccc(S(=O)(=O)C4CC4)cc3)nc2)c1] | 565.2 | 3-[6-[[2-(4-cyclopropylsulfonylphenyl)-2-(2,4-difluorophenoxy)acetyl]amino]-3-pyridyl]benzoic acid |
| B52 | 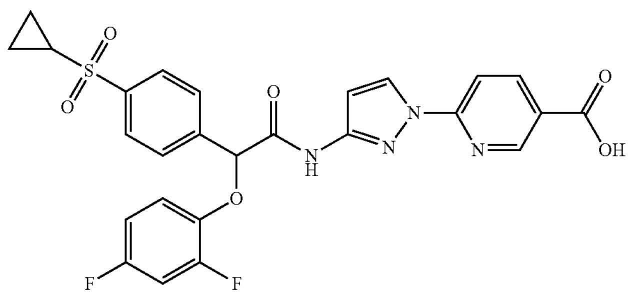 [SMILES: O=C(O)c1ccc(-n2ccc(NC(=O)C(Oc3ccc(F)cc3F)c3ccc(S(=O)(=O)C4CC4)cc3)n2)nc1] | 554.9 | 6-[3-[[2-(4-cyclopropylsulfonylphenyl)-2-(2,4-difluorophenoxy)acetyl]amino]pyrazol-1-yl]pyridine-3-carboxylic acid |
| B53 | 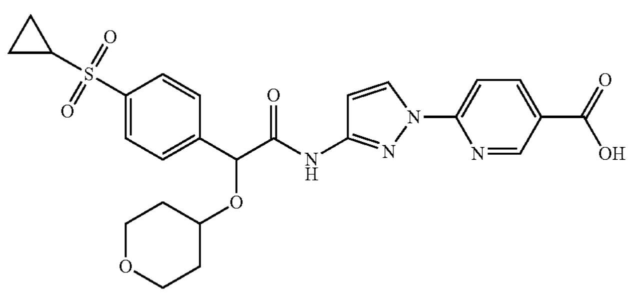 [SMILES: O=C(O)c1ccc(-n2ccc(NC(=O)C(OC3CCOCC3)c3ccc(S(=O)(=O)C4CC4)cc3)n2)nc1] | 526.9 | 6-[3-[[2-(4-cyclopropylsulfonylphenyl)-2-tetrahydropyran-4-yloxy-acetyl]amino]pyrazol-1-yl]pyridine-3-carboxylic acid |
| B54 | 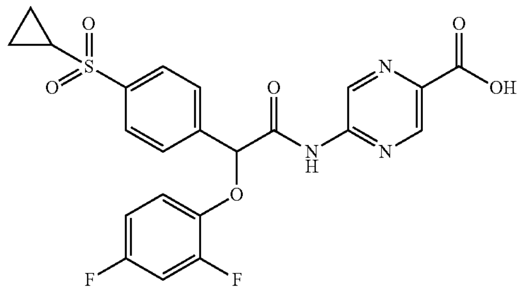 [SMILES: O=C(O)c1cnc(NC(=O)C(Oc2ccc(F)cc2F)c2ccc(S(=O)(=O)C3CC3)cc2)cn1] | 490.1 | 5-[[2-(4-cyclopropylsulfonylphenyl)-2-(2,4-difluorophenoxy)acetyl]amino]pyrazine-2-carboxylic acid |

-continued

| Example No. | Structure | MS (EI) m/z: (M + 1). | IUPAC Name |
|---|---|---|---|
| B55 | 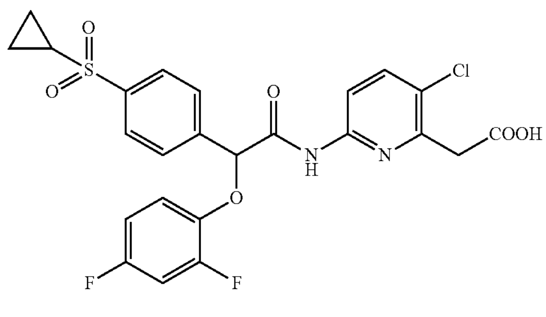 [SMILES: O=C(O)Cc1nc(NC(=O)C(Oc2ccc(F)cc2F)c2ccc(S(=O)(=O)C3CC3)cc2)ccc1Cl] | 537.1 ($^{35}$Cl) | 2-[3-chloro-6-[[2-(4-cyclopropylsulfonylphenyl)-2-(2,4-difluorophenoxy)acetyl]amino]-2-pyridyl]acetic acid |
| B56 | 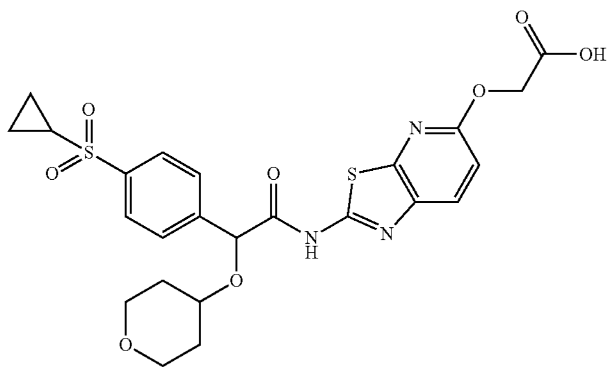 [SMILES: O=C(O)COc1ccc2nc(NC(=O)C(OC3CCOCC3)c3ccc(S(=O)(=O)C4CC4)cc3)sc2n1] | 548.2 | 2-[2-[[2-(4-cyclopropylsulfonylphenyl)-2-tetrahydropyran-4-yloxy-acetyl]amino]thiazolo[5,4-b]pyridin-5-yl]oxyacetic acid |
| B57 | 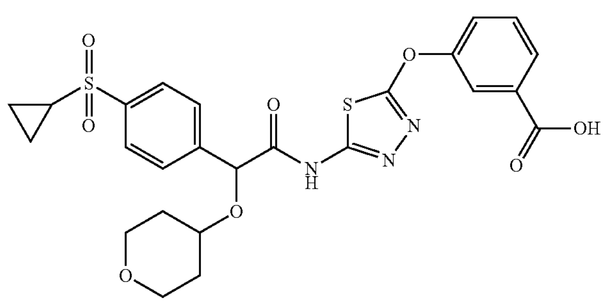 [SMILES: O=C(O)c1cccc(Oc2nnc(NC(=O)C(OC3CCOCC3)c3ccc(S(=O)(=O)C4CC4)cc3)s2)c1] | 560.1 | 3-[[5-[[2-(4-cyclopropylsulfonylphenyl)-2-tetrahydropyran-4-yloxy-acetyl]amino]-1,3,4-thiadiazol-2-yl]oxy]benzoic acid |
| B58 | 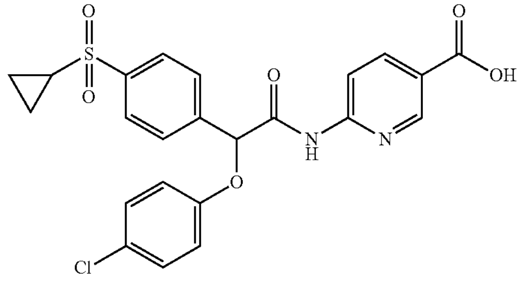 [SMILES: O=C(O)c1ccc(NC(=O)C(Oc2ccc(Cl)cc2)c2ccc(S(=O)(=O)C3CC3)cc2)nc1] | 487.0 ($^{35}$Cl) | 6-[[2-(4-chlorophenoxy)-2-(4-cyclopropylsulfonylphenyl)acetyl]amino]pyridine-3-carboxylic acid |

| Example No. | Structure | MS (EI) m/z: (M + 1) | IUPAC Name |
|---|---|---|---|
| B59 | 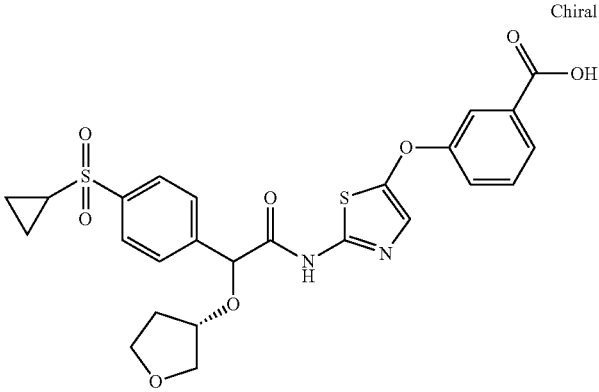 [SMILES: O=C(O)c1cccc(Oc2cnc(NC(=O)C(O[C@H]3CCOC3)c3ccc(S(=O)(=O)C4CC4)cc3)s2)c1] Chiral | 545.3 | 3-[2-[[2-(4-cyclopropylsulfonylphenyl)-2-[(3S)-tetrahydrofuran-3-yl]oxy-acetyl]amino]thiazol-5-yl]oxybenzoic acid |
| B60 | 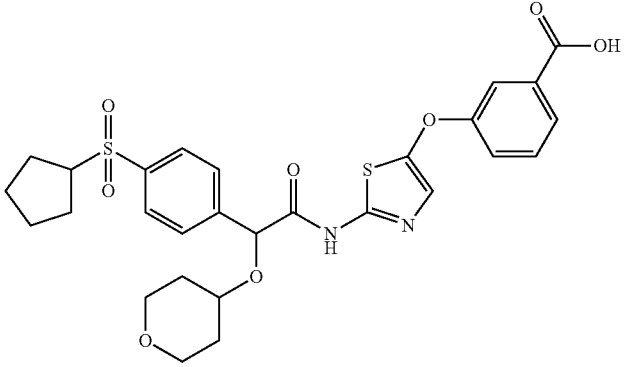 [SMILES: O=C(O)c1cccc(Oc2cnc(NC(=O)C(OC3CCOCC3)c3ccc(S(=O)(=O)C4CCCC4)cc3)s2)c1] | 587.3 | 3-[2-[[2-(4-cyclopentylsulfonylphenyl)-2-tetrahydropyran-4-yloxy-acetyl]amino]thiazol-5-yl]oxybenzoic acid |
| B61 | 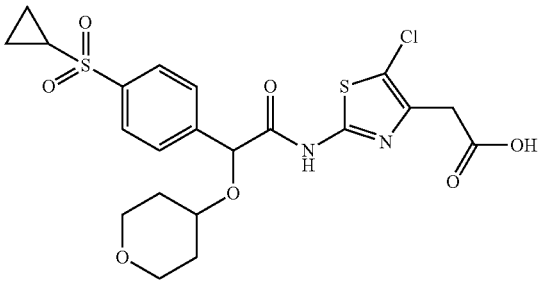 [SMILES: O=C(O)Cc1nc(NC(=O)C(OC2CCOCC2)c2ccc(S(=O)(=O)C3CC3)cc2)sc1Cl] | 514.9 ($^{35}$Cl) | 2-[5-chloro-2-[[2-(4-cyclopropylsulfonylphenyl)-2-tetrahydropyran-4-yloxy-acetyl]amino]thiazol-4-yl]acetic acid |

Example C

4-[2-[[2-(4-cyclopropylsulfonylphenyl)-2-tetrahydro-pyran-4-yloxy-acetyl]amino]thiazol-5-yl]oxy-N-isopropyl-benzamide

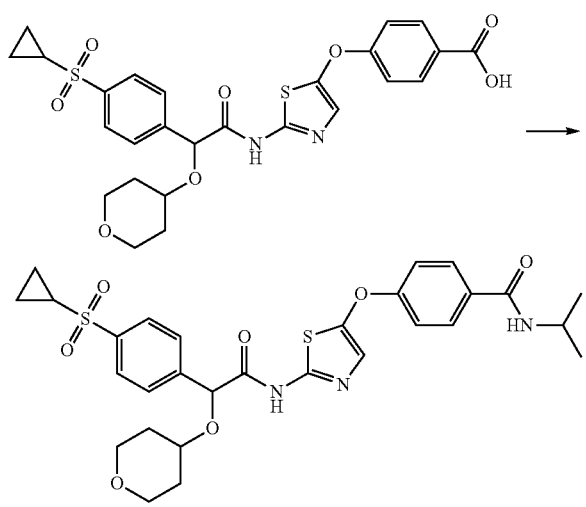

To a cooled solution of 4-[2-[[2-(4-cyclopropylsulfonylphenyl)-2-tetrahydropyran-4-yloxy-acetyl]amino]thiazol-5-yl]oxybenzoic acid (Example B1; 0.3 g, 0.537 mmol) in dry DCM (10 mL) was added triethyl amine (0.09 mL, 0.644 mmol) and Ethyl chloroformate (0.061 mL, 0.644 mmol), and mixture was stirred for 1 hour at 25° C. under argon atmosphere. Isopropyl amine (0.06 mL, 0.644 mmol) was added slowly and reaction mixture was stirred for more 16 h. Formation of product was confirmed by TLC. Reaction mixture was diluted with DCM (20 mL) and washed with 1N HCl (10 mL), water (15 mL), and brine solution (15 mL), dried over anhydrous sodium sulfate, filtered and concentrated under reduced pressure. The residue was purified on preparative TLC plate using mobile phase 5% methanol in DCM to give the title compound (0.120 g).

$^1$H NMR (400 MHz, DMSO-d$_6$): δ 0.99-1.07 (m, 2H), 1.07-1.18 (m, 8H), 1.42-1.61 (m, 2H), 1.8-1.96 (m, 2H), 2.8-2.88 (m, 1H), 3.22-3.21 (m, 2H), 3.58-3.68 (m, 1H), 3.74-3.84 (m, 2H), 4.0-4.08 (m, 1H), 5.47 (s, 1H), 7.14 (d, J=8.8 Hz, 2H), 7.34 (s, 1H) 7.76 (d, J=8.0 Hz, 2H), 7.83 (d, J=8.8 Hz, 2H), 7.92 (d, J=8.4 Hz, 2H), 8.16 (d, J=8.0 Hz, 1H), 12.5 (bs, 1H); MS (EI) m/z: 600.2 (M+1).

Examples C2 to C3 were prepared in analogues manner of example C1

| Example No. | Structure | MS (EI)m/z: (M + 1). | IUPAC Name |
|---|---|---|---|
| C2 | 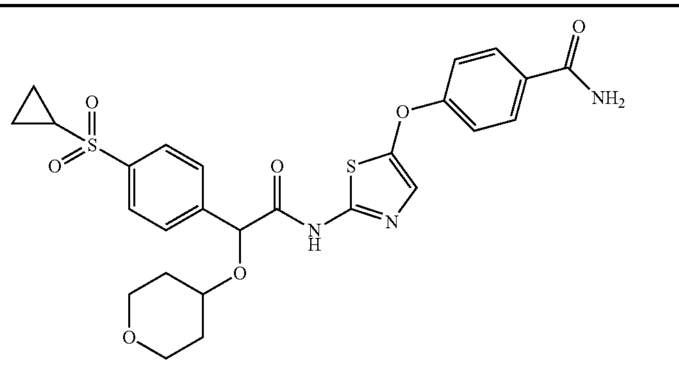 | 558.2 | 4-[2-[[2-(4-cyclopropylsulfonylphenyl)-2-2-tetrahydropyran-4-yloxy-acetyl]amino]thiazol-5-yl]oxybenzamide |
| C3 | 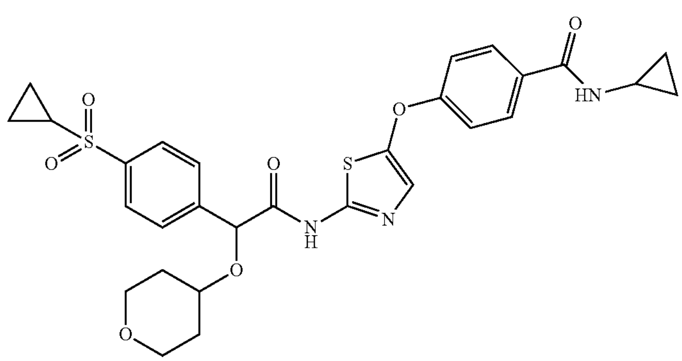 [SMILES: O=C(NC1CC1)c1ccc(Oc2cnc(NC(=O)C(OC3CCOCC3)c3ccc(S(=O)(=O)C4CC4)cc3)s2)cc1] | 598.2 | N-Cyclopropyl-4-[2-[[2-(4-cyclopropylsulfonylphenyl)-2-tetrahydropyran-4-yloxy-acetyl]amino]thiazol-5-yl]oxy-benzamide |

Example D1

2-(4-Cyclopropanesulfonyl-phenyl)-N-[5-(4-hydroxymethyl-phenoxy)-thiazol-2-yl]-2-(tetrahydro-pyran-4-yloxy)-acetamide

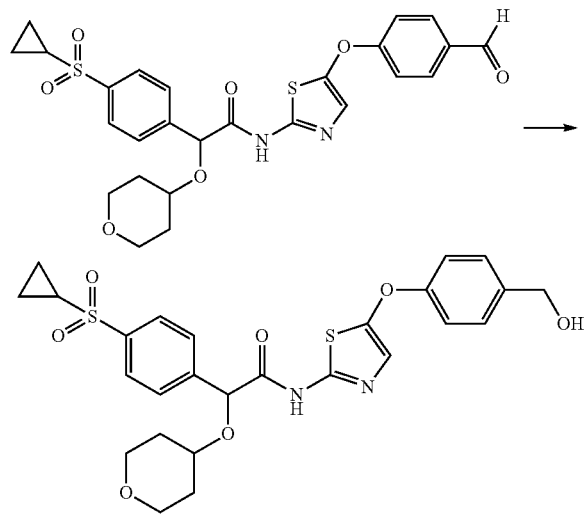

To a stirred solution of 2-(4-Cyclopropanesulfonyl-phenyl)-N-[5-(4-formyl-phenoxy)-thiazol-2-yl]-2-(tetrahydro-pyran-4-yloxy)-acetamide (Example A74; 0.2 g, 0.36 mmol) in 10 mL methanol, sodium borohydride (0.027 g, 0.73 mmol) was added in portions at 0° C. After complete addition reaction mixture was stirred for 1 hr at 0° C. to 10° C. Completion of the reaction was confirmed by TLC, then methanol was evaporated on rotavapour. Reaction mixture was diluted with ethyl acetate (3×20 mL), organic layer was washed with water and brine, dried (Na$_2$SO$_4$) and concentrated in vacuo. Purified by PREP TLC to afford title compound (0.110 g).

$^1$H NMR (400 MHz, CDCl$_3$): δ 1.04-1.06 (m, 2H), 1.35-1.37 (m, 2H), 1.69-1.76 (m, 2H), 1.84-1.88 (m, 1H), 2.01-2.04 (m, 1H), 2.43-2.46 (m, 1H), 3.35-3.42 (m, 2H), 3.65-3.69 (m, 1H), 3.94-4.02 (m, 2H), 4.65 (bs, 2H), 5.20 (s, 1H), 7.06 (d, J=8.8 Hz, 2H), 7.09 (s, 1H), 7.32 (d, J=8.8 Hz, 2H), 7.68 (d, J=7.6 Hz, 2H), 7.92 (d, J=8.4 Hz, 2H), (9.72 (bs, 1H). MS (EI) m/z: 545.2 (M+1).

Example D2

2-(4-Cyclopropanesulfonyl-phenyl)-N-(4-hydroxymethyl-5-methyl-thiazol-2-yl)-2-(tetrahydro-pyran-4-yloxy)-acetamide

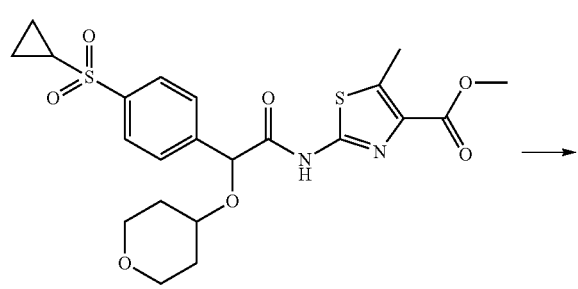

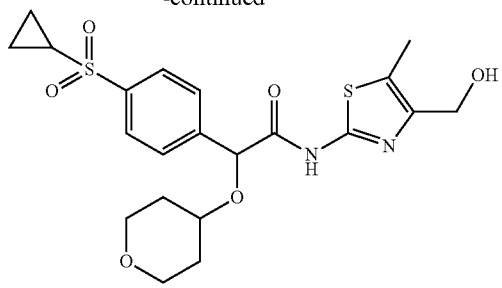

To a solution of 2-[2-(4-Cyclopropanesulfonyl-phenyl)-2-(tetrahydro-pyran-4-yloxy)-acetylamino]-5-methyl-thiazole-4-carboxylic acid methyl ester(Example A15) (0.23 g, 0.46 mmol) in toluene (5 mL) was added DIBALH (1M in toluene, 0.13 g, 0.93 mmol) at 0° C. and reaction mixture was stirred overnight at room temperature. Solvent was removed in vacuo and taken into water, extracted with ethyl acetate (10 mL×3), combined organic layers were washed with 1 N NaOH solution, water and brine, dried (Na$_2$SO$_4$) and concentrated in vacuo. Purified by preparative HPLC to afford title compound (0.012 g)

$^1$HNMR (CDCl$_3$, 400 MHz):—δ 1.02-1.05 (m, 2H), 1.33-1.36 (m, 2H), 1.67-1.79 (m, 2H), 1.81-1.85 (m, 1H), 1.89-2.30 (m, 1H), 2.35 (s, 3H), 2.40-2.47 (m, 1H), 3.34-3.42 (m, 2H), 3.61-3.65 (m, 1H), 3.93-4.02 (m, 2H), 4.60 (s, 2H), 5.20 (s, 1H), 7.67 (d, J=8.0 Hz, 2H), 7.91 (d, J=8.4 Hz, 2H); MS (EI) m/z: 467.20 (M+1).

Example D3

2-(4-cyclopropylsulfonylphenyl)-N-[5-[3-(hydroxymethyl)phenoxy]thiazol-2-yl]-2-tetrahydropyran-4-yloxy-acetamide

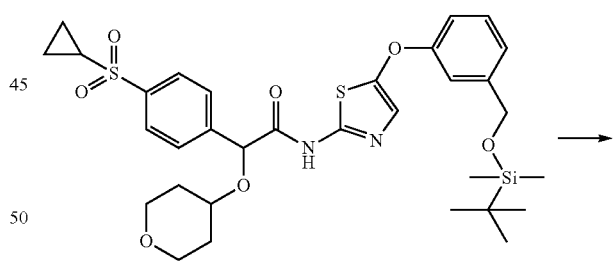

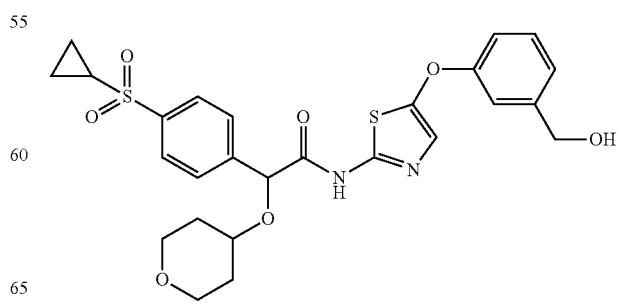

N-[5-[3-[[tert-butyl(dimethyl)silyl]oxymethyl]phenoxy]thiazol-2-yl]-2-(4-cyclopropylsulfonylphenyl)-2-tetrahydro-pyran-4-yloxy-acetamide (0.05 g, 0.0758 mmol) was taken in 3 mL of dry THF and to it tetra-n-butylammonium fluoride (0.16 mL, 0.16 mmol, 1M solution in THF) was added in inert atmosphere at 0° C. After complete addition the reaction was stirred for overnight at room temperature. TLC showed complete reaction. The reaction mixture was portioned between water and ethyl acetate. The aqueous layer was extracted with ethyl acetate. The combined organic layer was washed with brine and dried over anhydrous sodium sulfate. The solvent was removed on vacuo to get the crude product which was purified by preparative TLC to get the solid product (0.020 g).

$^1$H NMR (400 MHz, DMSOd$_6$): δ 1.00-1.06 (m, 2H), 1.08-1.12 (m, 2H), 1.4-1.6 (m, 2H), 1.81-1.94 (m, 2H), 2.8-2.87 (m, 1H), 3.26-3.32 (m, 2H), 3.58-3.65 (m, 1H), 3.75-3.84 (m, 2H), 4.44 (d, J=5.6 Hz, 2H), 5.24 (t, J=6.0 Hz, 1H), 5.41 (s, 1H), 6.95 (dd, J=8.0, 2.4 Hz, 1H), 7.02-7.06 (m, 2H), 7.27 (s, 1H), 7.29 (t, J=8.0, 1H), 7.75 (d, J=8.0 Hz, 2H), 7.91 (d, J=8.0 Hz, 2H), 12.45 (s, 1H); MS (EI) m/z: 545.1 (M+1).

Example E1

2-(4-Cyclopropanesulfonyl-phenyl)-N-[5-(1,2-dihydroxy-ethyl)-thiazol-2-yl]-2-(tetrahydro-pyran-4-yloxy)-acetamide

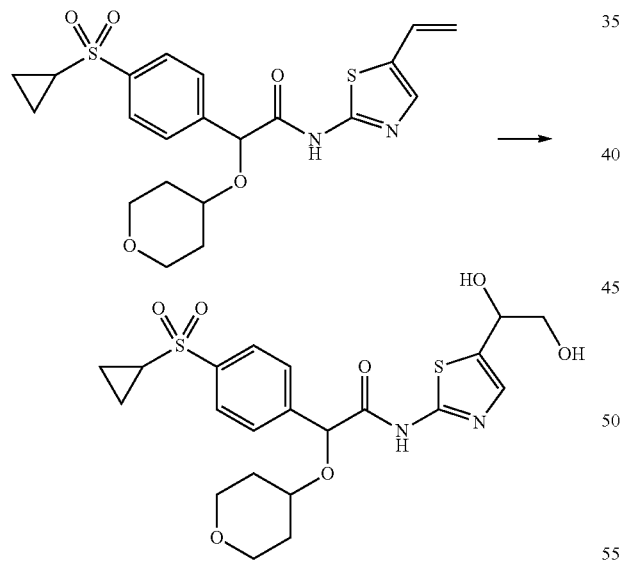

2-(4-Cyclopropanesulfonyl-phenyl)-2-(tetrahydro-pyran-4-yloxy)-N-(5-vinyl-thiazol-2-yl)-acetamide (Example A118) (0.107 g, 0.238 mmol), osmium tetroxide (0.0061 g, 0.0238 mmol) and N-methylmorpholine N-oxide (0.041 g, 0.353 mmol) were taken in 4 mL of THF and 1 mL of water and stirred at room temperature for 3 hrs. The reaction mixture was partioned between 10% sodium thiosulphate (10 mL) and ethyl acetate (10 mL). The layers were separated. Aq. layer was extracted with ethyl acetate (2×10 mL). The combined organic layer was washed with brine and dried over anhydrous sodium sulfate filtered and concentrated under reduced pressure to get a residue which was purified by preparative TLC to get the required product (0.070 g).

$^1$H NMR (400 MHz, DMSOd$_6$): δ 1.00-1.05 (m, 2H), 1.09-1.13 (m, 2H), 1.48-1.58 (m, 2H), 1.85-1.93 (m, 2H), 2.82-2.86 (m, 1H), 3.29-3.36 (m, 2H), 3.40-3.59 (m, 2H), 3.62-3.66 (m, 1H), 3.77-3.85 (m, 2H), 4.71 (q, J=5.2 Hz, 1H), 4.88 (q, J=5.6 Hz, 1H), 5.47 (s, 1H), 5.58 (t, J=4.4 Hz, 1H), 7.31 (s, 1H), 7.77 (d, J=8.4 Hz, 2H), 7.92 (d, J=8.4 Hz, 2H), 12.25 (s, 1H); MS (EI) m/z: 483.2 (M+1).

Example E2

2-(4-Cyclopropanesulfonyl-phenyl)-N-[5-(1,2-dihydroxy-ethyl)-thiazolo[5,4-b]pyridin-2-yl]-2-(tetrahydro-pyran-4-yloxy)-acetamide

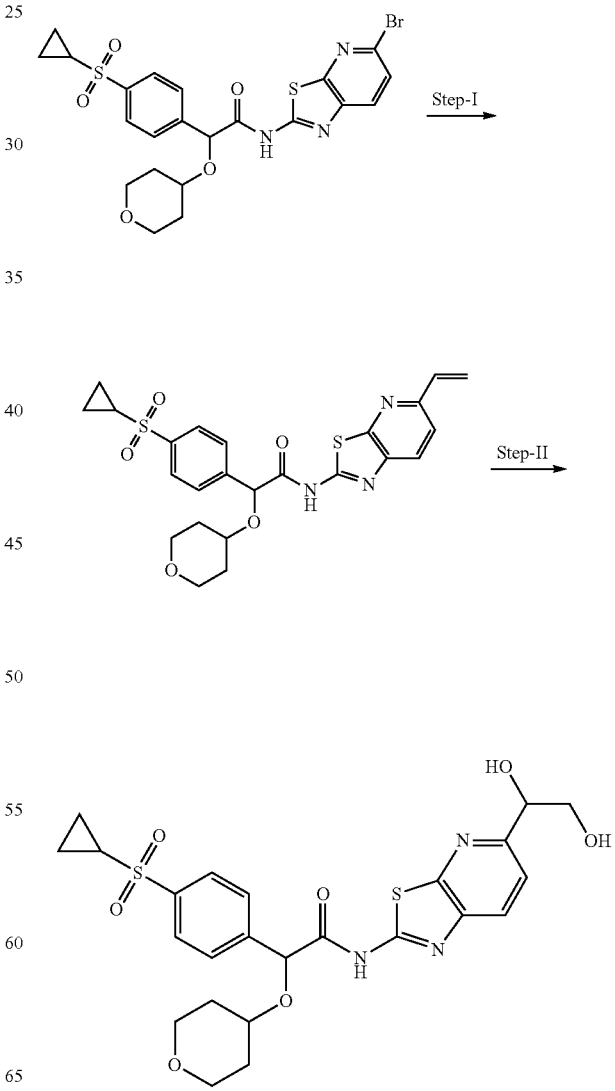

145

Step-I

2-(4-Cyclopropanesulfonyl-phenyl)-2-(tetrahydro-pyran-4-yloxy)-N-(5-vinyl-thiazolo[5,4-b]pyridin-2-yl)-acetamide

To mixture of N-(5-Bromo-thiazolo[5,4-b]pyridin-2-yl)-2-(4-cyclopropanesulfonyl-phenyl)-2-(tetrahydro-pyran-4-yloxy)-acetamide (Example-A95) (0.135 g, 0.24 mmol), Pd(PPh$_3$)$_4$ (0.014 g, 0.012 mmol) and LiCl (0.031 g, 0.73 mmol) in THF:DMF (1:1, 5 mL) under inert atmosphere was added tributyl(vinyl)stannane (0.23 g, 0.73 mmol) and heated under reflux for 8 hrs. Solvent was removed in vacuo and taken into brine and extracted with ethyl acetate (3×5 mL), washed with water and brine, dried (Na$_2$SO$_4$) and concentrated in vacuo to afford titled compound (0.080 g)

MS (EI) m/z: 500.20 (M+1).

146

Step-II

2-(4-Cyclopropanesulfonyl-phenyl)-N-[5-(1,2-dihydroxy-ethyl)-thiazolo[5,4-b]pyridin-2-yl]-2-(tetrahydro-pyran-4-yloxy)-acetamide

Prepared in analogues manner of Example E1

$^1$HNMR (DMSO-d$_6$, 400 MHz):—δ 1.00-1.06 (m, 2H), 1.10-1.1.14 (m, 2H), 1.47-1.64 (m, 2H), 1.84-2.02 (m, 2H), 2.83-2.89 (m, 1H), 3.25-3.35 (m, 2H), 3.51-3.57 (m, 1H), 3.65-3.72 (m, 2H), 3.78-3.87 (m, 2H), 4.66-4.74 (m, 2H), 5.54 (d, J=4.8 Hz, 1H), 5.56 (s, 1H), 7.59 (d, J=8.4 Hz, 1H), 7.81 (d, J=8.0 Hz, 2H), 7.95 (d, J=8.4 Hz, 2H), 8.11 (d, J=8.4 Hz, 1H), 12.78 (bs, 1H); MS (EI) m/z: 534.20 (M+1).

Examples E3 and E5 were prepared in analogues manner of example E1

| Example No. | Structure | Mass | IUPAC Name |
|---|---|---|---|
| E3 | 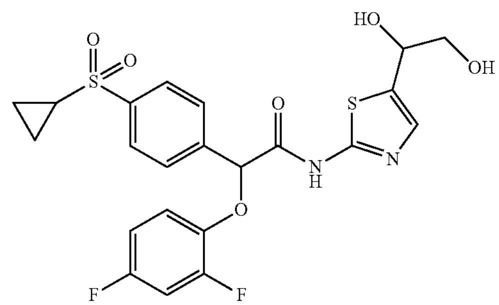 [SMILES: O=C(Nc1ncc(C(O)CO)s1)C(Oc1ccc(F)cc1F)c1ccc(S(=O)(=O)C2CC2)cc1] | 511.1 | 2-(4-cyclopropylsulfonylphenyl)-2-(2,4-difluorophenoxy)-N-[5-(1,2-dihydroxyethyl)thiazol-2-yl]acetamide |
| E4 | 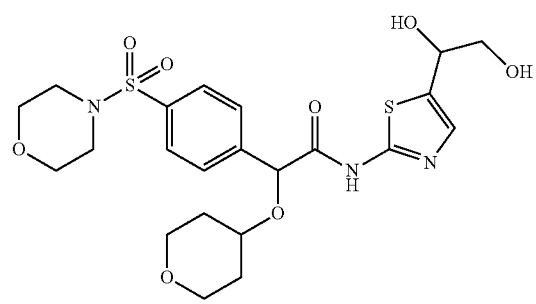 [SMILES: O=C(Nc1ncc(C(O)CO)s1)C(OC1CCOCC1)c1ccc(S(=O)(=O)N2CCOCC2)cc1] | 528.2 | N-[5-(1,2-Dihydroxy-ethyl)-thiazol-2-yl]-2-[4-(morpholine-4-sulfonyl)-phenyl]-2-(tetrahydro-pyran-4-yloxy)-acetamide |
| E5 | 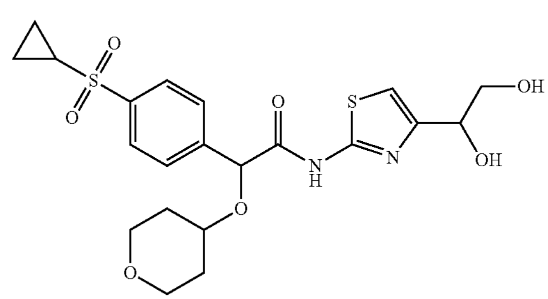 [SMILES: O=C(Nc1nc(C(O)CO)cs1)C(OC1CCOCC1)c1ccc(S(=O)(=O)C2CC2)cc1] | 483.1 | 2-(4-Cyclopropanesulfonyl-phenyl)-N-[4-(1,2-dihydroxy-ethyl)-thiazol-2-yl]-2-(tetrahydro-pyran-4-yloxy)-acetamide |

Example F1

2-(4-cyclopropylsulfonylphenyl)-2-tetrahydropyran-4-yloxy-N-[5-(2H-tetrazol-5-yl)-2-pyridyl]acetamide

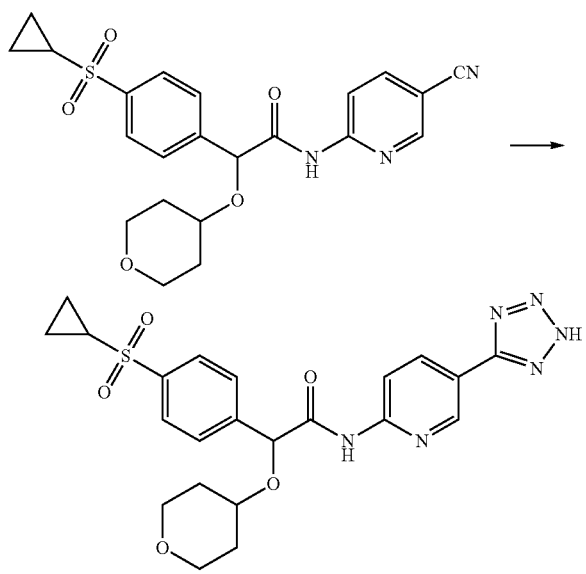

The mixture of N-(5-cyano-2-pyridyl)-2-(4-cyclopropylsulfonylphenyl)-2-tetrahydropyran-4-yloxy-acetamide (0.1 g, 0.22 mmol), sodium azide (0.03 g, 0.453 mmol) and ammonium chloride (0.024 g, 0.453 mmol) in DMF (8 mL) was heated at 110° C. for 16 h. After completion, reaction mixture was diluted with water (40 mL) and extracted with ethyl acetate (2×50 mL), combined organic layer was washed with water and brine, dried over sodium sulfate, filtered and concentrated in vacuo. Crude compound was purified by LCMS purification to afford title compound. (0.020 g).

$^1$H NMR (400 MHz, CD$_3$OD):—δ 1.03-1.08 (m, 2H), 1.21-1.25 (m, 2H), 1.66-1.84 (m, 2H), 1.90-1.97 (m, 1H), 2.07-2.14 (m, 1H), 2.64-2.71 (m, 1H), 3.40-3.51 (m, 2H), 3.76-3.84 (m, 1H), 3.89-4.01 (m, 2H), 5.39 (s, 1H), 7.83 (d, J=8.6 Hz, 2H), 7.94 (d, J=8.3 Hz, 2H), 8.31 (d, J=8.8 Hz, 1H), 8.38 (dd, J=8.8 Hz, 2.2 Hz, 1H), 8.99 (d, J=1.7 Hz, 1H), 9.05 (bs, 1H); HPLC MS (EI) m/z: 484.6. (M+1).

Example G1A/B-G27A/B Chirally Pure Compounds

Analytical Methods Used for Chiral Purification

Method-1:—Column-OJ-RH (150×4.6)mm, 5 μm, Flow: 1 mL min$^{-1}$, M.Phase: Methanol, Column Temp: 40° C., Detection wavelength: 220 nm.

Method-2:—Column-OJ-RH (150×4.6)mm, 5 μm, Flow: 0.8 mL min$^{-1}$, M.Phase: 0.05% FA in Methanol, Column Temp: 40° C., Detection wavelength: 224 nm.

Method-3:—Column-OJ-RH (150×4.6)mm, 5 μm, Flow: 1 ml min$^{-1}$, M.Phase: 0.05% FA in Methanol, Column Temp: Ambient, Detection wavelength: 220 nm.

Method-4:—Column-OJ-RH (150×4.6)mm, 5 μm, Flow: 1 ml min$^{-1}$, M.Phase: 0.05% FA in Methanol, Column Temp: 40° C., Detection wavelength: 224 nm.

Method-5:—Column-OJ-RH (150×4.6)mm, 5 μm, Flow: 1 ml min$^{-1}$, M.Phase: 0.05 FA in Methanol, Column Temp: 40° C., Detection wavelength: 220 nm Method-6:—Column-OJ-RH (150×4.6)mm, 5 μm, Flow: 1 ml min$^{-1}$, M.Phase: 0.05% FA in Water(05%): Methanol(95), Column Temp: 40° C., Detection wavelength: 220 nm, Resolution: 3.31.

Method-7:—Column-OJ-RH (150×4.6)mm, 5 μm, Flow: 1 ml min$^{-1}$, M.Phase: 0.05% TFA in Methanol, Column Temp: 40° C., Detection wavelength: 220 nm, Resolution: 3.45, Method-8:—Column-OJ-RH (150×4.6)mm, 5 μm, Flow: 1 ml min$^{-1}$, M.Phase: 0.05% TFA in Methanol, Column Temp: 40° C., Detection wavelength: 224 nm.

Method-9:—Column-OJ-RH (150×4.6)mm, 5 μm, Flow: 0.5 ml min$^{-1}$, M.Phase: Acetonitrile: 0.05% Formic acid in water (30:70) Column Temp.: 40, Detection wavelength: 220 nm; Resolution: 2.

Method-10:—Column-OJ-RH (150×4.6)mm, 5 μm, Flow: 0.5 ml min$^{-1}$, M.Phase: Acetonitrile: 0.05% Formic acid in water (40:60) Column Temp.: 40, Detection wavelength: 220 nm; Resolution: 2.46.

Method-11:—Column-Chiralpak IC-3 (150×4.6)mm, 3 μm, Flow: 1.5 ml min$^{-1}$, M.Phase: 0.1% TFA in n-Hexane (80%):Ethanol(20%), Column Temp: 40° C., Detection wavelength: 220 nm.

Method-12:—Column-Chiralpak IC-3 (150×4.6)mm, 3 μm, Flow: 1.2 ml min$^{-1}$, M.Phase: 0.1% TFA in n-Hexane (50%):IPA(50%), Column Temp: 40° C., Detection wavelength: 254 nm.

Method-13:—Column-OJ-RH (150×4.6)mm, Flow: 0.6 ml min$^{-1}$, M.Phase: 0.05% FA in Methanol, Column Temp: 40° C.; Detection wavelength: 220 nm,

| Example No. | Structure | MS (EI)m/z: (M + 1). | IUPAC Name | Examples Used/ Method Used |
|---|---|---|---|---|
| G1A | 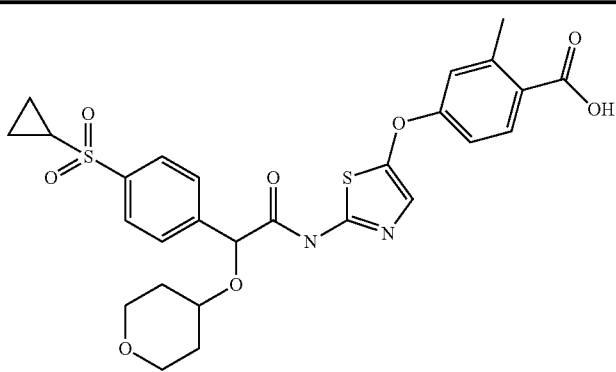<br>(+) Enantiomer | 573.2 | (+)4-[2-[[2-(4-cyclopropylsulfonylphenyl)-2-tetrahydropyran-4-yloxy-acetyl]amino]thiazol-5-yl]oxy-2-methyl-benzoic acid | B10/ Method-1 |

-continued

| Example No. | Structure | MS (EI)m/z: (M + 1). | IUPAC Name | Examples Used/ Method Used |
|---|---|---|---|---|
| G1B | (−) Enantiomer | 573.2 | (−)4-[2-[[2-(4-cyclopropylsulfonylphenyl)-2-tetrahydropyran-4-yloxy-acetyl]amino]thiazol-5-yl]oxy-2-methyl-benzoic acid | |
| G2A | (+) Enantiomer | 514.9 ($^{35}$Cl) | (+)2-[5-chloro-2-[[2-(4-cyclopropylsulfonylphenyl)-2-tetrahydropyran-4-yloxy-acetyl]amino]thiazol-4-yl]acetic acid | B 61/ Method-9 |
| G2B | (−) Enantiomer | 514.9 ($^{35}$Cl) | (−)2-[5-chloro-2-[[2-(4-cyclopropylsulfonylphenyl)-2-tetrahydropyran-4-yloxy-acetyl]amino]thiazol-4-yl]acetic acid | |
| G3A | (+) Enantiomer | 558.2 | (+)2-[5-chloro-2-[[2-[4-(1-piperidylsulfonyl)phenyl]-2-tetrahydropyran-4-yloxy-acetyl]amino]thiazol-4-yl]acetic acid | B12/ Method-10 |

-continued

| Example No. | Structure | MS (EI)m/z: (M + 1). | IUPAC Name | Examples Used/ Method Used |
|---|---|---|---|---|
| G3B | (−) Enantiomer | 558.2 | (−)2-[5-chloro-2-[[2-[4-(1-piperidylsulfonyl)phenyl]-2-tetrahydropyran-4-yloxy-acetyl]amino]thiazol-4-yl]acetic acid | |
| G4A | (+) Enantiomer | 517.1 | (+)2-(4-cyclopropylsulfonylphenyl)-2-(2,4-difluorophenoxy)-N-(5-pyrazol-1-ylthiazol-2-yl)acetamide | A64/ Method-1 |
| G4B | (−) Enantiomer | 517.1 | (−)2-(4-cyclopropylsulfonylphenyl)-2-(2,4-difluorophenoxy)-N-(5-pyrazol-1-ylthiazol-2-yl)acetamide | |
| G5A | (+) Enantiomer | 601.3 | (+)2-[4-[2-[[2-(4-cyclopropylsulfonylphenyl)-2-tetrahydropyran-4-yloxy-acetyl]amino]thiazol-5-yl]oxyphenyl]-2-methyl-propanoic acid | B13/ Method-2 |

-continued

| Example No. | Structure | MS (EI)m/z: (M + 1). | IUPAC Name | Examples Used/ Method Used |
|---|---|---|---|---|
| G5B | 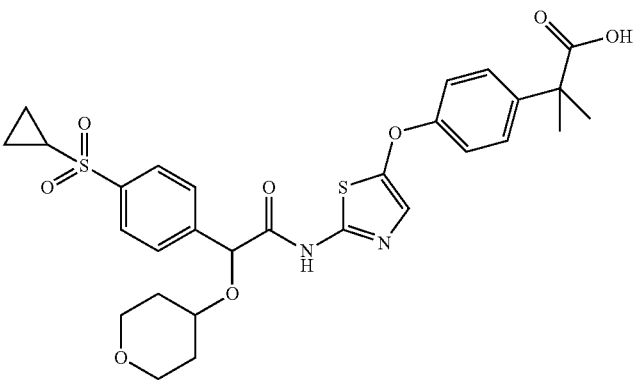<br>(−) Enantiomer | 601.3 | (−)2-[4-[2-[[2-(4-cyclopropylsulfonylphenyl)-2-tetrahydropyran-4-yloxy-acetyl]amino]thiazol-5-yl]oxyphenyl]-2-methyl-propanoic acid | |
| G6A | 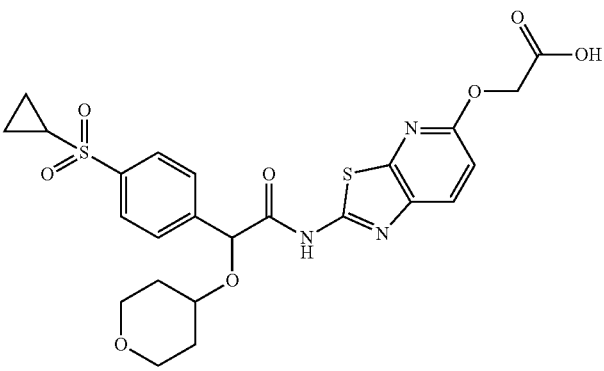<br>(+) Enantiomer | 548.1 | (+)2-[2-[[2-(4-cyclopropylsulfonylphenyl)-2-tetrahydropyran-4-yloxy-acetyl]amino]thiazolo[5,4-b]pyridin-5-yl]oxyacetic acid | B56/ Method-3 |
| G6B | 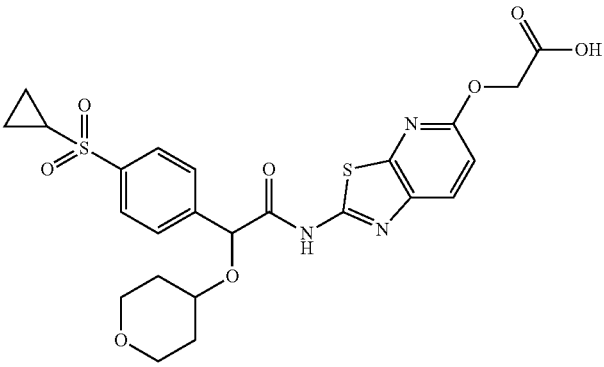<br>(−) Enantiomer | 548.2 | (−)2-[2-[[2-(4-cyclopropylsulfonylphenyl)-2-tetrahydropyran-4-yloxy-acetyl]amino]thiazolo[5,4-b]pyridin-5-yl]oxyacetic acid | |

| Example No. | Structure | MS (EI)m/z: (M + 1) | IUPAC Name | Examples Used/ Method Used |
|---|---|---|---|---|
| G7A | 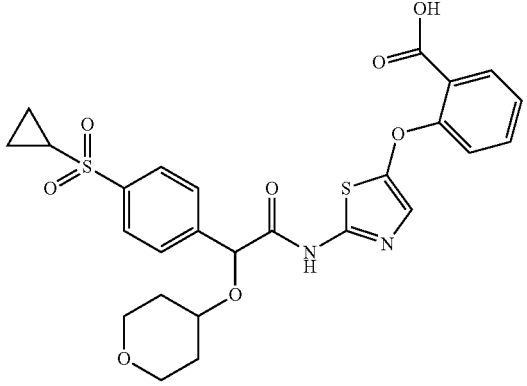 (+) Enantiomer | 559.2 | (+)2-[2-[[2-(4-cyclopropylsulfonylphenyl)-2-tetrahydropyran-4-yloxy-acetyl]amino]thiazol-5-yl]oxybenzoic acid | B18/ Method-4 |
| G7B | 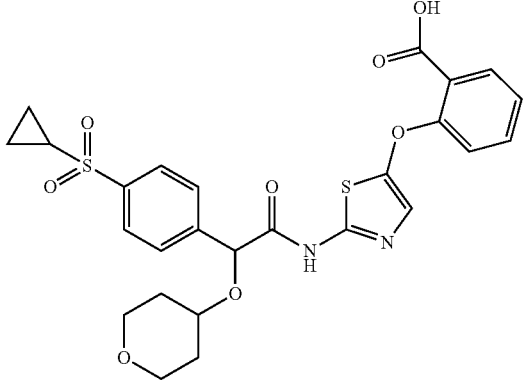 (-) Enantiomer | 559.2 | (−)2-[2-[[2-(4-cyclopropylsulfonylphenyl)-2-tetrahydropyran-4-yloxy-acetyl]amino]thiazol-5-yl]oxybenzoic acid | |
| G8A | 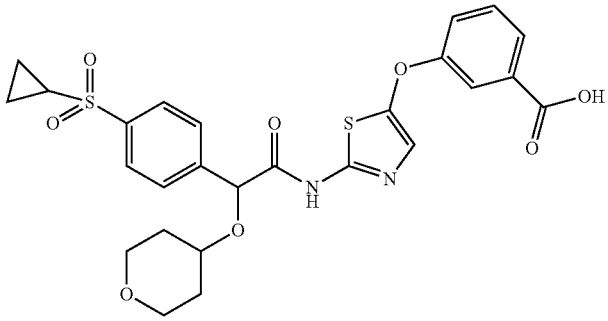 (+) Enantiomer | 559.2 | (+)3-[2-[[2-(4-cyclopropylsulfonylphenyl)-2-tetrahydropyran-4-yloxy-acetyl]amino]thiazol-5-yl]oxybenzoic acid | B1/ Method-8 |

-continued

| Example No. | Structure | MS (EI)m/z: (M + 1). | IUPAC Name | Examples Used/ Method Used |
|---|---|---|---|---|
| G8B | 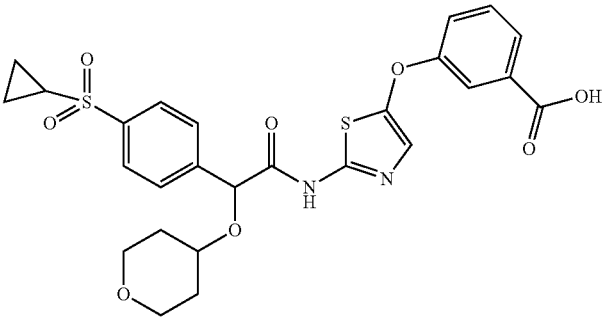 (−) Enantiomer | 559.2 | (−)3-[2-[[2-(4-cyclopropylsulfonylphenyl)-2-tetrahydropyran-4-yloxy-acetyl]amino]thiazol-5-yl]oxybenzoic acid | |
| G9A | 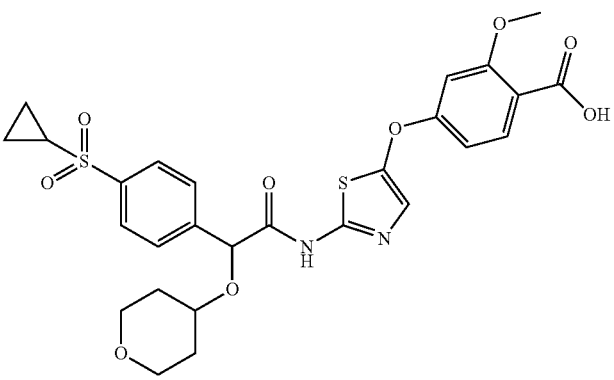 (+) Enantiomer | 589.2 | (+)4-[2-[[2-(4-cyclopropylsulfonylphenyl)-2-tetrahydropyran-4-yloxy-acetyl]amino]thiazol-5-yl]oxy-2-methoxy-benzoic acid | B24/ Method-7 |
| G9B | 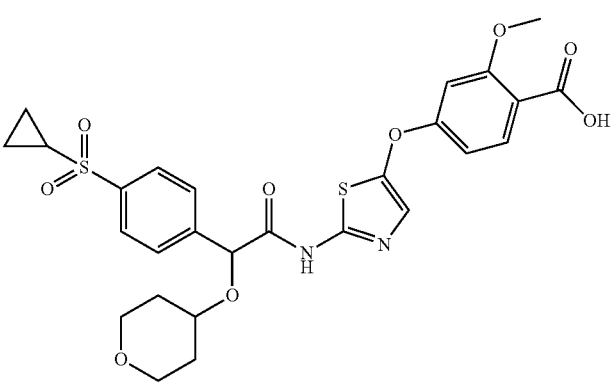 (−) Enantiomer | 589.2 | (−)4-[2-[[2-(4-cyclopropylsulfonylphenyl)-2-tetrahydropyran-4-yloxy-acetyl]amino]thiazol-5-yl]oxy-2-methoxy-benzoic acid | |

-continued

| Example No. | Structure | MS (EI)m/z: (M + 1). | IUPAC Name | Examples Used/ Method Used |
|---|---|---|---|---|
| G10A | 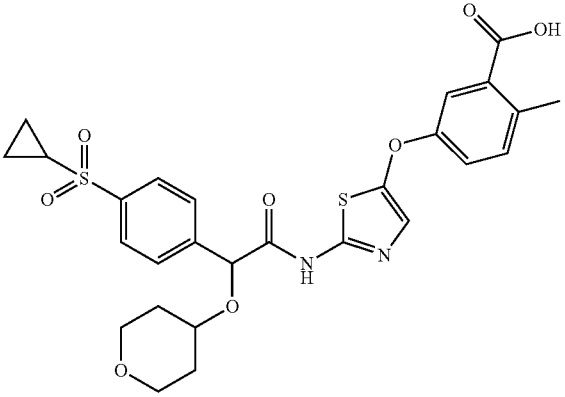<br>(+) Enantiomer | 573.2 | (+)5-[2-[[2-(4-cyclopropylsulfonylphenyl)-2-tetrahydropyran-4-yloxy-acetyl]amino]thiazol-5-yl]oxy-2-methyl-benzoic acid | B28/ Method-8 |
| G10B | 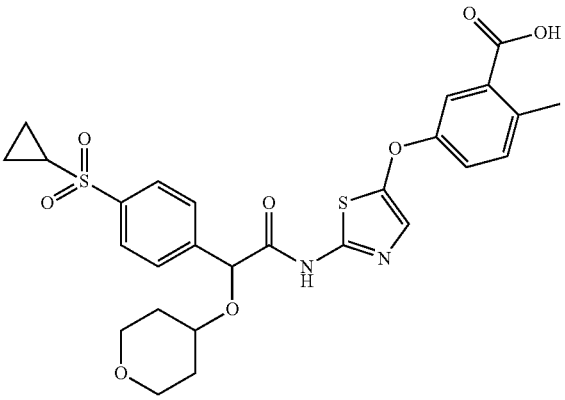<br>(-) Enantiomer | 573.2 | (−)5-[2-[[2-(4-cyclopropylsulfonylphenyl)-2-tetrahydropyran-4-yloxy-acetyl]amino]thiazol-5-yl]oxy-2-methyl-benzoic acid | |
| G11A | Chiral<br>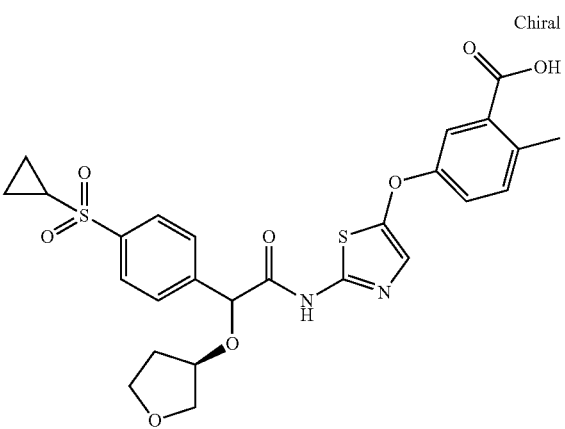<br>(+) Enantiomer | 559.2 | (+)5-[2-[[2-(4-cyclopropylsulfonylphenyl)-2-[(3R)-tetrahydrofuran-3-yl]oxy-acetyl]amino]thiazol-5-yl]oxy-2-methyl-benzoic acid | B2/ Method-7 |

-continued

| Example No. | Structure | MS (EI)m/z: (M + 1). | IUPAC Name | Examples Used/ Method Used |
|---|---|---|---|---|
| G11B | 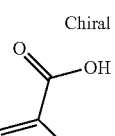<br>(-) Enantiomer | 559.2 | (−)5-[2-[[2-(4-cyclopropylsulfonylphenyl)-2-[(3R)-tetrahydrofuran-3-yl]oxy-acetyl]amino]thiazol-5-yl]oxy-2-methyl-benzoic acid | |
| G12A | 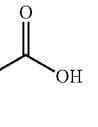<br>(+) Enantiomer | 533.2 | (+)1-[2-[[2-(4-cyclopropylsulfonylphenyl)-2-tetrahydropyran-4-yloxy-acetyl]amino]thiazol-5-yl]pyrazole-4-carboxylic acid | B3/ Method-5 |
| G12B | 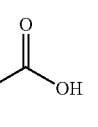<br>(−) Enantiomer | 533.2 | (−)1-[2-[[2-(4-cyclopropylsulfonylphenyl)-2-tetrahydropyran-4-yloxy-acetyl]amino]thiazol-5-yl]pyrazole-4-carboxylic acid | |

-continued

| Example No. | Structure | MS (EI)m/z: (M + 1). | IUPAC Name | Examples Used/ Method Used |
|---|---|---|---|---|
| G13A | *Chiral HPLC RT = 4.26 min* | 587.2 | 4-[2-[[2-(4-cyclopropylsulfonylphenyl)-2-tetrahydropyran-4-yloxy-acetyl]amino]-4-methyl-thiazol-5-yl]oxy-2-methyl-benzoic acid | B31/ Method-5 |
| G13B | *Chiral HPLC RT = 6.37 min* | 587.2 | 4-[2-[[2-(4-cyclopropylsulfonylphenyl)-2-tetrahydropyran-4-yloxy-acetyl]amino]-4-methyl-thiazol-5-yl]oxy-2-methyl-benzoic acid | |
| G14A | Chiral  (+) Enantiomer | 559.2 | (+)4-[2-[[2-(4-cyclopropylsulfonylphenyl)-2-[(3R)-tetrahydrofuran-3-yl]oxy-acetyl]amino]thiazol-5-yl]oxy-2-methyl-benzoic acid | B30/ Method-5 |

| Example No. | Structure | MS (EI)m/z: (M + 1). | IUPAC Name | Examples Used/ Method Used |
|---|---|---|---|---|
| G14B | 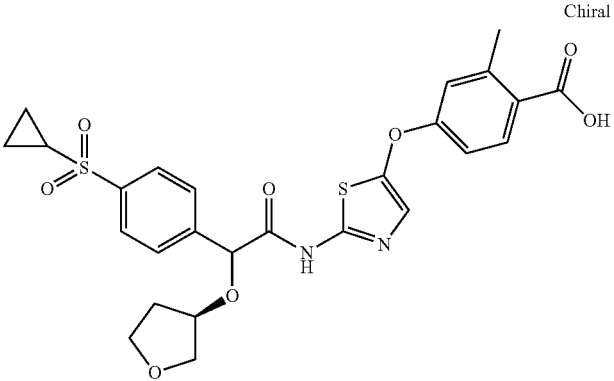 (−) Enantiomer | 559.2 | (−)4-[2-[[2-(4-cyclopropylsulfonylphenyl)-2-[(3R)-tetrahydrofuran-3-yl]oxy-acetyl]amino]thiazol-5-yl]oxy-2-methyl-benzoic acid | |
| G15A | 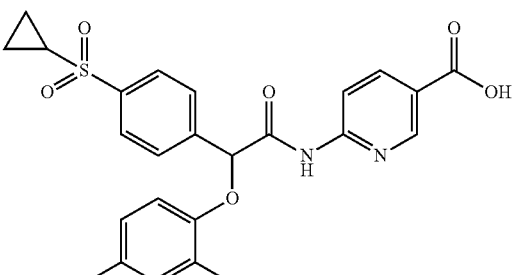 (−) Enantiomer | 489.1 | (−)6-[[2-(4-cyclopropylsulfonylphenyl)-2-(2,4-difluorophenoxy)acetyl]amino]pyridine-3-carboxylic acid | B5/ Method-11 |
| G15B | 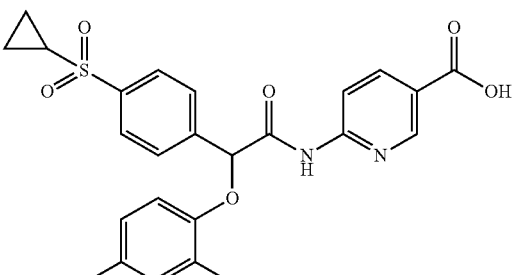 (+) Enantiomer | 489.1 | (+)6-[[2-(4-cyclopropylsulfonylphenyl)-2-(2,4-difluorophenoxy)acetyl]amino]pyridine-3-carboxylic acid | |
| G16A | 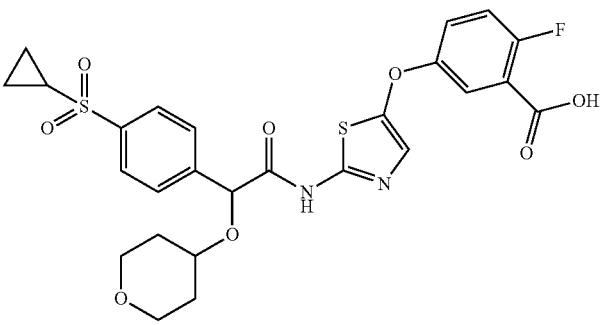 (+) Enantiomer | 577.2 | (+)5-[2-[[2-(4-cyclopropylsulfonylphenyl)-2-tetrahydropyran-4-yloxy-acetyl]amino]thiazol-5-yl]oxy-2-fluoro-benzoic acid | B37/ Method-7 |

-continued

| Example No. | Structure | MS (EI)m/z: (M + 1). | IUPAC Name | Examples Used/ Method Used |
|---|---|---|---|---|
| G16B | (−) Enantiomer | 577.2 | (−)5-[2-[[2-(4-cyclopropylsulfonylphenyl)-2-tetrahydropyran-4-yloxy-acetyl]amino]thiazol-5-yl]oxy-2-fluoro-benzoic acid | |
| G17A | (−) Enantiomer | 461.2 | (−)6-[[2-(4-cyclopropylsulfonylphenyl)-2-tetrahydropyran-4-yloxy-acetyl]amino]pyridine-3-carboxylic acid | B29/ Method-12 |
| G17B | (+) Enantiomer | 461.2 | (+)6-[[2-(4-cyclopropylsulfonylphenyl)-2-tetrahydropyran-4-yloxy-acetyl]amino]pyridine-3-carboxylic acid | |
| G18A | Chiral HPLC RT = 2.93 min | 475.1 | 2-[6-[[2-(4-cyclopropylsulfonylphenyl)-2-tetrahydropyran-4-yloxy-acetyl]amino]-2-pyridyl]acetic acid | B7/ Method-7 |

| Example No. | Structure | MS (EI)m/z: (M + 1). | IUPAC Name | Examples Used/ Method Used |
|---|---|---|---|---|
| G18B | Chiral HPLC RT = 4.09 min | 475.2 | 2-[6-[[2-(4-cyclopropylsulfonylphenyl)-2-tetrahydropyran-4-yloxy-acetyl]amino]-2-pyridyl]acetic acid | |
| G19A | (+) Enantiomer | 587.2 | (+)ethyl 3-[2-[[2-(4-cyclopropylsulfonylphenyl)-2-tetrahydropyran-4-yloxy-acetyl]amino]thiazol-5-yl]oxybenzoate | A2/ Method-8 |
| G19B | (-) Enantiomer | 587.2 | (−)ethyl 3-[2-[[2-(4-cyclopropylsulfonylphenyl)-2-tetrahydropyran-4-yloxy-acetyl]amino]thiazol-5-yl]oxybenzoate | |
| G20A | (+) Enantiomer | 545.2 | (+)2-(4-cyclopropylsulfonylphenyl)-N-[5-[3-(hydroxymethyl)phenoxy]thiazol-2-yl]-2-tetrahydropyran-4-yloxy-acetamide | D3/ Method-1 |

-continued

| Example No. | Structure | MS (EI)m/z: (M + 1). | IUPAC Name | Examples Used/ Method Used |
|---|---|---|---|---|
| G20B | 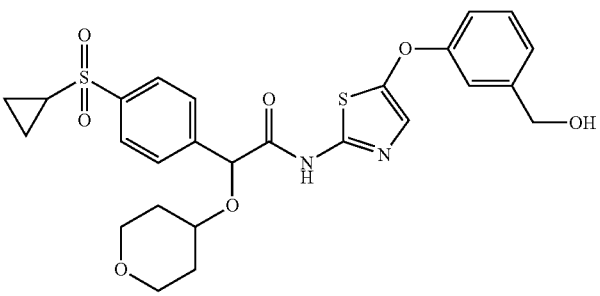<br>(−) Enantiomer | 545.2 | (−)2-(4-cyclopropylsulfonylphenyl)-N-[5-[3-(hydroxymethyl)phenoxy]thiazol-2-yl]-2-tetrahydro-pyran-4-yloxy-acetamide | |
| G21A | Chiral<br>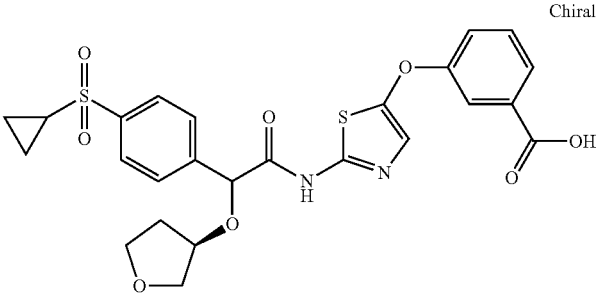<br>(+) Enantiomer | 545.2 | (+)3-[2-[[2-(4-cyclopropylsulfonylphenyl)-2-[(3R)-tetrahydrofuran-3-yl]oxy-acetyl]amino]thiazol-5-yl]oxybenzoic acid | B44/ Method-6 |
| G21B | Chiral<br>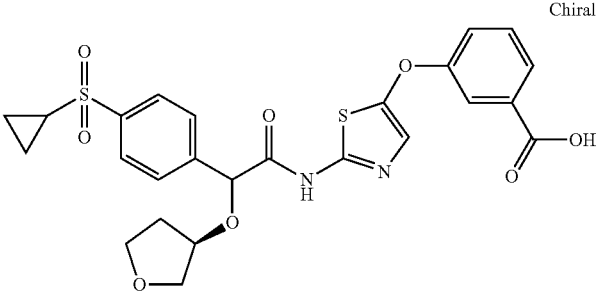<br>(−) Enantiomer | 545.2 | (−)3-[2-[[2-(4-cyclopropylsulfonylphenyl)-2-[(3R)-tetrahydrofuran-3-yl]oxy-acetyl]amino]thiazol-5-yl]oxybenzoic acid | |
| G22A | 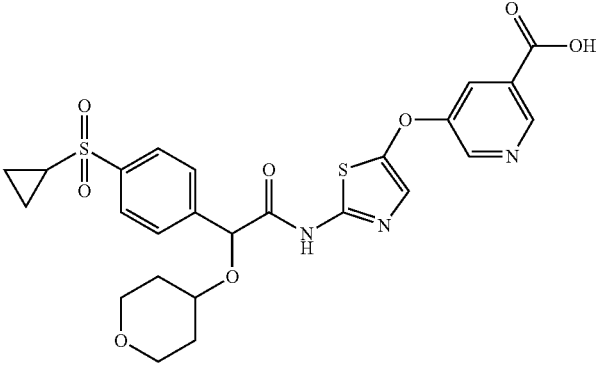<br>(+) Enantiomer | 560.1 | (+)5-[2-[[2-(4-cyclopropylsulfonylphenyl)-2-tetrahydropyran-4-yloxy-acetyl]amino]thiazol-5-yl]oxypyridine-3-carboxylic acid | B47/ Method-2 |

-continued

| Example No. | Structure | MS (EI)m/z: (M + 1). | IUPAC Name | Examples Used/ Method Used |
|---|---|---|---|---|
| G22B | (−) Enantiomer | 560.1 | (−)5-[2-[[2-(4-cyclopropylsulfonylphenyl)-2-tetrahydropyran-4-yloxy-acetyl]amino]thiazol-5-yl]oxypyridine-3-carboxylic acid | |
| G23A | (+) Enantiomer | 601.2 | (+)iso-propyl 3-[2-[[2-(4-cyclopropylsulfonylphenyl)-2-tetrahydropyran-4-yloxy-acetyl]amino]thiazol-5-yl]oxybenzoate | Synthesized from G8A |
| G24A | (+) Enantiomer | 615.2 | (+)-isobutyl 3-[2-[[2-(4-cyclopropylsulfonylphenyl)-2-tetrahydropyran-4-yloxy-acetyl]amino]thiazol-5-yl]oxybenzoate | Synthesized from G8A |

| Example No. | Structure | MS (EI)m/z: (M + 1). | IUPAC Name | Examples Used/ Method Used |
|---|---|---|---|---|
| G25A | 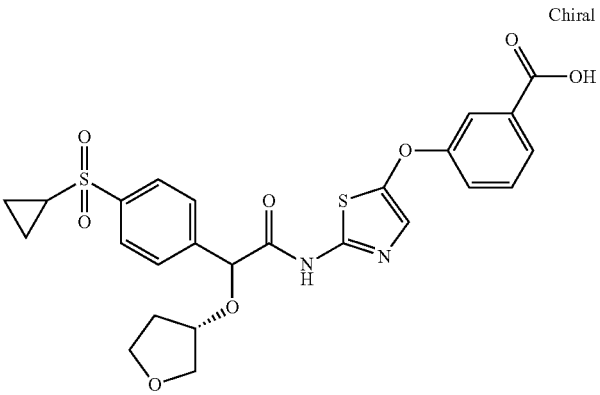<br>(+) Enantiomer | 545.2 | (+)-3-[2-[[2-(4-cyclopropylsulfonylphenyl)-2-[(3S)-tetrahydrofuran-3-yl]oxy-acetyl]amino]thiazol-5-yl]oxybenzoic acid | B59/ Method-8 |
| G25B | 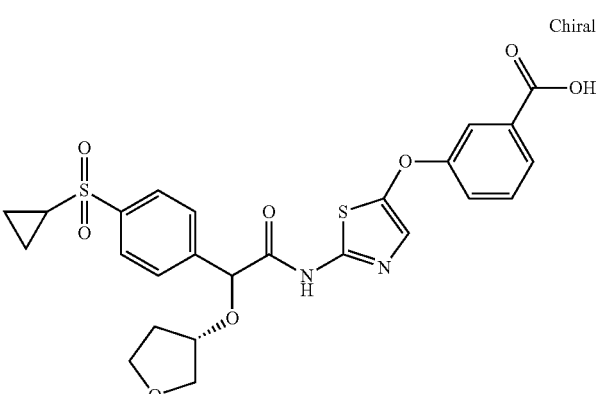<br>(-) Enantiomer | 545.2 | (-)-3-[2-[[2-(4-cyclopropylsulfonylphenyl)-2-[(3S)-tetrahydrofuran-3-yl]oxy-acetyl]amino]thiazol-5-yl]oxybenzoic acid | |
| G26A | 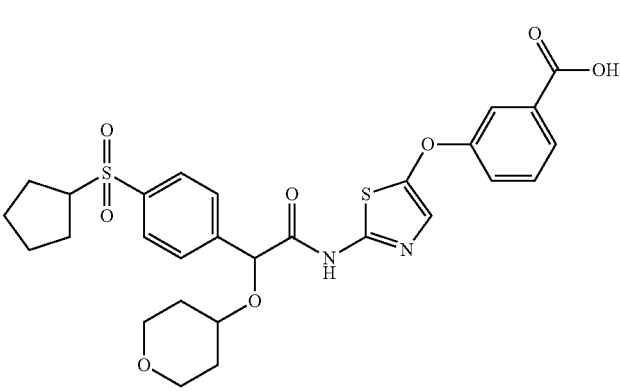<br>(+) Enantiomer | 587.3 | (+)-3-[2-[[2-(4-cyclopentylsulfonylphenyl)-2-tetrahydropyran-4-yloxy-acetyl]amino]thiazol-5-yl]oxybenzoic acid | B60/ Method-7 |

| Example No. | Structure | MS (EI)m/z: (M + 1). | IUPAC Name | Examples Used/ Method Used |
|---|---|---|---|---|
| G26B | (-) Enantiomer | 587.3 | (−)-3-[2-[[2-(4-cyclopentylsulfonylphenyl)-2-tetrahydropyran-4-yloxy-acetyl]amino]thiazol-5-yl]oxybenzoic acid | |
| G27A | 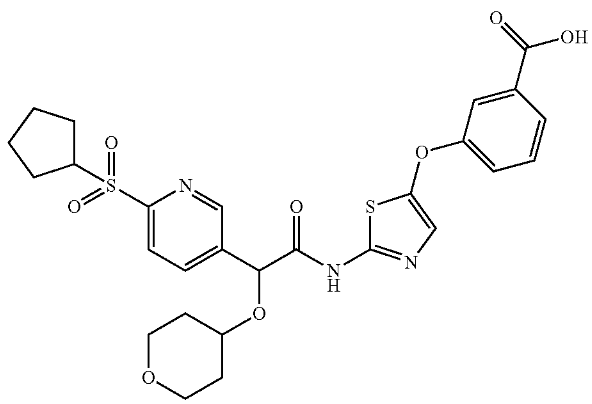 [SMILES: O=C(O)c1cccc(Oc2cnc(NC(=O)C(OC3CCOCC3)c3ccc(S(=O)(=O)C4CCCC4)nc3)s2)c1] | 588.3 | (+)-3-[2-[[2-(6-cyclopentylsulfonyl-3-pyridyl)-2-tetrahydropyran-4-yloxy-acetyl]amino]thiazol-5-yl]oxybenzoic acid | B8/ Method-13 |
| G27B | 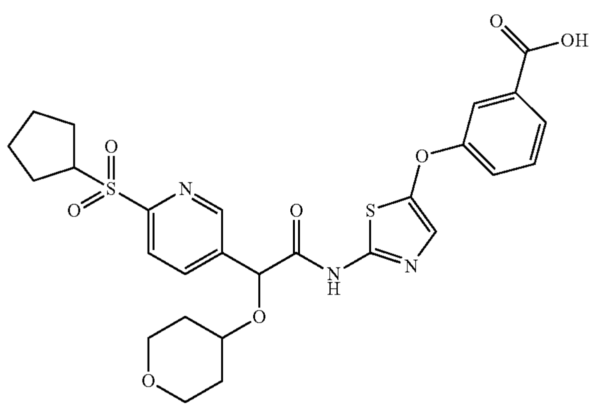 [SMILES: O=C(O)c1cccc(Oc2cnc(NC(=O)C(OC3CCOCC3)c3ccc(S(=O)(=O)C4CCCC4)nc3)s2)c1] | 588.2 | (−)-3-[2-[[2-(6-cyclopentylsulfonyl-3-pyridyl)-2-tetrahydropyran-4-yloxy-acetyl]amino]thiazol-5-yl]oxybenzoic acid | |

Glucokinase Activity Assay:

The glucokinase (GK) assay is a coupled enzymatic assay. GK catalyzes the first step of glycolysis, the conversion of glucose to glucose-6-phosphate (G6P) in the presence of ATP. G6P in turn is converted by glucose-6-phosphate dehydrogenase (G6PD) to 6-phosphogluconate, a process that requires NAD, resulting in NADH formation. Since the GK-catalyzed step is the rate-limiting step of this coupled enzymatic process, the rate of accumulation of 6-phosphogluconate and NADH is directly proportional to the rate of glucose phosphorylation by GK. The rate of the GK-catalyzed reaction can therefore be measured by monitoring the increase in NADH absorbance at 340 nm.

The assay is carried out according to the protocol outlined in Hariharan et al (1997), Diabetes 46: 11-16. Briefly, the test compounds are incubated in a reaction mix containing 25 mM HEPES (pH 7.2), 10 mM $MgCl_2$, 100 mM KCl, 5 mM ATP, 2 mM DTT, 0.5 mM NAD, 1 U/mL *Leuconostoc mesenteroides* G6PD, 0.3 U/mL of purified human recombinant GK, and different concentrations of glucose. Enzymatic activity is calculated from the initial reaction velocity, measured from the change in NADH absorbance as a function of time.

Compounds described in formula (I), in concentration ranges from 1.0 nM to 500 μM, are tested in the purified human recombinant glucokinase assay described above.

A compound is considered to be a glucokinase activator if it, in its testable range of concentrations, yields a higher rate of glucose phosphorylation than in its absence at a particular glucose concentration, for example at 5 mM glucose.

Characterization of Glucokinase Activators from the In Vitro Glucokinase Assay:

Compounds of general formula (I) are tested in the in vitro GK enzymatic assay to monitor dose-dependent effect on glucokinase activation (in kinetic mode), as described above, at various glucose concentrations. The $S_{0.5}$ of glucokinase for glucose at different concentration of each compound of interest is calculated from the following modified version of the Michaelis-Menten equation, $V=V_{max} [S]^n/(S_{0.5}{}^n+[S]^n)$, where [S] is the glucose concentration and n is the Hill coefficient (taken as 1.7 to account for the sigoidal kinetics of glucokinase with respect to glucose). The $S_{0.5}$ is plotted against the log of the compound concentration. The change in the $S_{0.5}$ of glucokinase ($\Delta S_{0.5}$) for glucose is calculated by subtracting the $S_{0.5}$ at each concentration of the compound from the $S_{0.5}$ in the vehicle control. The $\Delta S_{0.5}$ is then normalized to a percent scale, where the $S_{0.5}$ in the vehicle control is set to 0% and 0 mM glucose is set to 100%. The % $\Delta S_{0.5}$ is then plotted against the log of the compound concentration. The $EC_{50}$ and $E_{max}$ of % change in $S_{0.5}$ is obtained from the sigoidal fit of the data. Detailed protocol has been described in our copending application no. 409/CHE/2007 which is incorporated herein by reference. Characterization data of some representative glucokinase activators of the present disclosure, which are illustrative but not limiting, are given in table I below.

The glucokinase activation data of some representative compounds of the present disclosure, which are illustrative but not to be construed as limiting the scope or spirit of the disclosure, are given in the table I below.

TABLE I $EC_{50}$ and $E_{max}$ (with respect to % $\Delta S_{0.5}$) of GK activators

| Example-No. | $EC_{50}$ (μM) | % $E_{max}$ |
|---|---|---|
| A-1 | 1.4 | 89 |
| A-11 | 0.95 | 85 |
| A-12 | 0.66 | 88 |
| A-32 | >10 | |
| A-58 | >10 | |
| B-4 | 3.7 | 83 |
| B-9 | 0.093 | 89 |
| B-12 | 1.12 | 90 |
| B-20 | 0.59 | 94 |
| B-23 | 0.48 | 94 |
| B-26 | 0.22 | 92 |
| B-49 | 0.57 | 92 |
| B-58 | 0.74 | 89 |
| C3 | 0.13 | 94 |
| D1 | 0.1 | 91 |
| D3 | 0.14 | 92 |
| E2 | 1.5 | 93 |
| E3 | 1.2 | 88 |
| G1A | 0.087 | 97 |
| G1B) | 0.33 | 92 |
| G3B | 0.42 | 94 |
| G4A | 0.26 | 91 |
| G4B | 0.64 | 79 |
| G5A | 0.094 | 91 |
| G8A | 0.19 | 91 |
| G9A | 0.27 | 92 |
| G10A | 0.23 | 93 |
| G11A | 0.57 | 92 |

TABLE I-continued $EC_{50}$ and $E_{max}$ (with respect to % $\Delta S_{0.5}$) of GK activators

| Example-No. | $EC_{50}$ (μM) | % $E_{max}$ |
|---|---|---|
| G12A | 0.3 | 90 |
| G14A | 0.38 | 99 |
| G15A | 0.48 | 90 |
| G16A | 0.27 | 93 |
| G19A | 0.1 | 95 |
| G20A | 0.064 | 93 |
| G22A | 0.29 | 95 |
| G25A | 0.2 | 95 |
| G26A | 0.18 | 94 |
| G27A | 0.13 | 95 |

Measurement of Glycogen Synthesis in Primary Rat Hepatocytes:

The glycogen deposition assay was carried out with few modifications in the original protocol as described in "Biochem J. 1990 Feb. 15; 266(1): 91-102". In brief, primary hepatocytes were collected from male Wistar rats, and were seeded in a 48-well plate at a density of 150,000 cells/well in Minimal Essential Medium (MEM) containing 10% foetal calf serum (FCS) 100 nM insulin and 10 nM dexamethasone. followed by incubation for 4 hours at 37° C. The medium was replaced with fresh MEM containing 10% FCS and 10 nM dexamethasone and the cells were further incubated for 16 hours at 37° C. Following day, the medium was replaced with fresh MEM (serum-free) containing 2 μCi/ml of D-[U$^{14}$C]-glucose in the presence of the test compound. Hepatocytes were incubated for 3 hours at 37° C. followed by washing with 150 mM NaCl. Cells were lysed with 0.1 N NaOH, and the lysate was precipitated with 80% w/v trichloroacetic acid (TCA). Cell debris was pelleted by centrifugation, the supernatant was removed, and the glycogen was precipitated with 66% ethanol followed by drying overnight. Samples were dissolved in MiliQ water and transferred to 96 well reading plate, 100 μL scintillant was added per well and the plate was read in scintillation counter (MicroBeta Trilux, Perkin Elmer). Data was expressed as fold increase in glycogen synthesis over DMSO control (untreated hepatocytes).

A compound is considered to be a glucokinase activator in a cellular environment if it demonstrates significant increase in glycogen synthesis over DMSO control in the hepatocytes.

The glycogen synthesis data of some representative compounds of the present invention, which are illustrative but not limiting, that have shown glycogen synthesis greater than 2.5 fold at 10 μM concentration, is given in Table 2 below:

TABLE 2

Glycogen synthesis data

| | |
|---|---|
| Illustrative examples that have shown Glycogen synthesis greater than 2.5 fold at 10 μM concentration | G1A, G1B, G8A, G9A, G10A, G15A, G16A, G20A, G21A, G25A, G26A, G27A |

Although the subject matter has been described in considerable details with reference to certain preferred embodiments thereof, other embodiment are possible. As such, the spirit and scope of the appended claims should not be limited to the description of the preferred embodiments contained therein.

We claim:

1. A compound of formula (I)

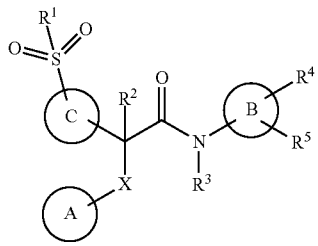

or its stereoisomers, tautomers, prodrugs, pharmaceutically acceptable salts, solvates and formulations wherein, ring A and ring C are monocyclic ring independently selected from aryl, heteroaryl or heterocyclyl;

wherein rings A and C are optionally substituted with 1 to 4 substituents independently selected from halogen, monohaloalkyl, dihaloalkyl or perhaloalkyl, monohaloalkoxy, dihaloalkoxy or perhaloalkoxy, cyano, nitro, alkyl, alkenyl, alkynyl, methylenedioxy, amidino —$NR^6R^7$, —$OR^6$, —$NR^6C(O)R^7$, —$(CR^8R^9)_nC(O)OR^6$, —$(CR^8R^9)_nC(O)NR^6R^7$, —$(CR^8R^9)_nC(O)R^6$, cycloalkyl, heterocyclyl, aryl or heteroaryl groups; n=0-4;

$R^6$ and $R^7$ are independently selected from the group consisting of hydrogen, alkyl, alkenyl, alkynyl, aryl, arylalkyl, heteroaryl, heteroarylalkyl, cycloalkyl, cycloalkylalkyl, heterocyclyl and heterocyclylalkyl; wherein $R^6$ and $R^7$ is each optionally substituted with one or more substituents selected from halo, straight chain or branched chain alkyl, cycloalkyl, aryl, heteroaryl, heterocycle, alkylsulfonyl, oxo, nitro, cyano, —$(CR^8R^9)_nCOOR^6$, —$(CR^8R^9)_nC(O)NR^6R^7$, —$OR^6$, —$SR^6$ or —$NR^6R^7$; or $R^6$ and $R^7$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, nitro, cyano, —$OR^6$, —$SR^6$, —$NR^6R^7$, oxo, alkylsulfonyl, —$COOR^6$, —$C(O)NR^6R^7$, cycloalkyl, aryl, heterocyclyl or heteroaryl;

wherein $R^6$ and $R^7$ are as described above;

$R^8$ and $R^9$ are independently selected from the group consisting of hydrogen, fluorine, $OR^6$, alkyl and perfluoroalkyl; or $R^8$ and $R^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, nitro, cyano, oxo, —$OR^6$, —$SR^6$, —$NR^6R^7$, alkylsulfonyl, —$COOR^6$, —$C(O)NR^6R^7$, cycloalkyl, aryl, heterocyclyl or heteroaryl;

wherein $R^6$ and $R^7$ are as described above;

ring-B is an optionally substituted 4-12 membered mono or bicyclic ring containing 1-4 hetero atoms selected from N, O, S with at least one nitrogen in the ring;

X represents O or $NR^6$;

wherein $R^6$ is as described above;

$R^1$ is selected from cycloalkyl or heterocyclyl;

$R^2$ is hydrogen;

$R^3$ is selected from the group consisting of hydrogen, alkyl and perfluoroalkyl;

$R^4$ and $R^5$ are independently selected from the group consisting of hydrogen, halogen, alkyl, alkenyl, alkynyl, cycloalkyl, cycloalkylalkyl, heterocyclyl, heterocycloalkyl, aryl, arylalkyl, heteroaryl, heteroarylalkyl, mono, di or tri substituted haloalkyl, nitrile, nitro, oxo, —$NR^6R^7$, —$OR^6$, —$S(O)_pR^6$, —$S(O)_pNR^6R^7$, —$NR^6S(O)_pR^7$, —$NR^6C(O)R^7$, —$OS(O)_pR^7$, —$NR^6C(O)OR^7$, —$(CR^8R^9)_nC(O)OR^6$, —$(CR^8R^9)_n(CO)NR^6R^7$, —$(CR^8R^9)_nS(O)_pNR^6R^7$, —$(CR^8R^9)_nN(R^6)C(O)R^6$, —$(CR^8R^9)_nOR^6$, —$C(R^8R^9)_nNR^6R^7$, —$C(R^8R^9)_nCO(R^6)$ and —$S(O)_pC(R^8R^9)_nC(O)OR^6$;

wherein $R^4$ and $R^5$ is each optionally substituted with one or more substituents selected from halo, straight chain or branched chain alkyl, alkenyl, alkynyl, cycloalkyl, aryl, heteroaryl, heterocycle, alkylsulfonyl, oxo, nitro, cyano, —$(CR^8R^9)_nCOOR^6$, —$(CR^8R^9)_nC(O)NR^6R^7$, —$OR^6$, —$SR^6$ or —$NR^6R^7$;

wherein n=0-4;

$R^6$, $R^7$, $R^8$ and $R^9$ are as described above; and in addition to $R^4$ and $R^5$, ring-B is further optionally substituted with one or more substituents selected from halo, straight chain or branched chain alkyl, alkenyl, alkynyl, cycloalkyl, aryl, heteroaryl, heterocyclyl, alkylsulfonyl, oxo, nitro, cyano, —$COOR^6$, —$C(O)NR^6R^7$, —$OR^6$, —$SR^6$ or —$NR^6R^7$.

2. The compound as claimed in claim 1, or its stereoisomers, tautomers, prodrugs, pharmaceutically acceptable salts, solvates and formulations thereof wherein ring-A is selected from

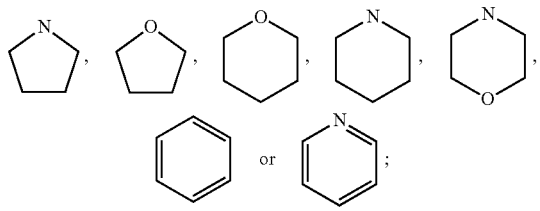

ring-B is selected from

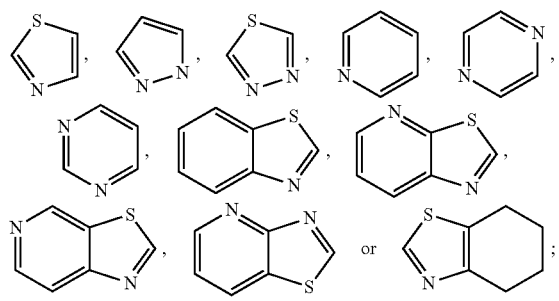

ring-C is

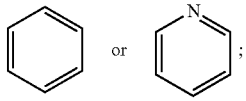 [SMILES: c1ccccc1 ; c1ccncc1]

ring A is optionally substituted with 1 to 4 substituents independently selected from alkyl, halogen, monohaloalkyl, dihaloalkyl or perhaloalkyl, nitrile, nitro, —NR$^6$R$^7$, —OR$^6$, —NR$^6$C(O)R$^7$, —NR$^6$C(O)OR$^7$, —(CR$^8$R$^9$)$_n$C(O)OR$^6$, —(CR$^8$R$^9$)$_n$C(O)NR$^6$R$^7$, —(CR$^8$R$^9$)$_n$C(O)R$^6$, cycloalkyl or cycloalkylalkyl;

ring C is optionally substituted with up 1 to 4 substituents independently selected from alkyl, halogen, mono, di or perhaloalkyl, nitrile, nitro, —NR$^6$R$^7$, —OR$^6$, —NR$^6$C(O)R$^7$, —NR$^6$C(O)OR$^7$, —(CR$^8$R$^9$)$_n$C(O)OR$^6$, —(CR$^8$R$^9$)$_n$C(O)NR$^6$R$^7$, —(CR$^8$R$^9$)$_n$C(O)R$^6$, cycloalkyl, or cycloalkylalkyl;

wherein n=0-4;

X represents O or NR$^6$;

R$^1$ is selected from C$_3$-C$_6$ cycloalkyl or heterocyclyl;

R$^2$ and R$^3$ are hydrogen;

R$^4$ and R$^5$ are independently selected from the group consisting of hydrogen, halogen, alkyl, cycloalkyl, cycloalkylalkyl, aryl, arylalkyl, heterocyclyl, heterocyclylalkyl, heteroaryl, heteroarylalkyl, —OR$^6$, —S(O)$_p$R$^6$, —NR$^6$C(O)R$^7$, —(CR$^8$R$^9$)$_n$C(O)OR$^6$, —(CR$^8$R$^9$)$_n$OR$^6$, and —C(R$^8$R$^9$)$_n$CO(R$^6$), wherein n=0-4; wherein each of R$^4$ and R$^5$ is optionally substituted with one or more substituents selected from halo, straight chain or branched chain alkyl, alkenyl, alkynyl, cycloalkyl, aryl, heteroaryl, heterocycle, alkylsulfonyl, oxo, nitro, cyano, —(CR$^8$R$^9$)—COOR$^6$, —(CR$^8$R$^9$)$_n$C(O)NR$^6$R$^7$, —OR$^6$, —SR$^6$ or —NR$^6$R$^7$;

R$^6$ and R$^7$ are independently selected from the group consisting of hydrogen, alkyl, cycloalkyl, aryl, heterocyclyl and heteroaryl; wherein R$^6$ and R$^7$ is each optionally substituted with one or more substituents selected from halo, straight chain or branched chain alkyl, cycloalkyl, aryl, heteroaryl, heterocycle, alkylsulfonyl, oxo, nitro, cyano, —(CR$^8$R$^9$)$_n$COOR$^6$, —(CR$^8$R$^9$)$_n$C(O)NR$^6$R$^7$, —OR$^6$, —SR$^6$ or —NR$^6$R$^7$; or R$^6$ and R$^7$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, cyano, —OR$^6$, —SR$^6$, —NR$^6$R$^7$, —COOR$^6$, —C(O)NR$^6$R$^7$, cycloalkyl, aryl, arylalkyl, heterocyclyl or heteroaryl; and R$^8$ and R$^9$ are independently selected from the group consisting of hydrogen, fluorine, OR$^6$, alkyl and perfluoroalkyl.

3. The compound of formula (Ia) as claimed in claim 1, or its prodrugs, pharmaceutically acceptable salts, solvates and formulations

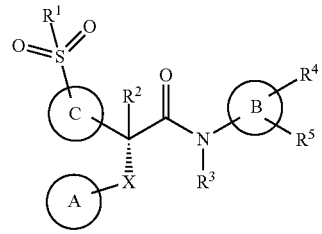

(Ia)

wherein ring-A is selected from

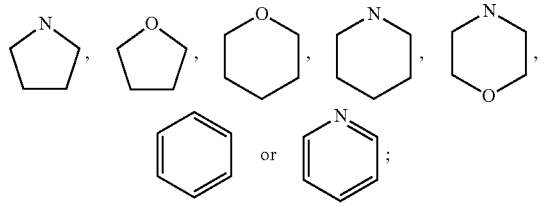

ring-B is selected from

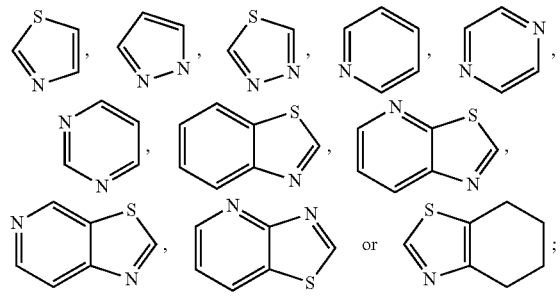

ring-C is

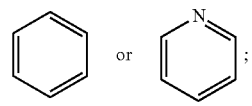 [SMILES: c1ccccc1 ; c1ccncc1]

ring A is optionally substituted with 1 to 4 substituents independently selected from alkyl, halogen, monohaloalkyl, dihaloalkyl or perhaloalkyl, nitrile, nitro, —NR$^6$R$^7$, —OR$^6$, —(CR$^8$R$^9$)$_n$C(O)OR$^6$, —(CR$^8$R$^9$)$_n$C(O)NR$^6$R$^7$, or —(CR$^8$R$^9$)$_n$C(O)R$^6$;

wherein n=0-4;

ring C is optionally substituted with 1 to 4 substituents independently selected from alkyl, halogen, mono, di or perhaloalkyl;

X represents 0 or NR$^6$;

R$^1$ is selected from cyclopropyl, cyclopentyl, cyclohexyl, pyrrolidinyl, tetrahydrofurnyl, piperidinyl, piperazinyl, tetrahydropyranyl or morpholinyl;

R$^2$ and R$^3$ are hydrogen;

R$^4$ and R$^5$ are independently selected from the group consisting of hydrogen, halogen, alkyl, cycloalkyl, cycloalkylalkyl, aryl, arylalkyl, heterocyclyl, heterocyclylalkyl, heteroaryl, heteroarylalkyl, —OR$^6$, —S(O)$_p$R$^6$, —NR$^6$C(O)R$^7$, —(CR$^8$R$^9$)$_n$C(O)OR$^6$,

185

—(CR⁸R⁹)ₙOR⁶, and —C(R⁸R⁹)ₙCO(R⁶), wherein n=0-4; wherein each of R⁴ and R⁵ is optionally substituted with one or more substituents selected from halo, straight chain or branched chain alkyl, alkenyl, alkynyl, cycloalkyl, aryl, heteroaryl, heterocycle, alkylsulfonyl, oxo, nitro, cyano, —(CR⁸R⁹)ₙCOOR⁶, —(CR⁸R⁹)ₙC(O)NR⁶R⁷, —OR⁶, —SR⁶ or —NR⁶R⁷;

R⁶ and R⁷ are independently selected from the group consisting of hydrogen, alkyl, cycloalkyl, aryl, heterocyclyl and heteroaryl; wherein R⁶ and R⁷ is each optionally substituted with one or more substituents selected from halo, straight chain or branched chain alkyl, cycloalkyl, aryl, heteroaryl, heterocycle, alkylsulfonyl, oxo, nitro, cyano, —(CR⁸R⁹)ₙCOOR⁶, —(CR⁸R⁹)ₙC(O)NR⁶R⁷, —OR⁶, —SR⁶ or —NR⁶R⁷; or R⁶ and R⁷ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, cyano, —OR⁶, —SR⁶, —NR⁶R⁷, —COOR⁶, —C(O)NR⁶R⁷, cycloalkyl, aryl, arylalkyl, heterocyclyl or heteroaryl;

R⁸ and R⁹ are independently selected from the group consisting of hydrogen, fluorine, OR⁶, alkyl and perfluoroalkyl.

4. The compound of formula (Ib) as claimed in claim 1, or its prodrugs, pharmaceutically acceptable salts, solvates and formulations thereof,

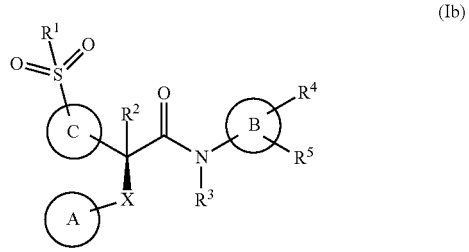

(Ib)

wherein ring-A is selected from

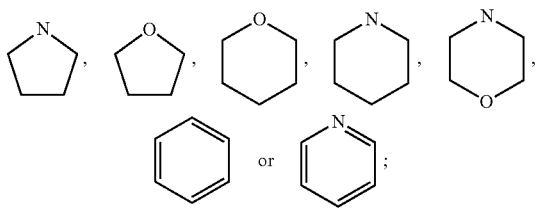

ring-B is selected from

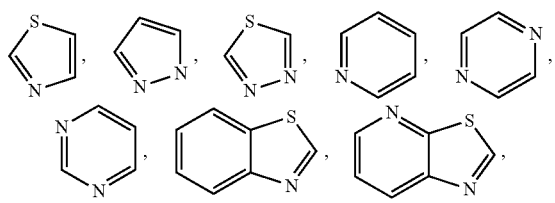

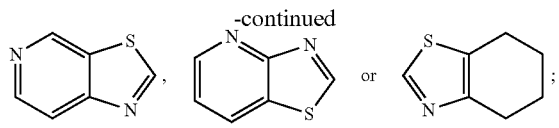

ring-C is

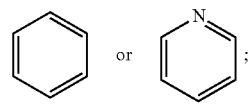 [SMILES: c1ccccc1 ; c1ccncc1]

ring A is optionally substituted with 1 to 4 substituents independently selected from alkyl, halogen, monohaloalkyl, dihaloalkyl or perhaloalkyl, nitrile, nitro, —NR⁶R⁷, —OR⁶, —(CR⁸R⁹)ₙC(O)OR⁶, —(CR⁸R⁹)ₙC(O)NR⁶R⁷, or —(CR⁸R⁹)ₙC(O)R⁶;

wherein n=0-4;

ring C is optionally substituted with 1 to 4 substituents independently selected from alkyl, halogen, mono, di or perhaloalkyl;

X represents O or NR⁶;

R¹ is selected from cyclopropyl, cyclopentyl, cyclohexyl, pyrrolidinyl, tetrahydrofurnyl, piperidinyl, piperazinyl, tetrahydropyranyl or morpholinyl;

R² and R³ are hydrogen;

R⁴ and R⁵ are independently selected from the group consisting of hydrogen, halogen, alkyl, cycloalkyl, cycloalkylalkyl, aryl, arylalkyl, heterocyclyl, heterocyclylalkyl, heteroaryl, heteroarylalkyl, —OR⁶, —S(O)ₚR⁶, —NR⁶C(O)R⁷, —(CR⁸R⁹)ₙC(O)OR⁶, —(CR⁸R⁹)ₙOR⁶, and —C(R⁸R⁹)ₙCO(R⁶), wherein n=0-4; wherein each of R⁴ and R⁵ is optionally substituted with one or more substituents selected from halo, straight chain or branched chain alkyl, alkenyl, alkynyl, cycloalkyl, aryl, heteroaryl, heterocycle, alkylsulfonyl, oxo, nitro, cyano, —(CR⁸R⁹)ₙCOOR⁶, —(CR⁸R⁹)ₙC(O)NR⁶R⁷, —OR⁶, —SR⁶ or —NR⁶R⁷;

R⁶ and R⁷ are independently selected from the group consisting of hydrogen, alkyl, cycloalkyl, aryl, heterocyclyl and heteroaryl; wherein R⁶ and R⁷ is each optionally substituted with one or more substituents selected from halo, straight chain or branched chain alkyl, cycloalkyl, aryl, heteroaryl, heterocycle, alkylsulfonyl, oxo, nitro, cyano, —(CR⁸R⁹)ₙCOOR⁶, —(CR⁸R⁹)ₙC(O)NR⁶R⁷, —OR⁶, —SR⁶ or —NR⁶R⁷; or R⁶ and R⁷ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, cyano, —OR⁶, —SR⁶, —NR⁶R⁷, —COOR⁶, —C(O)NR⁶R⁷, cycloalkyl, aryl, arylalkyl, heterocyclyl or heteroaryl; and R⁸ and R⁹ are independently selected from the group consisting of hydrogen, fluorine, OR⁶, alkyl and perfluoroalkyl.

5. A compound as claimed in claim 1 which is
2-(4-Cyclopropylsulfonylphenyl)-2-tetrahydropyran-4-yloxy-N-thiazol-2-yl-acetamide and its (+) and (−) enantiomers;
Methyl 5-[2-[[2-(4-cyclopropylsulfonylphenyl)-2-[(3R)-tetrahydrofuran-3-yl]oxy-acetyl]amino]thiazol-5-yl]oxy-2-methyl-benzoate and its (+) and (−) enantiomers;

2-(4-Morpholinosulfonylphenyl)-2-tetrahydropyran-4-yloxy-N-thiazolo[5,4-b]pyridin-2-yl-acetamide and its (+) and (−) enantiomers;
Ethyl 1-[2-[[2-(4-cyclopropylsulfonylphenyl)-2-tetrahydropyran-4-yloxy-acetyl]amino]thiazol-5-yl]pyrazole-4-carboxylate and its (+) and (−) enantiomers;
Methyl 2-[[2-(4-cyclopropylsulfonylphenyl)-2-tetrahydropyran-4-yloxy-acetyl]amino]-4,5,6,7-tetrahydro-1,3-benzothiazole-6-carboxylate and its (+) and (−) enantiomers;
tert-butyl 6-[[2-(4-cyclopropylsulfonylphenyl)-2-(2,4-difluorophenoxy)acetyl]amino]pyridine-3-carboxylate and its (+) and (−) enantiomers;
tert-Butyl 6-[[2-(4-cyclopropylsulfonylphenyl)-2-(2,4-difluoroanilino)acetyl]amino]pyridine-3-carboxylate and its (+) and (−) enantiomers;
Ethyl 2-[6-[[2-(4-cyclopropylsulfonylphenyl)-2-tetrahydropyran-4-yloxy-acetyl]amino]-2-pyridyl]acetate and its (+) and (−) enantiomers;
Methyl 3-[2-[[2-(6-cyclopentylsulfonyl-3-pyridyl)-2-tetrahydropyran-4-yloxy-acetyl]amino]thiazol-5-yl]oxybenzoate and its (+) and (−) enantiomers;
N-(5-fluorothiazol-2-yl)-2-(4-morpholinosulfonylphenyl)-2-tetrahydropyran-4-yloxy-acetamide and its (+) and (−) enantiomers;
N-(5-methoxythiazolo[5,4-b]pyridin-2-yl)-2-(4-morpholinosulfonylphenyl)-2-tetrahydropyran-4-yloxy-acetamide and its (+) and (−) enantiomers;
Methyl 4-[2-[[2-(4-cyclopropylsulfonylphenyl)-2-(2,4-difluorophenoxy)acetyl]amino]thiazol-5-yl]oxy-2-methyl-benzoate and its (+) and (−) enantiomers;
Methyl 4-[2-[[2-(4-cyclopropylsulfonylphenyl)-2-tetrahydropyran-4-yloxy-acetyl]amino]thiazol-5-yl]oxy-2-methyl-benzoate and its (+) and (−) enantiomers;
Methyl 2-[[2-(4-cyclopropylsulfonylphenyl)-2-tetrahydropyran-4-yloxy-acetyl]amino]-5-methyl-thiazole-4-carboxylate and its (+) and (−) enantiomers;
2-(4-Cyclopropylsulfonylphenyl)-2-[(2R,3S,4R)-3-hydroxy-2-(hydroxymethyl)tetrahydropyran-4-yl]oxy-N-thiazolo[5,4-b]pyridin-2-yl-acetamide and its (+) and (−) enantiomers;
Ethyl 2-[5-chloro-2-[[2-[4-(1-piperidylsulfonyl)phenyl]-2-tetrahydropyran-4-yloxy-acetyl]amino]thiazol-4-yl]acetate and its (+) and (−) enantiomers;
Ethyl 2-[4-[2-[[2-(4-cyclopropylsulfonylphenyl)-2-tetrahydropyran-4-yloxy-acetyl]amino]thiazol-5-yl]oxyphenyl]-2-methyl-propanoate and its (+) and (−) enantiomers;
Ethyl 2-[2-[[2-(4-cyclopropylsulfonylphenyl)-2-tetrahydropyran-4-yloxy-acetyl]amino]thiazol-4-yl]-2-methyl-propanoate and its (+) and (−) enantiomers;
Ethyl 2-[2-[[2-(4-cyclopropylsulfonylphenyl)-2-tetrahydropyran-4-yloxy-acetyl]amino]-5-fluoro-thiazol-4-yl]-2-methyl-propanoate and its (+) and (−) enantiomers;
Ethyl 2-[2-[[2-(4-cyclopropylsulfonylphenyl)-2-tetrahydropyran-4-yloxy-acetyl]amino]thiazol-4-yl]-2-isopropoxy-acetate and its (+) and (−) enantiomers;
Ethyl 2-[2-[[2-(4-cyclopropylsulfonylphenyl)-2-(2,4-difluorophenoxy)acetyl]amino]thiazol-4-yl]-2-methyl-propanoate and its (+) and (−) enantiomers;
Ethyl 2-[2-[[2-(4-cyclopropylsulfonylphenyl)-2-tetrahydropyran-4-yloxy-acetyl]amino]thiazol-5-yl]oxybenzoate and its (+) and (−) enantiomers;
Ethyl 2-[5-chloro-2-[[2-(4-cyclopropylsulfonylphenyl)-2-tetrahydropyran-4-yloxy-acetyl]amino]thiazol-4-yl]acetate and its (+) and (−) enantiomers;
Ethyl 2-[[2-(4-cyclopropylsulfonylphenyl)-2-tetrahydropyran-4-yloxy-acetyl]amino]-5-(4-fluorophenoxy)thiazole-4-carboxylate and its (+) and (−) enantiomers;
Methyl 2-chloro-4-[2-[[2-(4-cyclopropylsulfonylphenyl)-2-tetrahydropyran-4-yloxy-acetyl]amino]thiazol-5-yl]oxy-benzoate and its (+) and (−) enantiomers;
Ethyl 2-[2-[[2-(4-cyclopropylsulfonylphenyl)-2-tetrahydropyran-4-yloxy-acetyl]amino]thiazol-4-yl]propanoate and its (+) and (−) enantiomers;
Ethyl 2-[5-chloro-2-[[2-tetrahydropyran-4-yloxy-2-(4-tetrahydropyran-4-ylsulfonylphenyl)acetyl]amino]thiazol-4-yl]acetate and its (+) and (−) enantiomers;
Methyl 2-chloro-5-[2-[[2-(4-cyclopropylsulfonylphenyl)-2-tetrahydropyran-4-yloxy-acetyl]amino]thiazol-5-yl]oxy-benzoate and its (+) and (−) enantiomers;
Methyl 4-[2-[[2-(4-cyclopropylsulfonylphenyl)-2-tetrahydropyran-4-yloxy-acetyl]amino]thiazol-5-yl]oxy-2-methoxy-benzoate and its (+) and (−) enantiomers;
Ethyl 2-[2-[[2-(4-cyclopropylsulfonylphenyl)-2-tetrahydropyran-4-yloxy-acetyl]amino]thiazol-4-yl]-2-hydroxy-acetate and its (+) and (−) enantiomers;
2-(4-Cyclopropylsulfonylphenyl)-N-(5-fluorothiazol-2-yl)-2-[(1-methyl-4-piperidyl)oxy]acetamide and its (+) and (−) enantiomers;
Ethyl 3-[4-[2-[[2-(4-cyclopropylsulfonylphenyl)-2-tetrahydropyran-4-yloxy-acetyl]amino]thiazol-5-yl]oxyphenyl]isoxazole-5-carboxylate and its (+) and (−) enantiomers;
Methyl 5-[2-[[2-(4-cyclopropylsulfonylphenyl)-2-tetrahydropyran-3-yloxy-acetyl]oxythiazol-5-yl]oxy-2-methyl-benzoate and its (+) and (−) enantiomers;
Methyl 5-[2-[[2-(4-cyclopropylsulfonylphenyl)-2-tetrahydropyran-4-yloxy-acetyl]amino]thiazol-5-yl]oxy-2-methyl-benzoate and its (+) and (−) enantiomers;
tert-Butyl 6-[[2-(4-cyclopropylsulfonylphenyl)-2-tetrahydropyran-4-yloxy-acetyl]amino]pyridine-3-carboxylate and its (+) and (−) enantiomers;
Methyl 4-[2-[[2-(4-cyclopropylsulfonylphenyl)-2-[(3R)-tetrahydrofuran-3-yl]oxy-acetyl]amino]thiazol-5-yl]oxy-2-methyl-benzoate and its (+) and (−) enantiomers;
Methyl 4-[2-[[2-(4-cyclopropylsulfonylphenyl)-2-tetrahydropyran-4-yloxy-acetyl]amino]-4-methyl-thiazol-5-yl]oxy-2-methyl-benzoate and its (+) and (−) enantiomers;
Ethyl 3-[[2-(4-cyclopropylsulfonylphenyl)-2-tetrahydropyran-4-yloxy-acetyl]amino]-1-[(4-methoxyphenyl)methyl]pyrazole-4-carboxylate and its (+) and (−) enantiomers;
Ethyl 2-[[2-(4-cyclopropylsulfonylphenyl)-2-tetrahydropyran-4-yloxy-acetyl]amino]-4,5,6,7-tetrahydro-1,3-benzothiazole-4-carboxylate and its (+) and (−) enantiomers;
tert-Butyl 4-[[6-[[2-(4-cyclopropylsulfonylphenyl)-2-tetrahydropyran-4-yloxy-acetyl]amino]-3-pyridyl]oxy]-2-methyl-benzoate and its (+) and (−) enantiomers;
tert-Butyl 3-[[6-[[2-(4-cyclopropylsulfonylphenyl)-2-tetrahydropyran-4-yloxy-acetyl]amino]-3-pyridyl]oxy]benzoate and its (+) and (−) enantiomers;
tert-Butyl 3-[[6-[[2-(4-cyclopropylsulfonylphenyl)-2-(2,4-difluorophenoxy)acetyl]amino]-3-pyridyl]oxy]benzoate and its (+) and (−) enantiomers;
Methyl 5-[2-[[2-(4-cyclopropylsulfonylphenyl)-2-tetrahydropyran-4-yloxy-acetyl]amino]thiazol-5-yl]oxy-2-fluoro-benzoate and its (+) and (−) enantiomers;
Ethyl 2-[[2-(4-cyclopropylsulfonylphenyl)-2-tetrahydropyran-4-yloxy-acetyl]amino]thiazolo[5,4-b]pyridine-5-carboxylate and its (+) and (−) enantiomers;

Ethyl 2-[2-[[2-(4-cyclopropylsulfonylphenyl)-2-tetrahydropyran-4-yloxy-acetyl]amino]-4,5,6,7-tetrahydro-1,3-benzothiazol-4-yl]acetate and its (+) and (−) enantiomers;

tert-Butyl 2-[[6-[[2-(4-cyclopropylsulfonylphenyl)-2-(2,4-difluorophenoxy)acetyl]amino]-3-pyridyl]oxy]-2-methyl-propanoate and its (+) and (−) enantiomers;

tert-Butyl 2-[[6-[[2-(4-cyclopropylsulfonylphenyl)-2-tetrahydropyran-4-yloxy-acetyl]amino]-3-pyridyl]oxy]-2-methyl-propanoate and its (+) and (−) enantiomers;

Ethyl 2-[[2-(4-cyclopropylsulfonylphenyl)-2-tetrahydropyran-4-yloxy-acetyl]amino]thiazolo[5,4-b]pyridine-6-carboxylate and its (+) and (−) enantiomers;

Ethyl 2-[3-chloro-6-[[2-(4-cyclopropylsulfonylphenyl)-2-tetrahydropyran-4-yloxy-acetyl]amino]-2-pyridyl]acetate and its (+) and (−) enantiomers;

Ethyl 3-[2-[[2-(4-cyclopropylsulfonylphenyl)-2-[(3R)-tetrahydrofuran-3-yl]oxy-acetyl]amino]thiazol-5-yl]oxybenzoate and its (+) and (−) enantiomers;

tert-Butyl 3-[2-[[2-(4-cyclopropylsulfonylphenyl)-2-tetrahydropyran-4-yloxy-acetyl]amino]-6-methyl-pyrimidin-4-yl]oxybenzoate and its (+) and (−) enantiomers;

Methyl 3-[2-[[2-(4-cyclopropylsulfonylphenyl)-2-tetrahydropyran-4-yloxy-acetyl]amino]thiazol-5-yl]oxy-5-isopropoxy-benzoate and its (+) and (−) enantiomers;

Methyl 5-[2-[[2-(4-cyclopropylsulfonylphenyl)-2-tetrahydropyran-4-yloxy-acetyl]amino]thiazol-5-yl]oxypyridine-3-carboxylate and its (+) and (−) enantiomers;

Methyl 3-[6-[[2-(4-cyclopropylsulfonylphenyl)-2-tetrahydropyran-4-yloxy-acetyl]amino]-3-pyridyl]benzoate and its (+) and (−) enantiomers;

Methyl 4-[2-[[2-(4-cyclopropylsulfonylphenyl)-2-tetrahydropyran-4-yloxy-acetyl]amino]thiazol-5-yl]oxypyridine-2-carboxylate and its (+) and (−) enantiomers;

2-(4-Cyclopropylsulfonylphenyl)-N-(5-methyl-2-pyridyl)-2-tetrahydropyran-4-yloxy-acetamide and its (+) and (−) enantiomers;

tert-Butyl 6-[[2-(2,4-difluorophenoxy)-2-(4-morpholinosulfonylphenyl)acetyl]amino]pyridine-3-carboxylate and its (+) and (−) enantiomers;

Methyl 3-[6-[[2-(4-cyclopropylsulfonylphenyl)-2-(2,4-difluorophenoxy)acetyl]amino]-3-pyridyl]benzoate carboxylate and its (+) and (−) enantiomers;

tert-Butyl 6-[3-[[2-(4-cyclopropylsulfonylphenyl)-2-(2,4-difluorophenoxy)acetyl]amino]pyrazol-1-yl]pyridine-3-carboxylate carboxylate and its (+) and (−) enantiomers;

tert-Butyl 6-[3-[[2-(4-cyclopropylsulfonylphenyl)-2-tetrahydropyran-4-yloxy-acetyl]amino]pyrazol-1-yl]pyridine-3-carboxylate carboxylate and its (+) and (−) enantiomers;

Methyl 5-[[2-(4-cyclopropylsulfonylphenyl)-2-(2,4-difluorophenoxy)acetyl]amino]pyrazine-2-carboxylate carboxylate and its (+) and (−) enantiomers;

Ethyl 2-[3-chloro-6-[[2-(4-cyclopropylsulfonylphenyl)-2-(2,4-difluorophenoxy)acetyl]amino]-2-pyridyl]acetate carboxylate and its (+) and (−) enantiomers;

2-(4-cyclopropylsulfonylphenyl)-2-tetrahydropyran-4-yloxy-N-(5-vinylthiazol-2-yl)acetamide carboxylate and its (+) and (−) enantiomers;

Methyl 3-[2-[[2-(4-cyclopentylsulfonylphenyl)-2-tetrahydropyran-4-yloxy-acetyl]amino]thiazol-5-yl]oxybenzoate carboxylate and its (+) and (−) enantiomers;

Ethyl 3-[2-[[2-(4-cyclopropylsulfonylphenyl)-2-[(3S)-tetrahydrofuran-3-yl]oxy-acetyl]amino]thiazol-5-yl]oxybenzoate carboxylate and its (+) and (−) enantiomers;

2-(4-cyclopropylsulfonylphenyl)-N-[5-(4-formylphenoxy)thiazol-2-yl]-2-tetrahydropyran-4-yloxy-acetamide carboxylate and its (+) and (−) enantiomers;

N-[5-[3-[[tert-butyl(dimethyl)silyl]oxymethyl]phenoxy]thiazol-2-yl]-2-(4-cyclopropylsulfonylphenyl)-2-tetrahydropyran-4-yloxy-acetamide carboxylate and its (+) and (−) enantiomers;

Ethyl 2-[5-chloro-2-[[2-(4-cyclopropylsulfonylphenyl)-2-tetrahydropyran-4-yloxy-acetyl]amino]thiazol-4-yl]acetate carboxylate and its (+) and (−) enantiomers;

Ethyl 2-[2-[[2-(4-cyclopropylsulfonylphenyl)-2-tetrahydropyran-4-yloxy-acetyl]amino]thiazolo[5,4-b]pyridin-5-yl]oxyacetate carboxylate and its (+) and (−) enantiomers;

tert-butyl 6-[[2-(4-chlorophenoxy)-2-(4-cyclopropylsulfonylphenyl)acetyl]amino]pyridine-3-carboxylate carboxylate and its (+) and (−) enantiomers;

Ethyl 3-[[5-[[2-(4-cyclopropylsulfonylphenyl)-2-tetrahydropyran-4-yloxy-acetyl]amino]-1,3,4-thiadiazol-2-yl]oxy]benzoate carboxylate and its (+) and (−) enantiomers;

4 5-[2-[[2-(4-Cyclopropylsulfonylphenyl)-2-[(3R)-tetrahydrofuran-3-yl]oxy-acetyl]amino]thiazol-5-yl]oxy-2-methyl-benzoic acid carboxylate and its (+) and (−) enantiomers;

2-[[2-(4-Cyclopropylsulfonylphenyl)-2-tetrahydropyran-4-yloxy-acetyl]amino]-4,5,6,7-tetrahydro-1,3-benzothiazole-6-carboxylic acid carboxylate and its (+) and (−) enantiomers;

6-[[2-(4-Cyclopropylsulfonylphenyl)-2-(2,4-difluoroandino)acetyl]amino]pyridine-3-carboxylic acid carboxylate and its (+) and (−) enantiomers;

4-[2-[[2-(4-Cyclopropylsulfonylphenyl)-2-(2,4-difluorophenoxy)acetyl]amino]thiazol-5-yl]oxy-2-methyl-benzoic acid carboxylate and its (+) and (−) enantiomers;

2-[[2-(4-Cyclopropylsulfonylphenyl)-2-tetrahydropyran-4-yloxy-acetyl]amino]-5-methyl-thiazole-4-carboxylic acid carboxylate and its (+) and (−) enantiomers;

2-[2-[[2-(4-Cyclopropylsulfonylphenyl)-2-tetrahydropyran-4-yloxy-acetyl]amino]thiazol-4-yl]-2-methyl-propanoic acid carboxylate and its (+) and (−) enantiomers;

2-[2-[[2-(4-Cyclopropylsulfonylphenyl)-2-tetrahydropyran-4-yloxy-acetyl]amino]-5-fluoro-thiazol-4-yl]-2-methyl-propanoic acid carboxylate and its (+) and (−) enantiomers;

2-[2-[[2-(4-Cyclopropylsulfonylphenyl)-2-tetrahydropyran-4-yloxy-acetyl]amino]thiazol-4-yl]-2-isopropoxy-acetic acid carboxylate and its (+) and (−) enantiomers;

2-[2-[[2-(4-Cyclopropylsulfonylphenyl)-2-(2,4-difluorophenoxy)acetyl]amino]thiazol-4-yl]-2-methyl-propanoic acid carboxylate and its (+) and (−) enantiomers;

2-[[2-(4-Cyclopropylsulfonylphenyl)-2-tetrahydropyran-4-yloxy-acetyl]amino]-5-(4-fluorophenoxy)thiazole-4-carboxylic acid carboxylate and its (+) and (−) enantiomers;

2-Chloro-4-[2-[[2-(4-cyclopropylsulfonylphenyl)-2-tetrahydropyran-4-yloxy-acetyl]amino]thiazol-5-yl]oxy-benzoic acid carboxylate and its (+) and (−) enantiomers;

2-[2-[[2-(4-Cyclopropylsulfonylphenyl)-2-tetrahydropyran-4-yloxy-acetyl]amino]thiazol-4-yl]propanoic acid carboxylate and its (+) and (−) enantiomers;

2-[5-Chloro-2-[[2-tetrahydropyran-4-yloxy-2-(4-tetrahydropyran-4-ylsulfonylphenyl)acetyl]amino]thiazol-4-yl]acetic acid carboxylate and its (+) and (−) enantiomers;

2-Chloro-5-[2-[[2-(4-cyclopropylsulfonylphenyl)-2-tetrahydropyran-4-yloxy-acetyl]amino]thiazol-5-yl]oxybenzoic acid carboxylate and its (+) and (−) enantiomers;

2-[2-[[2-(4-Cyclopropylsulfonylphenyl)-2-tetrahydropyran-4-yloxy-acetyl]amino]thiazol-4-yl]-2-hydroxyacetic acid carboxylate and its (+) and (−) enantiomers;

3-[4-[2-[[2-(4-Cyclopropylsulfonylphenyl)-2-tetrahydropyran-4-yloxy-acetyl]amino]thiazol-5-yl]oxyphenyl]isoxazole-5-carboxylic acid carboxylate and its (+) and (−) enantiomers;

5-[2-[2-(4-Cyclopropylsulfonylphenyl)-2-tetrahydropyran-3-yloxy-acetyl]oxythiazol-5-yl]oxy-2-methyl-benzoic acid carboxylate and its (+) and (−) enantiomers;

3-[[2-(4-Cyclopropylsulfonylphenyl)-2-tetrahydropyran-4-yloxy-acetyl]amino]-1-[(4-methoxyphenyl)methyl]pyrazole-4-carboxylic acid carboxylate and its (+) and (−) enantiomers;

2-[[2-(4-Cyclopropylsulfonylphenyl)-2-tetrahydropyran-4-yloxy-acetyl]amino]-4,5,6,7-tetrahydro-1,3-benzothiazole-4-carboxylic acid carboxylate and its (+) and (−) enantiomers;

4-[[6-[[2-(4-Cyclopropylsulfonylphenyl)-2-tetrahydropyran-4-yloxy-acetyl]amino]-3-pyridyl]oxy]-2-methyl-benzoic acid carboxylate and its (+) and (−) enantiomers;

3-[[6-[[2-(4-Cyclopropylsulfonylphenyl)-2-tetrahydropyran-4-yloxy-acetyl]amino]-3-pyridyl]oxy]benzoic acid carboxylate and its (+) and (−) enantiomers;

3-[[6-[[2-(4-Cyclopropylsulfonylphenyl)-2-(2,4-difluorophenoxy)acetyl]amino]-3-pyridyl]oxy]benzoic acid carboxylate and its (+) and (−) enantiomers;

2-[[2-(4-Cyclopropylsulfonylphenyl)-2-tetrahydropyran-4-yloxy-acetyl]amino]thiazolo[5,4-b]pyridine-5-carboxylic acid carboxylate and its (+) and (−) enantiomers;

2-[6-[[2-(4-Cyclopropylsulfonylphenyl)-2-tetrahydropyran-4-yloxy-acetyl]amino]-2-pyridyl]acetic acid carboxylate and its (+) and (−) enantiomers;

2-[[6-[[2-(4-Cyclopropylsulfonylphenyl)-2-(2,4-difluorophenoxy)acetyl]amino]-3-pyridyl]oxy]-2-methyl-propanoic acid carboxylate and its (+) and (−) enantiomers;

2-[[6-[[2-(4-Cyclopropylsulfonylphenyl)-2-tetrahydropyran-4-yloxy-acetyl]amino]-3-pyridyl]oxy]-2-methyl-propanoic acid carboxylate and its (+) and (−) enantiomers;

2-[[2-(4-Cyclopropylsulfonylphenyl)-2-tetrahydropyran-4-yloxy-acetyl]amino]thiazolo[5,4-b]pyridine-6-carboxylic acid carboxylate and its (+) and (−) enantiomers;

2-[3-Chloro-6-[[2-(4-cyclopropylsulfonylphenyl)-2-tetrahydropyran-4-yloxy-acetyl]amino]-2-pyridyl]acetic acid carboxylate and its (+) and (−) enantiomers;

3-[2-[[2-(4-Cyclopropylsulfonylphenyl)-2-tetrahydropyran-4-yloxy-acetyl]amino]-6-methyl-pyrimidin-4-yl]oxybenzoic acid carboxylate and its (+) and (−) enantiomers;

3-[2-[[2-(4-Cyclopropylsulfonylphenyl)-2-tetrahydropyran-4-yloxy-acetyl]amino]thiazol-5-yl]oxy-5-isopropoxy-benzoic acid carboxylate and its (+) and (−) enantiomers;

3-[6-[[2-(4-Cyclopropylsulfonylphenyl)-2-tetrahydropyran-4-yloxy-acetyl]amino]-3-pyridyl]benzoic acid carboxylate and its (+) and (−) enantiomers;

4-[2-[[2-(4-Cyclopropylsulfonylphenyl)-2-tetrahydropyran-4-yloxy-acetyl]amino]thiazol-5-yl]oxypyridine-2-carboxylic acid carboxylate and its (+) and (−) enantiomers;

6-[[2-(2,4-Difluorophenoxy)-2-(4-morpholinosulfonylphenyl)acetyl]amino]pyridine-3-carboxylic acid carboxylate and its (+) and (−) enantiomers;

3-[6-[[2-(4-Cyclopropylsulfonylphenyl)-2-(2,4-difluorophenoxy)acetyl]amino]-3-pyridyl]benzoic acid carboxylate and its (+) and (−) enantiomers;

6-[3-[[2-(4-Cyclopropylsulfonylphenyl)-2-(2,4-difluorophenoxy)acetyl]amino]pyrazol-1-yl]pyridine-3-carboxylic acid carboxylate and its (+) and (−) enantiomers;

6-[3-[[2-(4-Cyclopropylsulfonylphenyl)-2-tetrahydropyran-4-yloxy-acetyl]amino]pyrazol-1-yl]pyridine-3-carboxylic acid carboxylate and its (+) and (−) enantiomers;

5-[[2-(4-Cyclopropylsulfonylphenyl)-2-(2,4-difluorophenoxy)acetyl]amino]pyrazine-2-2-[3-Chloro-6-[[2-(4-cyclopropylsulfonylphenyl)-2-(2,4-difluorophenoxy)acetyl]amino]-2-pyridyl]acetic acid carboxylate and its (+) and (−) enantiomers;

3-[[5-[[2-(4-Cyclopropylsulfonylphenyl)-2-tetrahydropyran-4-yloxy-acetyl]amino]-1,3,4-thiadiazol-2-yl]oxy]benzoic acid carboxylate and its (+) and (−) enantiomers;

6-[[2-(4-Chlorophenoxy)-2-(4-cyclopropylsulfonylphenyl)acetyl]amino]pyridine-3-carboxylic acid carboxylate and its (+) and (−) enantiomers;

4-[2-[[2-(4-Cyclopropylsulfonylphenyl)-2-tetrahydropyran-4-yloxy-acetyl]amino]thiazol-5-yl]oxy-N-isopropyl-benzamide carboxylate and its (+) and (−) enantiomers;

4-[2-[[2-(4-Cyclopropylsulfonylphenyl)-2-tetrahydropyran-4-yloxy-acetyl]amino]thiazol-5-yl]oxybenzamide carboxylate and its (+) and (−) enantiomers;

N-Cyclopropyl-4-[2-[[2-(4-cyclopropylsulfonylphenyl)-2-tetrahydropyran-4-yloxy-acetyl]amino]thiazol-5-yl]oxy-benzamide carboxylate and its (+) and (−) enantiomers;

2-(4-Cyclopropanesulfonyl-phenyl)-N-[5-(4-hydroxymethyl-phenoxy)-thiazol-2-yl]-2-(tetrahydro-pyran-4-yloxy)-acetamide carboxylate and its (+) and (−) enantiomers;

2-(4-Cyclopropanesulfonyl-phenyl)-N-(4-hydroxymethyl-5-methyl-thiazol-2-yl)-2-(tetrahydro-pyran-4-yloxy)-acetamide carboxylate and its (+) and (−) enantiomers;

2-(4-Cyclopropanesulfonyl-phenyl)-N-[5-(1,2-dihydroxy-ethyl)-thiazol-2-yl]-2-(tetrahydro-pyran-4-yloxy)-acetamide carboxylate and its (+) and (−) enantiomers;

2-(4-Cyclopropanesulfonyl-phenyl)-N-[5-(1,2-dihydroxy-ethyl)-thiazolo[5,4-b]pyridin-2-yl]-2-(tetrahydro-pyran-4-yloxy)-acetamide carboxylate and its (+) and (−) enantiomers;

2-(4-cyclopropylsulfonylphenyl)-2-(2,4-difluorophenoxy)-N-[5-(1,2-dihydroxyethyl)thiazol-2-yl]acetamide carboxylate and its (+) and (−) enantiomers;

N-[5-(1,2-Dihydroxy-ethyl)-thiazol-2-yl]-2-[4-(morpholine-4-sulfonyl)-phenyl]-2-(tetrahydro-pyran-4-yloxy)-acetamide carboxylate and its (+) and (−) enantiomers;

2-(4-Cyclopropanesulfonyl-phenyl)-N-[4-(1,2-dihydroxy-ethyl)-thiazol-2-yl]-2-(tetrahydro-pyran-4-yloxy)-acetamide carboxylate and its (+) and (−) enantiomers;

2-(4-Cyclopropylsulfonylphenyl)-2-tetrahydropyran-4-yloxy-N-[5-(2H-tetrazol-5-yl)-2-pyridyl]acetamide carboxylate and its (+) and (−) enantiomers;

4-[2-[[2-(4-Cyclopropylsulfonylphenyl)-2-tetrahydropyran-4-yloxy-acetyl]amino]thiazol-5-yl]oxy-2-methyl-benzoic acid carboxylate and its (+) and (−) enantiomers;

2-[5-Chloro-2-[[2-(4-cyclopropylsulfonylphenyl)-2-tetrahydropyran-4-yloxy-acetyl]amino]thiazol-4-yl]acetic acid carboxylate and its (+) and (−) enantiomers;

2-[5-Chloro-2-[[2-[4-(1-piperidylsulfonyl)phenyl]-2-tetrahydropyran-4-yloxy-acetyl]amino]thiazol-4-yl]acetic acid carboxylate and its (+) and (−) enantiomers;

2-(4-Cyclopropylsulfonylphenyl)-2-(2,4-difluorophenoxy)-N-(5-pyrazol-1-ylthiazol-2-yl)acetamide carboxylate and its (+) and (−) enantiomers;

2-[4-[2-[[2-(4-Cyclopropylsulfonylphenyl)-2-tetrahydropyran-4-yloxy-acetyl]amino]thiazol-5-yl]oxyphenyl]-2-methyl-propanoic acid carboxylate and its (+) and (−) enantiomers;

2-[2-[[2-(4-Cyclopropylsulfonylphenyl)-2-tetrahydropyran-4-yloxy-acetyl]amino]thiazolo[5,4-b]pyridin-5-yl]oxyacetic acid carboxylate and its (+) and (−) enantiomers;

2-[2-[[2-(4-Cyclopropylsulfonylphenyl)-2-tetrahydropyran-4-yloxy-acetyl]amino]thiazol-5-yl]oxybenzoic acid carboxylate and its (+) and (−) enantiomers;

3-[2-[[2-(4-Cyclopropylsulfonylphenyl)-2-tetrahydropyran-4-yloxy-acetyl]amino]thiazol-5-yl]oxybenzoic acid carboxylate and its (+) and (−) enantiomers;

4-[2-[[2-(4-Cyclopropylsulfonylphenyl)-2-tetrahydropyran-4-yloxy-acetyl]amino]thiazol-5-yl]oxy-2-methoxy-benzoic acid carboxylate and its (+) and (−) enantiomers;

5-[2-[[2-(4-Cyclopropylsulfonylphenyl)-2-tetrahydropyran-4-yloxy-acetyl]amino]thiazol-5-yl]oxy-2-methyl-benzoic acid carboxylate and its (+) and (−) enantiomers;

5-[2-[[2-(4-Cyclopropylsulfonylphenyl)-2-[(3R)-tetrahydrofuran-3-yl]oxy-acetyl]amino]thiazol-5-yl]oxy-2-methyl-benzoic acid carboxylate and its (+) and (−) enantiomers;

1-[2-[[2-(4-Cyclopropylsulfonylphenyl)-2-tetrahydropyran-4-yloxy-acetyl]amino]thiazol-5-yl]pyrazole-4-carboxylic acid carboxylate and its (+) and (−) enantiomers;

4-[2-[[2-(4-Cyclopropylsulfonylphenyl)-2-tetrahydropyran-4-yloxy-acetyl]amino]-4-methyl-thiazol-5-yl]oxy-2-methyl-benzoic acid carboxylate and its (+) and (−) enantiomers;

4-[2-[[2-(4-Cyclopropylsulfonylphenyl)-2-[(3R)-tetrahydrofuran-3-yl]oxy-acetyl]amino]thiazol-5-yl]oxy-2-methyl-benzoic acid carboxylate and its (+) and (−) enantiomers;

6-[[2-(4-Cyclopropylsulfonylphenyl)-2-(2,4-difluorophenoxy)acetyl]amino]pyridine-3-carboxylic acid carboxylate and its (+) and (−) enantiomers;

5-[2-[[2-(4-Cyclopropylsulfonylphenyl)-2-tetrahydropyran-4-yloxy-acetyl]amino]thiazol-5-yl]oxy-2-fluoro-benzoic acid carboxylate and its (+) and (−) enantiomers;

6-[[2-(4-Cyclopropylsulfonylphenyl)-2-tetrahydropyran-4-yloxy-acetyl]amino]pyridine-3-carboxylic acid carboxylate and its (+) and (−) enantiomers;

2-[6-[[2-(4-Cyclopropylsulfonylphenyl)-2-tetrahydropyran-4-yloxy-acetyl]amino]-2-pyridyl]acetic acid carboxylate and its (+) and (−) enantiomers;

Ethyl 3-[2-[[2-(4-cyclopropylsulfonylphenyl)-2-tetrahydropyran-4-yloxy-acetyl]amino]thiazol-5-yl]oxybenzoate carboxylate and its (+) and (−) enantiomers;

2-(4-Cyclopropylsulfonylphenyl)-N-[5-[3-(hydroxymethyl)phenoxy]thiazol-2-yl]-2-tetrahydropyran-4-yloxy-acetamide carboxylate and its (+) and (−) enantiomers;

3-[2-[[2-(4-Cyclopropylsulfonylphenyl)-2-[(3R)-tetrahydrofuran-3-yl]oxy-acetyl]amino]thiazol-5-yl]oxybenzoic acid carboxylate and its (+) and (−) enantiomers;

5-[2-[[2-(4-Cyclopropylsulfonylphenyl)-2-tetrahydropyran-4-yloxy-acetyl]amino]thiazol-5-yl]oxypyridine-3-carboxylic acid carboxylate and its (+) and (−) enantiomers;

iso-propyl 3-[2-[[2-(4-cyclopropylsulfonylphenyl)-2-tetrahydropyran-4-yloxy-acetyl]amino]thiazol-5-yl]oxy-benzoate carboxylate and its (+) and (−) enantiomers;

isobutyl 3-[2-[[2-(4-cyclopropylsulfonylphenyl)-2-tetrahydropyran-4-yloxy-acetyl]amino]thiazol-5-yl]oxy-benzoate carboxylate and its (+) and (−) enantiomers;

3-[2-[[2-(4-Cyclopropylsulfonylphenyl)-2-[(3S)-tetrahydrofuran-3-yl]oxy-acetyl]amino]thiazol-5-yl]oxybenzoic acid carboxylate and its (+) and (−) enantiomers;

3-[2-[[2-(4-Cyclopentylsulfonylphenyl)-2-tetrahydropyran-4-yloxy-acetyl]amino]thiazol-5-yl]oxybenzoic acid carboxylate and its (+) and (−) enantiomers; or 3-[2-[[2-(6-Cyclopentylsulfonyl-3-pyridyl)-2-tetrahydropyran-4-yloxy-acetyl]amino]thiazol-5-yl]oxybenzoic acid carboxylate and its (+) and (−) enantiomers.

6. A method of activating Glucokinase in a subject, the method comprising administering to the subject a compound of formula (I), as claimed in any one of the claims 1 to 5, or its stereoisomers, tautomers, prodrugs, pharmaceutically acceptable salts, solvates and formulations thereof.

7. A method of treating hyperglycemia or diabetes or type II diabetes in a subject, the method comprising administering to the subject a compound of formula (I), as claimed in any one of the claims 1 to 5, or its stereoisomers, tautomers, prodrugs, pharmaceutically acceptable salts, solvates and formulations thereof.

8. A method of treating a subject demonstrating pre-diabetic hyperglycemia or impaired glucose tolerance, the method comprising administering to the subject a compound of formula (I), as claimed in any one of the claims 1 to 5, or its stereoisomers, tautomers, prodrugs, pharmaceutically acceptable salts, solvates and formulations thereof.

9. A method of treating diabetes and obesity in a subject, the method comprising administering to the subject a compound of formula (I), as claimed in any one of the claims 1 to 5, or its stereoisomers, tautomers, prodrugs, pharmaceutically acceptable salts, solvates and formulations thereof.

10. A compound of formula (I), as claimed in any one of the claims 1 to 5, or its stereoisomers, tautomers, prodrugs, pharmaceutically acceptable salts, solvates and formulations thereof.

11. A compound of formula (I), as claimed in any one of the claims 1 to 5, or its stereoisomers, tautomers, prodrugs, pharmaceutically acceptable salts, solvates and formulations thereof.

12. A compound of formula (I), as claimed in any one of the claims 1 to 5, or its stereoisomers, tautomers, prodrugs, pharmaceutically acceptable salts, solvates and formulations thereof.

13. A method of enhancing the secretion of enteroincretins in a subject, the method comprising administering to the subject a compound of formula (I), as claimed in any one of the claims 1 to 5, or its stereoisomers, tautomers, prodrugs, pharmaceutically acceptable salts, solvates and formulations thereof, wherein the enteroincretin is optionally selected from the group consisting of GLP-1 and GIP.

14. A pharmaceutical composition comprising, as an active ingredient, at least one compound of formula (I), as claimed in any one of the claims 1 to 5, or its stereoisomers, tautomers, prodrugs, pharmaceutically acceptable salts, and solvates thereof, together with one or more pharmaceutically acceptable carriers or excipients.

15. A pharmaceutical composition comprising, as an active ingredient, at least one compound of formula (I), as claimed in any one of the claims 1 to 5, or its stereoisomers, tautomers, prodrugs, pharmaceutically acceptable salts, and solvates thereof, in combination with one or more pharmaceutically acceptable therapeutically active agents.

16. The pharmaceutical composition as claimed in claim 15 wherein, the pharmaceutically acceptable therapeutically active agent is selected from anti-diabetic agents, anti-hyperglycemic agents, anti-obesity agents, anti-hypertensive agents or anti-dyslipidemic agents.

17. The pharmaceutical composition as claimed in claim 16 wherein the pharmaceutically acceptable therapeutically active agent is selected from insulin secretagogues sulfonylureas, insulinotropic sulfonyl urea receptor ligands, biguanides, glucagon antagonists, peptide glucagon antagonist, non-peptide glucagon antagonist, glucosidase inhibitors, glucose sensitive insulinotropic agents, insulin sensitizers dipeptidyl peptidase-IV inhibitors, fibrates, niacin, statins, cholesterol absorption inhibitors, bile acid sequestrants, diuretics, angiotensin converting enzyme (ACE) inhibitors, angiotensin-II receptor type-I blockers (ARB), rennin inhibitors, calcium channel blockers, aldosterone receptor antagonist, and aldosterone synthase inhibitors.

18. A process for the preparation of a compound of formula (I) as claimed in any one of the claims 1 to 5 or its stereoisomers, tautomers, prodrugs, pharmaceutically acceptable salts, and solvates thereof, said process comprising:

reacting an acid of formula (II)

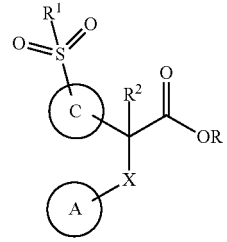

(II)

wherein R is hydrogen, alkyl or arylalkyl, with a compound of formula (III)

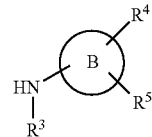

(III)

in presence of a suitable amide coupling reagent, optionally hydrolysing and optionally further coupling with an amine of formula $NHR^6R^7$ to obtain the compound of formula (I)

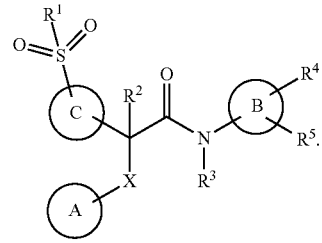

(I)

* * * * *